(12) United States Patent
Kiuchi et al.

(10) Patent No.: US 10,012,777 B2
(45) Date of Patent: Jul. 3, 2018

(54) RESIN COMPOSITION

(71) Applicant: KONICA MINOLTA, INC., Chiyoda-ku, Tokyo (JP)

(72) Inventors: Hiroyoshi Kiuchi, Hachioji (JP); Takatugu Suzuki, Hachioji (JP); Kiyoshi Fukusaka, Fussa (JP); Rie Fujisawa, Ebina (JP); Hiroshi Kita, Hachioji (JP); Issei Nakahara, Hino (JP)

(73) Assignee: KONICA MINOLTA, INC., Tokyo (JP)

( * ) Notice: Subject to any disclaimer, the term of this patent is extended or adjusted under 35 U.S.C. 154(b) by 67 days.

(21) Appl. No.: 14/758,750

(22) PCT Filed: Jan. 9, 2014

(86) PCT No.: PCT/JP2014/050202
§ 371 (c)(1),
(2) Date: Jun. 30, 2015

(87) PCT Pub. No.: WO2014/109350
PCT Pub. Date: Jul. 17, 2014

(65) Prior Publication Data
US 2015/0338563 A1 Nov. 26, 2015

(30) Foreign Application Priority Data

Jan. 10, 2013 (JP) ................................ 2013-002358
May 31, 2013 (JP) ................................ 2013-115431
Jul. 31, 2013 (JP) ................................ 2013-158421

(51) Int. Cl.
| | |
|---|---|
| G02B 5/30 | (2006.01) |
| C08K 5/3472 | (2006.01) |
| C07D 249/04 | (2006.01) |
| H01L 51/00 | (2006.01) |
| G02F 1/13363 | (2006.01) |
| C07D 403/00 | (2006.01) |
| C08J 5/18 | (2006.01) |
| C08K 5/34 | (2006.01) |
| C08L 1/08 | (2006.01) |

(Continued)

(52) U.S. Cl.
CPC ......... *G02B 5/3083* (2013.01); *C07D 207/32* (2013.01); *C07D 249/04* (2013.01); *C07D 249/08* (2013.01); *C07D 249/10* (2013.01); *C07D 249/12* (2013.01); *C07D 249/14* (2013.01); *C07D 271/10* (2013.01); *C07D 285/08* (2013.01); *C07D 401/04* (2013.01); *C07D 403/00* (2013.01); *C07D 403/10* (2013.01); *C07D 403/12* (2013.01); *C07D 403/14* (2013.01); *C07D 405/04* (2013.01); *C07D 407/04* (2013.01); *C07D 409/04* (2013.01); *C07D 413/04* (2013.01); *C07D 417/04* (2013.01); *C08J 5/18* (2013.01); *C08K 5/34* (2013.01); *C08K 5/3472* (2013.01); *C08L 1/08* (2013.01); *C08L 1/10* (2013.01); *C08L 1/12* (2013.01); *C08L 1/28* (2013.01); *C08L 101/14* (2013.01); *G02B 5/30* (2013.01); *G02B 5/305* (2013.01); *G02F 1/133634* (2013.01); *H01L 51/0034* (2013.01); *H01L 51/0067* (2013.01); *G02F 1/13363* (2013.01); *G02F 2001/133541* (2013.01); *G02F 2001/133638* (2013.01)

(58) Field of Classification Search
None
See application file for complete search history.

(56) References Cited

U.S. PATENT DOCUMENTS

| | | | |
|---|---|---|---|
| 3,718,640 | A | 2/1973 | Roueche |
| 3,926,969 | A | 12/1975 | Fleck |

(Continued)

FOREIGN PATENT DOCUMENTS

| | | |
|---|---|---|
| CN | 100462750 C | 2/2009 |
| GB | 1300328 A | 12/1972 |

(Continued)

OTHER PUBLICATIONS

International Preliminary Report on Patentability (IPRP) including Written Opinion (in English) dated Jul. 14, 2015, issued in parent International Application No. PCT/JP2014/050202.
Korean Office Action dated Nov. 17, 2016 (and English translation thereof) issued in counterpart Korean Application No. 10-2015-7017496.
Chinese Office Action (and English translation thereof) dated May 25, 2016, issued in counterpart Chinese Application No. 201480004298.1.
Taiwanese Office Action (and English translation thereof) dated Feb. 23, 2016, issued in counterpart Taiwanese Application No. 103100533.
Chinese Office Action (and English translation thereof) dated Feb. 16, 2017, issued in counterpart Chinese Application No. 201480004298.1.

(Continued)

*Primary Examiner* — Yun Qian
(74) *Attorney, Agent, or Firm* — Holtz, Holtz & Volek PC

(57) ABSTRACT

The present invention provides a resin composition capable of forming a film exhibiting a small humidity-dependent variation in optical values; a triazole compound to be incorporated into the resin composition; an optical film and an optical lens, each of which is prepared from the resin composition and exhibits a small humidity-dependent variation in optical values; and a polarizing plate, a circularly polarizing plate, and an image display device, each of which includes the optical film and exhibits excellent moisture resistance. The resin composition of the present invention contains a resin and a compound having a 5-membered or 6-membered aromatic hydrocarbon or heterocyclic ring, wherein the resin is a hygroscopic resin, the compound has at least three specific aromatic rings having a specific NICS value, and the specific aromatic rings are bonded to one another via a single bond or one or two atoms.

7 Claims, 4 Drawing Sheets

(51) Int. Cl.

| | | |
|---|---|---|
| C08L 101/14 | (2006.01) |
| C07D 403/12 | (2006.01) |
| C07D 401/04 | (2006.01) |
| C07D 403/10 | (2006.01) |
| C07D 403/14 | (2006.01) |
| C07D 405/04 | (2006.01) |
| C07D 407/04 | (2006.01) |
| C07D 409/04 | (2006.01) |
| C07D 413/04 | (2006.01) |
| C07D 417/04 | (2006.01) |
| C07D 249/08 | (2006.01) |
| C07D 249/10 | (2006.01) |
| C07D 249/12 | (2006.01) |
| C07D 249/14 | (2006.01) |
| C07D 271/10 | (2006.01) |
| C07D 207/32 | (2006.01) |
| C07D 285/08 | (2006.01) |
| C08L 1/10 | (2006.01) |
| C08L 1/12 | (2006.01) |
| C08L 1/28 | (2006.01) |
| G02F 1/1335 | (2006.01) |

(56) References Cited

U.S. PATENT DOCUMENTS

| | | | |
|---|---|---|---|
| 5,792,567 | A | 8/1998 | Kido et al. |
| 2005/0222136 | A1* | 10/2005 | Buschmann ......... A61K 31/415 514/221 |
| 2009/0142395 | A1 | 6/2009 | Zadok et al. |
| 2009/0227647 | A1 | 9/2009 | Lake et al. |
| 2011/0076423 | A1 | 3/2011 | Nagura et al. |
| 2012/0204757 | A1 | 8/2012 | Nagura et al. |
| 2012/0251739 | A1 | 10/2012 | Kato et al. |
| 2014/0053755 | A1 | 2/2014 | Nagura et al. |

FOREIGN PATENT DOCUMENTS

| | | | |
|---|---|---|---|
| JP | 07207169 A | 8/1995 |
| JP | 09286980 A | 11/1997 |
| JP | 2000056123 A | 2/2000 |
| JP | 2002352957 A | 12/2002 |
| JP | 2006342227 A | 12/2006 |
| JP | 2008106124 A | 5/2008 |
| JP | 2009139812 A | 6/2009 |
| JP | 2011008017 A | 1/2011 |
| JP | 2011094114 A | 5/2011 |
| JP | 2012123292 A | 6/2012 |
| JP | 2012208173 A | 10/2012 |
| JP | 2012215817 A | 11/2012 |
| JP | 2012234159 A | 11/2012 |
| WO | 9525097 A1 | 9/1995 |
| WO | 2010035282 A1 | 4/2010 |

OTHER PUBLICATIONS

Korshak, et al., "Synthesis and Investigation of New Highly Fused Polyheteroarylenes", Macromolecules, vol. 4, No. 4, pp. 626-632.
Extended European Search Report (EESR) including Written Opinion (in English) dated Oct. 12, 2016, issued in counterpart European Patent Application No. 14738171.9.
Chinese Office Action dated Sep. 5, 2017 issued in counterpart Chinese Application No. 201480004298.1.
Kiselyov, et al., "Synthesis of heteroaromatic 3,3'-bridged biscarbenes of the 1,2,4-triazole series and their properties", ARKIVOC, 2008, vol. 15, pp. 329-342.
Japanese Office Action dated Oct. 17, 2017 which issued in counterpart Japanese Application No. 2017-029287.
Knishevitsky, et al., "Copper (I) halide complexes of the new 4,4'-bridged heteroaromatic biscarbenes of the 1,2,4-triazole series", Journal of Organometallic Chemistry, 2008, v.693, pp. 1405-1411.
Korean Office Action (and English translation thereof) dated Jun. 28, 2017 issued in counterpart Korean Application No. 10-2015-7017496.
Japanese Office Action (and English translation thereof) dated Jul. 4, 2017 issued in counterpart Japanese Application No. 2014-556430.
El Sayed H. El Ashry, et al., "Corrosion inhibitors Part II: Quantum chemical studies on the corrosion inhibitions of steel in acidic medium by some triazole, oxadiazole and thiadiazole derivatives", Electrochimica Acta, 2006, 51, pp. 3957-3968.
International Search Report (ISR) dated Apr. 15, 2014 issued in International Application No. PCT/JP2014/050202.
M. Hajjizadeh, et al., "Electrocatalytic oxidation and determination of deferasirox and deferiprone on a nickel oxyhydroxide-modified electrode", Analytical Biochemistry, 2008, 373, pp. 337-348.
Japanese Office Action (and English translation thereof) dated Dec. 20, 2016 issued in Japanese counterpart Application No. 2014-556430.

* cited by examiner

RESIN COMPOSITION

TECHNICAL FIELD

The present invention relates to a resin composition, a triazole compound to be incorporated thereinto, an optical film and an optical lens, each of which is prepared from the resin composition, a polarizing plate, a circularly polarizing plate, and an image display device. In more specific, the present invention relates to a resin composition exhibiting a small humidity-dependent variation in optical values; a triazole compound to be incorporated thereinto; an optical film and an optical lens, each of which is prepared from the resin composition and exhibits a small humidity-dependent variation in optical values; and a polarizing plate, a circularly polarizing plate, and an image display device, each of which includes the optical film and exhibits excellent moisture resistance.

BACKGROUND ART

Resins, such as acrylic resins, polyesters, polycarbonates, cellulose derivatives, polyvinyl alcohol, and polyimides, are highly transparent, lighter than inorganic glass, and easy to mold. Thus, these resins are widely used in the fields of optical technology and information equipment relevant to recording, display, and transmission of information; for example, in optical disks, optical films for liquid crystal display devices and organic electroluminescent display devices (hereinafter also referred to as "organic EL display devices"), optical lenses, and optical fibers.

Such a resin has a hydrogen bond donor (e.g., the hydrogen atom of a hydroxy group or the hydrogen atom of an amido group) or a hydrogen bond acceptor (e.g., the carbonyl oxygen atom of an ester group or a nitrogen atom contained in an aromatic heterocyclic ring), and thus the resin forms a hydrogen bond with water to adsorb water (hereinafter the resin will be referred to as "hygroscopic resin"). The resin may therefore absorb water in association with a change in environmental humidity over time, leading to variations in dimensions and properties, including mechanical properties, such as rigidity and strength, electrical properties, such as resistivity, and optical properties, such as refractive index.

A variation in retardation is one of the problems caused by adsorption of water on a resin. A retardation film is used for increasing the viewing angle of a liquid crystal display device or preventing external light reflection in an organic EL display device. The retardation of the film is sensitive to the amount of water adsorbed on the resin, because the retardation depends on the birefringence of the film; i.e., the difference between the refractive index in the direction of molecular orientation and that in the direction orthogonal thereto.

Although acrylic resins, polycarbonates, or cellulose derivatives are used as hygroscopic resins for formation of retardation films, the cellulose derivatives, which have high water adsorption (high moisture content), cause large variations in retardation in association with changes in environmental humidity over time.

In recent years, liquid crystal display devices or organic EL display devices have been increasingly used for large-size and high-definition applications, such as television sets, and retardation films have accordingly been demanded to have higher quality. Liquid crystal display devices or organic EL display devices for large-size and high-definition applications are required to be used under severer conditions than conventional ones. Thus, retardation films used in these display devices are demanded to exhibit a small humidity-dependent variation in optical performance.

In view of these situations, several techniques have been proposed which involve incorporation of a specific additive into an optical film for reducing a humidity-dependent variation in optical performance.

PTL 1 discloses a cellulose ester film containing a polyester and a polyhydric alcohol ester or an aromatic-terminal ester.

PTL 2 discloses a cellulose ester film containing a compound having a specific value; i.e., quotient of the molecular weight of the compound divided by the total number of hydrogen bond donors and hydrogen bond acceptors of the compound.

PTL 3 discloses a cellulose ester film containing a highly hygroscopic compound exhibiting a difference between moisture contents determined under different conditions of 2% or more.

The present inventors have evaluated the cellulose ester films disclosed in PTLs 1 to 3 under severer conditions than conventional ones. Consequently, the present inventors have found that although these cellulose ester films exhibit some advantageous effects, the films need further improvements for use in recent display devices for high-definition applications.

A film used in such applications has been demanded to exhibit no variation in performance even under such a severe condition involving direct exposure of the film to water resulting from condensation during its conveyance. The present inventors have found that the conventional techniques disclosed in PTLs 1 to 3 are less effective under the severe condition; i.e., direct exposure to water.

CITATION LIST

Patent Literature

PTL 1: Japanese Unexamined Patent Application Publication No. 2006-342227

PTL 2: Japanese Unexamined Patent Application Publication No. 2011-94114

PTL 3: Japanese Unexamined Patent Application Publication No. 2012-215817

SUMMARY OF INVENTION

Problems to be Solved by Invention

The present invention has been attained in consideration of the problems and circumstances described above. An object of the present invention is to provide a resin composition exhibiting a small humidity-dependent variation in optical values, and a triazole compound to be incorporated thereinto. Another object of the present invention is to provide an optical film and an optical lens, each of which is prepared from the resin composition and exhibits a small humidity-dependent variation in optical values. Still another object of the present invention is to provide a polarizing plate, a circularly polarizing plate, and an image display device, each of which includes the optical film and exhibits excellent moisture resistance.

Means for Solving Problems

The present inventors have focused on the interaction between a hygroscopic resin and an additive, and have understood that a CH/π interaction occurs between CH moieties of a hygroscopic resin and π-electrons of a hydrophobic aromatic compound on the basis of unexpectedly good compatibility of the hygroscopic resin with the aromatic compound, which exhibits low hydrogen bonding ability or poor dipolar interaction. The present inventors have also understood that utilization of the CH/π interaction enables the interaction between the additive and the hygroscopic resin to be stronger than that between water molecules and the resin, resulting in prevention of intrusion of water between the resin and the additive, leading to stable optical properties. Thus, the present inventors have studied means for enhancing the CH/π interaction. The present inventors have assumed that the CH/π interaction can be particularly enhanced by an aromatic compound having at least three adjacently bonded specific aromatic rings each having a specific NICS value. On the basis of this assumption, the present inventors have examined various compounds, and have consequently found that the aforementioned aromatic compound is particularly effective for reducing a humidity-dependent variation in optical values. The present invention has been accomplished on the basis of this finding.

The technique according to the present invention has first provided a film which exhibits a small variation in retardation even under such a severe condition, that is, direct exposure of the film to water.

The problems described above are accordingly solved by the present invention which is characterized as follows:

1. A resin composition comprising:
    a resin; and
    a compound having a 5-membered or 6-membered aromatic hydrocarbon or heterocyclic ring,
    wherein the resin is a hygroscopic resin, the compound has at least three 5-membered or 6-membered aromatic hydrocarbon or heterocyclic rings having an NICS value equal to or smaller than that of a benzene ring, at least one of the rings has an NICS value smaller than that of the benzene ring, and the 5-membered or 6-membered aromatic hydrocarbon or heterocyclic rings are bonded to one another via a single bond or one or two atoms.

2. The resin composition according to item 1, wherein an optical film (sample film) prepared from the resin composition exhibits a percent reduction of a variation in retardation value (Ro or Rt) of 20 to 100% under the following conditions for measurement:
    (a) another optical film (reference film) is prepared in the same manner as the sample film, where the reference film has the same thickness as the sample film and does not contain a compound having a 5-membered or 6-membered aromatic hydrocarbon or heterocyclic ring;
    (b) the sample film and the reference film are immersed in pure water at 23° C. for 24 hours;
    (c) the retardation values Ro and Rt of each of the sample film and the reference film are determined at 23° C., 55% RH, and a light wavelength of 590 nm, and the absolute value ΔRo or ΔRt of the difference between the retardation value Ro or Rt before water immersion and that after water immersion is determined for each of the optical films; and
    (d) the percent reduction of a variation in retardation value (Ro or Rt) is determined by the following expression:

percent reduction of a variation in $Ro$ (%)={[(Δ$Ro$ of the reference film)−(Δ$Ro$ of the sample film)]÷(Δ$Ro$ of the reference film)}×100, or percent reduction of a variation in $Rt$ (%)={[(Δ$Rt$ of the reference film)−(Δ$Rt$ of the sample film)]÷(Δ$Rt$ of the reference film)}×100.

3. The resin composition according to item 1 or 2, wherein the hygroscopic resin exhibits a water absorption of 0.5 to 10 mass % at 23° C.

4. The resin composition according to any one of items 1 to 3, wherein the hygroscopic resin is a cellulose derivative.

5. The resin composition according to any one of items 1 to 4, wherein the hygroscopic resin is a cellulose ester.

6. The resin composition according to any one of items 1 to 5, wherein the compound has a pyrrole ring, a pyrazole ring, an imidazole ring, a 1,2,3-triazole ring, or a 1,2,4-triazole ring as a 5-membered or 6-membered aromatic hydrocarbon or heterocyclic ring having an NICS value smaller than that of a benzene ring.

7. The resin composition according to any one of items 1 to 6, wherein the compound having a 5-membered or 6-membered aromatic hydrocarbon or heterocyclic ring has a structure represented by Formula (1):

[F1]

$A_1$-$L_1$-$T_1$-$L_2$-$B$-($L_3$-$T_2$-$L_4$-$A_2$)$_n$    Formula (1)

wherein $A_1$ and $A_2$ each independently represent an alkyl group, a cycloalkyl group, an aromatic hydrocarbon ring, or an aromatic heterocyclic ring, B represents an aromatic hydrocarbon ring or an aromatic heterocyclic ring, $T_1$ and $T_2$ each independently represent a pyrrole ring, a pyrazole ring, an imidazole ring, a 1,2,3-triazole ring, or a 1,2,4-triazole ring, $L_1$, $L_2$, $L_3$, and $L_4$ each independently represent a single bond or a divalent linking group, and n represents an integer of 0 to 5.

8. The resin composition according to item 7, wherein $L_1$, $L_2$, $L_3$, and $L_4$ in Formula (1) each independently represent a single bond.

9. The resin composition according to item 7 or 8, wherein $T_1$ and $T_2$ each independently represent a pyrazole ring.

10. The resin composition according to any one of items 1 to 9, wherein the compound having a 5-membered or 6-membered aromatic hydrocarbon or heterocyclic ring has a structure represented by Formula (2):

[F2]

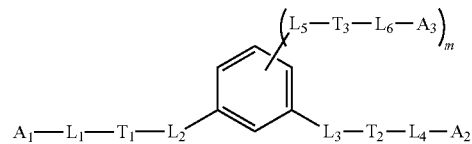

Formula(2)

wherein $A_1$, $A_2$, $T_1$, $T_2$, $L_1$, $L_2$, $L_3$, and $L_4$ have the same meanings as defined in Formula (1), $A_3$ and $T_3$ are the same as $A_1$ and $T_1$ in Formula (1), respectively, each of $L_5$ and $L_6$ is the same as $L_1$ in Formula (1), and m represents an integer of 0 to 4.

11. The resin composition according to item 7, wherein the compound having a structure represented by Formula (1) is a triazole compound having a structure represented by Formula (1.1):

[F3]

[$A_1$-$L_1$-$T_1$-$L_2$]$_k$B    Formula (1.1)

wherein $A_1$, B, $L_1$, and $L_2$ have the same meanings as defined in Formula (1), k represents an integer of 1 to 4, and $T_1$ represents a 1,2,4-triazole ring.

12. The resin composition according to item 11, wherein the triazole compound having a structure represented by Formula (1.1) is a triazole compound having a structure represented by Formula (1.2):

[F4]

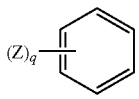

Formula(1.2)

wherein Z represents a structure represented by Formula (1.2a), q is 2 or 3, and at least two structures Z bonded to the benzene ring are located in the ortho- or meta-position relative to each other:

[F5]

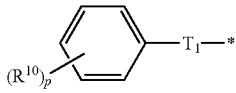

Formula(1.2a)

wherein $R^{10}$ represents a hydrogen atom, an alkyl group, or an alkoxy group, p represents an integer of 1 to 5, * represents a position at which the structure is bonded to the benzene ring, and $T_1$ represents a 1,2,4-triazole ring.

13. An optical film prepared from the resin composition according to any one of items 1 to 12.

14. The optical film according to item 13, containing the compound having a 5-membered or 6-membered aromatic hydrocarbon or heterocyclic ring in an amount of 1 to 15 mass % relative to the resin.

15. The optical film according to item 13 or 14, exhibiting an in-plane retardation value Ro represented by Expression (I) of 40 to 100 nm and a retardation value Rt across the thickness of the film represented by Expression (II) of 100 to 300 nm, the retardation values Ro and Rt being determined at 23° C., 55% RH, and a light wavelength of 590 nm:

$Ro=(n_x-n_y)\times d$      Expression (I)

$Rt=\{(n_x+n_y)/2-n_z\}\times d$      Expression (II)

wherein $n_x$ represents a refractive index in a direction x in which the refractive index is maximum in the in-plane direction of the film, $n_y$ represents a refractive index in a direction y orthogonal to the direction x in the in-plane direction of the film, $n_z$ represents a refractive index in a thickness direction z of the film, and d represents the thickness (nm) of the film.

16. The optical film according to any one of items 13 to 15, exhibiting in-plane retardation values Ro (450), Ro (550), and Ro (650) which are determined at 23° C. and 55% RH and respectively at light wavelengths of 450 nm, 550 nm, and 650 nm, and satisfy Expressions (a1) to (a3):

$110 \leq Ro(550) \leq 170$;      (a1)

$0.72 \leq Ro(450)/Ro(550) \leq 0.96$;      (a2)

and $0.83 Ro(550)/Ro(650) \leq 0.97$.      (a3)

17. A polarizing plate comprising:
   a polarizer; and
   the optical film according to any one of items 13 to 16 provided on at least one surface of the polarizer.

18. A circularly polarizing plate comprising:
   a polarizer; and
   the optical film according to any one of items 13 to 16 provided on at least one surface of the polarizer.

19. An image display device comprising the optical film according to item 15 or 16.

20. The image display device according to item 19, which is a liquid crystal display device comprising a liquid crystal cell and the polarizing plate according to item 17 provided on at least one surface of the liquid crystal cell.

21. The image display device according to item 20, wherein the liquid crystal cell is a VA-mode liquid crystal cell.

22. The image display device according to item 19, which is an organic electroluminescent display device comprising an organic electroluminescent element and the circularly polarizing plate according to item 18 provided on the organic electroluminescent element.

23. An optical lens prepared from the resin composition according to any one of items 1 to 12.

24. A triazole compound having a structure represented by Formula (1.2):

[F6]

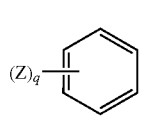

Formula(1.2)

wherein Z represents a structure represented by Formula (1.2a), q is 2 or 3, and at least two structures Z bonded to the benzene ring are located in the ortho- or eta-position relative to each other:

[F7]

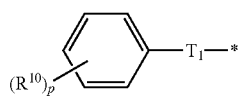

Formula(1.2a)

wherein $R^{10}$ represents a hydrogen atom, an alkyl group, or an alkoxy group, p represents an integer of 1 to 5, and * represents a position at which the structure is bonded to the benzene ring.

Effects of Invention

The present invention can provide a resin composition exhibiting a small humidity-dependent variation in optical values, and a triazole compound to be incorporated thereinto. The present invention can also provide an optical film and an optical lens, each of which is prepared from the resin composition and exhibits a small humidity-dependent variation in optical values. The present invention can also provide a polarizing plate, a circularly polarizing plate, and an image display device, each of which includes the optical film and exhibits excellent moisture resistance.

The mechanism by which the advantageous effects of the present invention are expressed is presumed as follows:

The present invention relates to a technique for achieving coexistence of an organic compound serving as an additive with a hygroscopic resin having high affinity for water molecules. The present inventors have understood that a variation in optical properties of an optical film, which would occur due to intrusion of water molecules into the film over time or during any treatment, can be reduced to a minimum possible extent by a plurality of sites of a special "CH/π interaction" between CH moieties of a hygroscopic resin and π-electrons of an additive, the interaction having not yet been recognized as a major resin-additive interaction.

MODES FOR CARRYING OUT THE INVENTION

Figure 1:
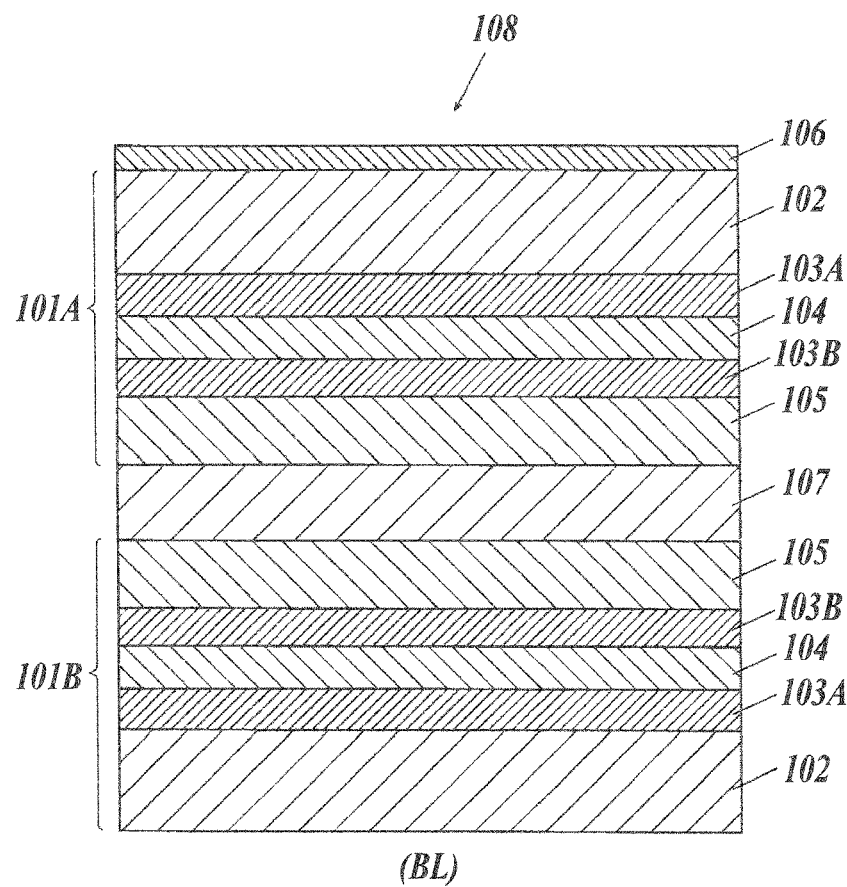
FIG. 1 is a schematic diagram of the configuration of a liquid crystal display device.

The resin composition of the present invention contains a resin and a compound having a 5-membered or 6-membered aromatic hydrocarbon or heterocyclic ring, wherein the resin is a hygroscopic resin, the compound has at least three 5-membered or 6-membered aromatic hydrocarbon or heterocyclic rings having an NICS value equal to or smaller than that of a benzene ring, at least one of the rings has an NICS value smaller than that of the benzene ring, and the 5-membered or 6-membered aromatic hydrocarbon or heterocyclic rings are bonded to one another via a single bond or one or two atoms. These technical characteristics are common to Aspects 1 to 24 of the present invention.

In the present invention, an optical film prepared from the resin composition preferably exhibits a percent reduction of a variation in retardation value (Ro or Rt) of 20 to 100% under the aforementioned measuring conditions. The hygroscopic resin preferably exhibits a water absorption of 0.5 to 10 mass % at 23° C. The hygroscopic resin is preferably a cellulose derivative or a cellulose ester for attaining the advantageous effects of the present invention.

The compound preferably has a pyrrole ring, a pyrazole ring, an imidazole ring, a 1,2,3-triazole ring, or a 1,2,4-triazole ring as a 5-membered or 6-membered aromatic hydrocarbon or heterocyclic ring having an NICS value smaller than that of a benzene ring. The compound having a 5-membered or 6-membered aromatic hydrocarbon or heterocyclic ring preferably has a structure represented by Formula (1). In Formula (1), preferably, $L_1$, $L_2$, $L_3$, and $L_4$ each independently represent a single bond. Preferably, $T_1$ and $T_2$ each independently represent a pyrazole ring.

The compound having a 5-membered or 6-membered aromatic hydrocarbon or heterocyclic ring preferably has a structure represented by Formula (2).

The compound having a structure represented by Formula (1) is preferably a triazole compound having a structure represented by Formula (1.1). The triazole compound having a structure represented by Formula (1.1) is preferably a triazole compound having a structure represented by Formula (1.2).

The resin composition is preferably used for preparation of an optical film. The optical film preferably has an in-plane retardation value Ro represented by Expression (I) of 40 to 100 nm and a retardation value Rt across the thickness of the film represented by Expression (II) of 100 to 300 nm, the retardation values Ro and Rt being determined at 23° C., 55% RH, and a light wavelength of 590 nm. In-plane retardation values Ro (450), Ro (550), and Ro (650), which are determined at 23° C. and 55% RH and respectively at light wavelengths of 450 nm, 550 nm, and 650 nm, preferably satisfy Expressions (a1) to (a3).

The optical film is preferably provided on a polarizing plate or a circularly polarizing plate of at least one surface of a polarizer. The optical film is also preferably provided in an image display device. The polarizing plate is preferably provided on at least one surface of a liquid crystal cell in a liquid crystal display device. The liquid crystal cell is preferably a VA-mode liquid crystal cell. The image display device is preferably an organic EL display device including an organic EL element and the circularly polarizing plate provided thereon.

The resin composition is preferably used for preparation of an optical lens.

The present invention, the contexture thereof, and embodiments and aspects for implementing the present invention will now be described in detail. As used herein, the term "to" between two numerical values indicates that the numeric values before and after the term are inclusive as the lower limit value and the upper limit value, respectively.

The resin composition of the present invention contains a resin and a compound having a 5-membered or 6-membered aromatic hydrocarbon or heterocyclic ring, wherein the resin is a hygroscopic resin, the compound has at least three 5-membered or 6-membered aromatic hydrocarbon or heterocyclic rings having an NICS value equal to or smaller than that of a benzene ring, at least one of the rings has an NICS value smaller than that of the benzene ring, and the 5-membered or 6-membered aromatic hydrocarbon or heterocyclic rings are bonded to one another via a single bond or one or two atoms.

Now will be described a CH/π interaction, which directly relates to the technical concept of the present invention.

<<CH/π Interaction>>

The present inventors have focused on the interaction between a hygroscopic resin and an additive, and have understood that a "CH/π interaction" occurs between CH moieties present in the main chain or side chains of a hygroscopic resin and π-electrons of a hydrophobic aromatic compound (i.e., additive) on the basis of unexpectedly good compatibility of the hygroscopic resin with the aromatic compound, which exhibits low hydrogen bonding ability or poor dipolar interaction. The CH/π interaction, which is a non-polar interaction largely attributed to the London dispersion force, is also effective in a polar solvent with high dielectric constant, such as water. The present inventors have also understood that utilization of the CH/π interaction enables the interaction between the additive and the hygroscopic resin to be stronger than that between water molecules and the resin, resulting in prevention of intrusion of water between the resin and the additive, whereby variations in optical properties, which is a problem involved in conventional techniques, can be reduced. On the basis of this conception, the present inventors have examined various compounds, and have consequently found that a specific compound is highly effective for reducing a variation in optical properties. The present invention has been accomplished on the basis of this finding.

Thus, the present invention relates to a technique for achieving coexistence of an organic compound serving as an additive with a hygroscopic resin having high affinity for water molecules. The present invention, which is based on a technical concept different from conventional ones, is characterized by the use of an additive that achieves a plurality of sites of a specific interaction regardless of the presence of water molecules. Specifically, the present invention is characterized by a plurality of sites of a special "CH/π interaction" between CH moieties of the resin and π-electrons of the additive, the interaction having not yet been regarded as a major resin-additive interaction. The present inventors have conceived that these CH/π interaction sites can reduce variations in optical properties of an optical film, which would occur due to intrusion of water molecules into the film over time or during any treatment.

If a resin composition containing a hygroscopic resin and an additive is used in an optical application requiring high transparency, such as an optical film or an optical lens, the hygroscopic resin must be compatibilized with the additive. In conventional techniques, an additive used in an optical film is compatibilized with a hygroscopic resin through formation of hydrogen bonds between the additive and the resin with a hydrogen bond donor (e.g., the hydrogen atom of a hydroxy group or the hydrogen atom of an amido group) or a hydrogen bond acceptor (e.g., the carbonyl oxygen atom of an ester group or a nitrogen atom contained in an aromatic heterocyclic ring), which is necessarily present in the hygroscopic resin.

It is known that the hygroscopic resin can be compatibilized with the additive even in the absence of hydrogen bonds. Specifically, the hygroscopic resin, which necessarily has a polar group (i.e., a moiety for electron localization), can have a large local or entire dipole moment, the additive also has a dipole moment corresponding to that of the resin, and the resultant "dipole-dipole interaction" is utilized as major stabilization means.

In contrast, a non-hygroscopic resin, such as polyethylene or cycloolefin polymer, cannot be readily compatibilized with an additive having hydrogen bonding ability, and thus such a resin is mixed with an additive which achieves compatibility through hydrophobic-hydrophobic interaction, which is quite different from the dipole-dipole interaction. In general, an additive incorporated into the resin exhibits special functions, such as plasticization, ultraviolet absorption, antioxidation, and/or optical property control functions, and the additive necessarily has a hydrogen bond donor or a hydrogen bond acceptor (i.e., the additive is not a compound formed only of hydrogen and carbon atoms). Thus, a simpler technique involves compatibilization of a hygroscopic resin with an additive. This technique is advantageous in that the additive can be selected from various compounds.

Compatibilization of a hygroscopic resin with an additive as described above requires hydrogen bonding or dipole-dipole interaction as an intermolecular force.

Now will be described the case where hydrogen bonding is used as an intermolecular force for achieving compatibilization. A water molecule has both a hydrogen bond donor (i.e., hydrogen atom) and a hydrogen bond acceptor (i.e., oxygen atom) and has a small size. When water molecules intrude into an optical film over time or during any treatment, the number of water molecules present in the film is much larger than that of hygroscopic resin molecules or additive molecules, and thus most hydrogen bond donors of the hygroscopic resin form hydrogen bonds with water molecules, whereby the hydrogen bonding ability of the resin is lowered. The hydrogen bonding ability of the additive is also lowered through formation of hydrogen bonds with water molecules, and no substantial interaction occurs between the hygroscopic resin and the additive. In fact, intrusion of water molecules into interfaces between the hygroscopic resin and the additive precludes the control of variations in optical properties.

In the case where a dipole-dipole interaction is used as an intermolecular force for achieving compatibilization, the number of localized electrons is decreased due to adsorption of water molecules (formation of hydrogen bonds) on the hygroscopic resin, leading to a reduction in dipole moment in the resin. The dipole moment in the additive is also reduced for the same reason. Thus, no substantial interaction occurs between the hygroscopic resin and the additive.

On the basis of the above-described hypothesis, the present inventors have inferred that if a special interaction which is not affected by the presence or absence of water molecules occurs between the hygroscopic resin and the additive, intrusion of water therebetween can be prevented, and the aforementioned problems can be overcome.

An interaction applicable to an organic compound will now be described.

The presence of a ring current derived from π-electrons in an aromatic compound causes an induced magnetic field. If a hydrogen atom (generally in the form of a C—H moiety) is present in a region in which the magnetic field acts, the CH moiety approaches a π-plane by an attractive force. This force is called "CH/π interaction."

The intensity of the CH/π interaction, which is basically attributed to π-electron spin, is constant whether water molecules are absorbed or not. The present inventors have assumed that utilization of this interaction between a hygroscopic resin and an additive can reduce variations in optical properties due to water molecules, which is a problem involved in conventional techniques.

Now will be described an example of stabilization of a molecular conformation with the CH/π interaction.

In a magenta dye containing an image stabilizing agent used for a color photographic photosensitive material, $CH_2$ protons of sulfomorpholine contained in the image stabilizing agent may be chemically shifted significantly by the π current effect of phenyl groups contained in the dye and facing the $CH_2$ protons. As used herein, the term "facing" refers to a state where $CH_2$ protons are located in the vicinity of the center of a phenyl group contained in the dye at a specific distance from the phenyl group (at a small distance sufficient for CH/π interaction). This phenomenon, which can also be confirmed in a molecular model, indicates that the CH/π interaction between CH moieties in the image stabilizing agent and phenyl groups (π-electrons) contained in the dye is an intermolecular force required for formation of the aforementioned molecular conformation.

Unlike the aforementioned case, when a compound has a structure similar to that of the dye but whose phenyl groups contained in the dye does not face the image stabilizing agent, sulfomorpholine rings do not face the phenyl groups. This demonstrates that molecules of the dye exhibiting no CH/π interaction are located away from molecules of the image stabilizing agent; i.e., the CH/π interaction can be an effective intermolecular force for binding different organic compounds.

Ring current effect will now be described.

From the viewpoint of generation of the CH/π interaction between CH moieties of a hygroscopic resin and π-electrons of an additive, the additive preferably exhibits a higher degree of π-electron contribution. The degree of π-electron contribution can be indicated by, for example, nucleus-independent chemical shift (NICS).

NICS values are used for quantification of aromaticity based on magnetic characteristics. An aromatic compound is strongly shielded at the center of the ring by its ring current effect, whereas an antiaromatic compound is deshielded (J. Am. Chem. Soc. 1996, 118, 6317). NICS values indicate the intensity of ring current; i.e., the degree of contribution of π-electrons to the aromaticity of a ring. Specifically, NICS values correspond to chemical shifts (calculated values) of virtual lithium ions disposed directly at the center of the ring. A more negative NICS value indicates a higher degree of π-electron contribution.

Several NICS measurements have been reported in, for example, Canadian Journal of Chemistry, 2004, 82, 50-69 (literature A) and The Journal of Organic Chemistry, 2000, 67, 1333-1338 (literature B).

In the present invention, NICS values are calculated with Gaussian 03 (Software Revision B.03, manufactured by Gaussian Inc., USA). Specifically, NICS values are calculated through NMR shielding constant calculation (GIAO method=Gauge-Independent Atomic Orbital method) on the basis of a structure optimized with B3LYP (density functional theory) and 6–31+G (split valence basis set with diffusion Gaussian function).

Table 1 shows the NICS values of typical ring structures calculated by this method.

TABLE 1

| Ring | NICS value |
| --- | --- |
| Pyrrole ring | −14.87 |
| Thiophene ring | −14.09 |
| Furan ring | −12.42 |
| Benzene ring | −7.98 |
| Naphthalene ring | −8.11 |
| Pyrazole ring | −13.82 |
| Imidazole ring | −13.28 |
| 1H-1,2,4-Triazole ring | −13.18 |
| 1,2,3-Oxadiazole ring | −12.74 |
| 1,2,5-Oxadiazole ring | −12.44 |
| 1,3-Thiazole ring | −12.82 |
| 1,2,4-Thiadizole ring | −13.23 |

As shown in Table 1, a 5-membered aromatic heterocyclic ring such as a pyrrole ring, a thiophene ring, or a furan ring has an NICS value more negative than that of an aromatic hydrocarbon ring such as a benzene ring or a naphthalene ring. Such a 5-membered aromatic heterocyclic ring is expected to enhance the CH/π interaction.

A π/π interaction is a π-electron-attributed intermolecular force other than the CH/π interaction. The π/π interaction is an intermolecular force between two aromatic rings. The π/π interaction is largely attributed to the London dispersion force because the aromatic rings have a large polarizability. Thus, the π/π interaction is readily provided by aromatic rings having a larger π-conjugated system because of their larger polarizability. In the case of benzene, which has a six-π-electron system, the most stable molecular conformation is such that one benzene ring is aligned perpendicular to another benzene ring, and a CH/π interaction occurs between a benzene ring and a hydrogen atom. In contrast, in the case of an aromatic compound having a larger π-conjugated system, such as naphthalene (10-π-electron system) or anthracene (14-π-electron system), the most stable molecular conformation is such that aromatic rings are disposed with each other through a π/π interaction. This indicates a strong π/π interaction occurs between aromatic rings having a larger π-conjugated system.

For generation of a CH/π interaction between CH moieties of a hygroscopic resin and π-electrons of an additive, a π/π interaction between additive molecules must be taken into consideration for the following reason. If the π/π interaction between additive molecules is stronger than the CH/π interaction between the hygroscopic resin and the additive, the π/π interaction becomes more dominant than the CH/π interaction. As indicated by the difference in most stable molecular conformation between benzene and naphthalene, an aromatic ring having a small π-conjugated system (six-π-electron system) is more advantageous than an aromatic ring having a large π-conjugated system (14-π-electron system or 10-π-electron system) for generation of the CH/π interaction.

[F8]

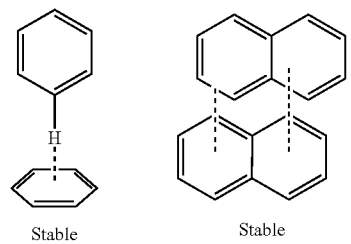

Stable conformation of benzene CH/π interaction

Stable conformation of naphthalene π/π interaction

The CH/π interaction is a weak intermolecular force as compared with, for example, hydrogen bonding, and thus difficulty is encountered in coordinating the additive to the resin only by this intermolecular force. However, a plurality of adjacently bonded aromatic rings would probably enhance the CH/π interaction between the resin and the additive. As a result of extensive studies, the present inventors have found that an effective technique involves use of a compound having at least three 5-membered or 6-membered aromatic hydrocarbon or heterocyclic rings having an NICS value equal to or smaller than that of a benzene ring, wherein at least one of the rings has an NICS value smaller than that of the benzene ring, and the 5-membered or 6-membered aromatic hydrocarbon or heterocyclic rings are bonded to one another via a single bond or one or two atoms.

As described above, the present invention provides a universal technique for maintaining stable optical properties of a resin composition during long-term storage or treatment with water. The technique involves application, to a hygroscopic resin, of a CH/π interaction, which is irrelevant to water molecules or undergoes no change in intensity even after adsorption of water molecules on the resin, and which has not yet been used as a means for achieving coexistence of the resin and an additive. The present invention is based on a technical concept quite different from techniques of using a hygroscopic resin and an aromatic compound in combination incidentally described in published literature (including patent literature). Thus, the present invention, which has been accomplished on the basis of a novel technical concept, should be regarded as an advanced and universal technique which will further develop in the future.
(Percent Reduction of Variation in Retardation Value (Ro or Rt))

An optical film (sample film) prepared from the resin composition of the present invention exhibits 20 to 100% reduction of a variation in retardation value (Ro or Rt) under the following conditions for measurement.

Ro represents an in-plane retardation value of the optical film, and Rt represents a retardation value across the thickness of the optical film, which will be detailed below.
Conditions for Measurement (a) Another optical film (reference film) is prepared in the same manner as the sample film, where the reference film has the same thickness as the sample film and does not contain a compound having a 5-membered or 6-membered aromatic hydrocarbon or heterocyclic ring.

(b) The sample film and the reference film are immersed in pure water at 23° C. for 24 hours.

(c) The retardation values Ro and Rt of each of the sample film and the reference film are determined at 23° C., 55% RH, and a light wavelength of 590 nm. The absolute value ΔRo or ΔRt of the difference between the retardation value Ro or Rt before water immersion and that after water immersion is determined for each of the optical films.

(d) The percent reduction of a variation in retardation value (Ro or Rt) is determined by the following expression.

Percent reduction of a variation in $Ro$ (%)={[($\Delta Ro$ of the reference film)–($\Delta Ro$ of the sample film)]÷($\Delta Ro$ of the reference film)}×100

Percent reduction of a variation in $Rt$ (%)={[($\Delta Rt$ of the reference film)–($\Delta Rt$ of the sample film)]÷($\Delta Rt$ of the reference film)}×100

The optical films (sample film and reference film) having a predetermined thickness can be prepared by any known method.

As used herein, the term "predetermined thickness" refers to a thickness within the range of 10 to 100 μm, preferably 20 to 70 μm, more preferably 30 to 50 μm from the viewpoint of rapid measurement.

The retardation values of the sample film and the reference film are determined under the same conditions.

The sample film used for the aforementioned measurement contains a compound having a 5-membered or 6-membered aromatic hydrocarbon or heterocyclic ring in an amount of preferably 1 to 15 mass %, more preferably 2 to 10 mass %, still more preferably 2 to 5 mass %, relative to the resin (100%). The compound contained in such a preferred amount exhibits good compatibility with the resin, and achieves an optical film exhibiting a small humidity-dependent variation in optical values and excellent bleeding-out resistance.

The optical film prepared from the resin composition of the present invention exhibits a percent reduction of a variation in retardation value (Ro or Rt) of more preferably 50 to 100%, still more preferably 70 to 100%. Particularly preferred is that both percent reduction of a variation in Ro and percent reduction of a variation in Rt fall within the aforementioned range.

In conventional techniques, a variation in retardation value in association with a change in environmental humidity is evaluated by the difference between retardation values measured at a constant temperature under low- and high-humidity conditions. In the present invention, a variation in retardation value is evaluated by the difference between retardation values before and after immersion of the optical film in water for a specific time period. Thus, in the present invention, a variation in retardation value is evaluated under severer conditions (i.e., direct exposure of the film to water) than conventional ones.
(Determination of Retardation Value)

The retardation value can be determined with an automatic birefringence analyzer (KOBRA-21ADH, manufactured by Oji Scientific Instruments) at a light wavelength of 590 nm.

Specifically, three-dimensional refractive indices of the optical film are measured at 10 points at 23° C. and 55% RH at a light wavelength of 590 nm, and the averages of the refractive indices $n_x$, $n_y$, and $n_z$ are determined. Thereafter, the in-plane retardation value Ro and the retardation value Rt across the thickness of the film are calculated by Expressions (I) and (II):

$$Ro(590)=(n_x-n_y)\times d \qquad \text{Expression (I)}$$

$$Rt(590)=\{(n_x+n_y)/2-n_z\}\times d \qquad \text{Expression (II)}$$

wherein $n_x$ represents a refractive index in a direction x in which the refractive index is maximum in the in-plane direction of the film; $n_y$ represents a refractive index in a direction y orthogonal to the direction x in the in-plane direction of the film; $n_z$ represents a refractive index in a thickness direction z of the film; and d represents the thickness (nm) of the film.

<<Resin Composition>>

The resin composition of the present invention contains a resin and a compound having a 5-membered or 6-membered aromatic hydrocarbon or heterocyclic ring. The resin is a hygroscopic resin. The compound (hereinafter also referred to as "additive N") has at least three 5-membered or 6-membered aromatic hydrocarbon or heterocyclic rings having an NICS value equal to or smaller than that of a benzene ring. At least one of the rings has an NICS value smaller than that of the benzene ring. The 5-membered or 6-membered aromatic hydrocarbon or heterocyclic rings are bonded to one another via a single bond or one or two atoms.

Such an additive is preferred in that coordination of the additive to the hygroscopic resin by a plurality of CH/n interaction sites prevents intrusion of water molecules between the resin and the additive, resulting in stable optical properties.

The 5-membered or 6-membered aromatic ring having an NICS value equal to or smaller than that of a benzene ring may be a monocyclic ring or may have one or more substituents. The substituents may be bonded together to form a ring, and the ring may have π-electrons.

The 5-membered or 6-membered aromatic ring having an NICS value equal to or smaller than that of a benzene ring preferably has a six-π-electron system. In the case of an aromatic ring having a larger π-conjugated system, such as a naphthalene ring (10-π-electron system), a benzoxazole ring (10-π-electron system), or an anthracene ring (14-π-electron system), a stronger π/π interaction occurs as described above, and thus the π/π interaction between additive molecules is stronger than the CH/π interaction between the hygroscopic resin and the additive. In contrast, an aromatic compound having a six-π-electron system tends to exhibit higher compatibility with the hygroscopic resin, and reduces bleeding-out of the resultant optical film over time.

Even if the additive is compatibilized with the hygroscopic resin, the distance therebetween decreases, resulting in stable optical properties.

Any aromatic ring structure may be used which has an NICS value smaller than that of a benzene ring. Examples of the aromatic ring structure include a pyrrole ring, a pyrazole ring, an imidazole ring, a 1,2,3-triazole ring, a 1,2,4-triazole ring, a tetrazole ring, a furan ring, an oxazole ring, an isoxazole ring, an oxadiazole ring, an isoxadiazole ring, a thiophene ring, a thiazole ring, an isothiazole ring, a thiadiazole ring, and an isothiadiazole ring. Of these, an aromatic ring containing only a nitrogen atom as a heteroatom other than a carbon atom is preferred, because the aromatic ring has a smaller NICS value and exhibits an excellent effect of reducing a variation in optical properties.

The aromatic ring containing only a nitrogen atom as a heteroatom other than a carbon atom is less likely to cause any reaction or degradation in coexistence with the hygroscopic resin, and enables preparation of a resin composition having excellent durability. Specifically, the aromatic ring having an NICS value smaller than that of a benzene ring is preferably a pyrrole ring, a pyrazole ring, an imidazole ring, a 1,2,3-triazole ring, or a 1,2,4-triazole ring.

If at least three 5-membered or 6-membered aromatic hydrocarbon or heterocyclic rings having an NICS value equal to or smaller than that of a benzene ring are bonded to one another via a single bond or one or two atoms, the CH/π interaction between the hygroscopic resin and the additive is strong, and a variation in optical properties is reduced. As used herein, the expression "via one or two atoms" refers to the case where the minimum number of atoms of a linking group between aromatic rings is one or two. Specifically, an ether group (—O—) has one linking atom, an ester group (—CO—O—) has two linking atoms, and a carbonate group (—O—CO—O—) has three linking atoms. A single bond is more preferred for further reducing a variation in optical properties.

If A, B, and C represent three 5-membered or 6-membered aromatic hydrocarbon or heterocyclic rings having an NICS value equal to or smaller than that of a benzene ring, A is bonded to B, and B is bonded to C, the dihedral angles between A and B and between B and C are preferably small for parallel formation of CH/π interaction sites by the respective aromatic rings. A significantly small dihedral angle may cause the π/π interaction to be dominant. Thus, the dihedral angle between A and B or between B and C is preferably 0° to 45°, more preferably 5° to 40°, still more preferably 10° to 35°.

<Compound Represented by Formula (1)>

In the resin composition of the present invention, it is particularly preferred that the additive N be a compound having a structure represented by Formula (1).

[F9]

$$A_1\text{-}L_1\text{-}T_1\text{-}L_2\text{-}B\text{-}(L_3\text{-}T_2\text{-}L_4\text{-}A_2)_n \qquad \text{Formula (1)}$$

In Formula (1), $A_1$, $A_2$, and B each independently represent an alkyl group (e.g., a methyl, ethyl group, n-propyl, isopropyl, tert-butyl, n-octyl group, or 2-ethylhexyl group), a cycloalkyl group (e.g., a cyclohexyl, cyclopentyl, or 4-π-dodecylcyclohexyl group), an aromatic hydrocarbon ring, or an aromatic heterocyclic ring. Of these, preferred is an aromatic hydrocarbon ring or an aromatic heterocyclic ring, and particularly preferred is a 5-membered or 6-membered aromatic hydrocarbon or heterocyclic ring having an NICS value equal to or smaller than that of a benzene ring.

Any 5-membered or 6-membered aromatic hydrocarbon or heterocyclic ring structure may be used which has an NICS value equal to or smaller than that of a benzene ring. Examples of the ring structure include a benzene ring, a pyrrole ring, a pyrazole ring, an imidazole ring, a 1,2,3-triazole ring, a 1,2,4-triazole ring, a tetrazole ring, a furan ring, an oxazole ring, an isoxazole ring, an oxadiazole ring, an isoxadiazole ring, a thiophene ring, a thiazole ring, an isothizole ring, a thiadiazole ring, and an isothiadiazole ring.

The 5-membered or 6-membered aromatic hydrocarbon or heterocyclic ring having an NICS value equal to or smaller than that of a benzene ring represented by $A_1$, $A_2$, or B may have a substituent. Examples of the substituent include halogen atoms (e.g., fluorine, chlorine, bromine, and iodine), alkyl groups (e.g., methyl, ethyl, n-propyl, isopropyl, tert-butyl, n-octyl, and 2-ethylhexyl), cycloalkyl groups (e.g., cyclohexyl, cyclopentyl, and 4-n-dodecylcyclohexyl), alkenyl groups (e.g., vinyl and allyl), cycloalkenyl groups (e.g., 2-cyclopenten-1-yl and 2-cyclohexen-1-yl), alkynyl groups (e.g., ethynyl and propargyl), aromatic hydrocarbon groups (e.g., phenyl, p-tolyl, and naphthyl), aromatic heterocyclic groups (e.g., 2-pyrrolyl, 2-furyl, 2-thienyl, pyrrolyl, imidazolyl, oxazolyl, thiazolyl, benzimidazolyl, benzoxazolyl, 2-benzothiazolyl, pyrazolinonyl, pyridyl, pyridinonyl, 2-pyrimidinyl, triazinyl, pyrazolyl, 1,2,3-triazolyl, 1,2,4-triazolyl, oxazolyl, isoxazolyl, 1,2,4-oxadiazolyl, 1,3,4-oxadiazolyl, thiazolyl, isothiazolyl, 1,2,4-thiadiazolyl, and 1,3,4-thiadiazolyl), a cyano group, a hydroxy group, a nitro group, a carboxyl group, alkoxy groups (e.g., methoxy, ethoxy, isopropoxy, tert-butoxy, n-octyloxy, and 2-methoxyethoxy), aryloxy groups (e.g., phenoxy, 2-methylphenoxy, 4-tert-butylphenoxy, 3-nitrophenoxy, and 2-tetradecanoylaminophenoxy), acyloxy groups (e.g., formyloxy, acetyloxy, pivaloyloxy, stearoyloxy, benzoyloxy, and p-methoxyphenylcabonyloxy), amino groups (e.g., amino, methylamino, dimethylamino, anilino, N-methyl-anilino, and diphenylamino), acylamino groups (e.g., formylamino, acetylamino, pivaloylamino, lauroylamino, and benzoylamino), alkyl and arylsulfonylamino groups (e.g., methylsulfonylamino, butylsulfonylamino, phenylsulfonylamino, 2,3,5-trichlorophenylsulfonylamino, and p-methylphenylsulfonylamino), a mercapto group, alkylthio groups (e.g., methylthio, ethylthio, and n-hexadecylthio), arylthio groups (e.g., phenylthio, p-chlorophenylthio, and m-methoxyphenylthio), sulfamoyl groups (e.g., N-ethylsulfamoyl, N-(3-dodecyloxypropyl)sulfamoyl, N,N-dimethylsulfamoyl, N-acetylsulfamoyl, N-benzoylsulfamoyl, and N—(N'-phenylcarbamoyl)sulfamoyl), a sulfo group, acyl groups (e.g., acetyl and pivaloylbenzoyl), and carbamoyl groups (e.g., carbamoyl, N-methylcarbamoyl, N,N-dimethylcarbamoyl, N,N-di-n-octylcarbamoyl, and N-(methylsulfonyl)carbamoyl).

Each of $A_1$, $A_2$, and B in Formula (1) is preferably a benzene ring, a pyrrole ring, a pyrazole ring, an imidazole ring, a 1,2,3-triazole ring, or a 1,2,4-triazole ring, for achieving a resin composition exhibiting stable optical properties and excellent durability.

Each of $T_1$ and $T_2$ in Formula (1) is preferably a pyrrole ring, a pyrazole ring, an imidazole ring, a 1,2,3-triazole ring, or a 1,2,4-triazole ring. Each of $T_1$ and $T_2$ is preferably a pyrazole ring or a 1,2,4-triazole ring, particularly preferably a pyrazole ring, for achieving a resin composition exhibiting further stabilization in optical properties and more excellent durability. The pyrazole ring, imidazole ring, 1,2,3-triazole ring, or 1,2,4-triazole ring represented by $T_1$ or $T_2$ may be a tautomer. Specific structures of the pyrrole, pyrazole, imidazole, 1,2,3-triazole, and 1,2,4-triazole rings are as follows:

[F10]

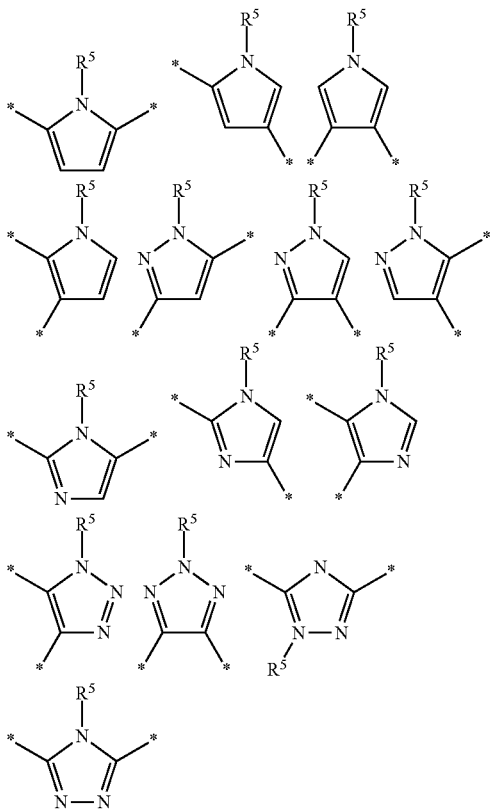

In each ring structure described above, the symbol "*" represents a position at which the structure is bonded to $L_1$, $L_2$, $L_3$, or $L_4$. $R^5$ represents a hydrogen atom or a non-aromatic substituent. The non-aromatic substituent represented by $R^5$ may be identical to any optional non-aromatic substituent on $A_1$ in Formula (1). If the substituent represented by $R^5$ has an aromatic group, torsion tends to occur between $A_1$ and $T_1$ or between B and $T_1$, resulting in failure to form CH/π interaction sites between the hygroscopic resin and $A_1$, B, and $T_1$, leading to difficulty in reducing variations in optical properties. For further reduction of variations in optical properties, $R^5$ is preferably a hydrogen atom, an alkyl group having one to five carbon atoms, or an acyl group having one to five carbon atoms, particularly preferably a hydrogen atom.

Each of $T_1$ and $T_2$ in Formula (1) may have a substituent. The substituent may be identical to any optional substituent on $A_1$ or $A_2$ in Formula (1).

In Formula (1), $L_1$, $L_2$, $L_3$, and $L_4$ each independently represent a single bond or a divalent linking group. The 5-membered or 6-membered aromatic hydrocarbon or heterocyclic rings are bonded to one another via one or two atoms. The expression "via one or two atoms" refers to the case where the minimum number of atoms of a linking group between aromatic rings is one or two. Any divalent linking group having one or two linking atoms may be used. The divalent linking group is selected from the group consisting of an alkylene group, an alkenylene group, an alkynylene group, O, (C=O), NR, S, and (O=S=O), or the divalent group is a combination of any two of these. R represents a hydrogen atom or a substituent. Examples of the substituent represented by R include alkyl groups (e.g., methyl, ethyl, n-propyl, isopropyl, tert-butyl, n-octyl, and 2-ethylhexyl), cycloalkyl groups (e.g., cyclohexyl, cyclopentyl, and 4-n-dodecylcyclohexyl), aromatic hydrocarbon groups (e.g., phenyl, p-tolyl, and naphthyl), aromatic heterocyclic groups (e.g., 2-furyl, 2-thienyl, 2-pyrimidinyl, 2-benzothiazolyl, and 2-pyridyl), and a cyano group. The divalent linking group represented by $L_1$, $L_2$, $L_3$, or $L_4$ may have any substituent. The substituent may be identical to any optional substituent on $A_1$ or $A_2$ in Formula (1).

High structural planarity of the compound represented by Formula (1) leads to a strong CH/π interaction between the compound and the hygroscopic resin, resulting in stable optical properties. Thus, each of $L_1$, $L_2$, $L_3$, and $L_4$ in Formula (1) is preferably a single bond, O, (C=O)—O, O—(C=O), (C=O)—NR, or NR—(C=O), more preferably a single bond.

In Formula (1), n represents an integer of 0 to 5. If n is an integer of 2 or more, $A_2$, $T_2$, $L_3$, and $L_4$ in Formula (1) may be identical to or different from one another. A larger integer n leads to a stronger CH/π interaction between the compound represented by Formula (1) and the hygroscopic resin, resulting in further stabilization in optical properties, whereas a smaller integer n leads to better compatibility between the compound and the hygroscopic resin. Thus, n is preferably an integer of 1 to 3, more preferably 1 or 2.

<Compound Represented by Formula (2)>

The compound represented by Formula (1) is preferably a compound represented by Formula (2).

[F11]

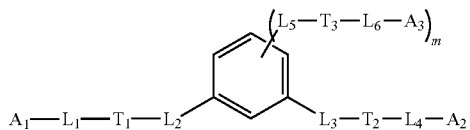

Formula (2)

In Formula (2), $A_1$, $A_2$, $T_1$, $T_2$, $L_1$, $L_2$, $L_3$, and $L_4$ have the same meanings as defined in Formula (1), $A_3$ and $T_3$ are the same as $A_1$ and $T_1$ in Formula (1), respectively, each of $L_5$ and $L_6$ is the same as $L_1$ in Formula (1), and m represents an integer of 0 to 4.

A smaller integer m leads to higher compatibility between the compound and a cellulose ester. Thus, m is preferably an integer of 0 to 2, more preferably 0 or 1.

<Compound Having Structure Represented by Formula (1.1)>

The compound having a structure represented by Formula (1) is preferably a triazole compound having a structure represented by Formula (1.1).

[F12]

$$[A_1\text{-}L_1\text{-}T_1\text{-}L_2\text{-}]_k B \qquad \text{Formula (1.1)}$$

In Formula (1.1), $A_1$, B, $L_1$, and $L_2$ have the same meanings as defined in Formula (1), k is an integer of 1 to 4, and $T_1$ represents a 1,2,4-triazole ring.

The triazole compound having a structure represented by Formula (1.1) is preferably a triazole compound having a structure represented by Formula (1.2).

[F13]

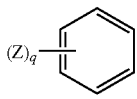

Formula(1.2)

In Formula (1.2), Z represents a structure represented by Formula (1.2a), q is 2 or 3, and at least two structures Z bonded to the benzene ring are located in the ortho- or meta-position relative to each other.

[F14]

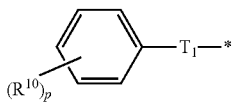

Formula(1.2a)

In Formula (1.2a), $R^{10}$ represents a hydrogen atom, an alkyl group, or an alkoxy group, p represents an integer of 1 to 5, * represents a position at which the structure is bonded to the benzene ring, and $T_1$ represents a 1,2,4-triazole ring.

The compound represented by Formula (1), (2), (1.1), or (1.2) may be in the form of a hydrate, a solvate, or a salt. In the present invention, the hydrate may contain an organic solvent, whereas the solvate may contain water. Thus, each of the "hydrate" and "solvate" contains a solvent mixture of water and an organic solvent. Examples of the salt include inorganic and organic acid addition salts. Examples of the inorganic acid include, but are not limited to, hydrohalic acids (e.g., hydrochloric acid and hydrobromic acid), sulfuric acid, and phosphoric acid. Examples of the organic acid include, but are not limited to, acetic acid, trifluoroacetic acid, propionic acid, butyric acid, oxalic acid, citric acid, benzoic acid, alkylsulfonic acids (e.g., methanesulfonic acid), and arylsulfonic acids (e.g., benzenesulfonic acid, 4-toluenesulfonic acid, and 1,5-naphthalenedisulfonic acid). Preferred salts are hydrochloride, acetate, propionate, and butyrate.

Examples of the salt include, but are not limited to salts prepared through substitution of an acid moiety of a parent compound with a metal ion (e.g., alkali metal ion, alkaline earth metal ion, or aluminum ion), such as alkali metal salts (e.g., sodium salts and potassium salts) and alkaline earth metal salts (e.g., calcium salts and magnesium salts); and salts prepared through reaction of a parent compound with an organic base (e.g., ethanolamine, diethanolamine, triethanolamine, morpholine, or piperidine). Of these, preferred are sodium salts and potassium salts.

The solvent contained in the solvate may be, for example, any common organic solvent. Specific examples of the organic solvent include alcohols (e.g., methanol, ethanol, 2-propanol, 1-butanol, 1-methoxy-2-propanol, and t-butanol), esters (e.g., ethyl acetate), hydrocarbons (e.g., toluene, hexane, and heptane), ethers (e.g., tetrahydrofuran), nitriles (e.g., acetonitrile), and ketones (e.g., acetone). Preferred are solvates of alcohols (e.g., methanol, ethanol, 2-propanol, 1-butanol, 1-methoxy-2-propanol, and t-butanol). The solvent contained in the solvate may be a solvent used for synthesis of the aforementioned compound or used for crystallization and purification after synthesis. Alternatively, the solvent may be any mixture of these solvents.

The solvate may contain two or more solvents in combination, or a mixture of water and a solvent (e.g., a mixture of water and an alcohol, such as methanol, ethanol, or t-butanol).

The compound represented by Formula (1), (2), (1.1), or (1.2) may be added in a water-, solvent- or salt-free form, or may form a hydrate, a solvate, or a salt in the resin composition or optical film of the present invention.

The compound represented by Formula (1), (2), (1.1), or (1.2) may have any molecular weight. A smaller molecular weight leads to better compatibility between the compound and the hygroscopic resin, whereas a larger molecular weight more effectively prevents variations in optical values in association with a change in environmental humidity. Thus, the molecular weight is preferably 150 to 2,000, more preferably 200 to 1,500, still more preferably 300 to 1,000.

Next will be described specific examples of the compound having a 5-membered or 6-membered aromatic hydrocarbon or heterocyclic ring according to the present invention. In particular, compounds represented by Formulae (1), (2), (1.1), and (1.2) are preferred. The compound having a 5-membered or 6-membered aromatic hydrocarbon or heterocyclic ring used in the present invention is not limited to specific examples described below. As described above, each of the below-exemplified compounds may be a tautomer, or may be in the form of a hydrate, a solvate, or a salt.

[F15]

1

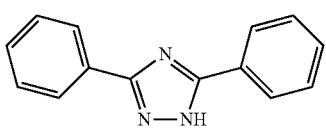

2

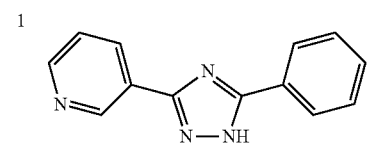

3

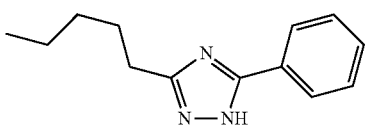

4

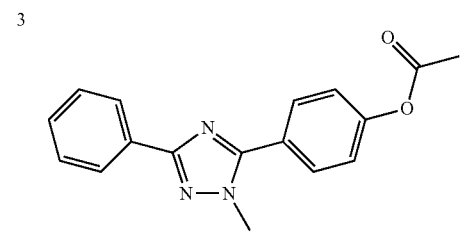

-continued
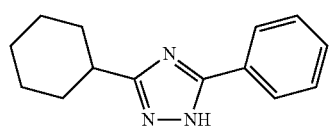 5
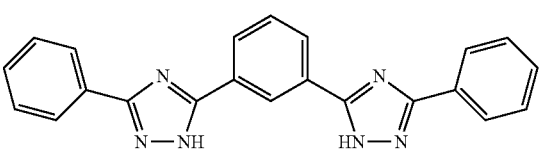 6
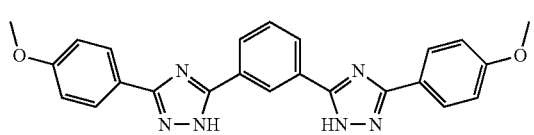 7
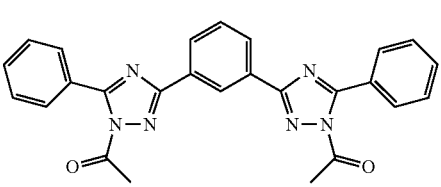 8
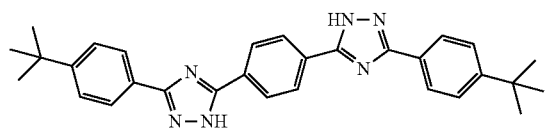 9
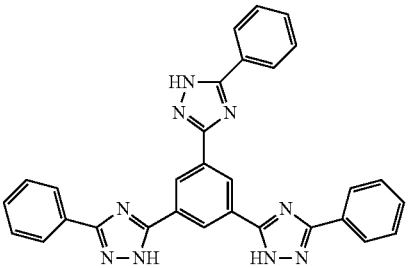 10
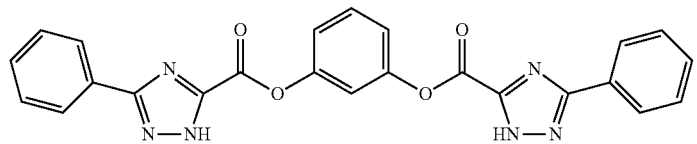 11
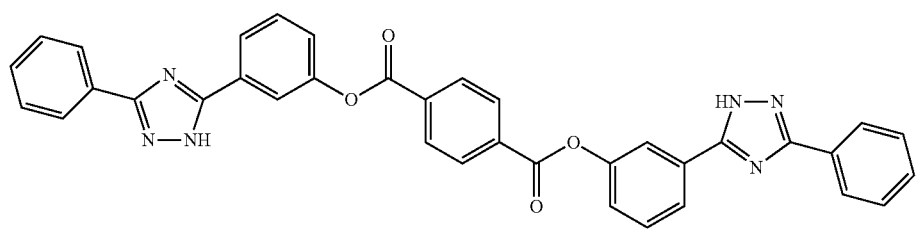 12
[F16]
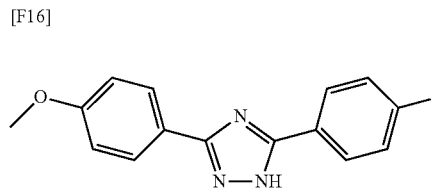 13
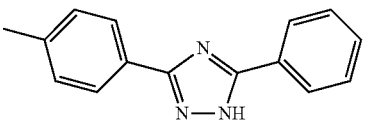 14
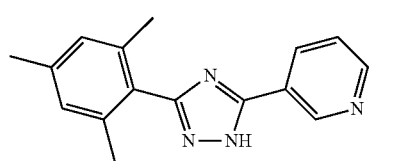 15
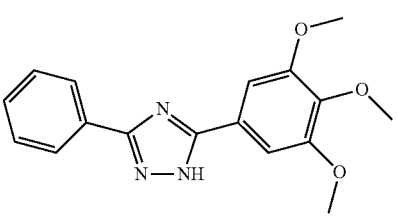 16
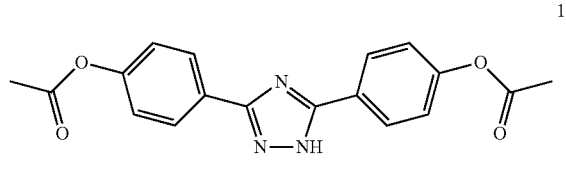 17
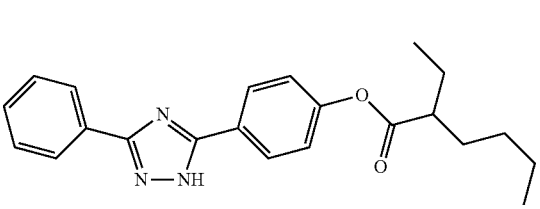 18

-continued
19
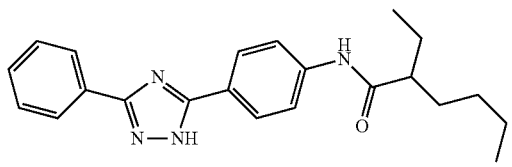
20
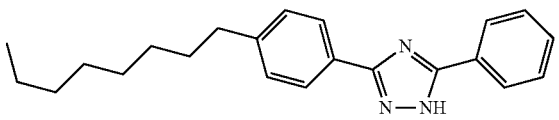
21
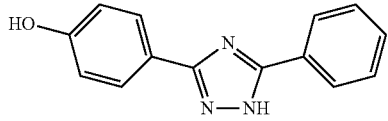
22
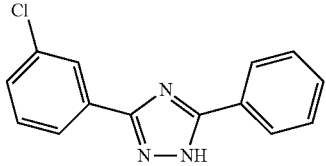
23
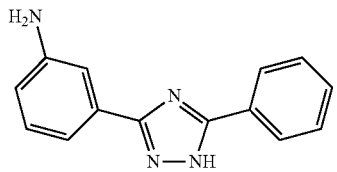
24
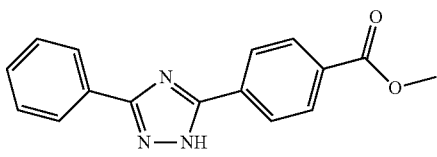
25
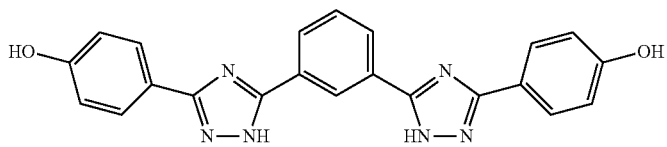
26
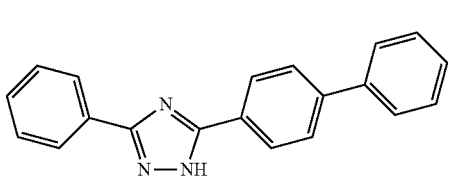
27
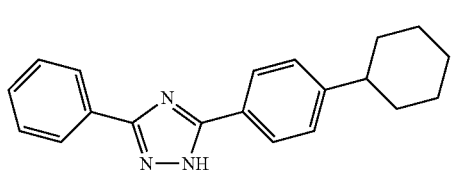
28
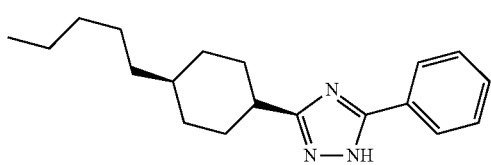
[F17]
29
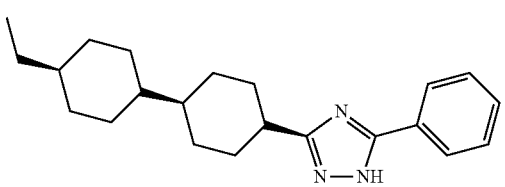
30
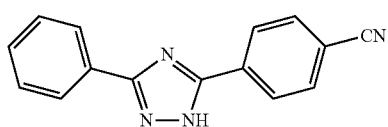
31
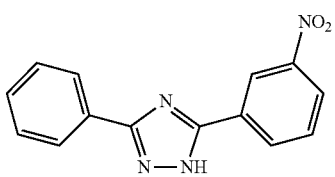
32
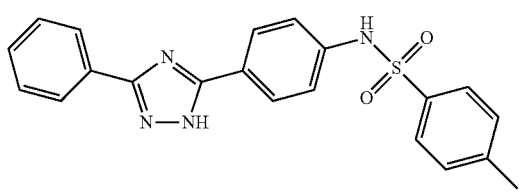
33
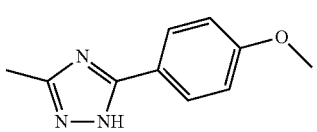
34

-continued
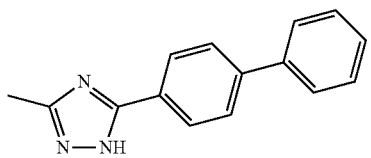
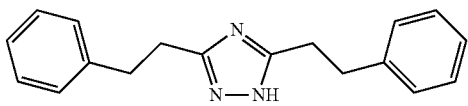
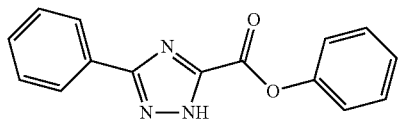
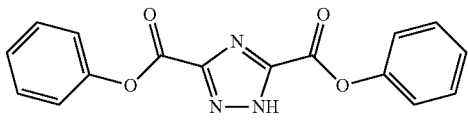
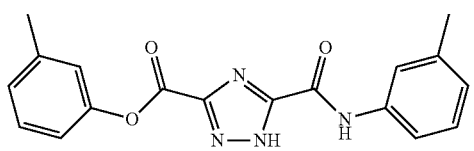
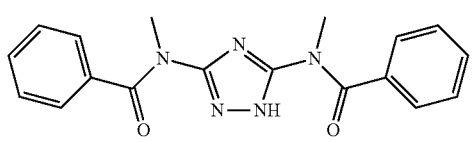
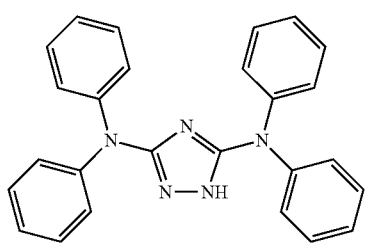
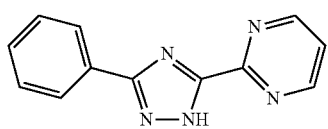
[F18]
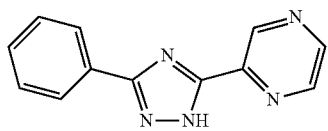
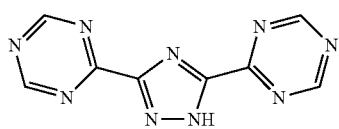
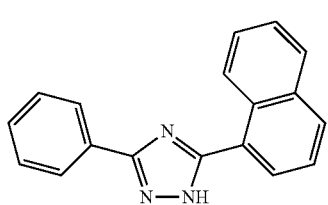
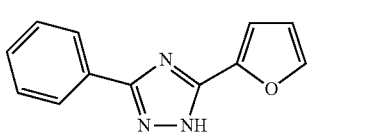

52
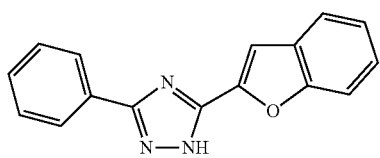
53
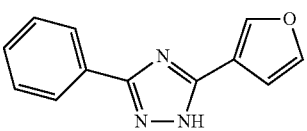
54
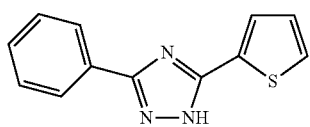
55
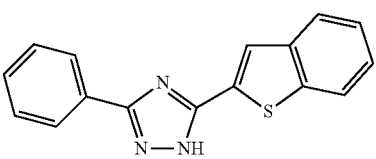
56
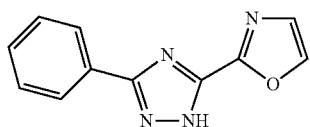
57
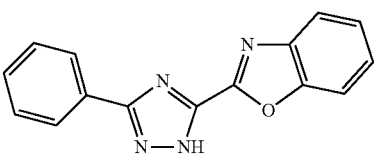
58
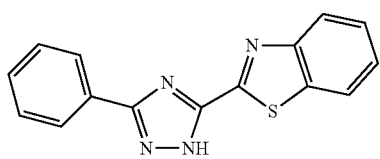
59
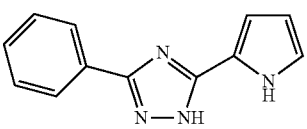
60
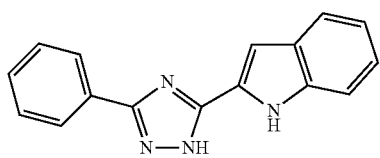
61
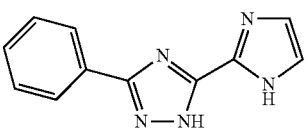
62
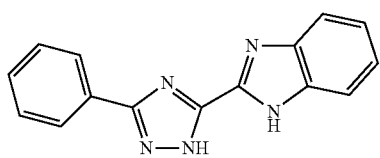
63
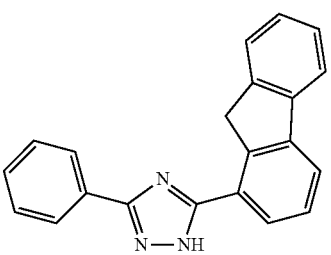
64
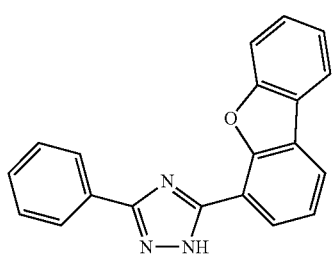
65
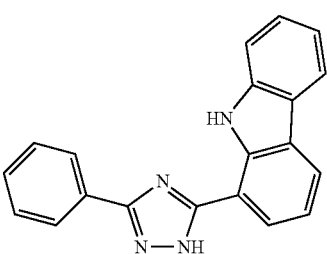
[F19]
66
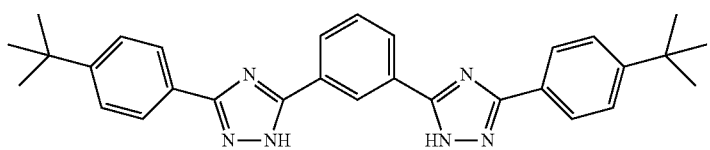

-continued
67
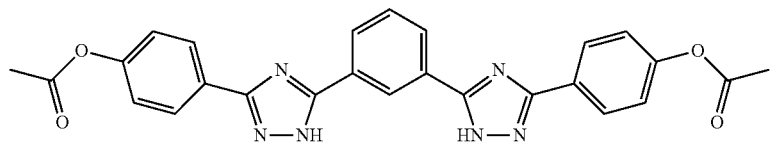
68
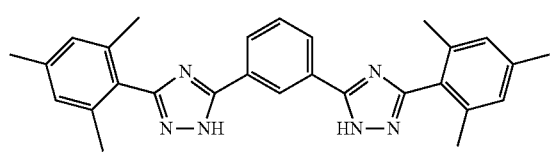
69
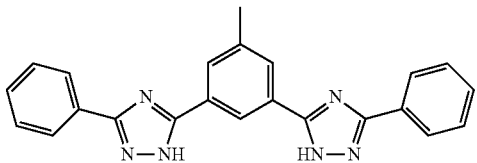
70
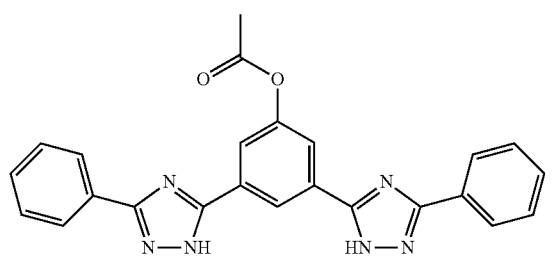
71
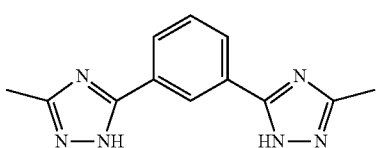
72
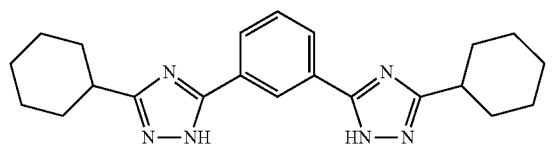
73
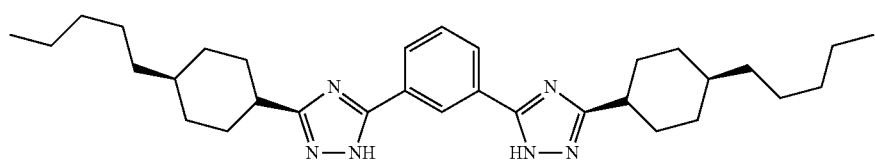
74
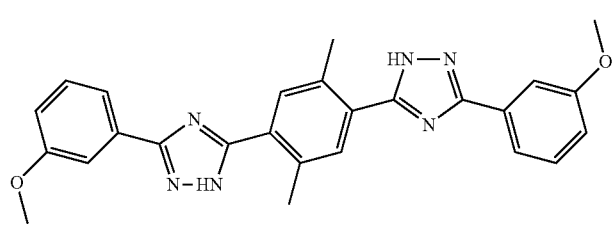
75
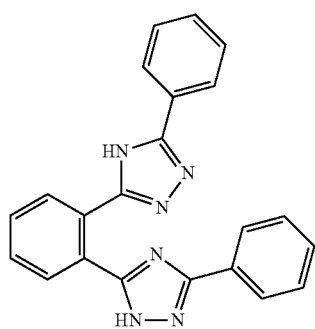
76
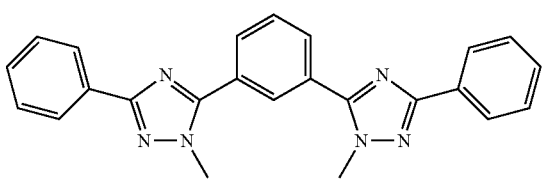

-continued
[F20]
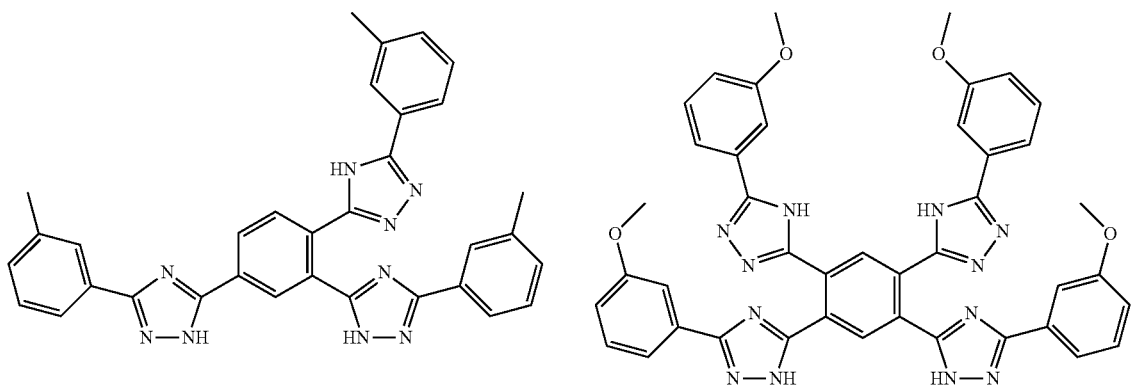
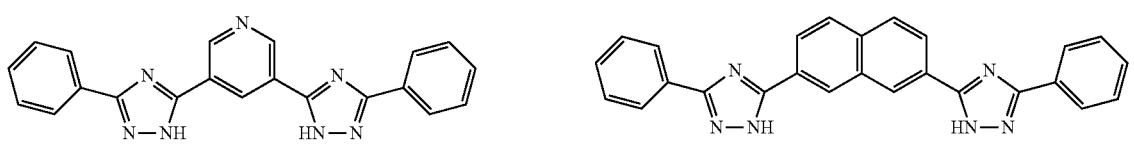
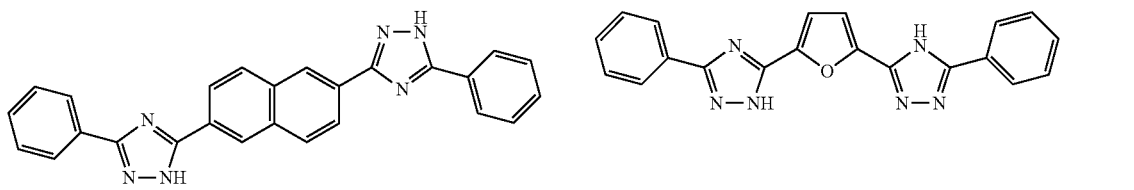
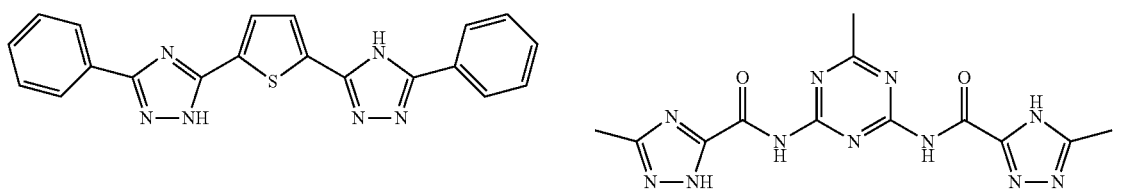
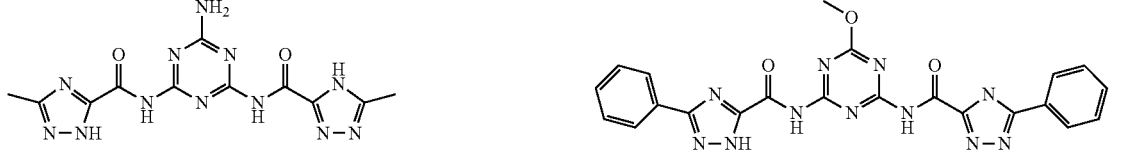
[F21]
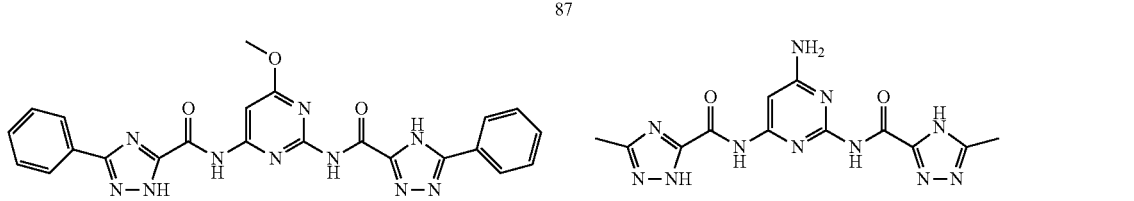
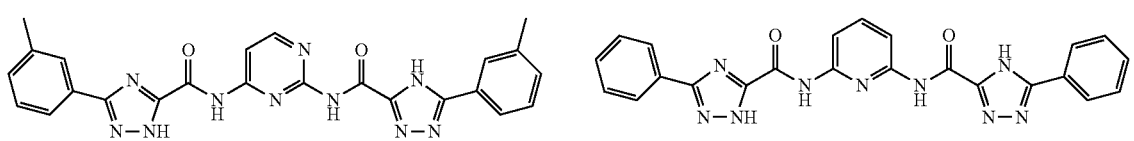

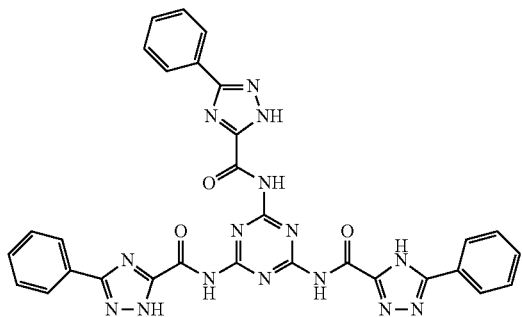
91
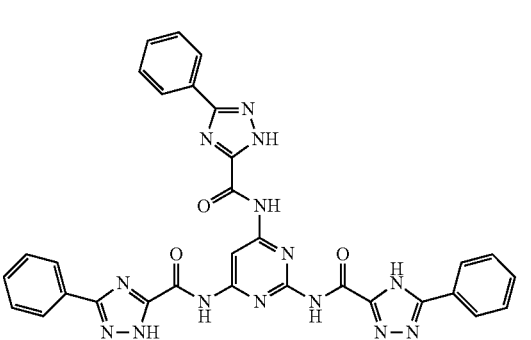
92
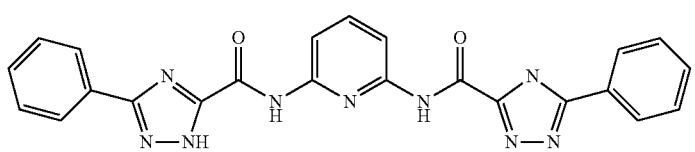
90
[F22]
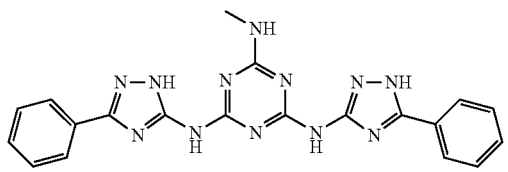
93
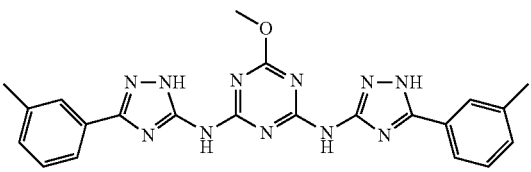
94
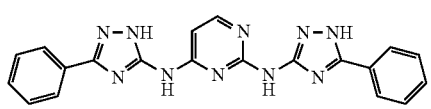
95
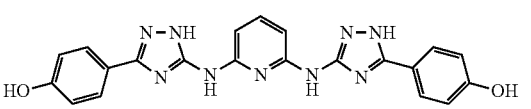
96
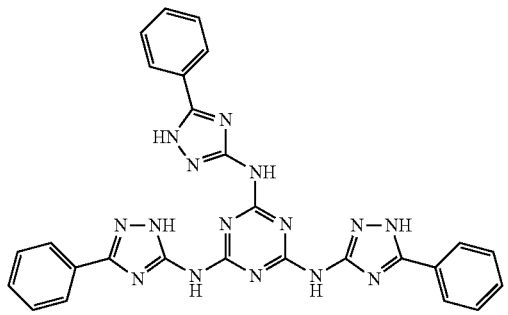
97
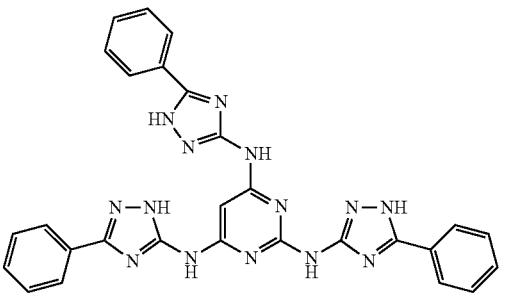
98
[F23]
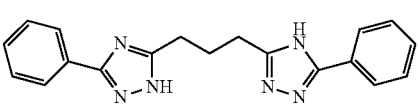
99
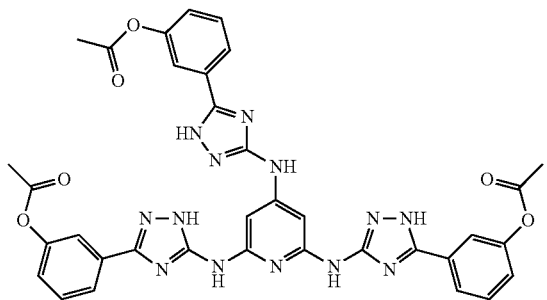
100

101
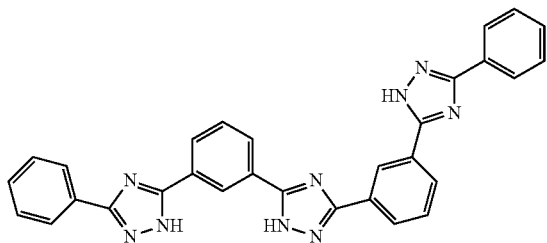
102
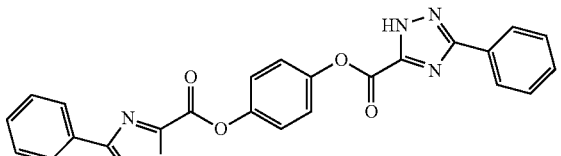
103
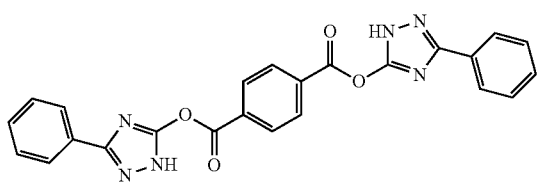
104
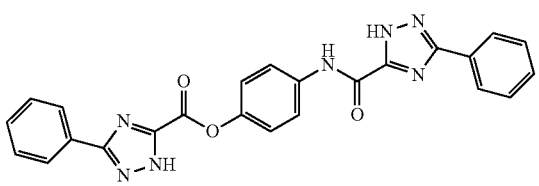
[F24]
105
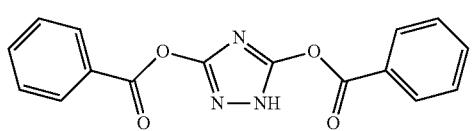
106
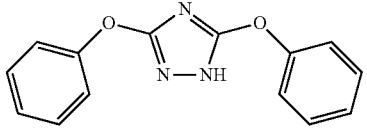
107
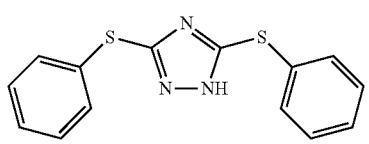
108
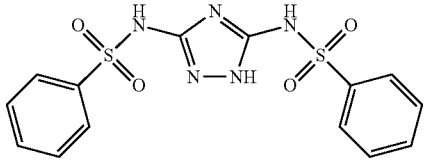
109
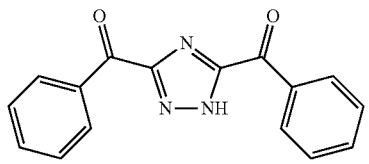
110
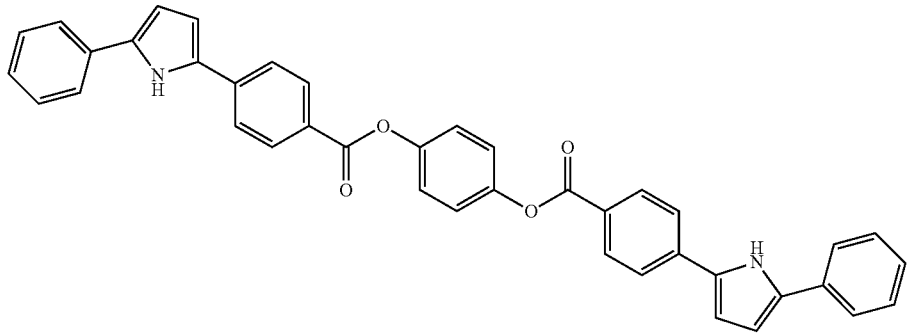
111
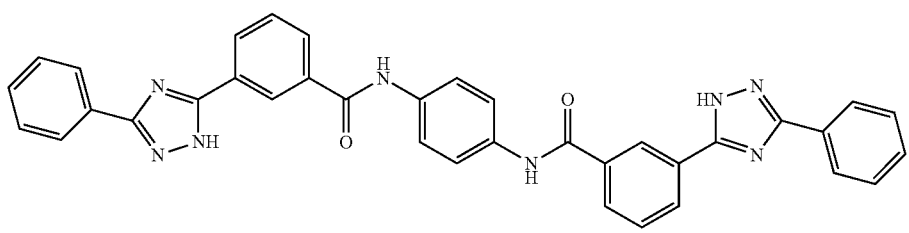

112
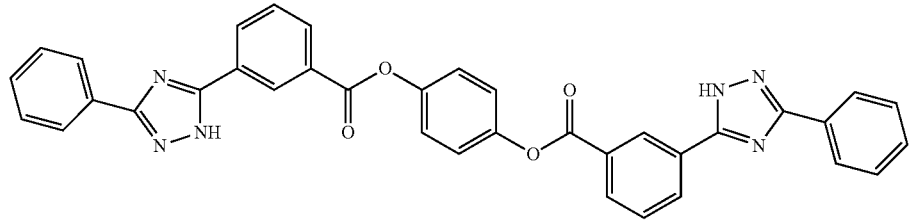
113
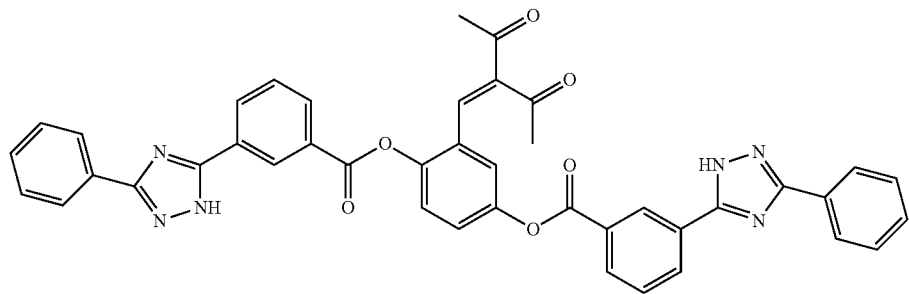
[F25]
114
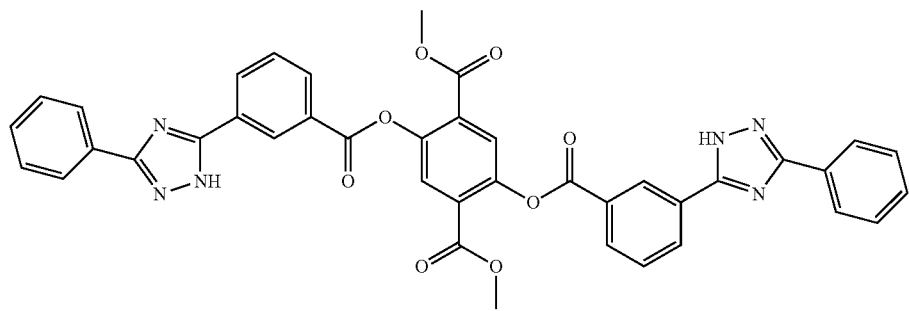
115
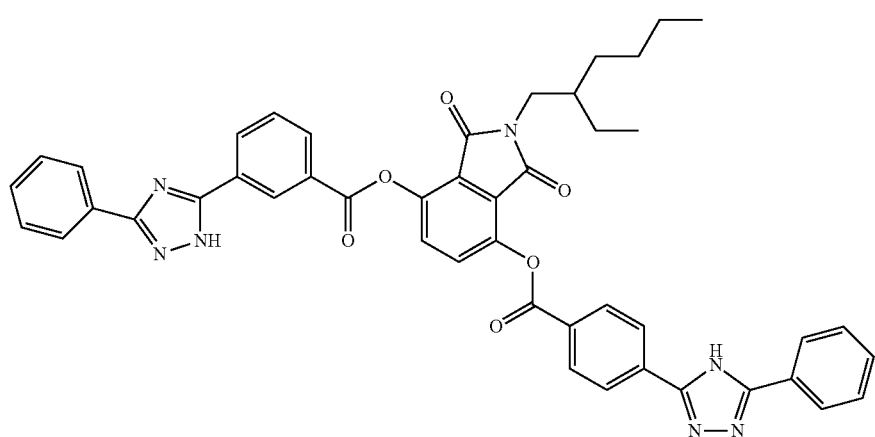

-continued
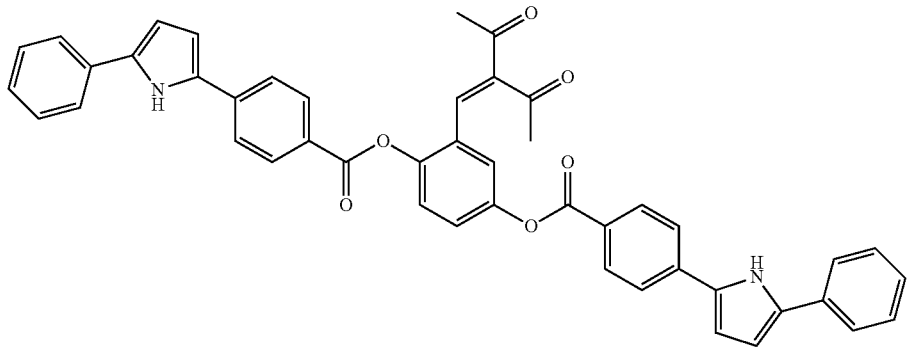
116
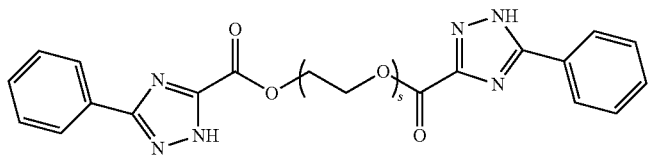
117: s = 1
118: s = 2
119: s = 3
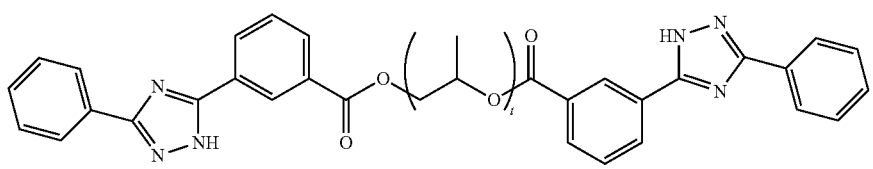
120: t = 1
121: t = 2
122: t = 3
[F26]
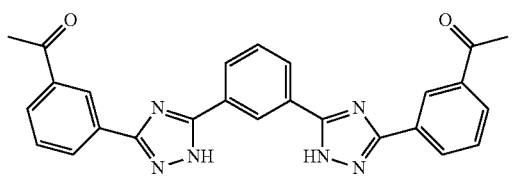
123
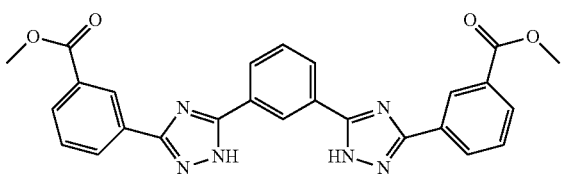
124
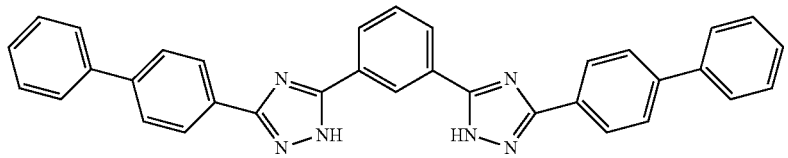
125
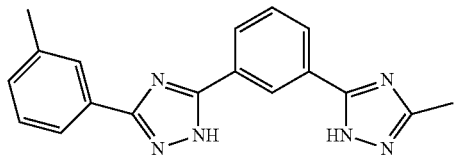
126
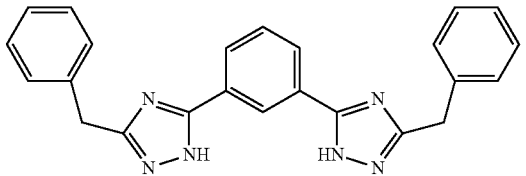
127
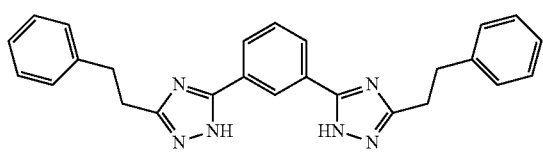
128
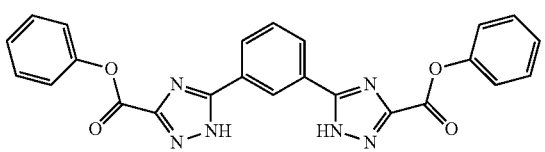
129

[F27]
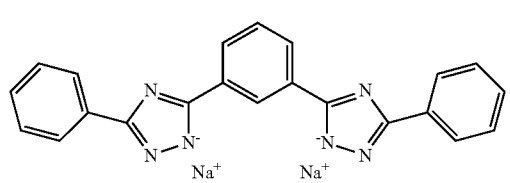
130
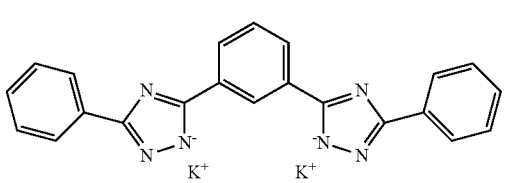
131
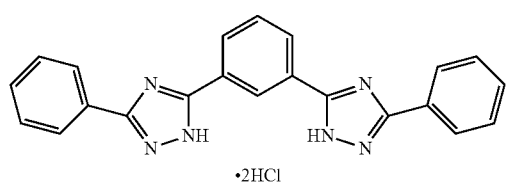
132
•2HCl
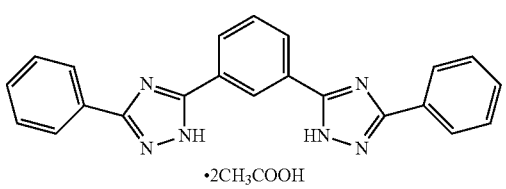
133
•2CH₃COOH
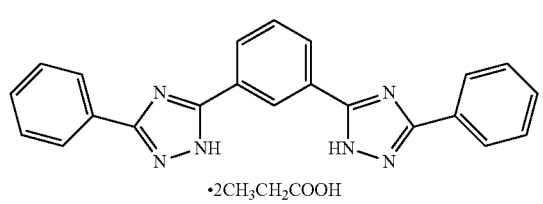
134
•2CH₃CH₂COOH
[F28]
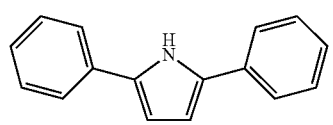
135
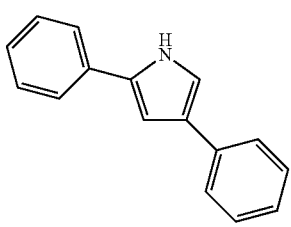
136
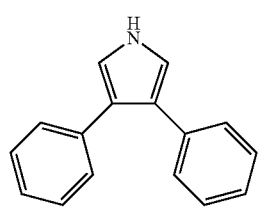
137
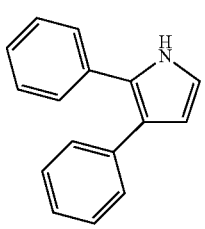
138
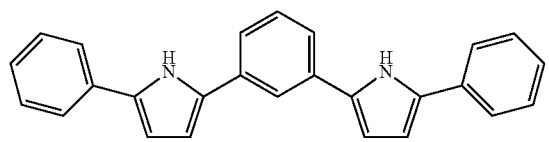
139
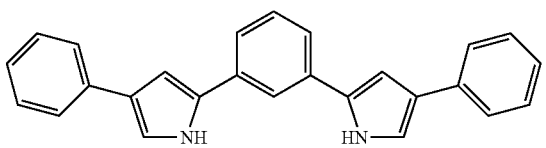
140
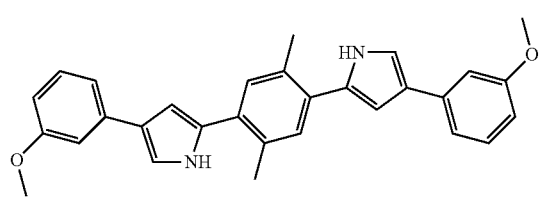
141
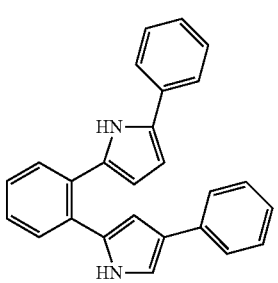
142

-continued
143
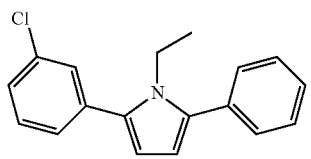
144
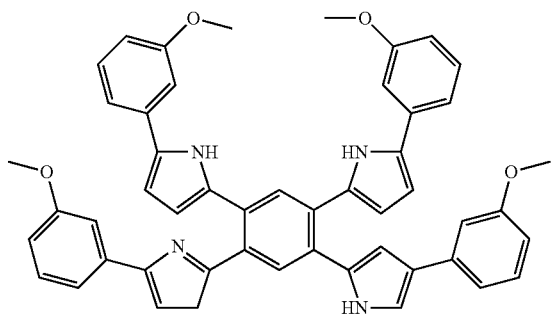
145
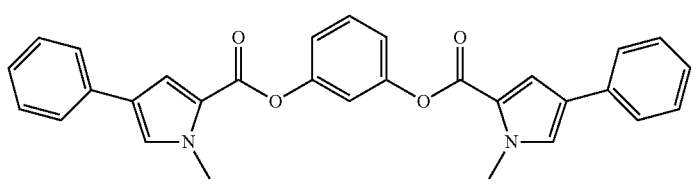
[F29]
146
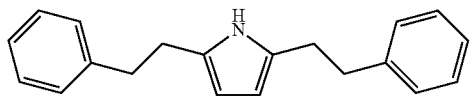
147
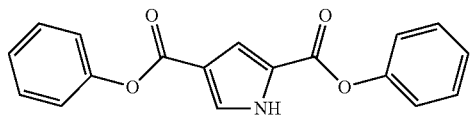
148
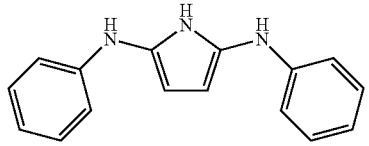
149
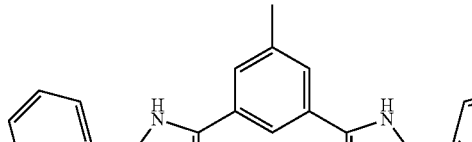
150
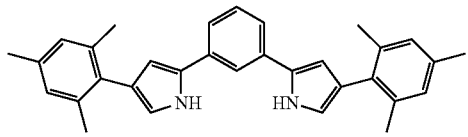
151
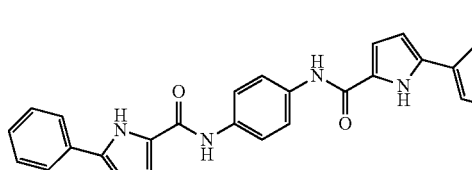
152
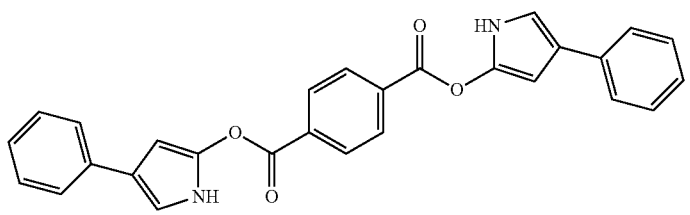
153
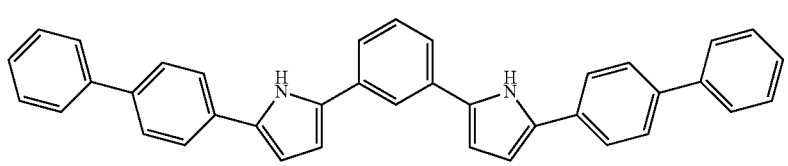

-continued
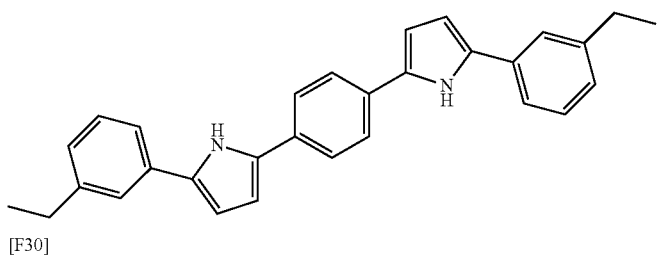
154
[F30]
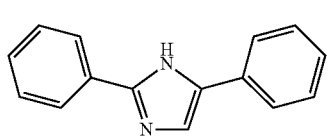
155
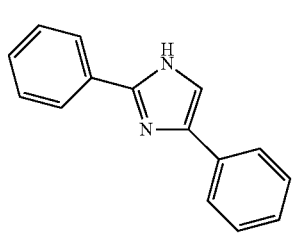
156
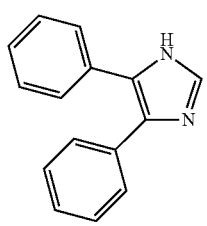
157
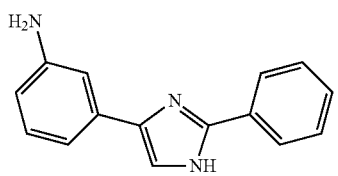
158
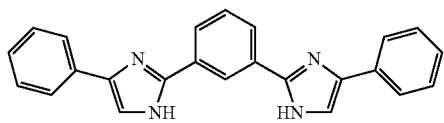
159
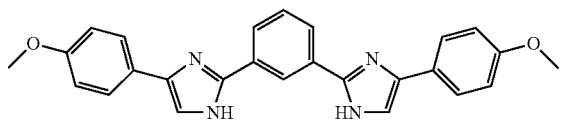
160
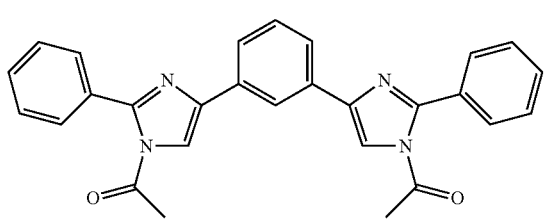
161
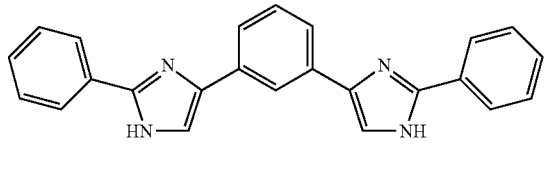
162
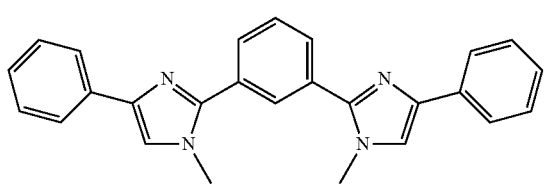
163
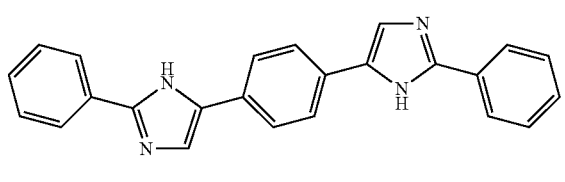
164
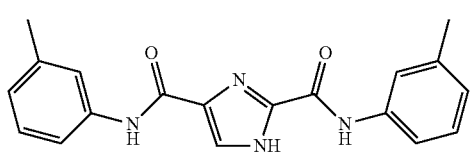
165
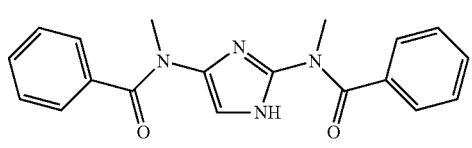
166

-continued
[F31]
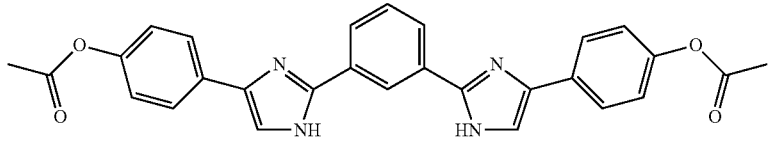
167
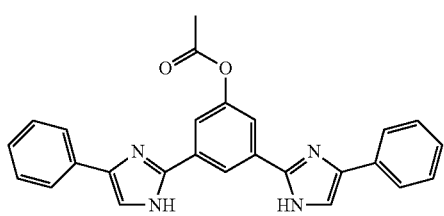
168
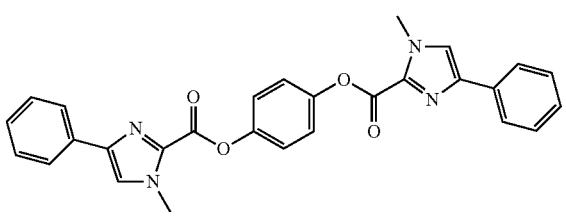
169
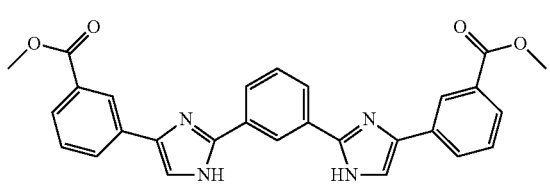
170
171
[F32]
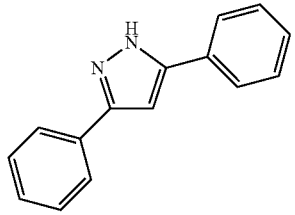
172
173
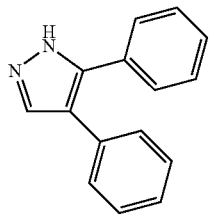
174
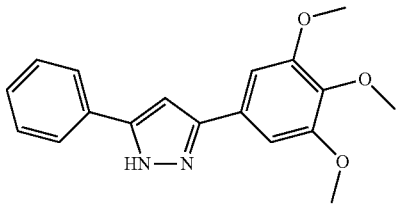
175
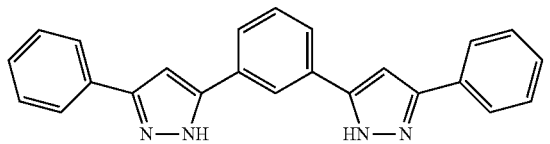
176
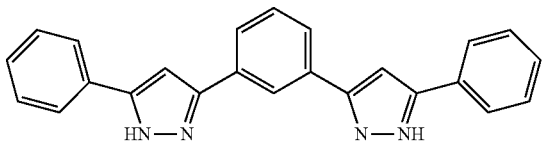
177
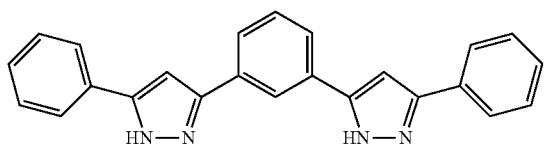
178
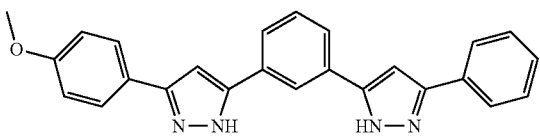
179

-continued
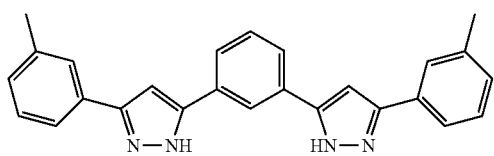
180
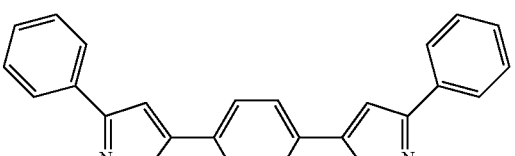
181
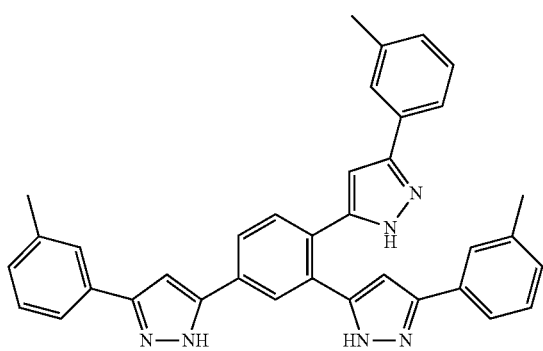
182
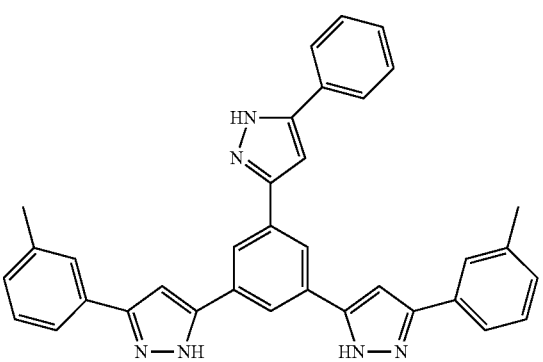
183
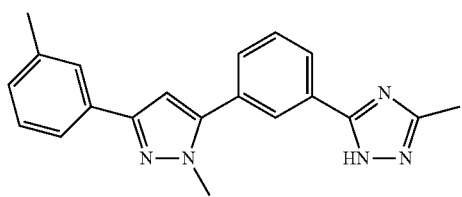
[F33]
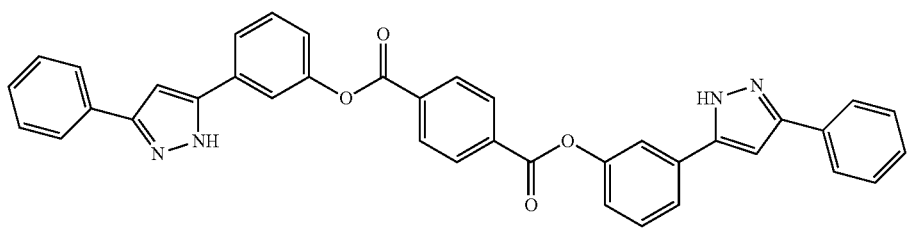
185
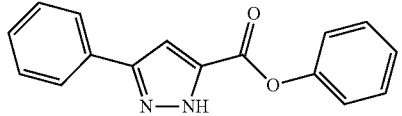
186
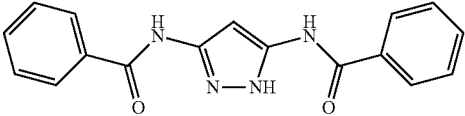
187
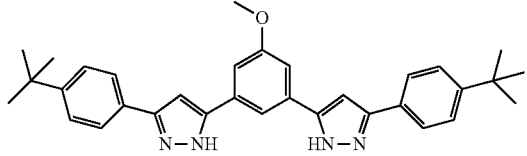
188
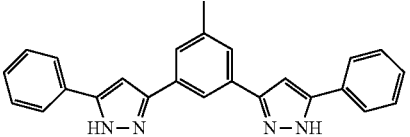
189
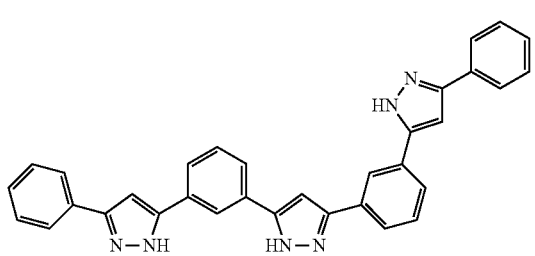
190
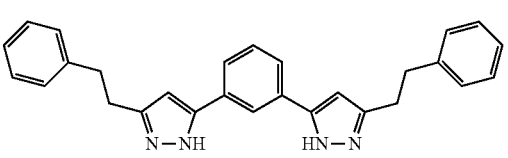
191

-continued
192 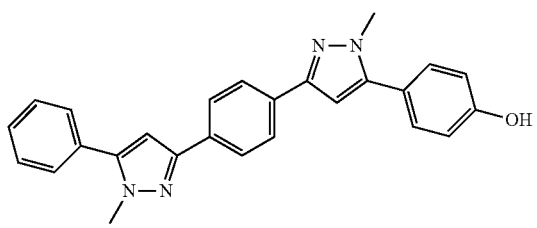
193 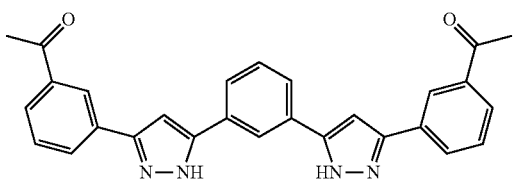
[F34]
194 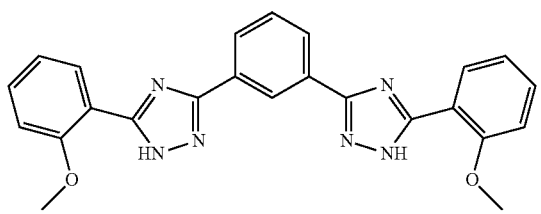
195 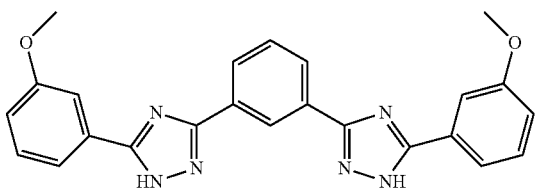
196 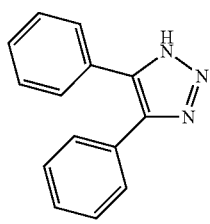
197 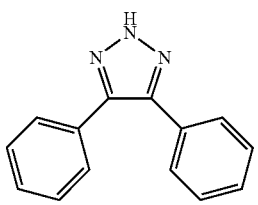
198 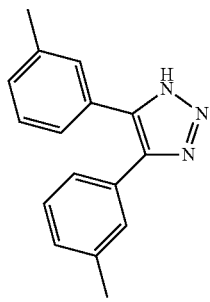
199 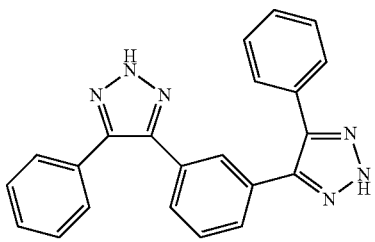
[F35]
200 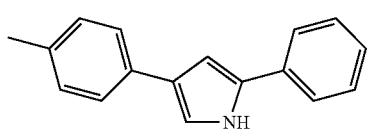
201 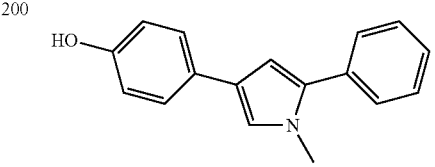
202 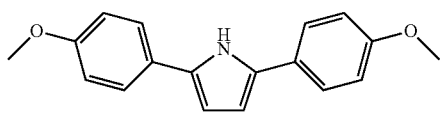
203 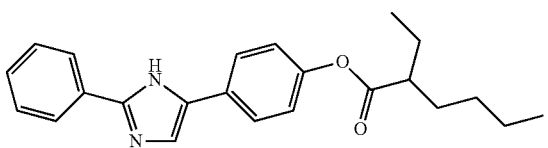
204 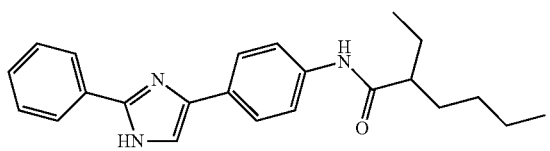
205 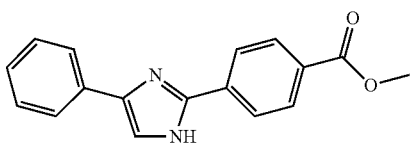

-continued

-continued
220 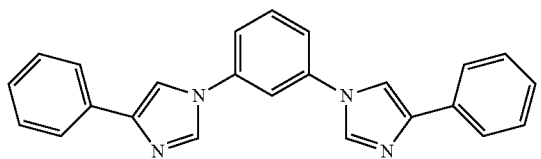
221 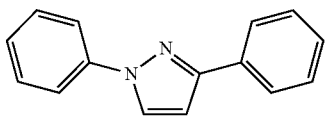
222 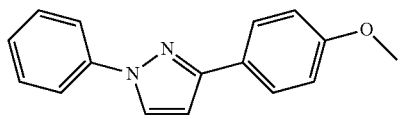
223 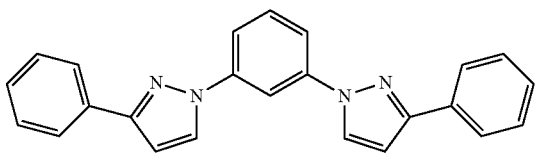
224 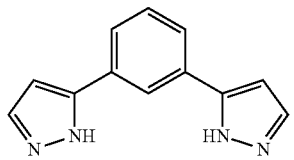
225 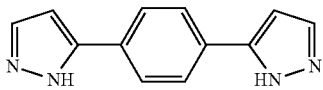
226 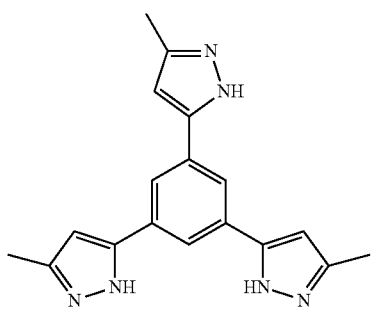
227 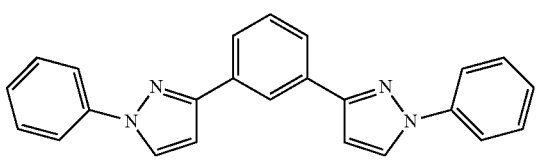
228 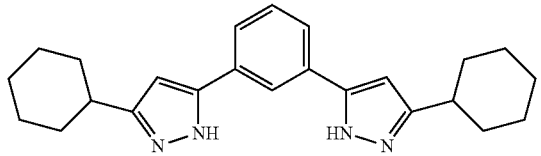
229 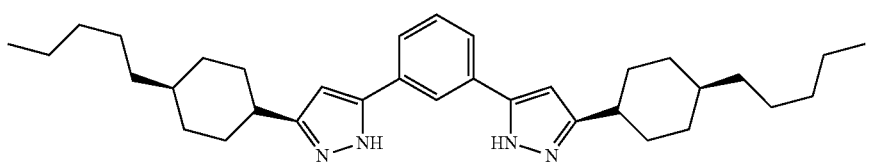
[F37]
230 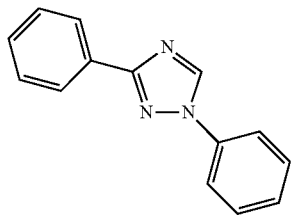
231 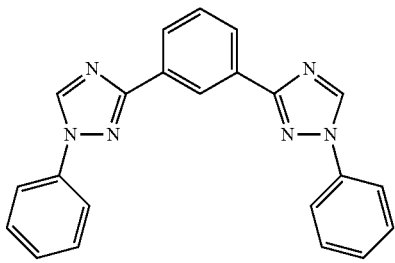

-continued
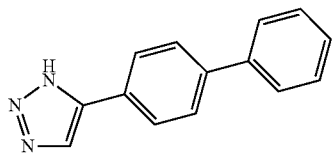
232
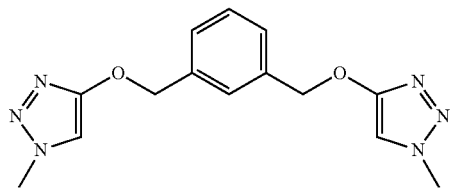
233
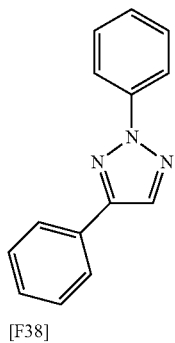
[F38]
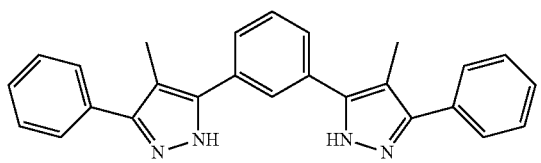
235
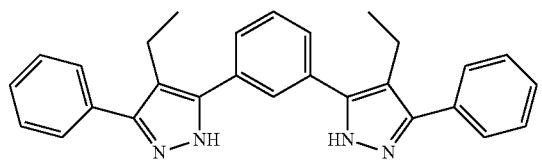
236
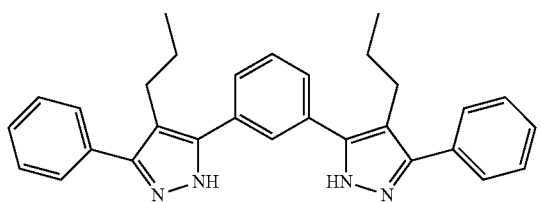
237
238
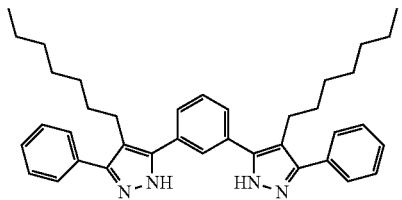
239
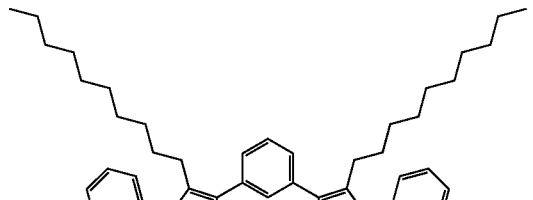
240
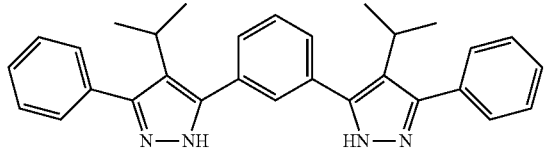
241
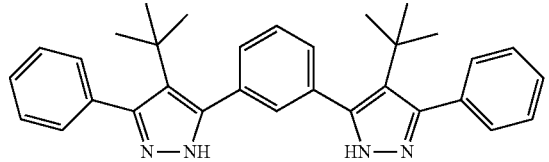
242

243 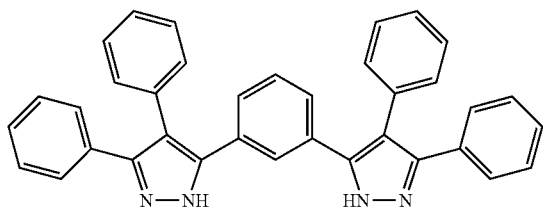
244 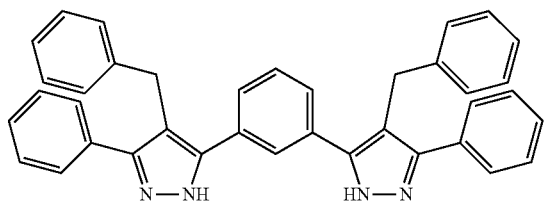
[F39]
245 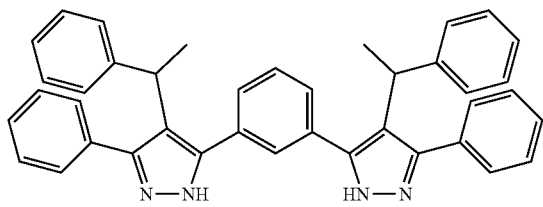
246 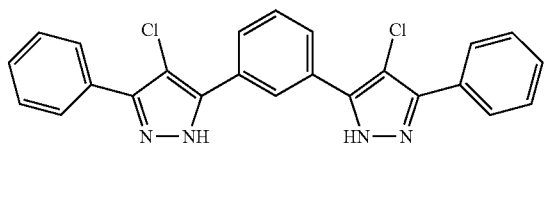
247 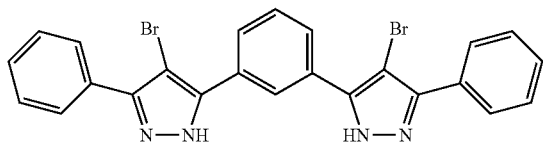
248 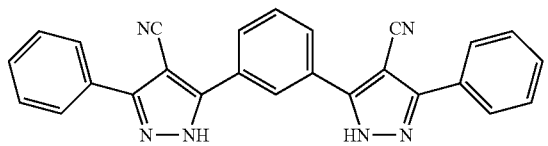
249 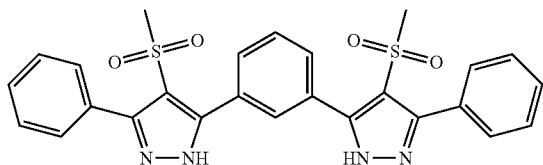
250 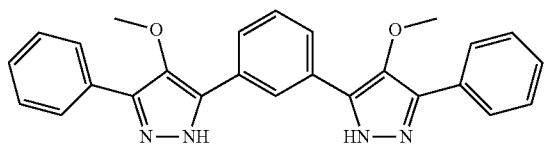
251 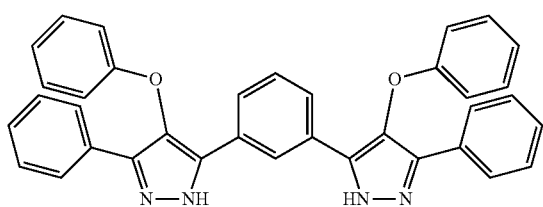
252 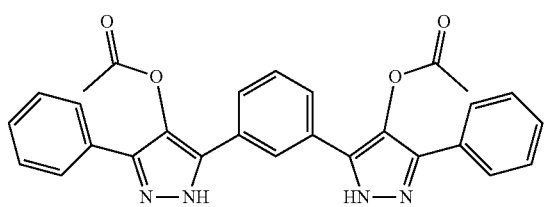
253 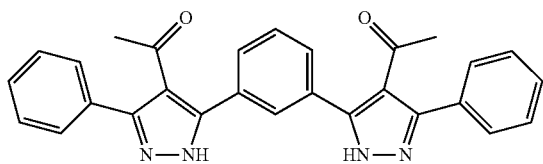
254 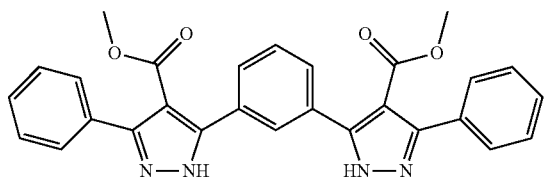
255 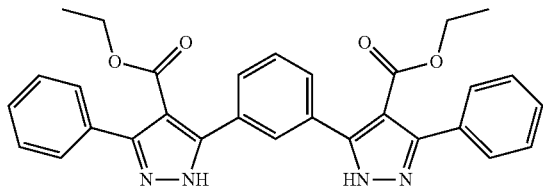
256 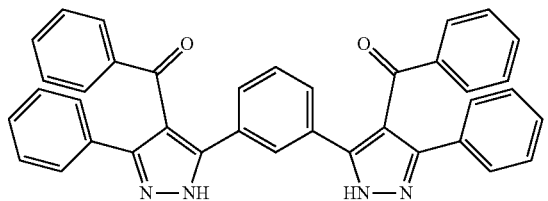

[F40]
257 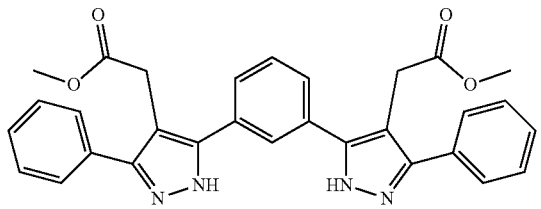
258 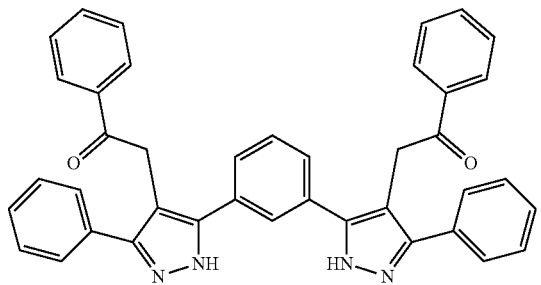
259 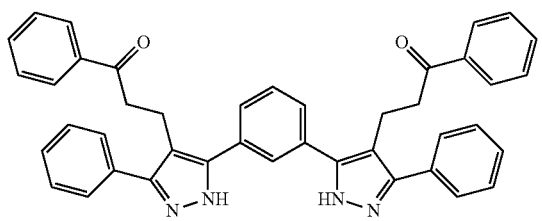
260 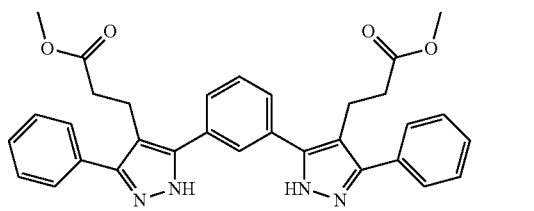
261 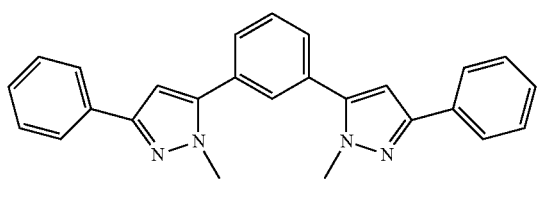
262 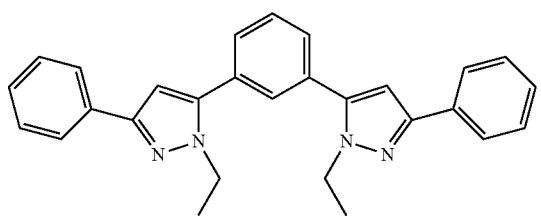
263 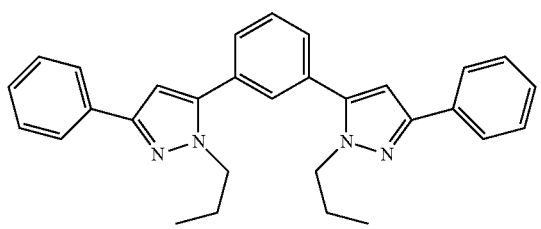
264 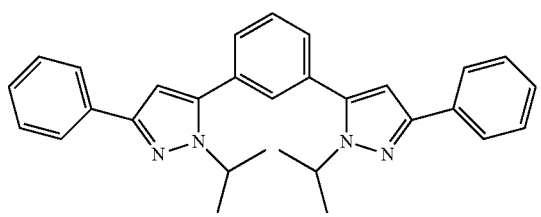
265 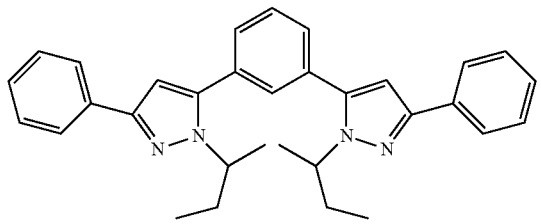
266 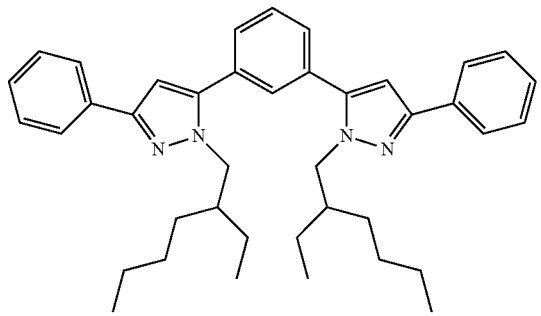

-continued
267 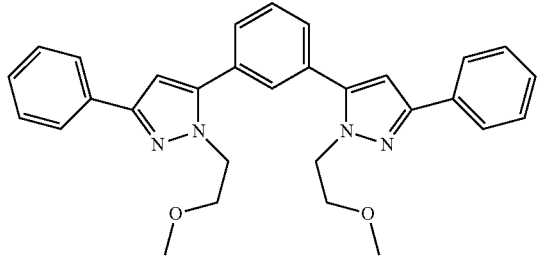
268 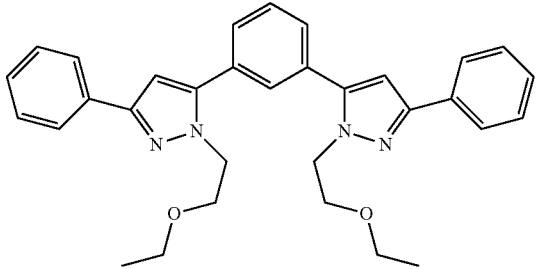
269 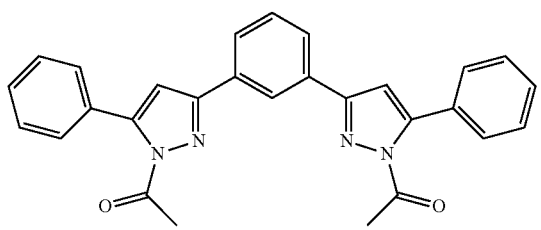
270 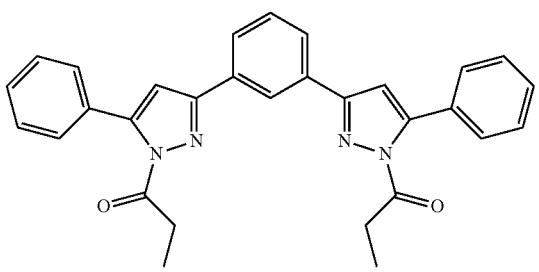
271 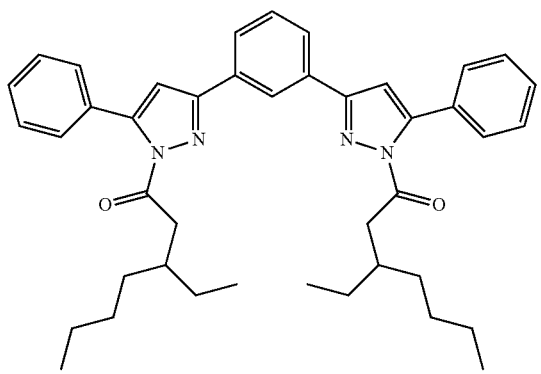
272 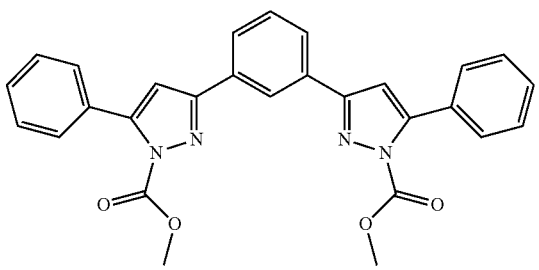
273 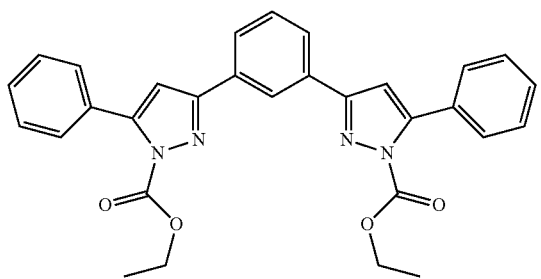
274 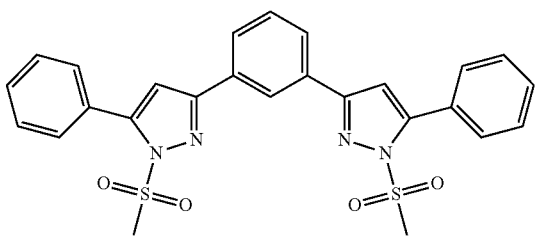
275 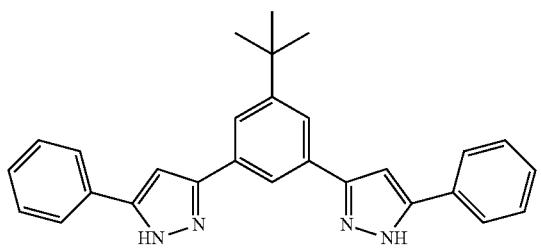
276 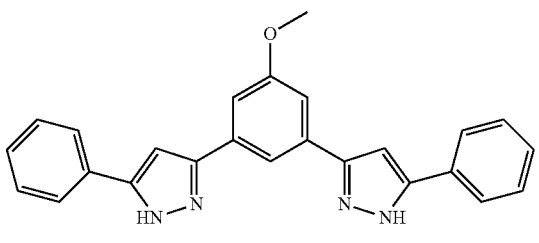

-continued
277 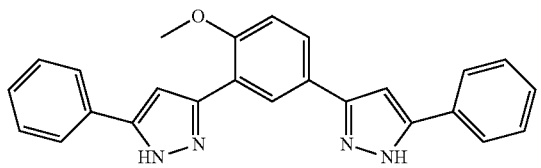
278 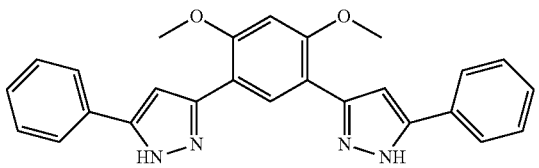
279 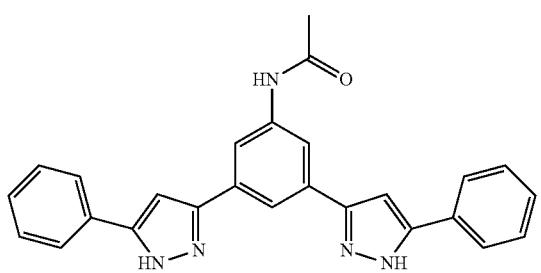
280 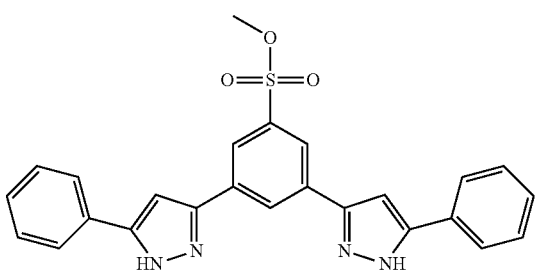
281 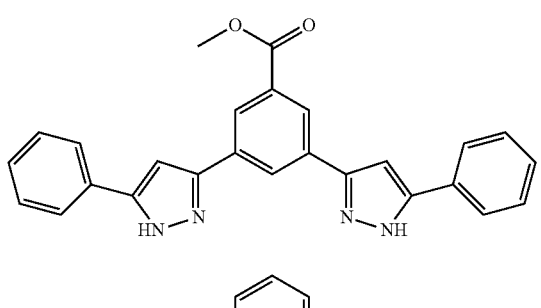
282 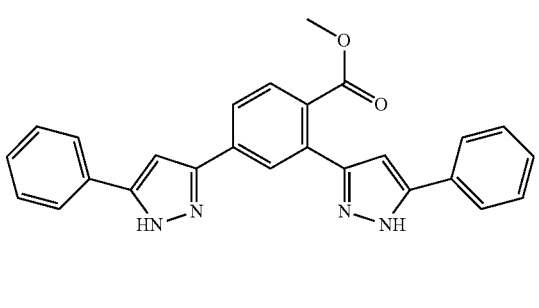
283 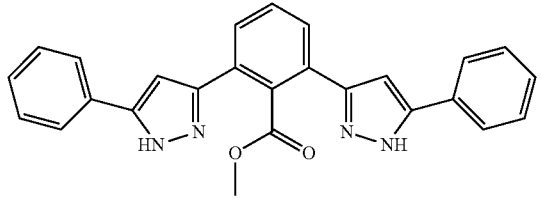
[F43]
284 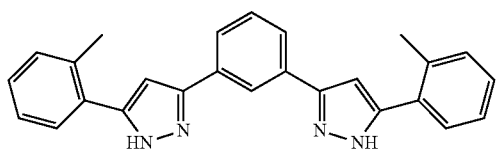
285 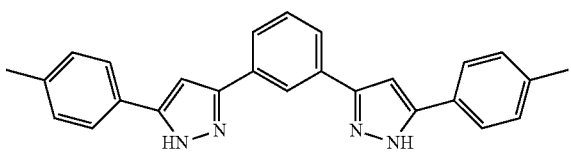
286 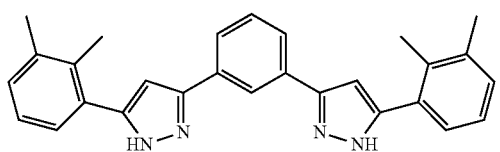
287 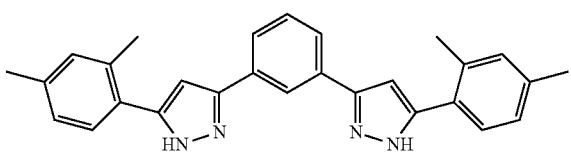
288 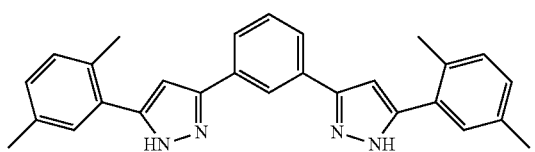
289 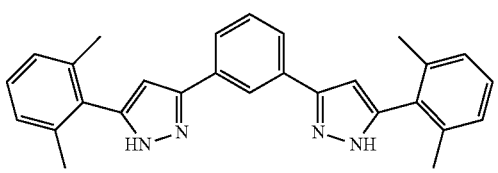

290 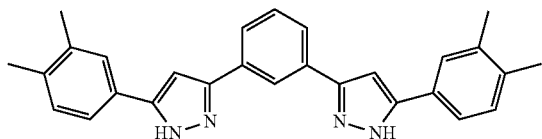
291 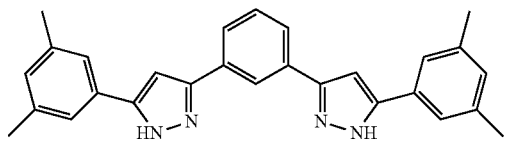
292 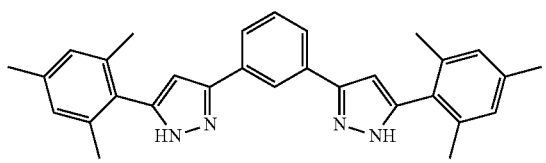
293 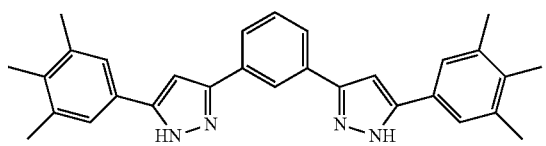
294 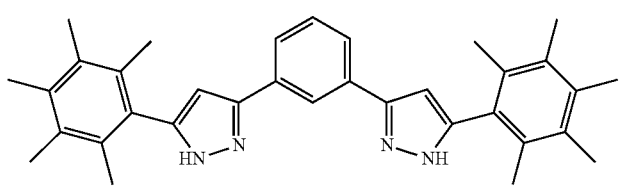
[F44]
295 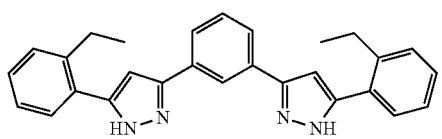
296 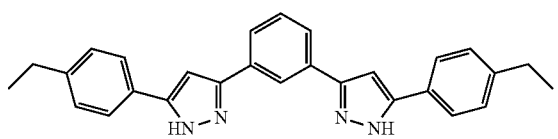
297 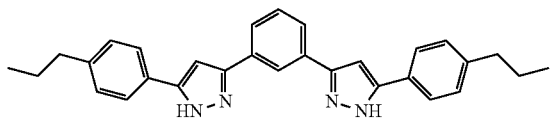
298 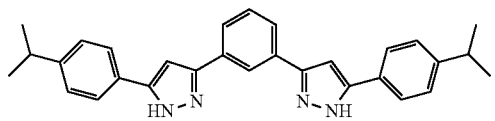
299 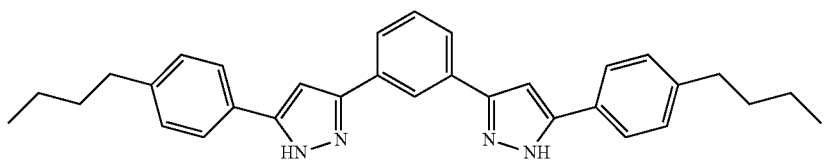
300 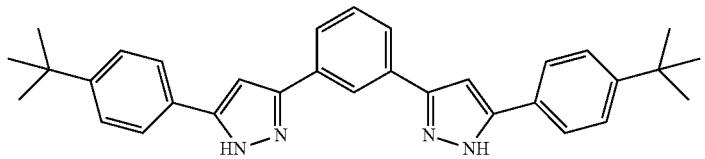
301 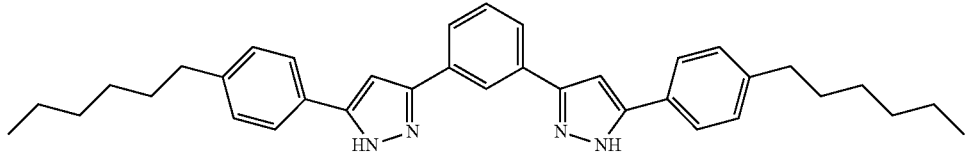
302 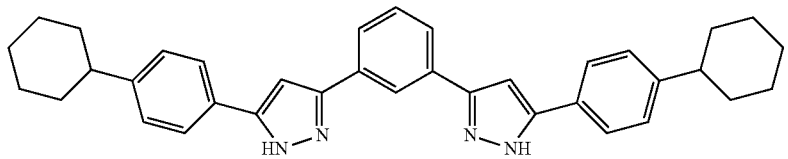

-continued
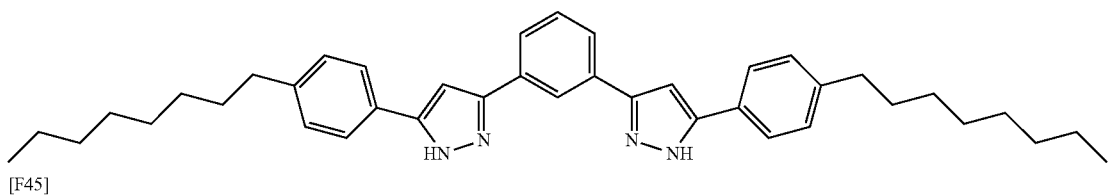
303
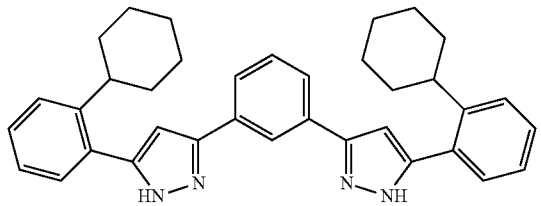
304
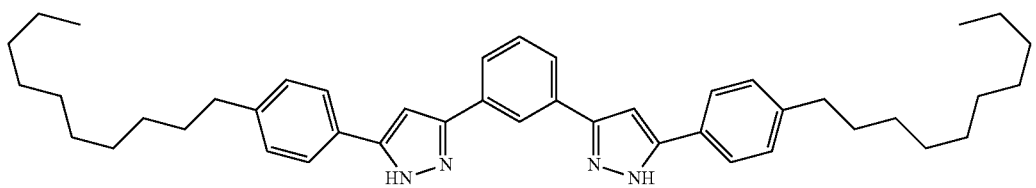
305
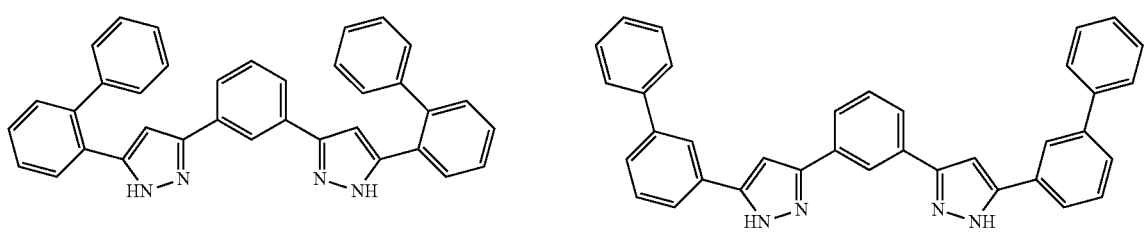
306    307
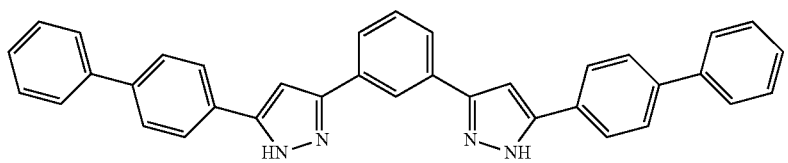
309
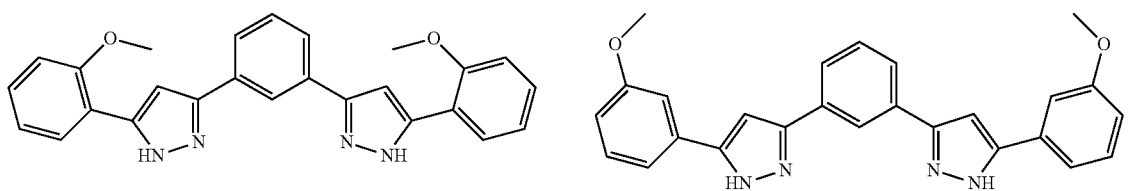
310    311
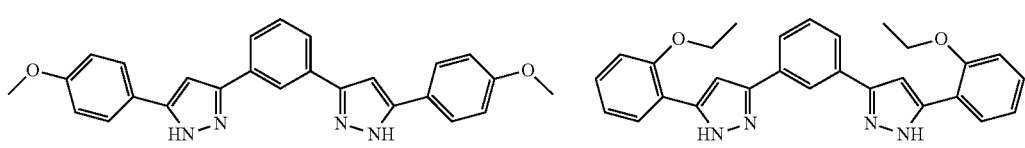
312    313
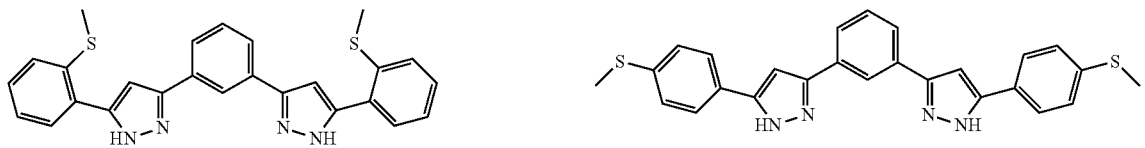
314

[F46]
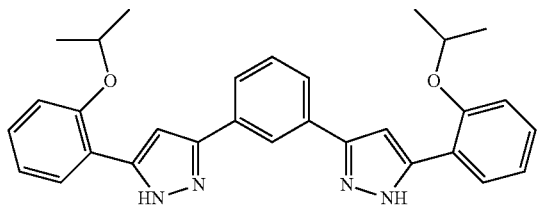
315
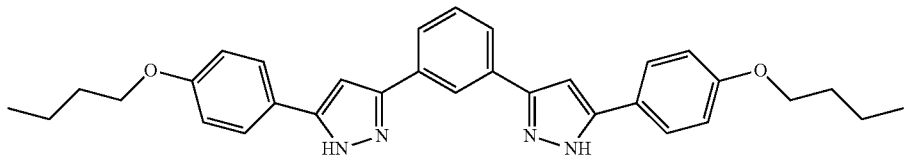
316
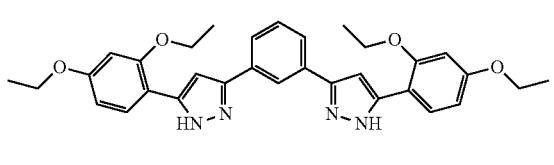
317
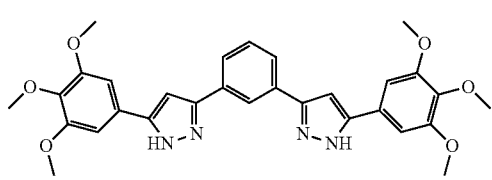
318
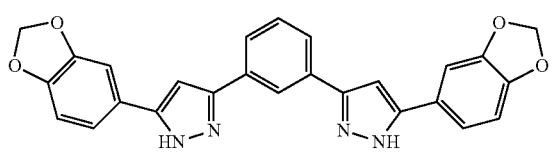
319
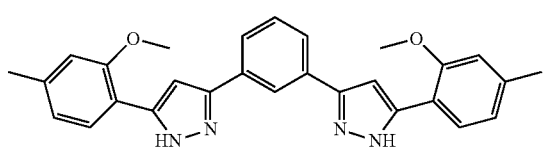
320
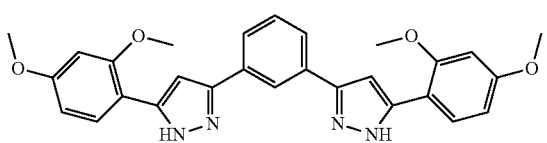
321
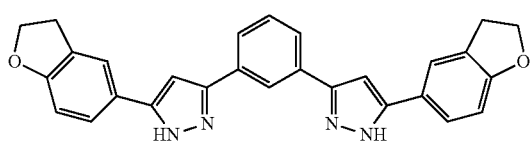
322
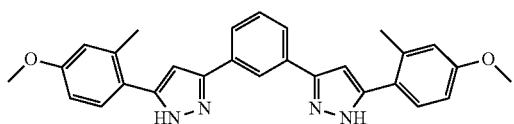
323
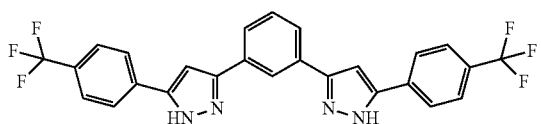
324
[F47]
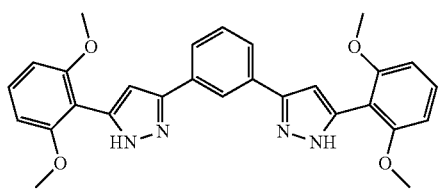
325
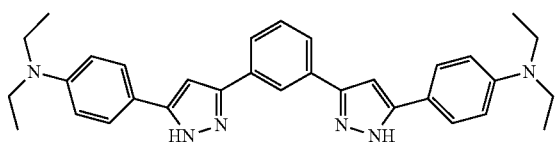
326
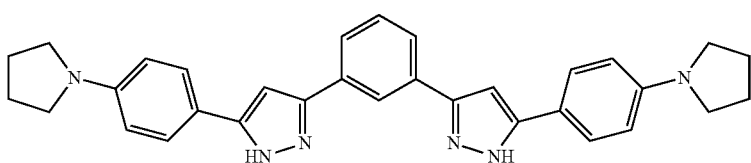
327

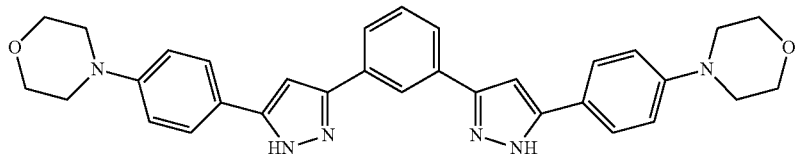
328
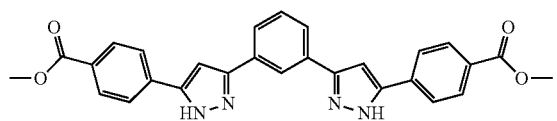
329
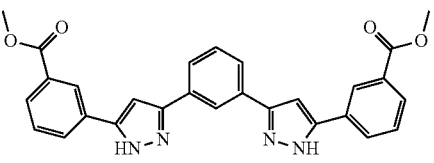
330
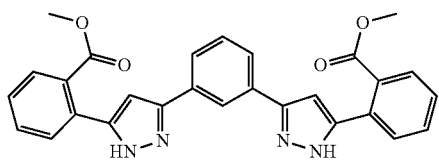
331
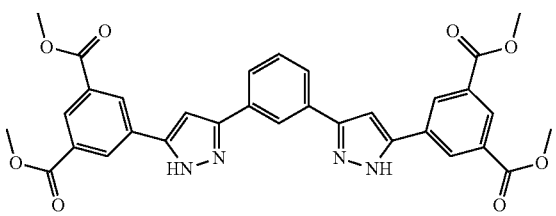
332
[F48]
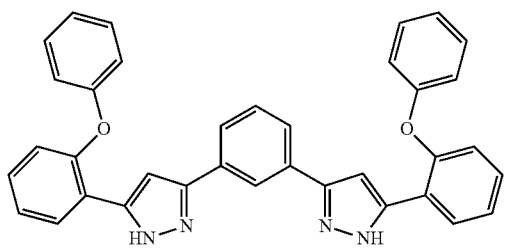
333
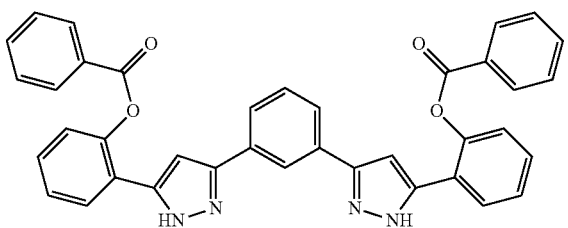
334
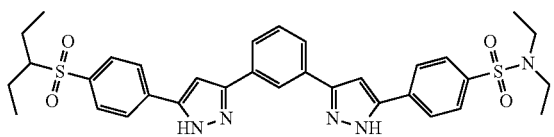
335
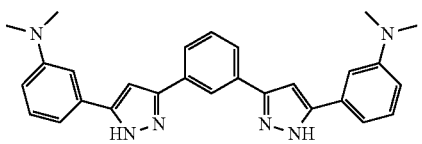
336
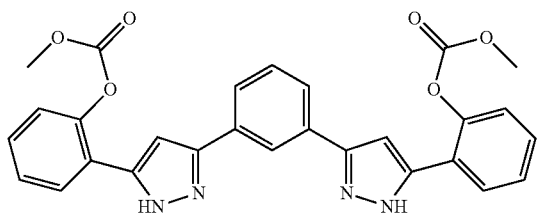
337
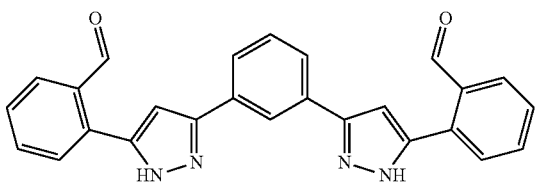
338
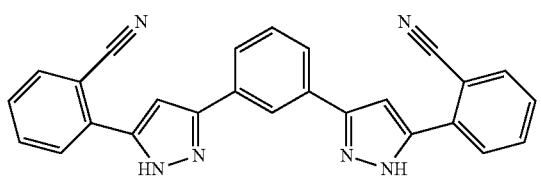
339

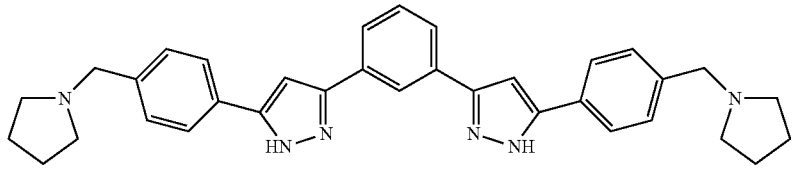
340
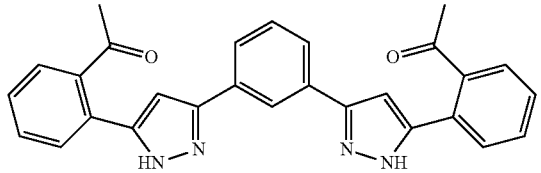
341
[F49]
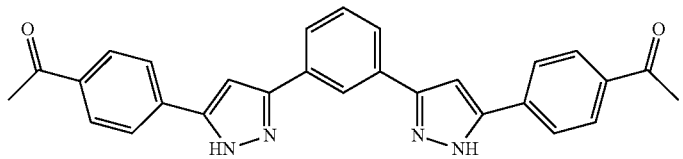
342
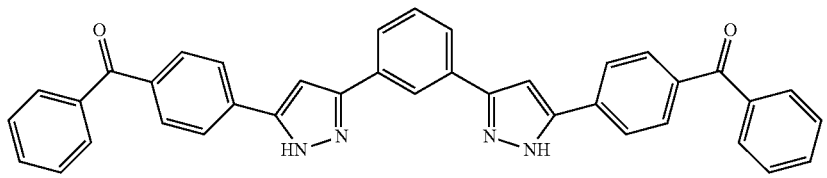
343
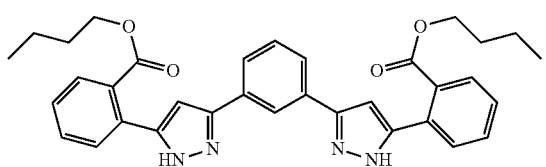
344
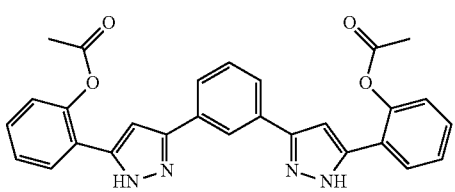
345
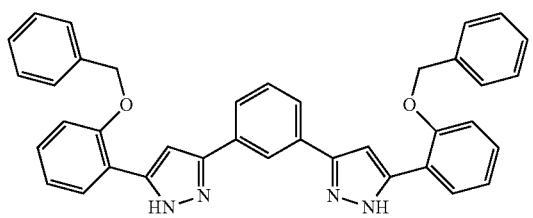
346
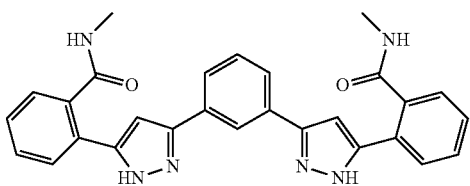
347
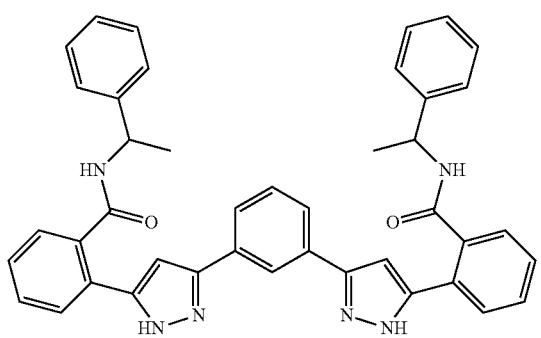
348

-continued
349
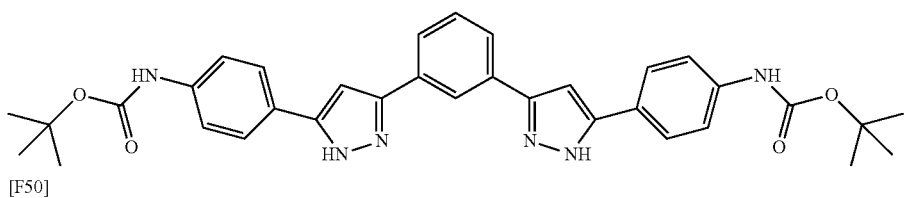
[F50]
350
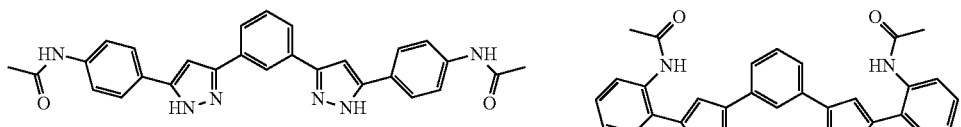
351
352
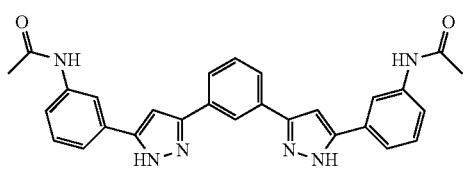
353
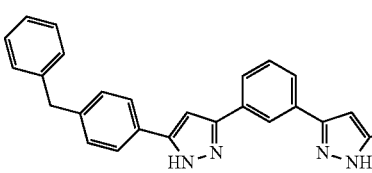
354
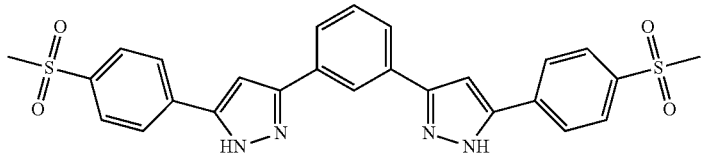
355
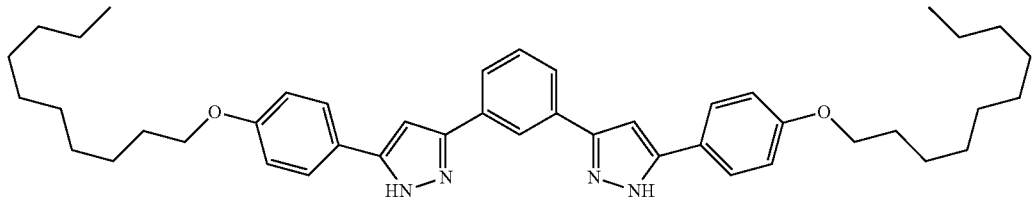
356
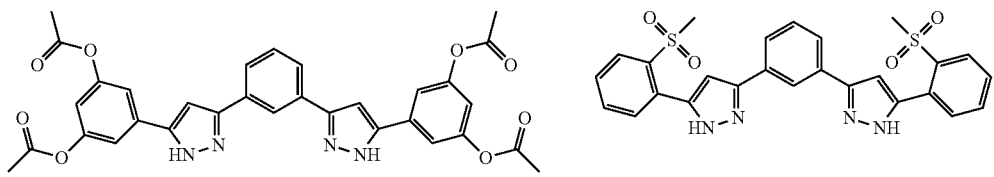
357
358
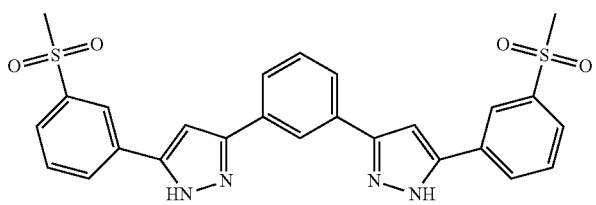
[F51]
359
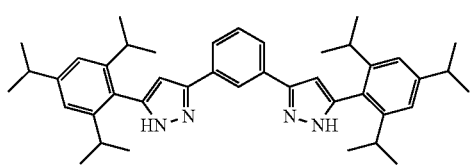
360
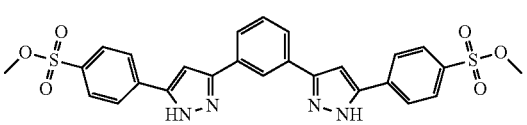

-continued
361
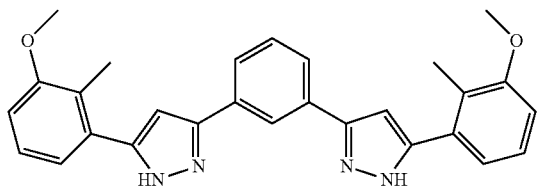
362
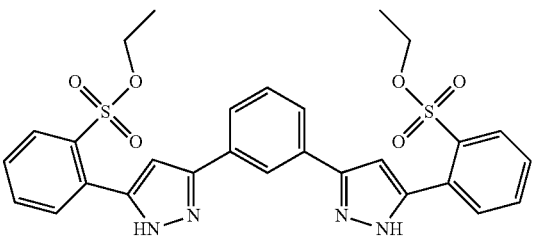
363
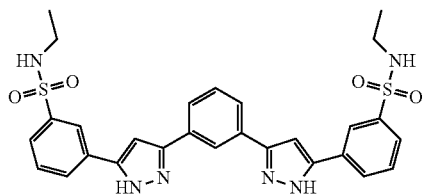
364
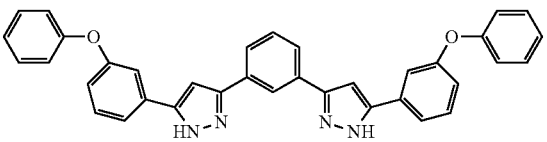
365
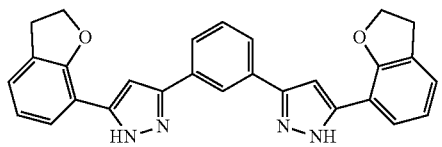
366
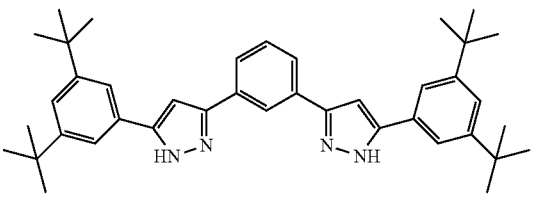
[F52]
367
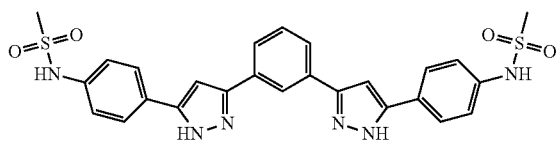
368
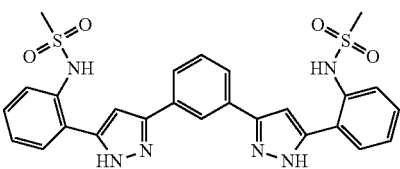
369
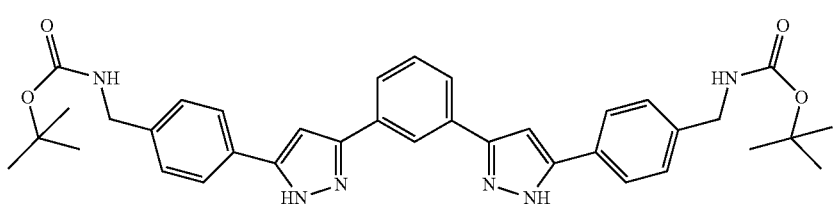
370
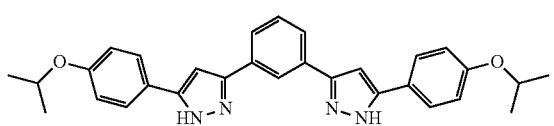
371
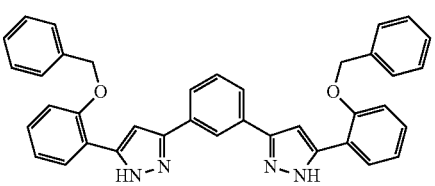
372
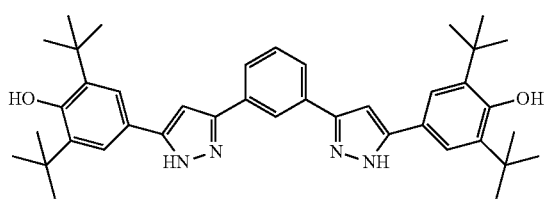
373
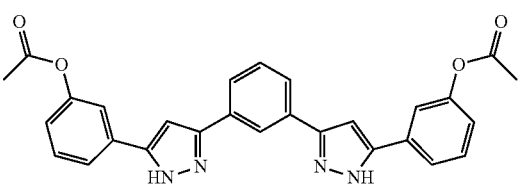

-continued
[F53]
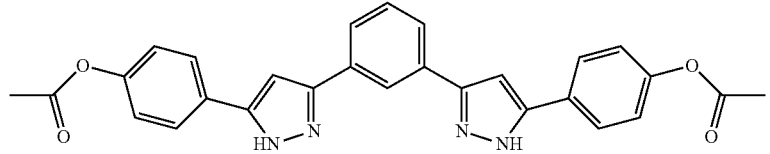
374
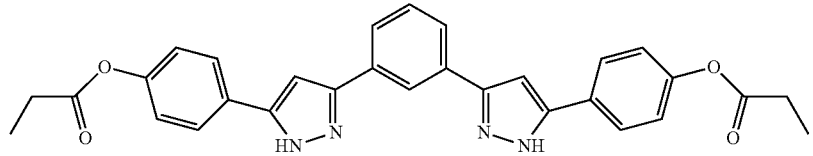
375
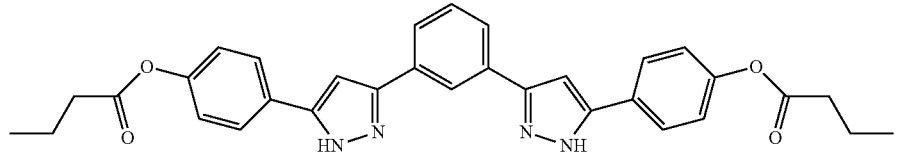
376
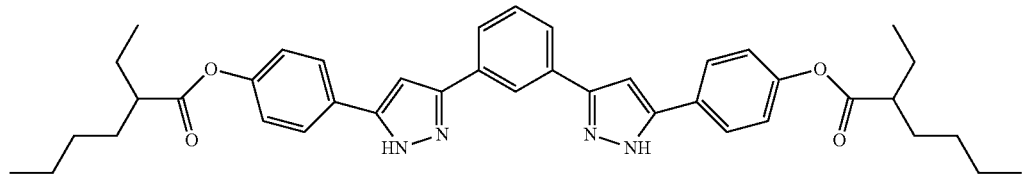
377
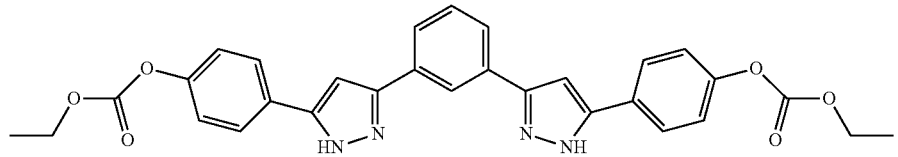
378
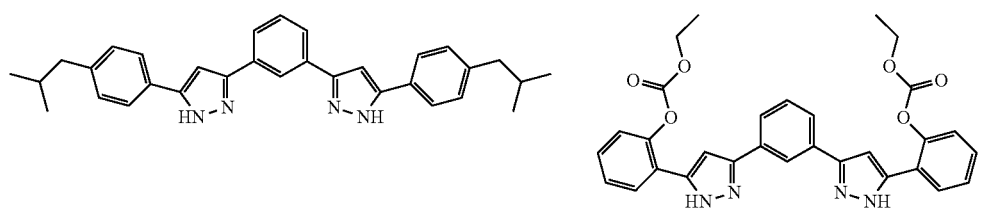
379 380
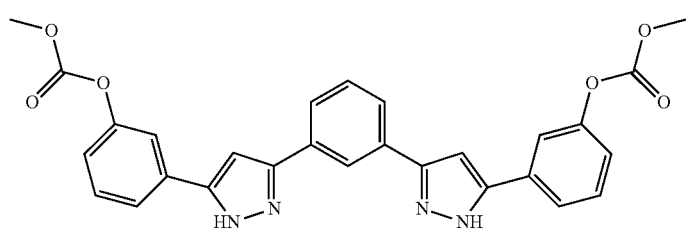
381
[F54]
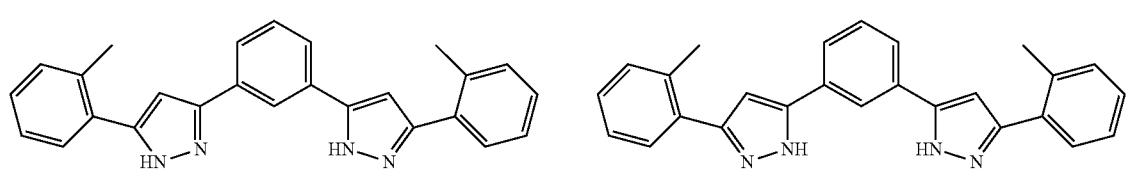
382 383

-continued
384
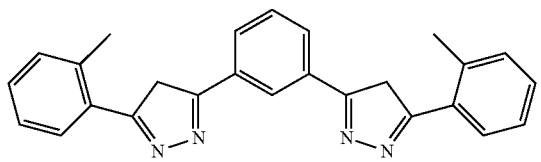
385
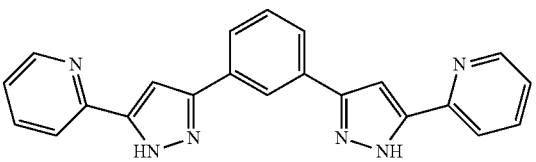
386
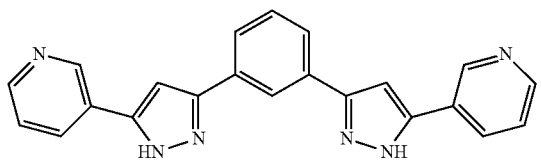
387
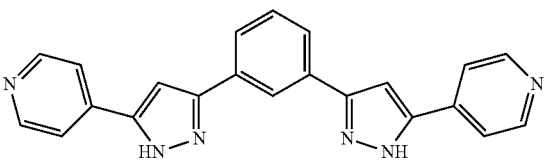
388
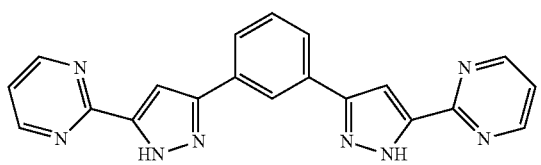
389
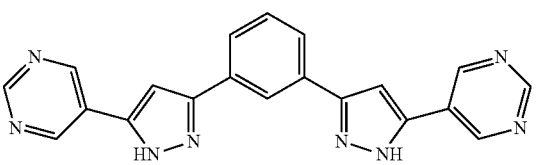
390
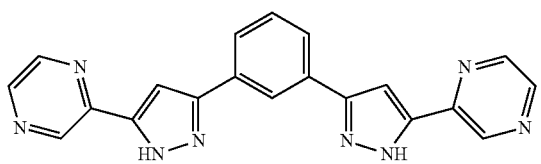
391
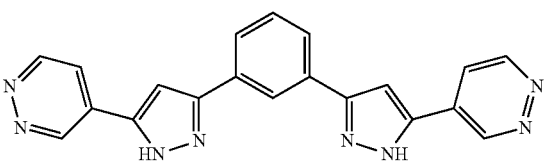
392
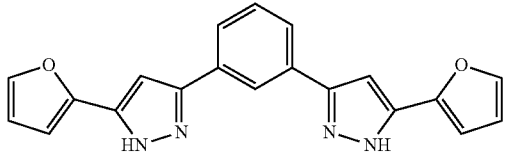
393
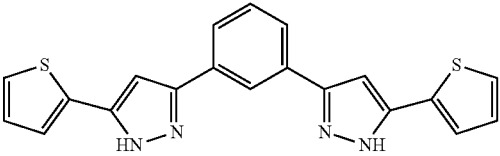
394
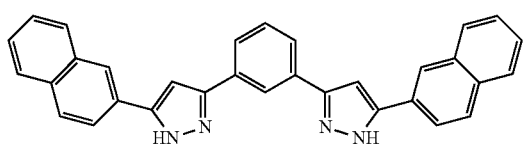
395
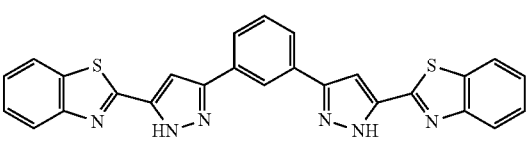
[F55]
396
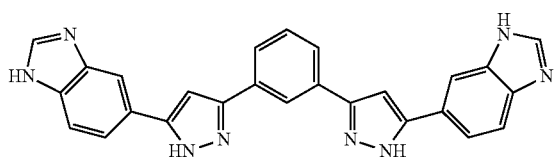
397
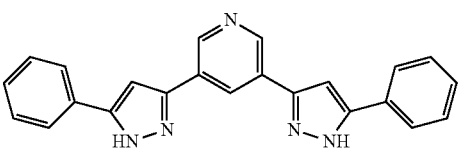
398
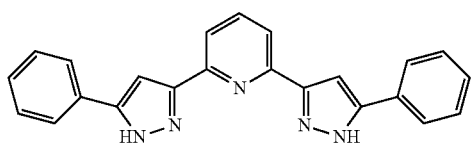
399
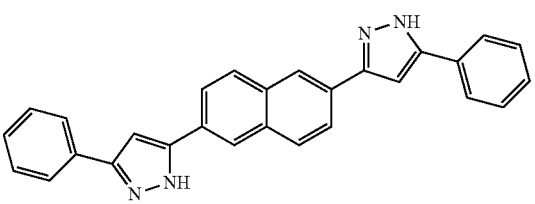

-continued
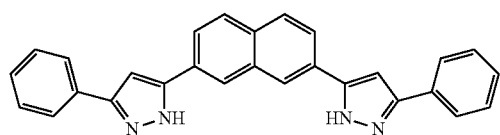
400
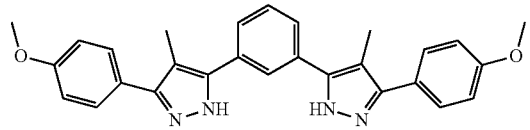
401
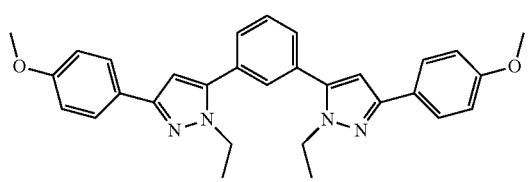
402
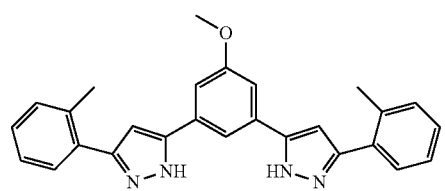
403
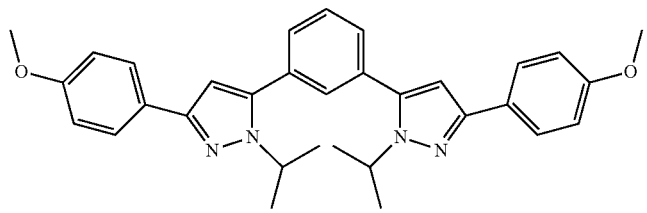
404
[F56]
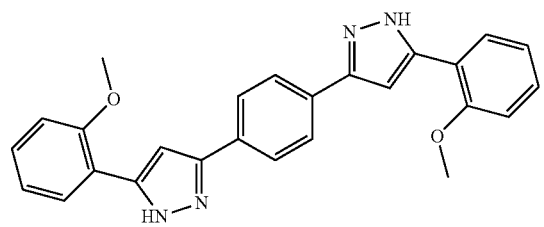
406
405
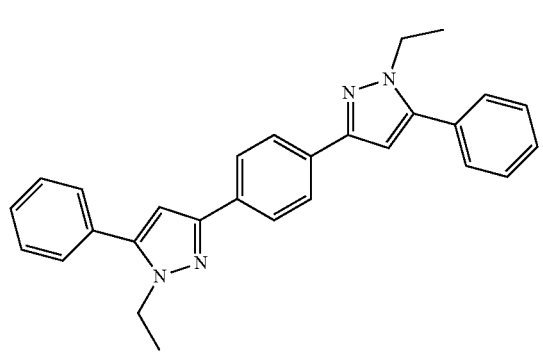
407
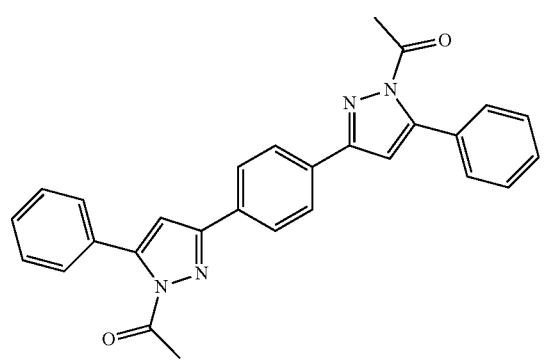
408
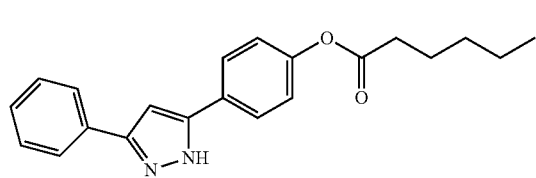
409
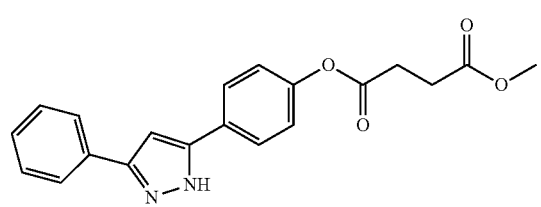
410

[F57]
411
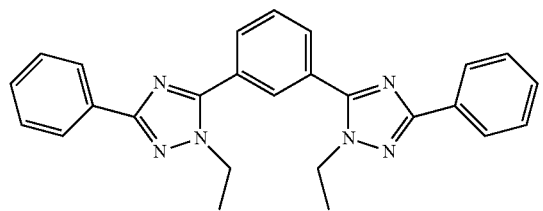
412
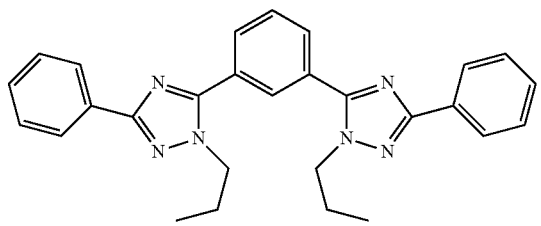
413
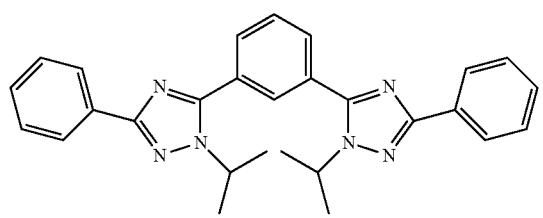
414
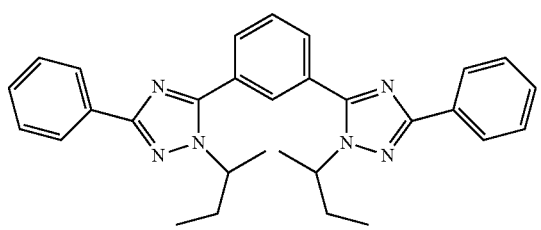
415
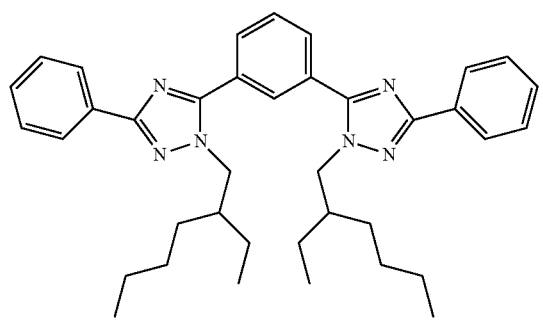
416
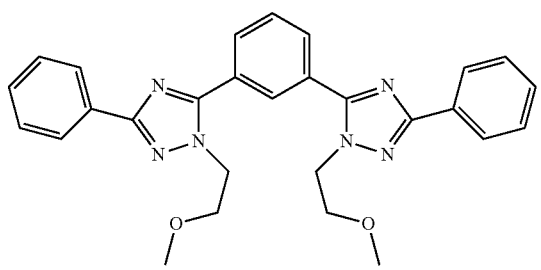
417
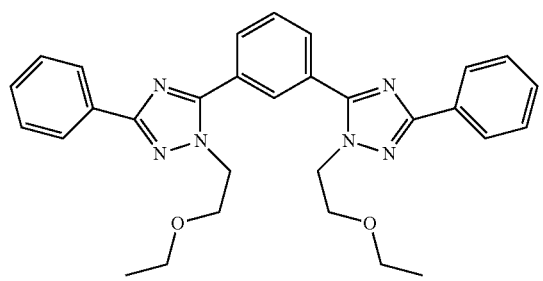
418
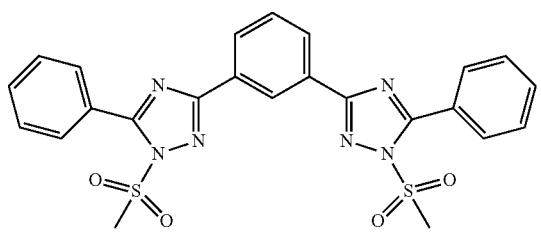
419
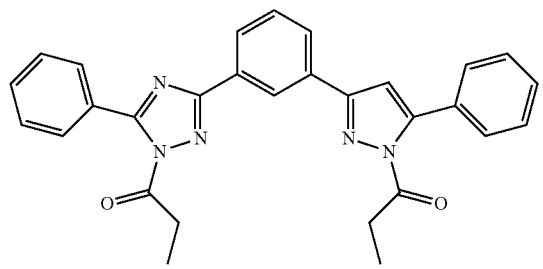
420
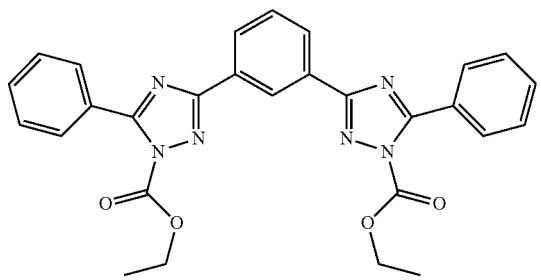

421
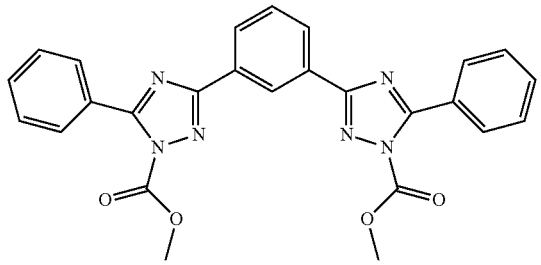
[F58]
422
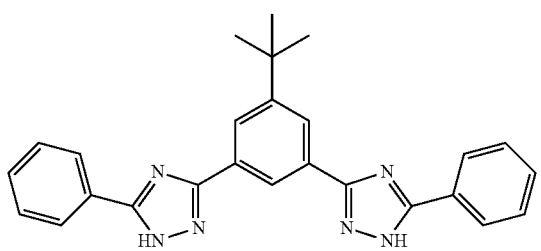
423
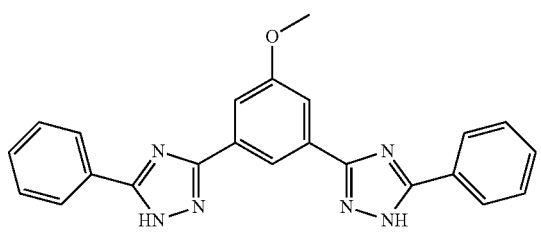
424
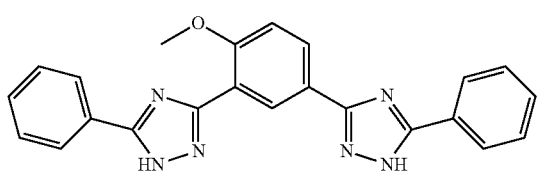
425
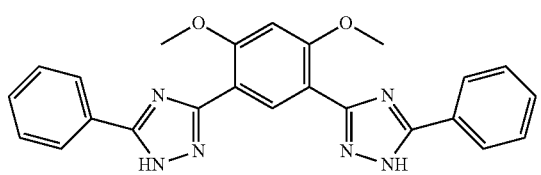
426
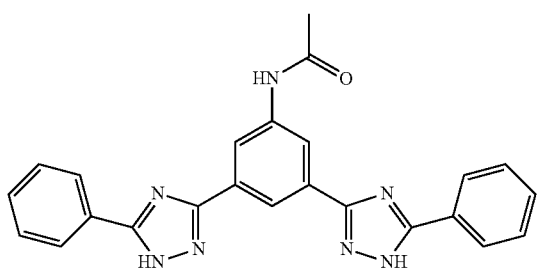
427
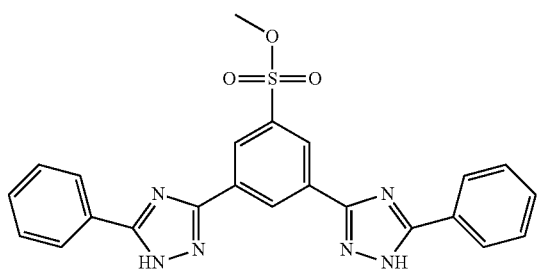
428
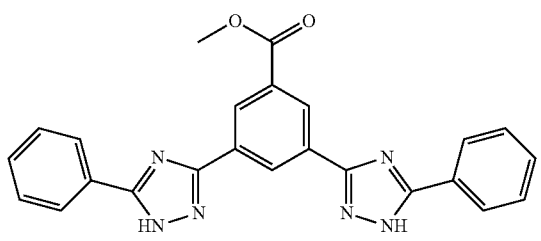
429
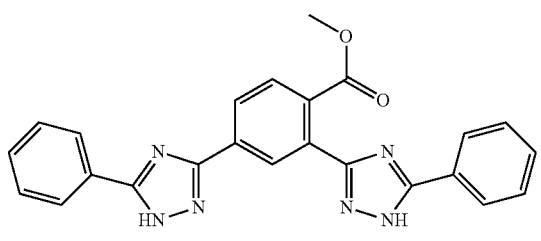
430
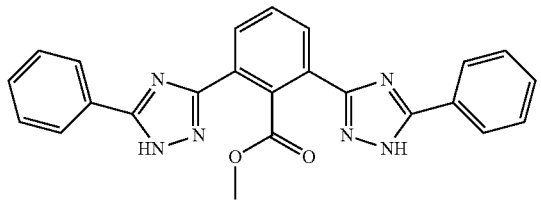

-continued
431
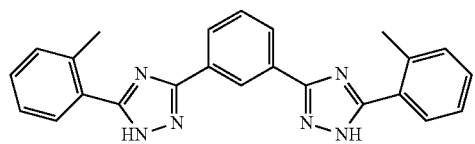
432
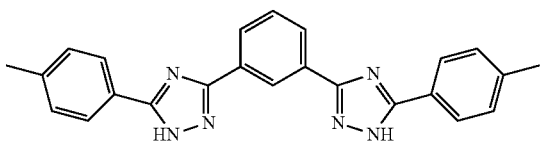
433
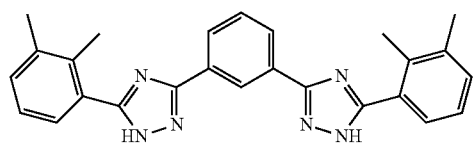
434
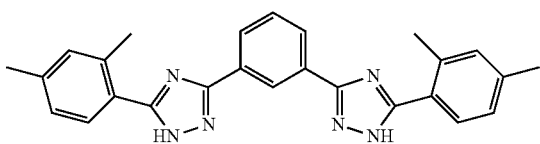
435
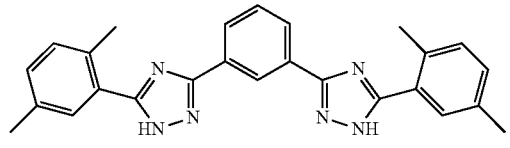
436
437
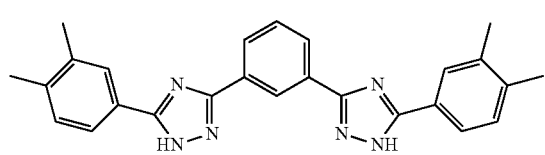
438
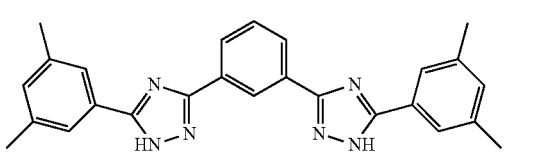
439
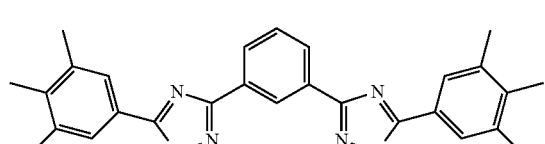
440
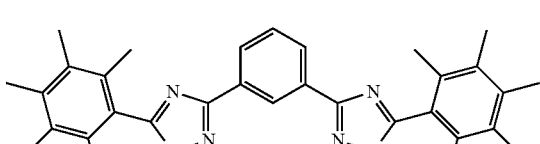
[F60]
441
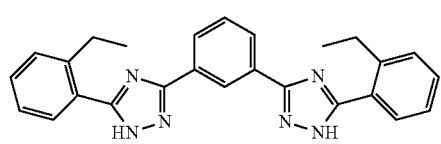
442
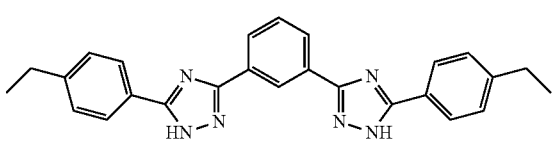
443
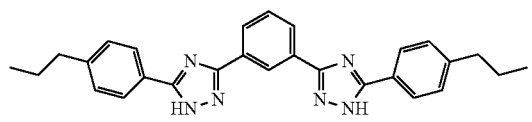
444
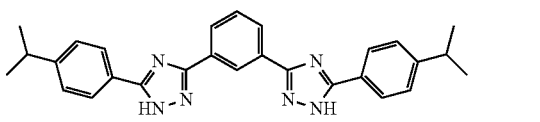
445
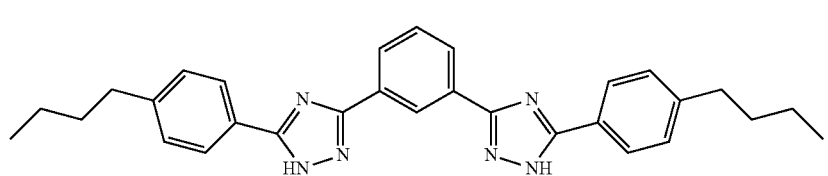
446
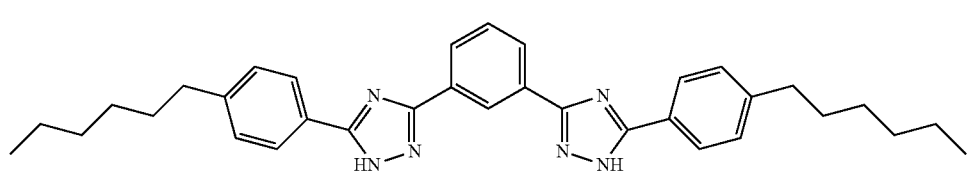

-continued
447
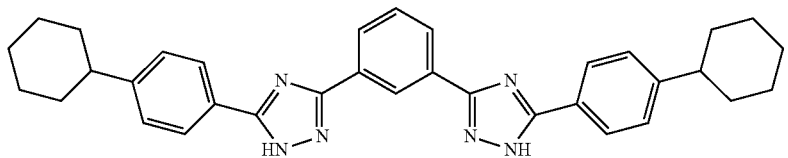
448
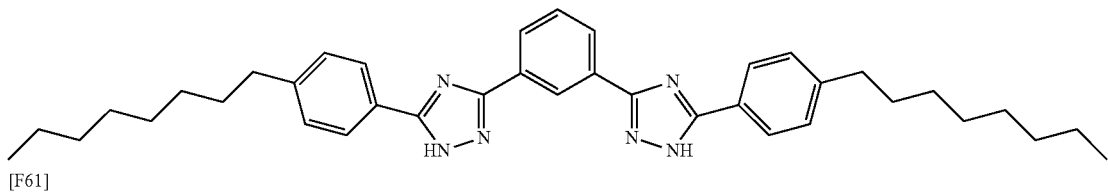
[F61]
449
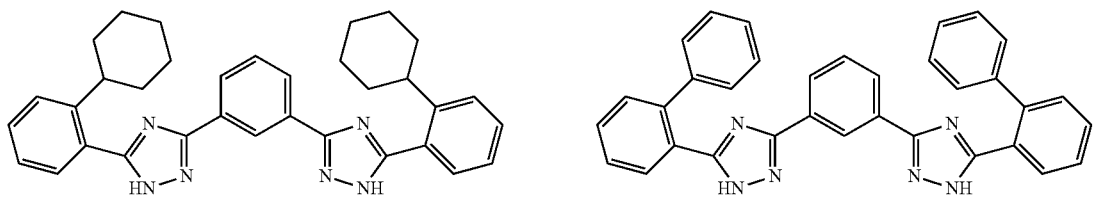
450
451
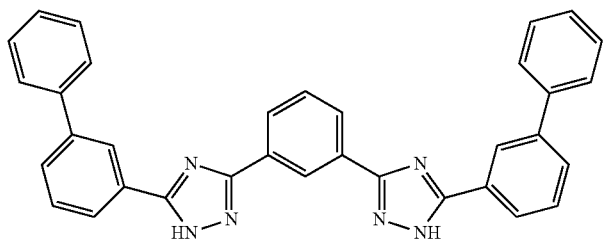
452
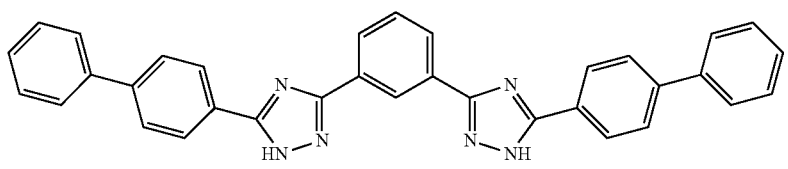
453
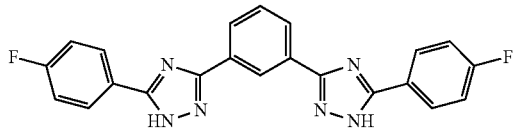
454
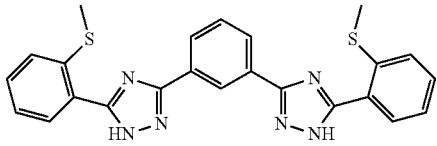
455
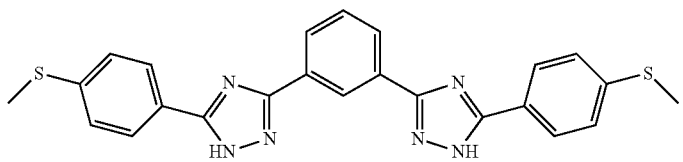
[F62]
456
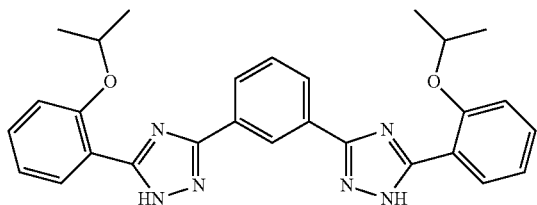

457
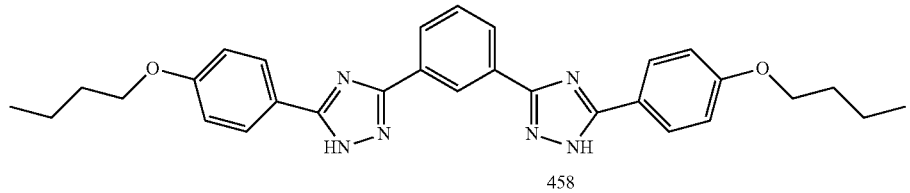
458
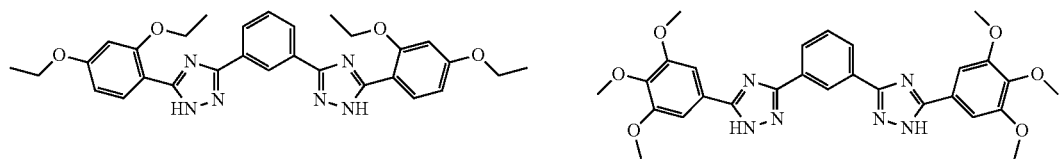
459
460
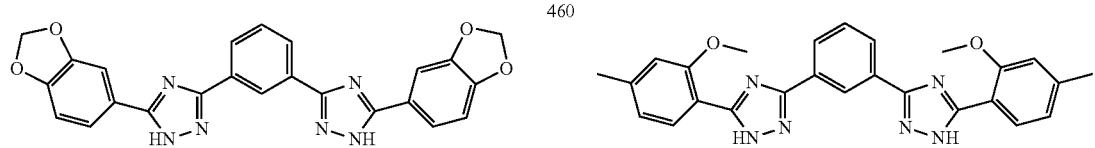
461
462
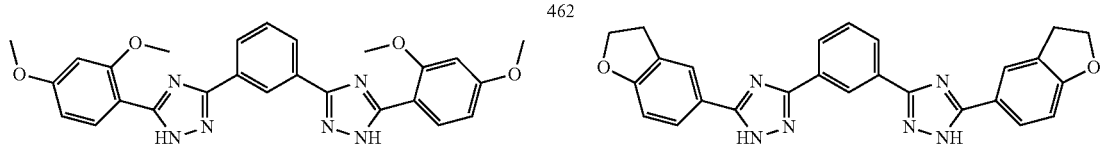
463
464
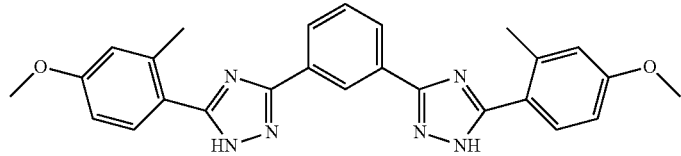
[F63]
465
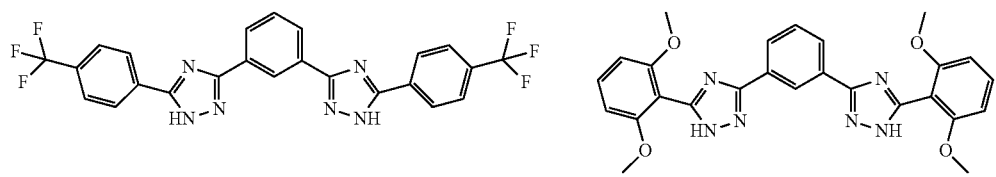
466
467
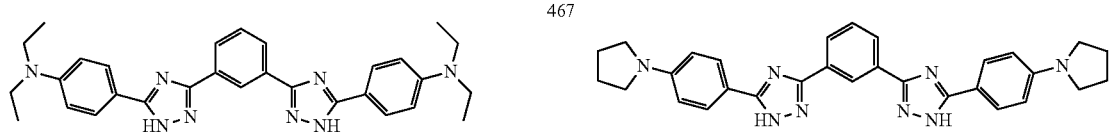
468
469
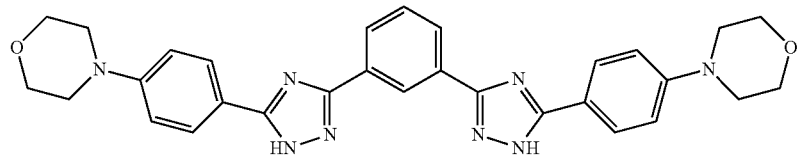
470
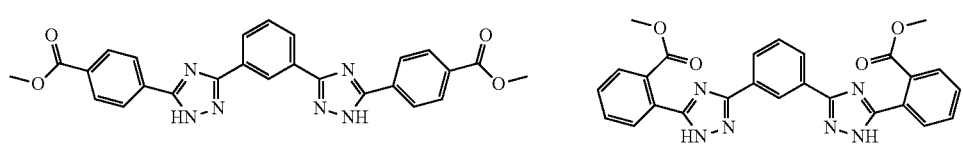
471

472
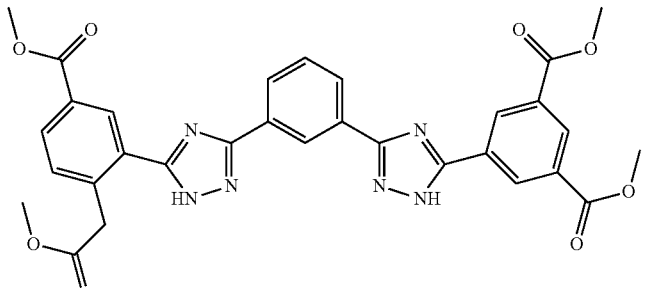
[F64]
473
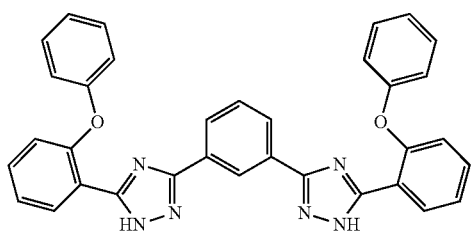
474
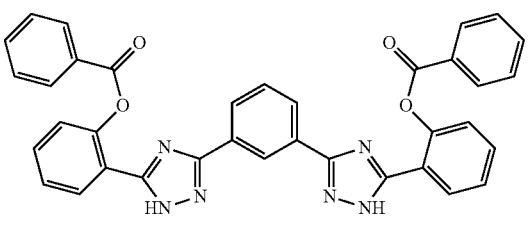
475
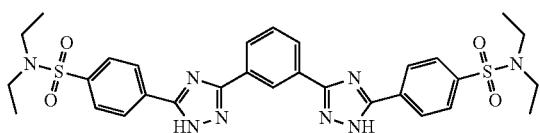
476
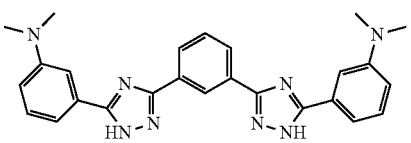
477
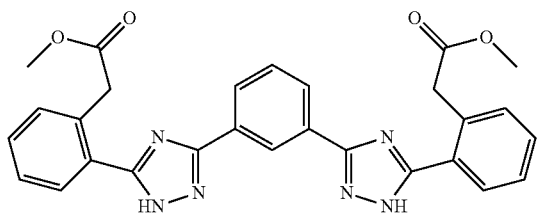
478
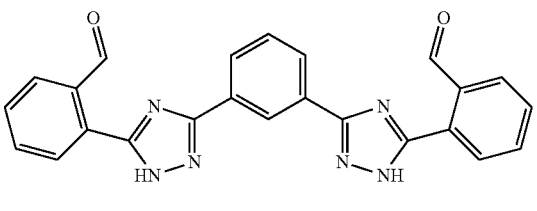
479
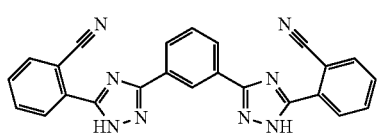
480
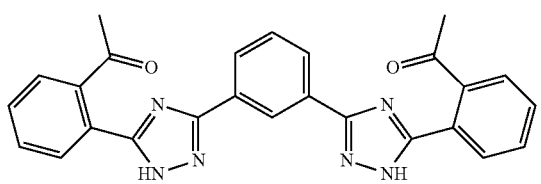
481
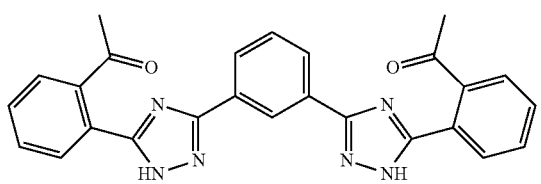
[F65]
482
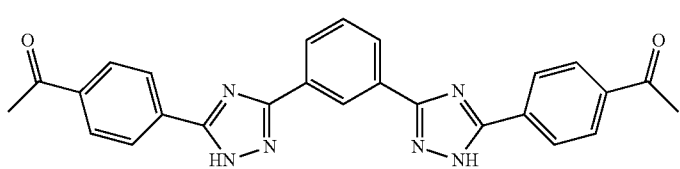

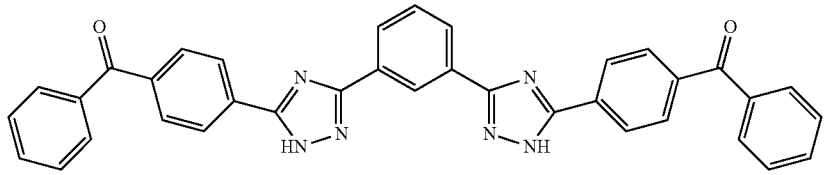
483
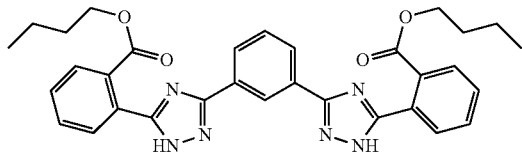
484
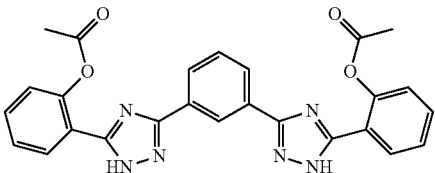
485
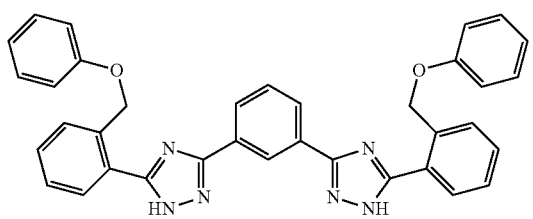
486
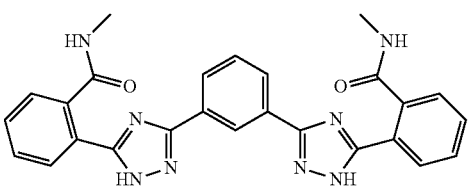
487
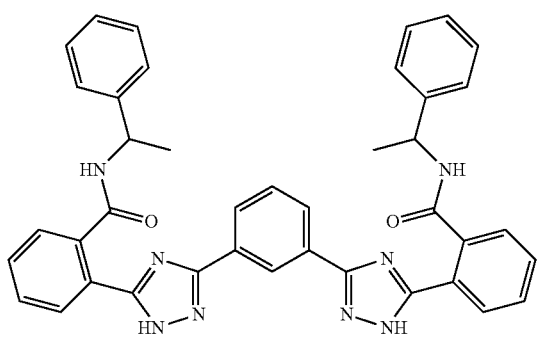
488
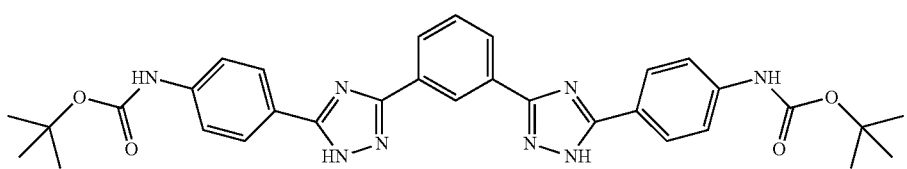
489
[F66]
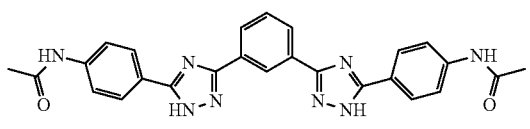
490
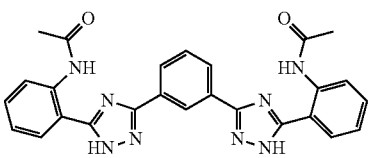
491
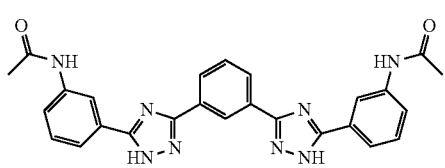
492
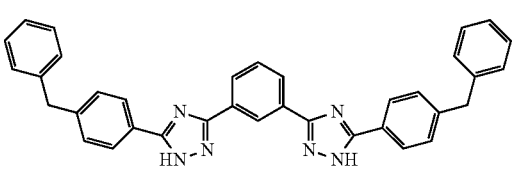
493

-continued
494
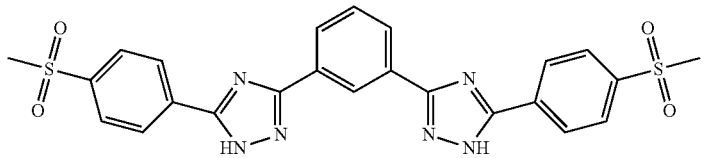
495
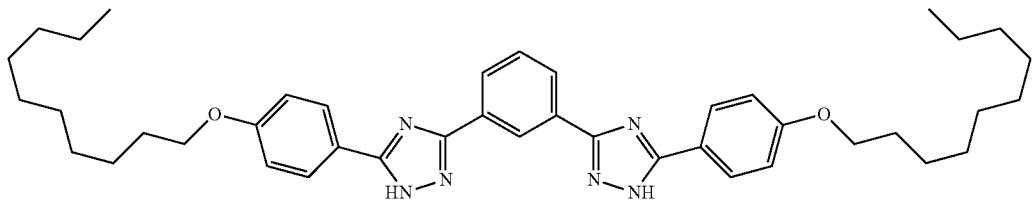
496
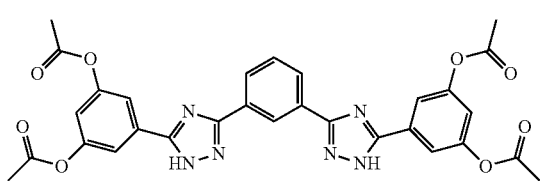
497
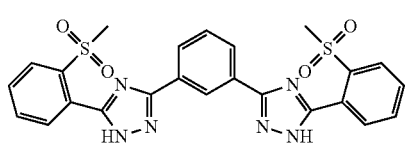
498
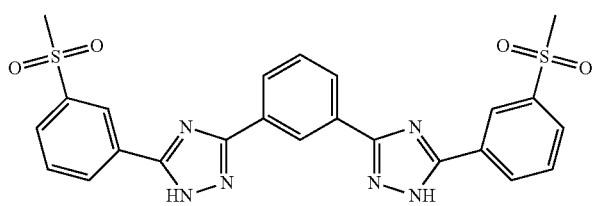
[F67]
499
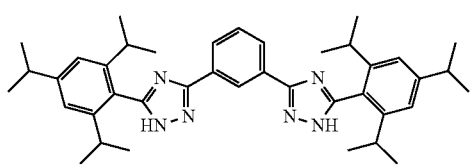
500
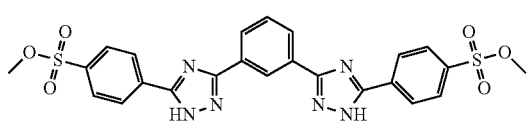
501
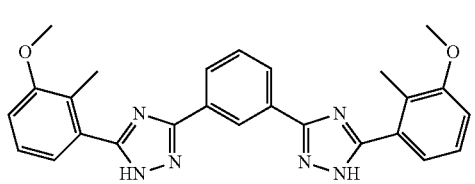
502
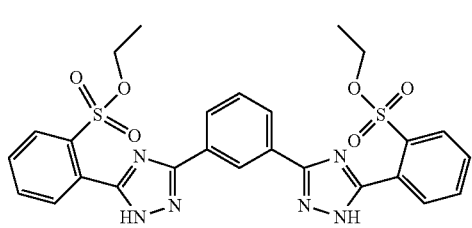
503
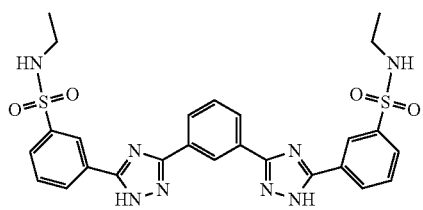
504
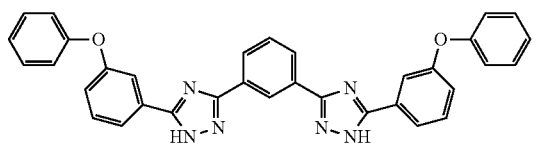

505 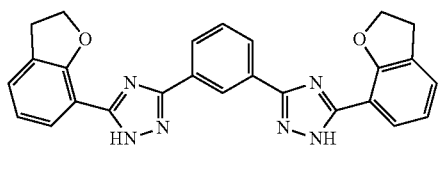
[F68]
506 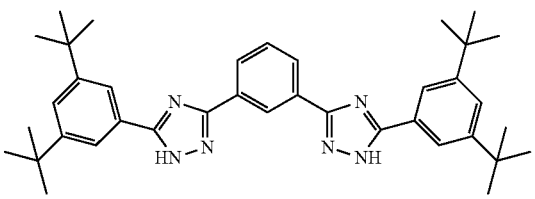
507 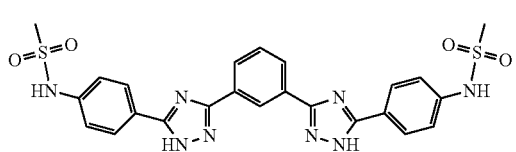
508 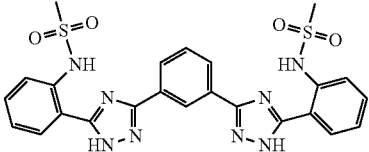
509 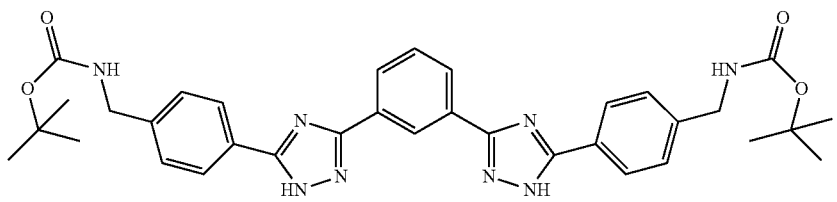
510 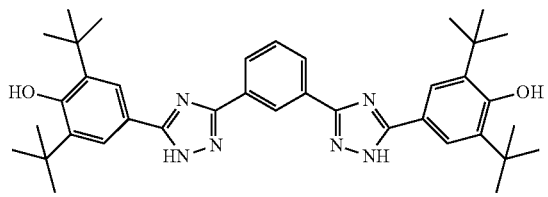
511 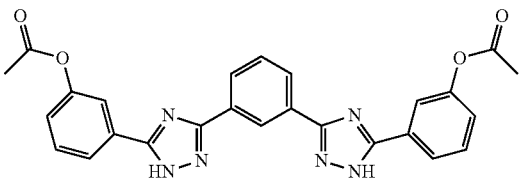
512 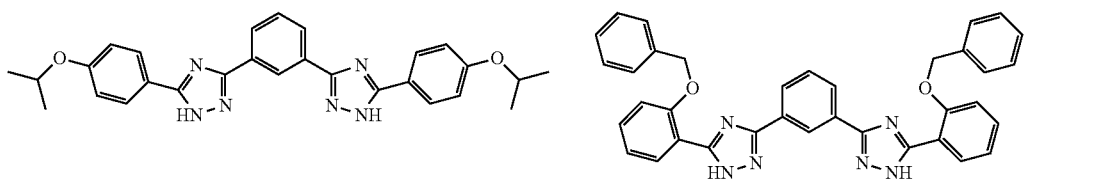
[F69]
513 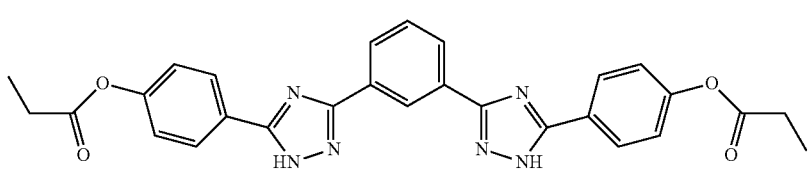
514 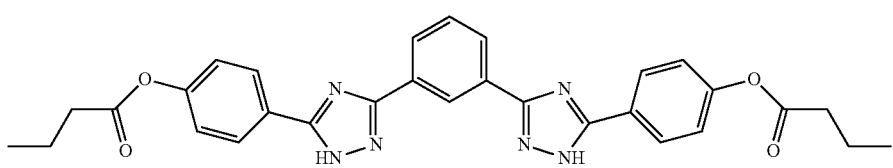
515 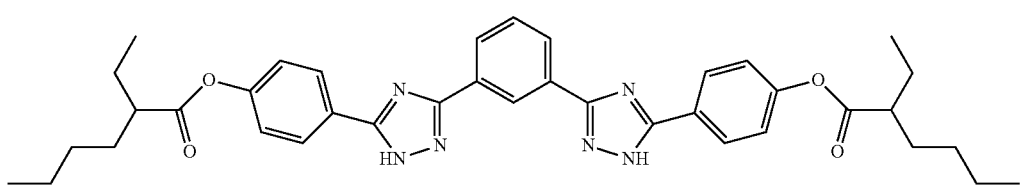
516

517
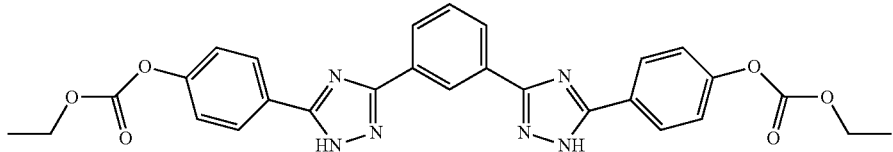
518
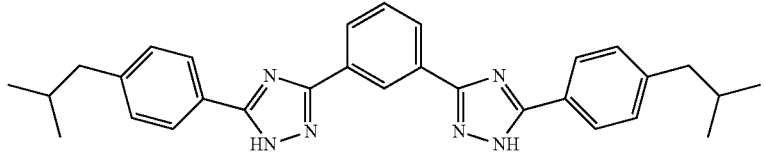
519
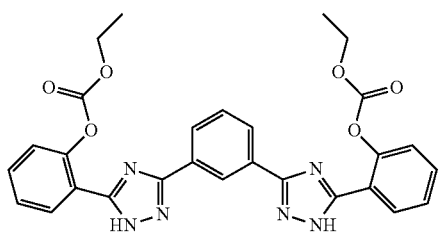
520
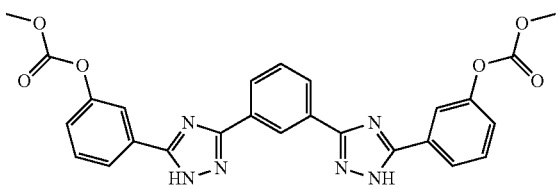
[F70]
521
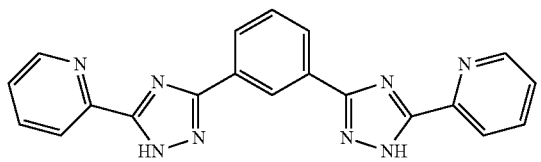
522
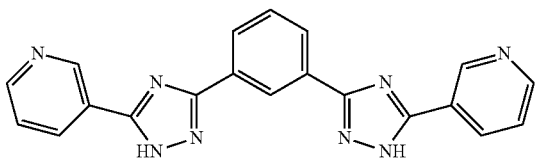
523
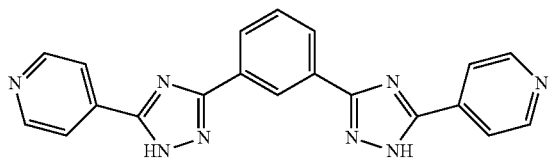
524
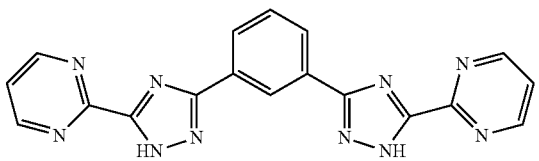
525
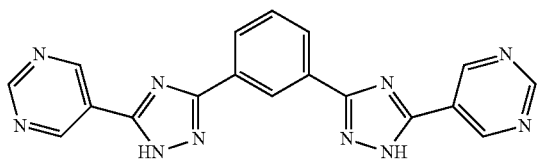
526
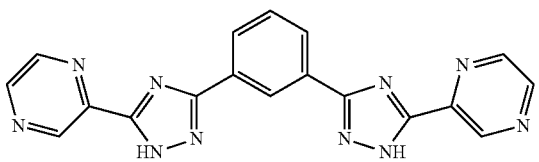
527
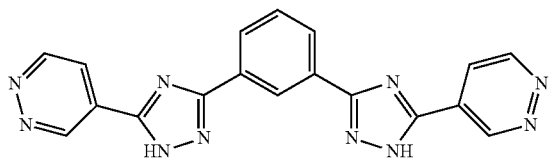
528
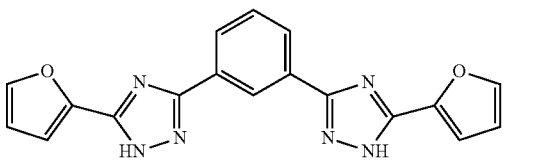
529
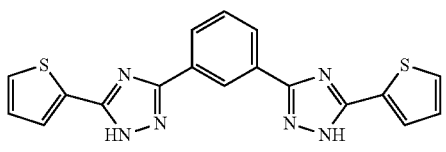
530
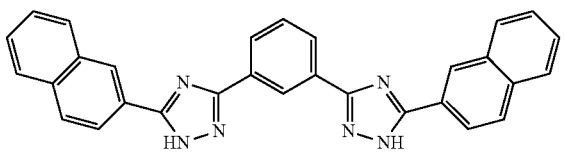

-continued
531
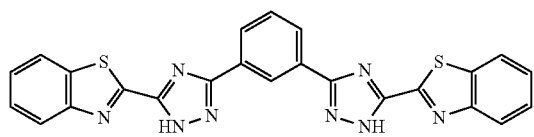
[F71]
532
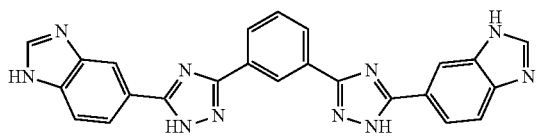
533
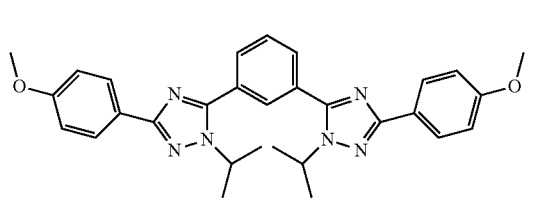
534
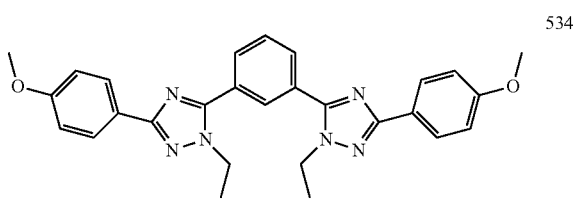
[F72]
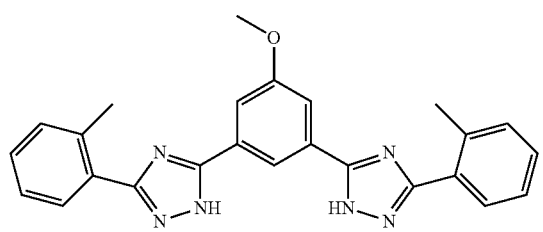
535
536
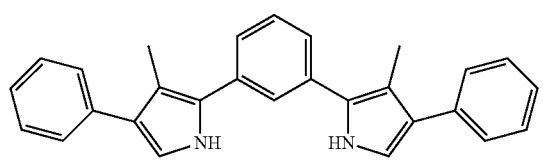
537
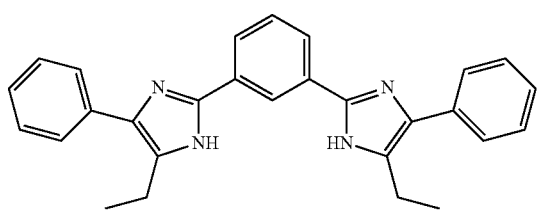
538
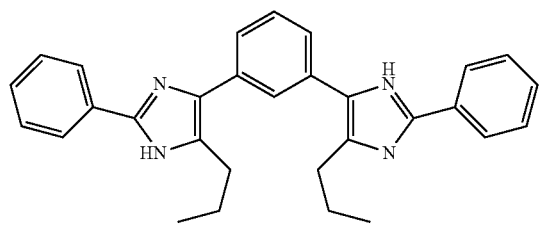
539
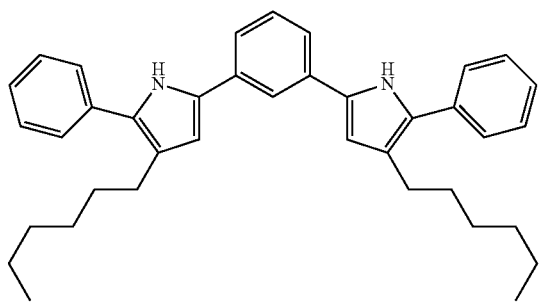
540
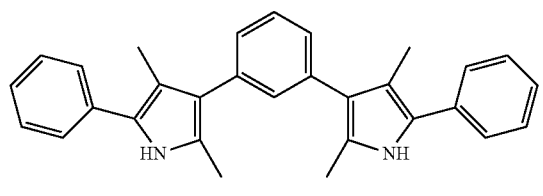
541
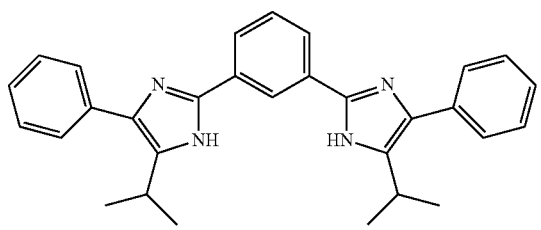

-continued
542
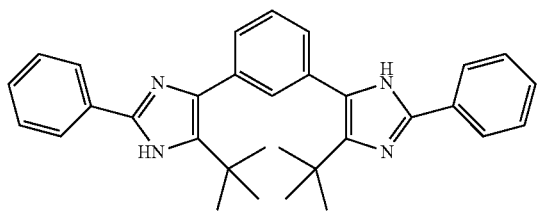
543
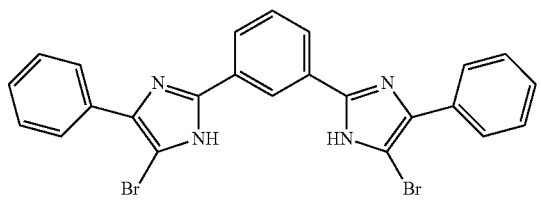
544
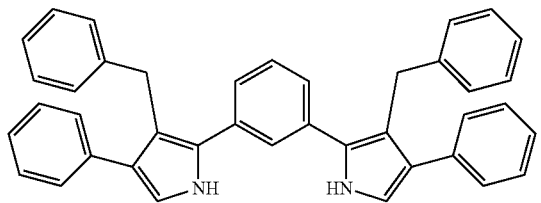
545
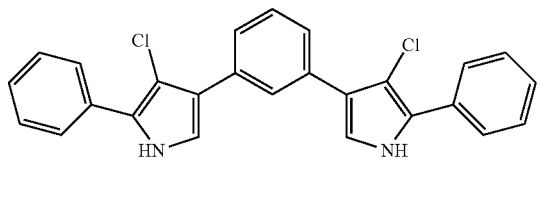
546
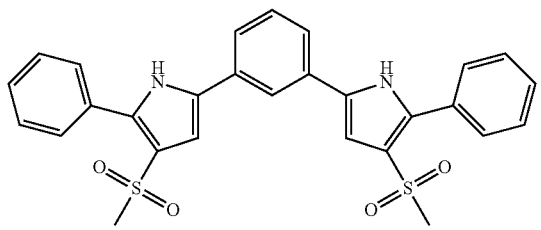
547
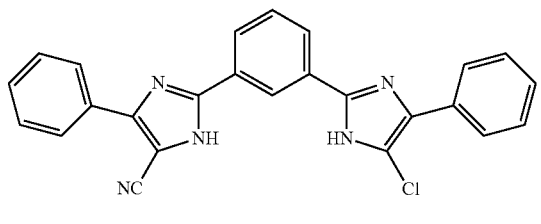
[F73]
548
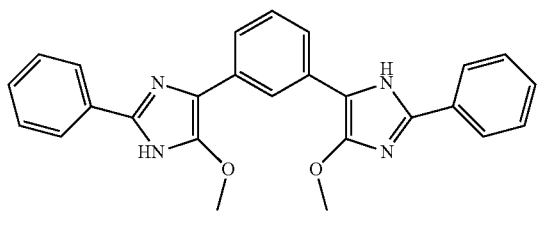
549
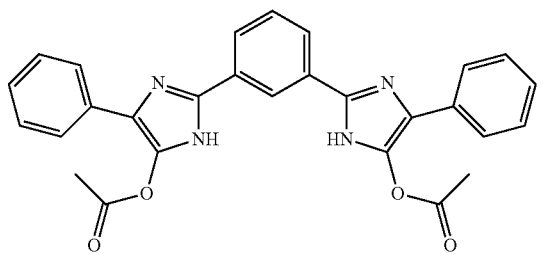
550
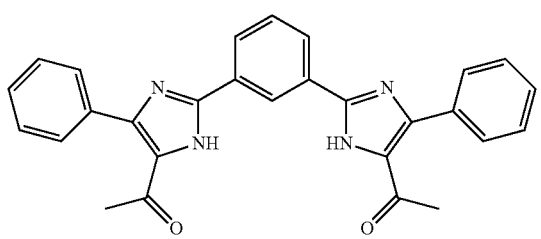
551
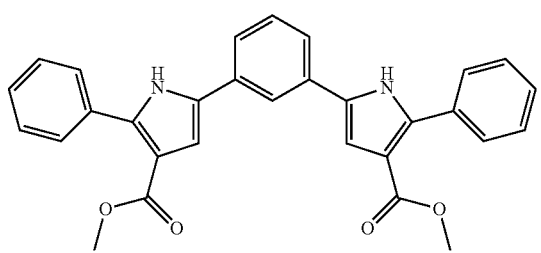
553
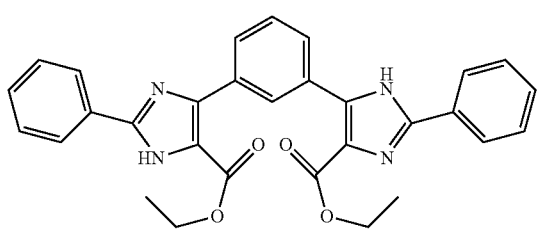
552
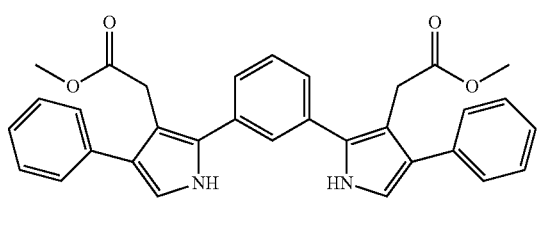

-continued
554
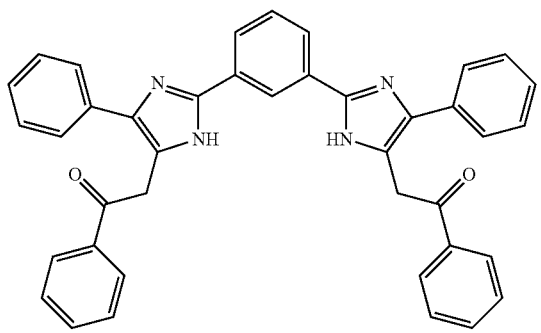
555
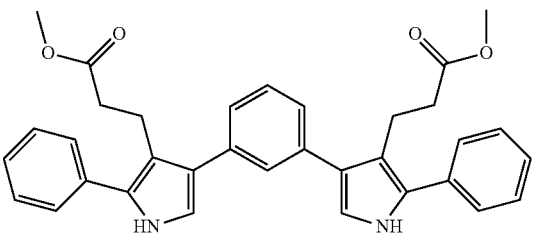
556
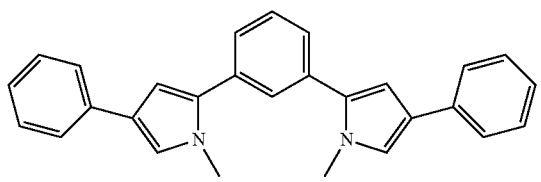
557
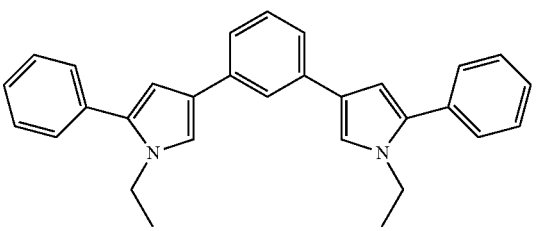
558
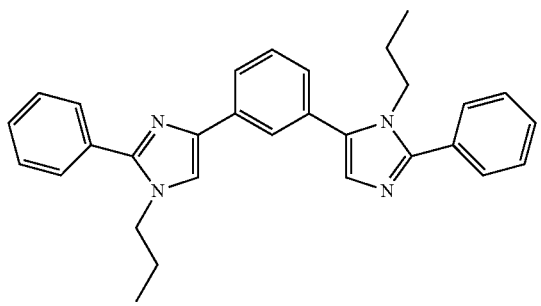
559
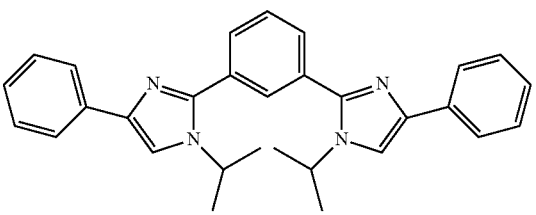
[F74]
560
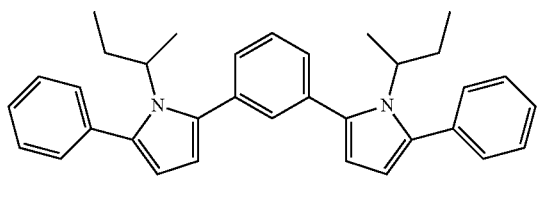
561
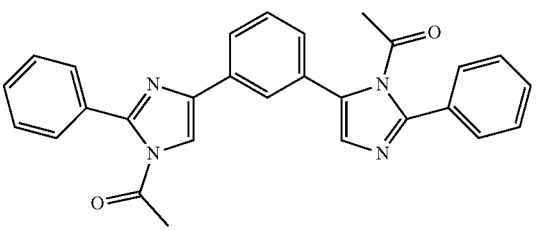
562
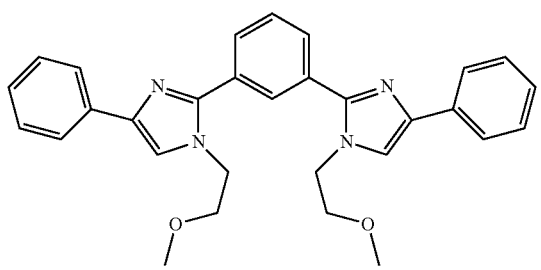
563
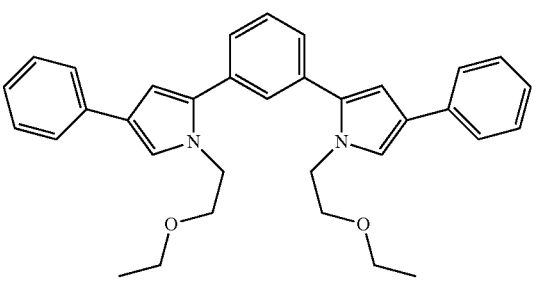

-continued
564
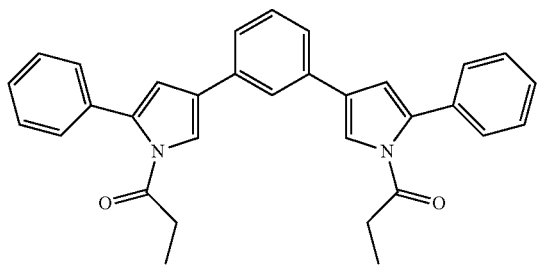
565
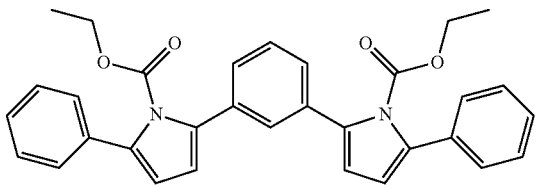
566
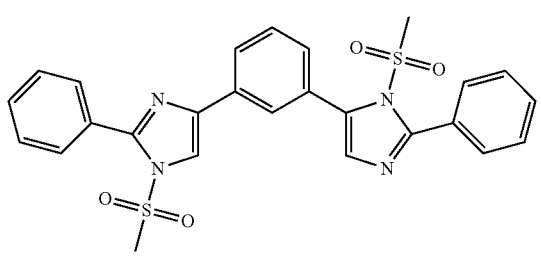
567
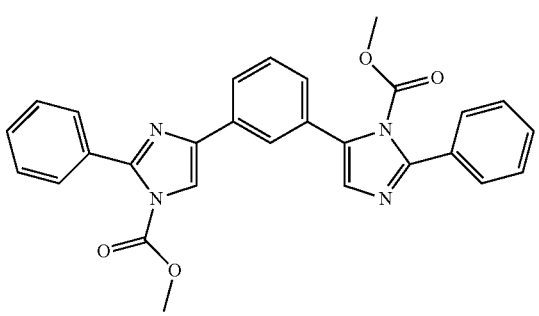
568
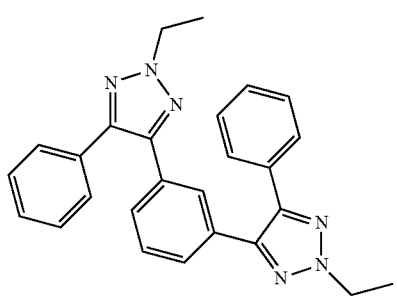
569
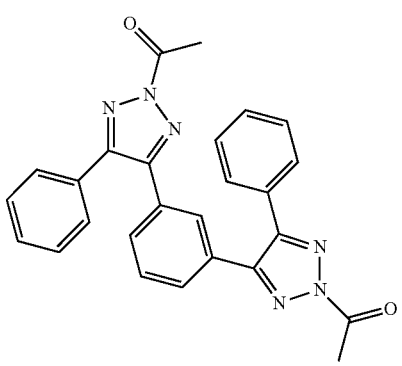
[F75]
570
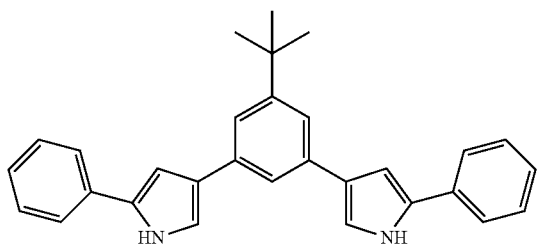
571
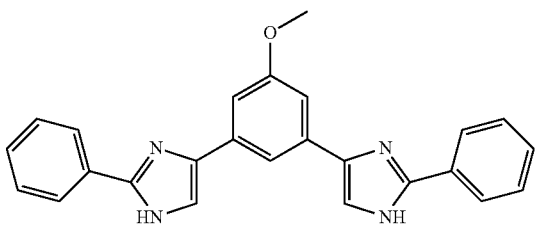
572
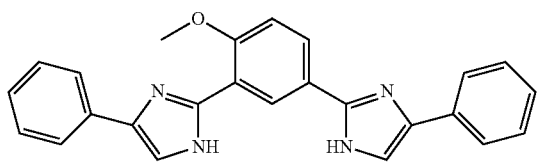
573
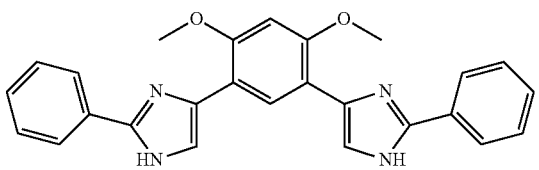

-continued
| 574 | 575 |
|---|---|
| 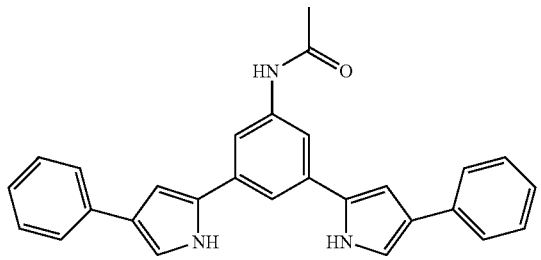 | 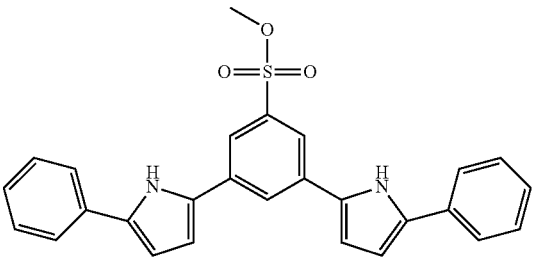 |
| 576 | 577 |
| 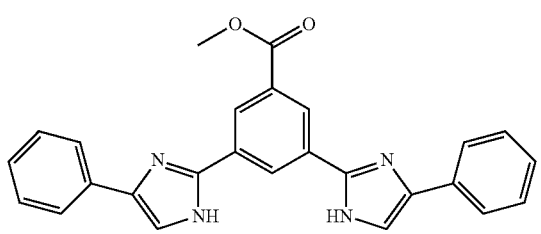 | 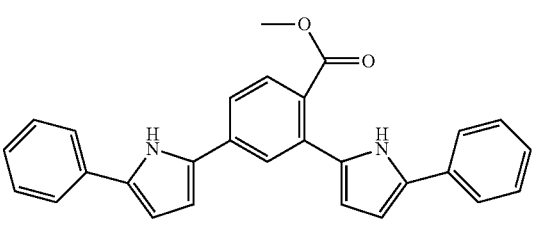 |
| 578 | 579 |
| 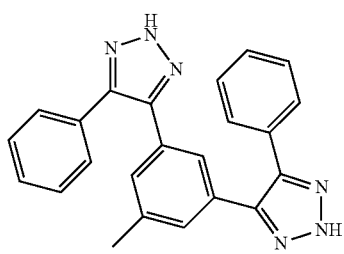 | 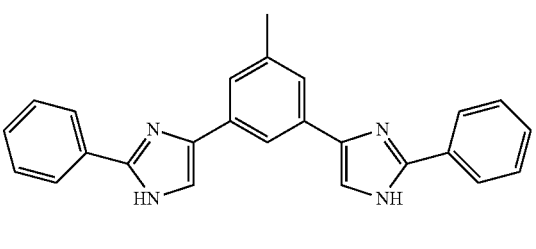 |
[F76]
| 580 | 581 |
|---|---|
| 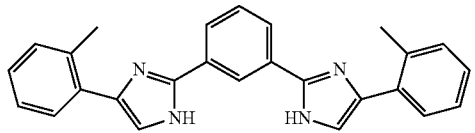 | 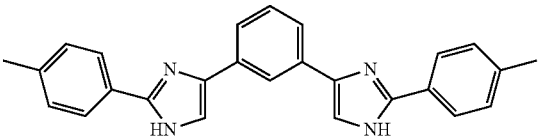 |
| 582 | 583 |
| 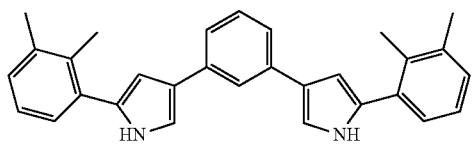 | 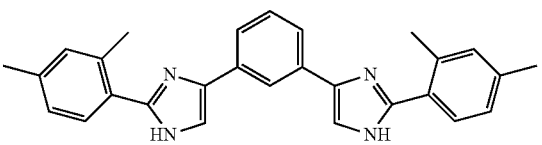 |
| 584 | 585 |
| 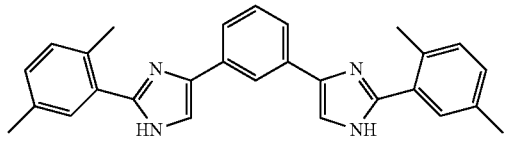 | 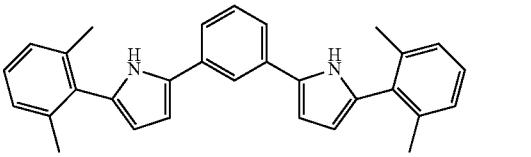 |
| 586 | 587 |
| 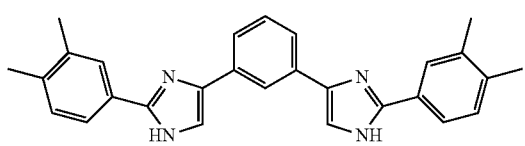 | 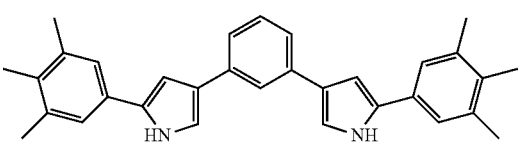 |

588 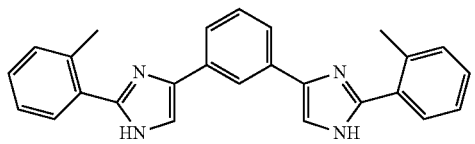
589 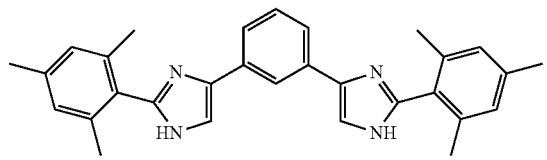
590 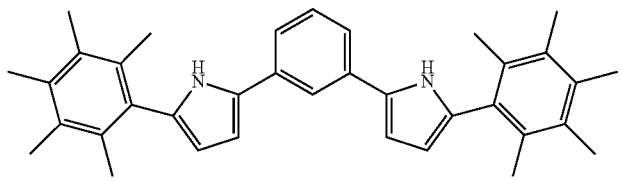
[F77]
591 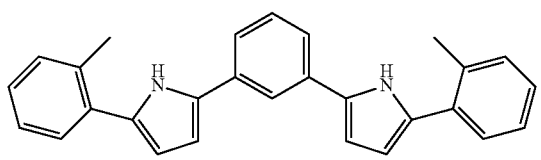
592 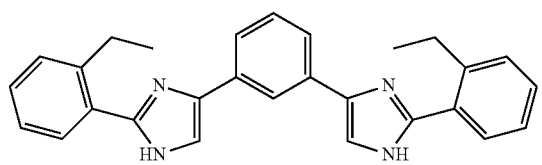
593 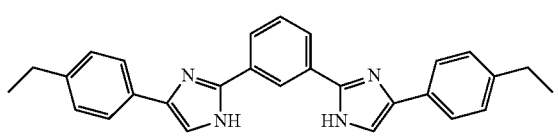
594 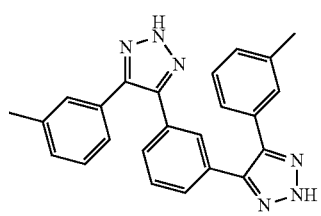
595 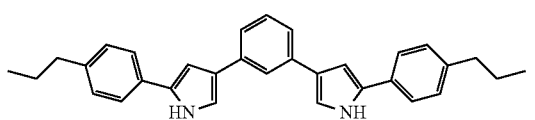
596 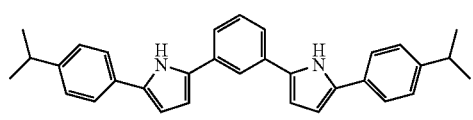
597 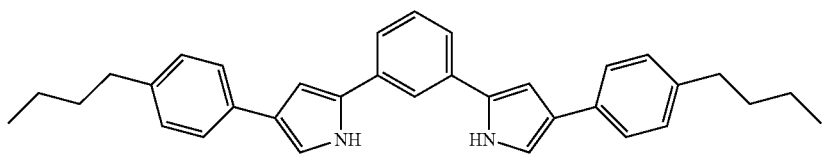
598 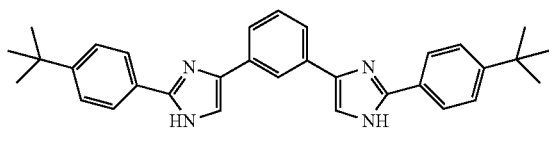
599 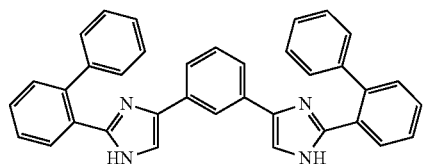
[F78]
600 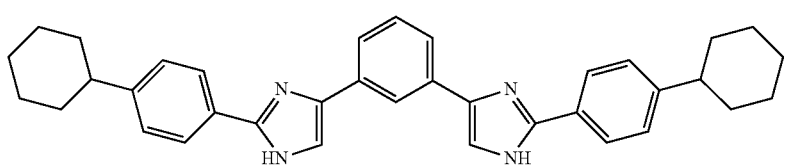

601
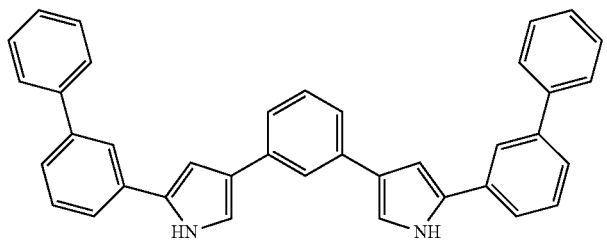
602
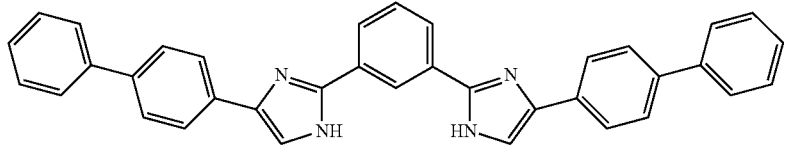
603
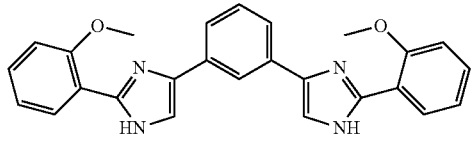
604
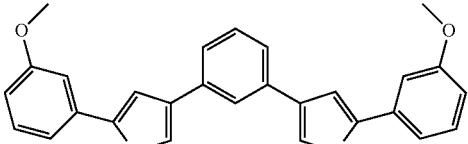
605
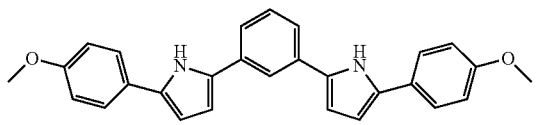
606
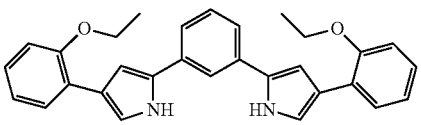
607
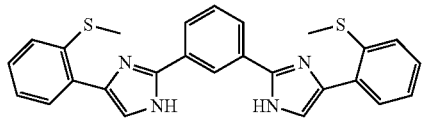
608
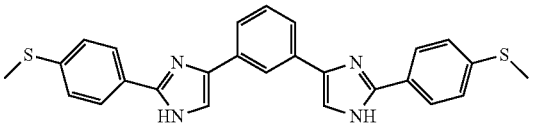
[F79]
609
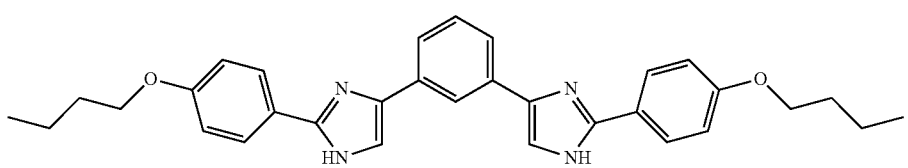
610
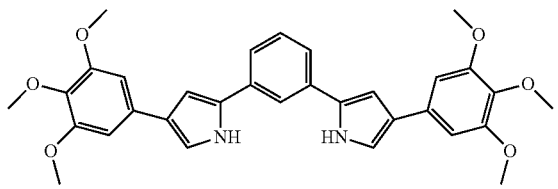
611
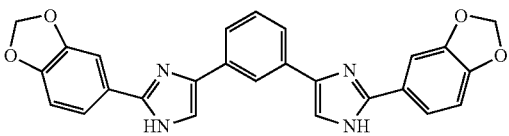
612
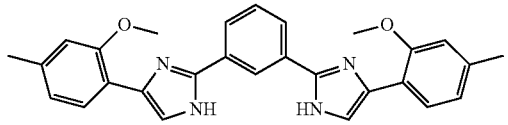
613
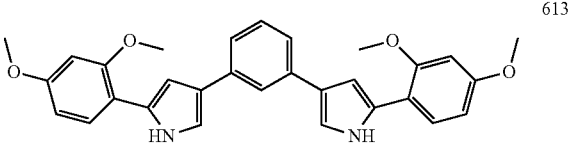
614
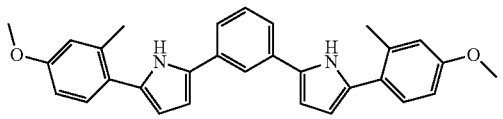
615
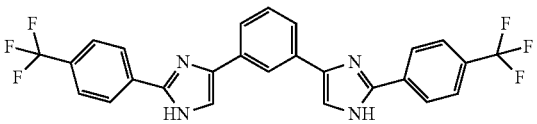

-continued
| 121 | 122 |
|---|---|
| 616 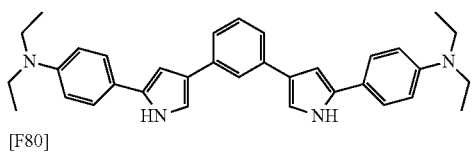 [F80] | 617 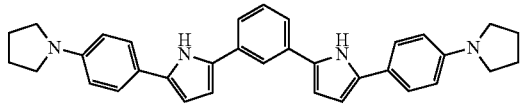 |
| 618 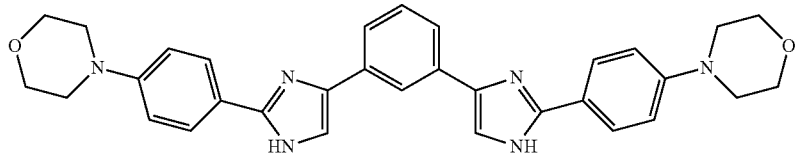 | |
| 619 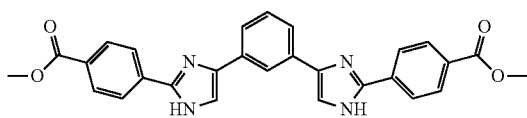 | 620 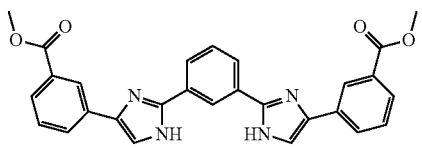 |
| 621 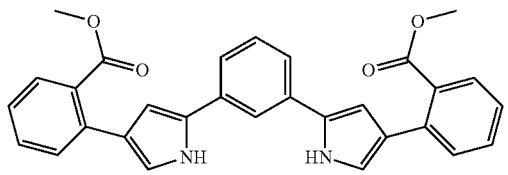 | 622 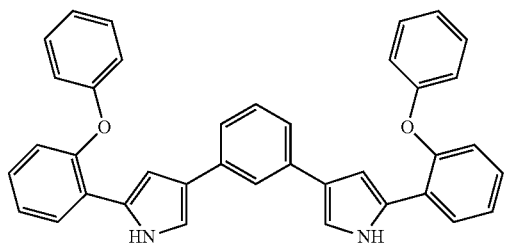 |
| 623 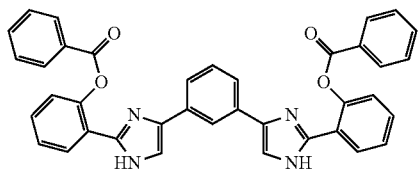 | 624 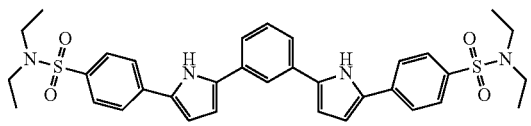 |
| 625 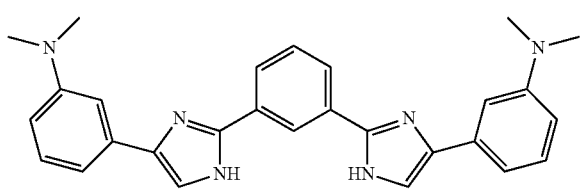 [F81] | |
| 626 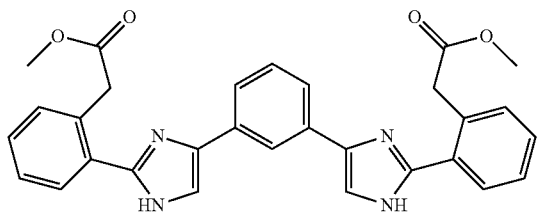 | 627 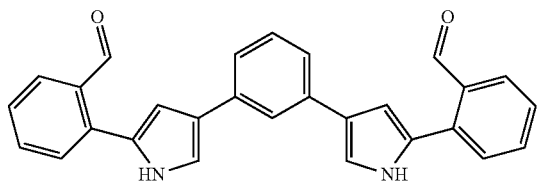 |
| 628 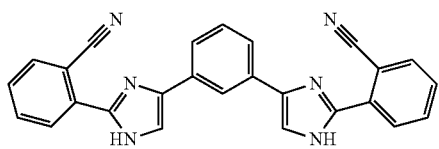 | 629 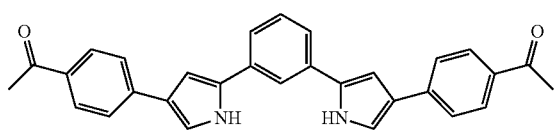 |

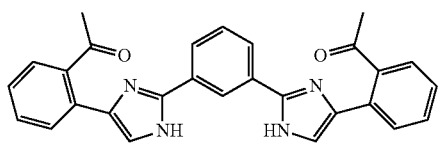
630
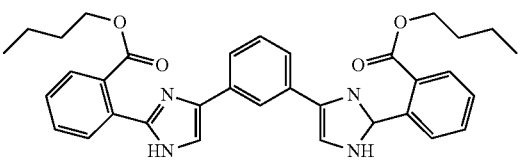
631
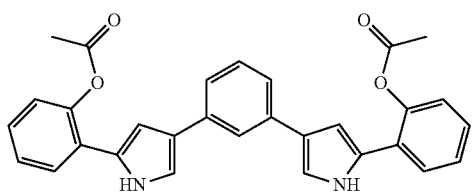
632
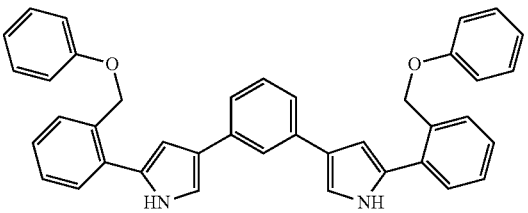
633
[F82]
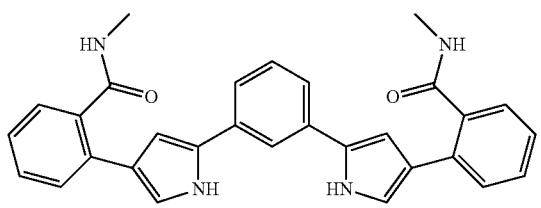
634
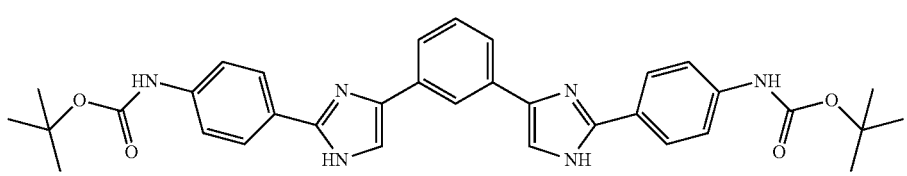
635
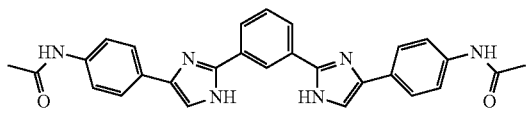
636
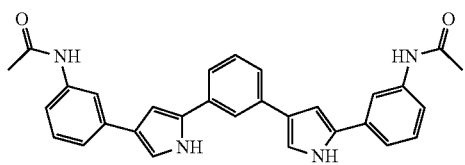
637
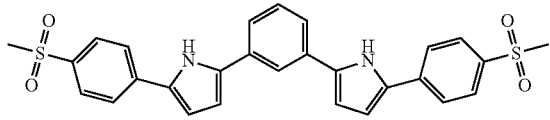
638
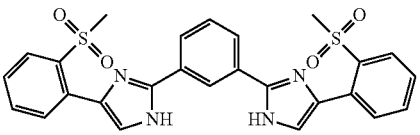
639
[F83]
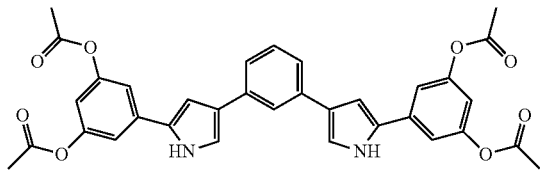
640
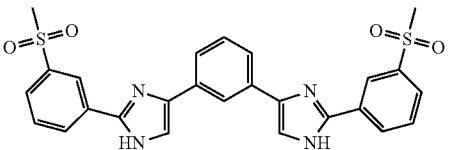
641

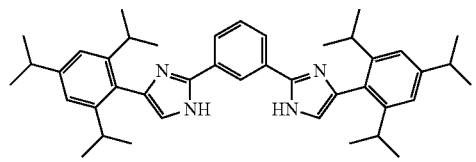
644
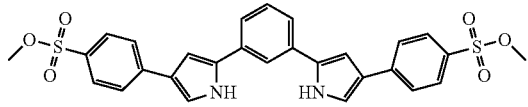
645
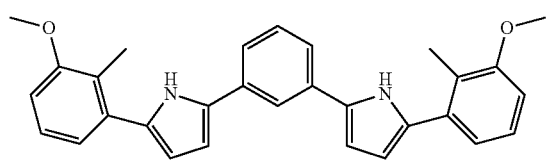
646
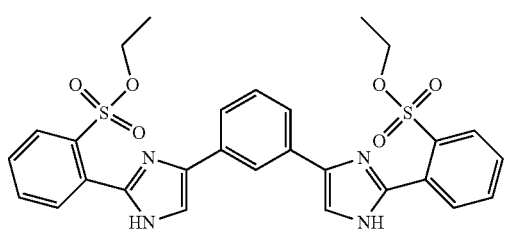
647
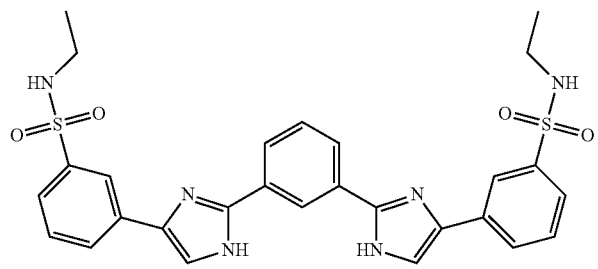
648
[F84]
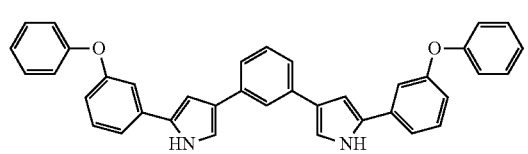
649
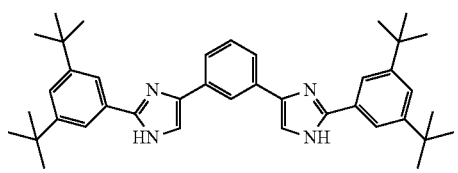
650
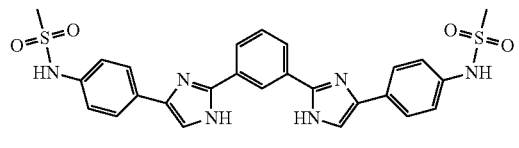
651
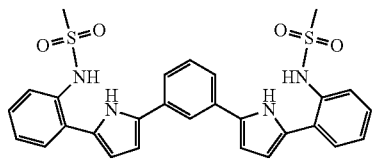
652
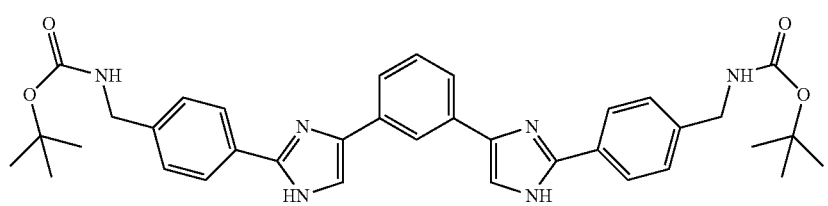
653
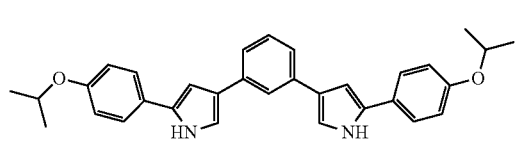
654
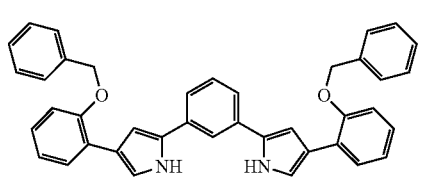
655

[F85]
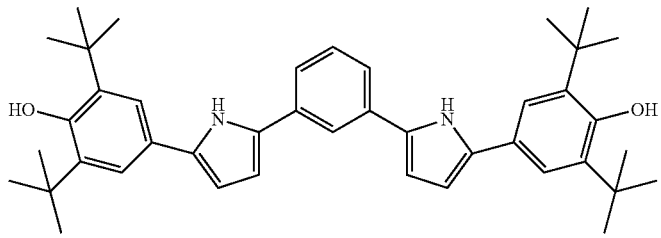
656
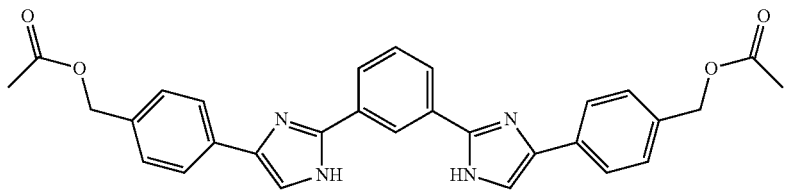
657
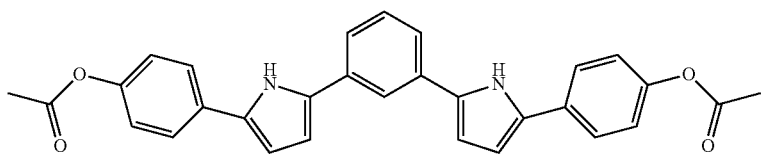
658
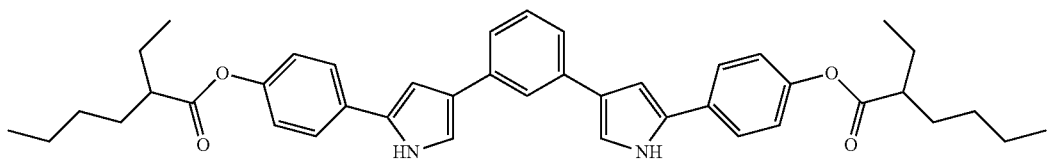
659
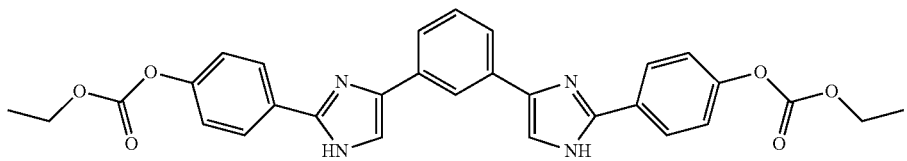
660
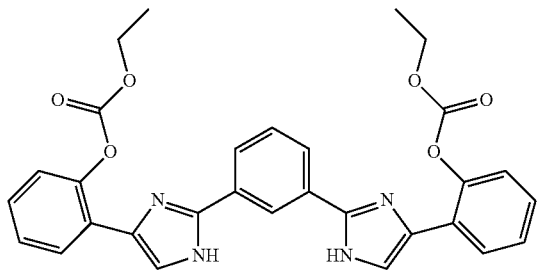
661
[F86]
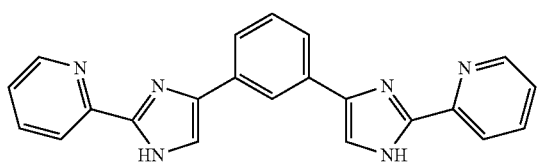
662
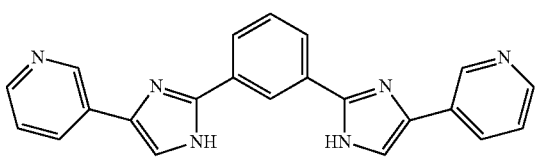
663

664
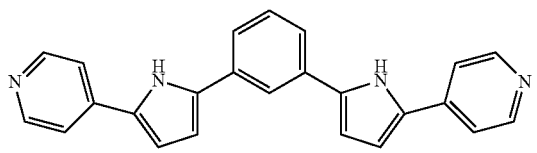
665
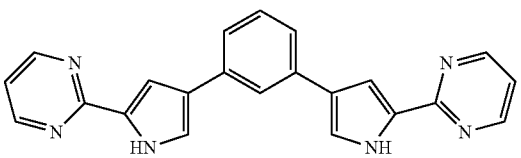
666
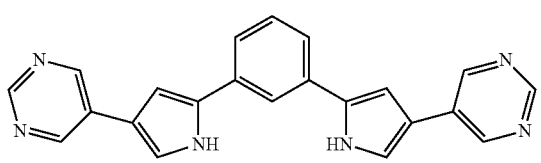
667
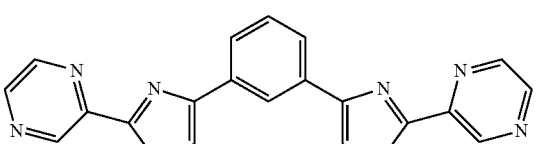
668
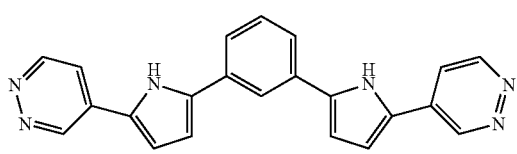
669
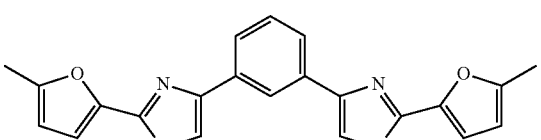
670
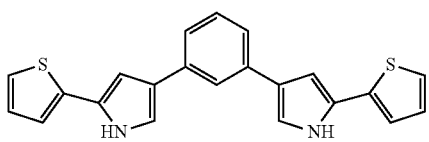
671
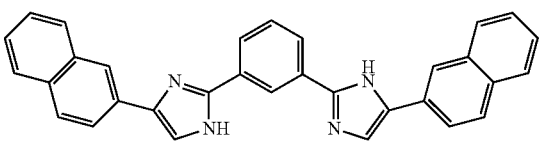
672
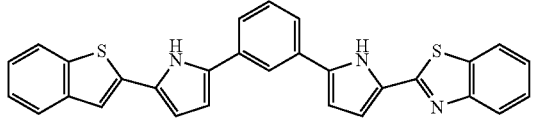
[F87]
673
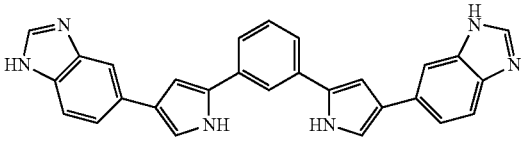
674
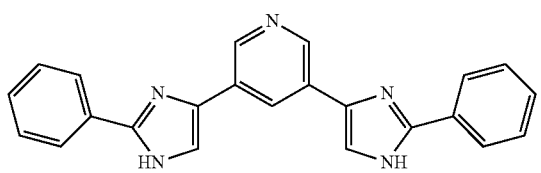
675
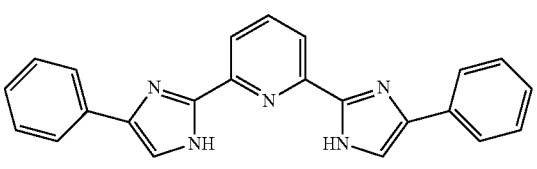
676
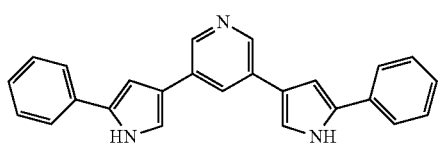
677
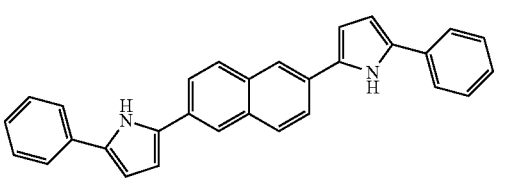
678
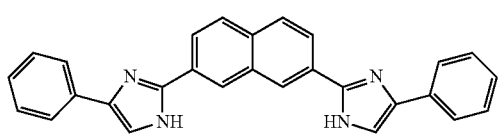
679
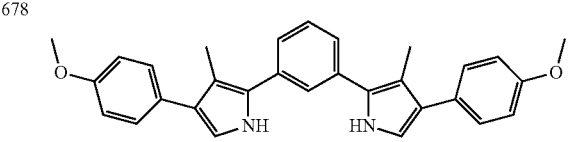

680
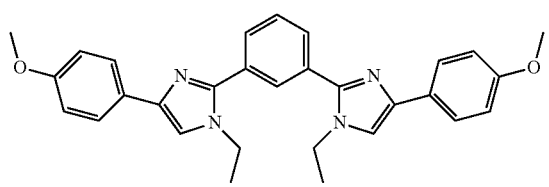
681
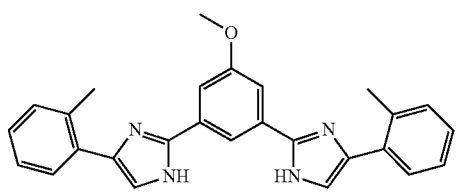
[F88]
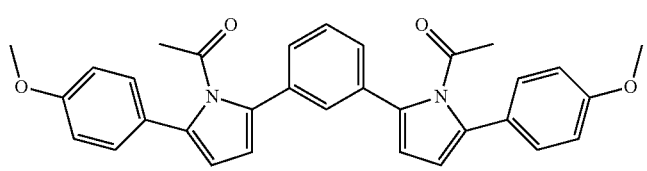
683
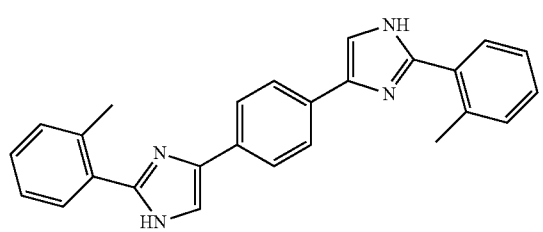
684
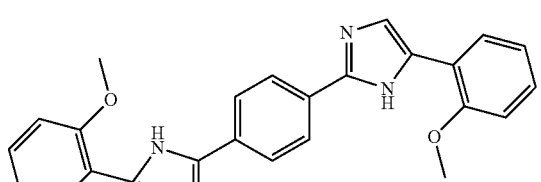
685
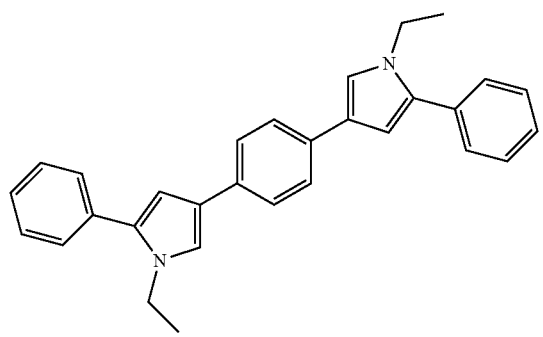
686
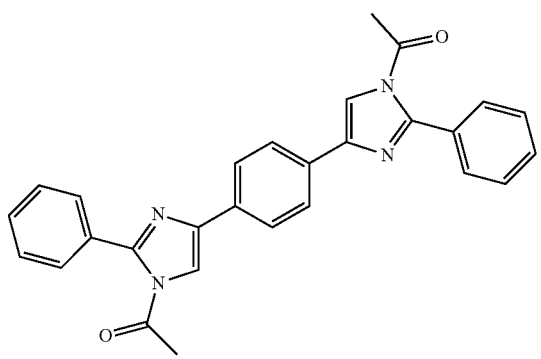
687
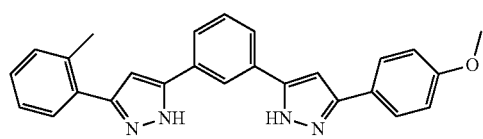
688
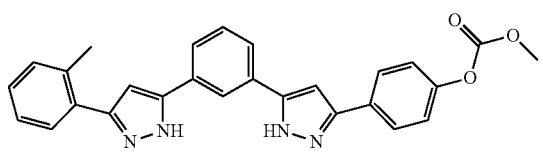
[F89]
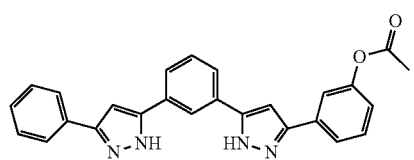
690
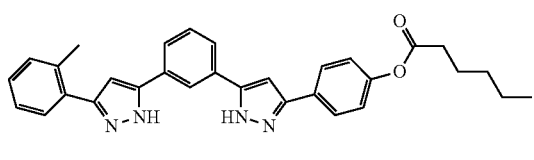
691
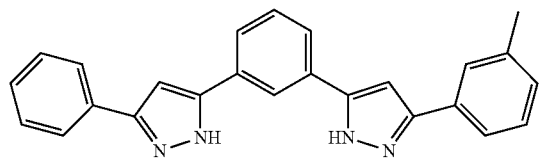
692
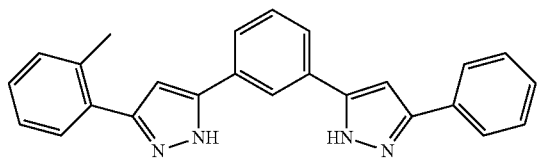

693

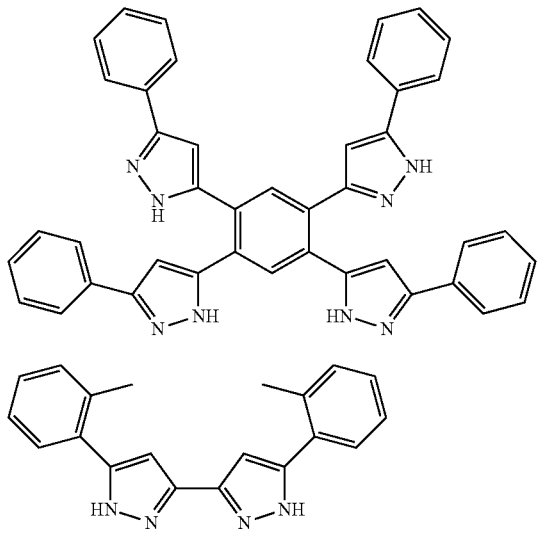

394

695

Now will be described a method for synthesizing the compound represented by Formula (1).

The compound represented by Formula (1) can be synthesized by a process known in the art.

Among compounds represented by Formula (1), a compound having a 1,2,4-triazole ring may be synthesized from any raw material, and is preferably synthesized through reaction between a hydrazide derivative and a nitrile derivative or an iminoether derivative. Any solvent inactive to the raw materials can be used for the reaction. Examples of the solvent include esters (e.g., ethyl acetate and methyl acetate), amides (e.g., dimethylformamide and dimethylacetamide), ethers (e.g., ethylene glycol dimethyl ether), alcohols (e.g., methanol, ethanol, propanol, 2-propanol, n-butanol, 2-butanol, ethylene glycol, and ethylene glycol monomethyl ether), aromatic hydrocarbons (e.g., toluene and xylene), and water. An alcohol solvent is preferably used. These solvents may be used in combination.

The solvent may be used in any amount. The amount is preferably 0.5 to 30 times, more preferably 1.0 to 25 times, particularly preferably 3.0 to 20 times of the hydrazide derivative used by mass.

The reaction between the nitrile derivative and the hydrazide derivative may be performed in the absence of a catalyst. For promotion of the reaction, a catalyst is preferably used. The catalyst may be an acid or a base. Examples of the acid include hydrochloric acid, sulfuric acid, nitric acid, and acetic acid. Hydrochloric acid is preferred. The acid may be added in the form of a dilute aqueous solution or may be fed in a gaseous state into the reaction system. Examples of the usable base include inorganic bases (e.g., potassium carbonate, sodium carbonate, potassium hydrogen carbonate, sodium hydrogen carbonate, potassium hydroxide, and sodium hydroxide) and organic bases (e.g., sodium methylate, sodium ethylate, potassium methylate, potassium ethylate, sodium butyrate, potassium butyrate, diisopropylethylamine, N,N'-dimethylaminopyridine, 1,4-diazabicyclo[2.2.2]octane, N-methylmorpholine, imidazole, N-methylimidazole, and pyridine). The inorganic base is preferably potassium carbonate, and the organic base is preferably sodium ethylate, sodium ethylate, or sodium butyrate. The inorganic base may be added in the form of powder or in the form of a dispersion in a solvent. The organic base may be added in the form of a solution in a solvent (e.g., 28% solution of sodium methylate in methanol).

The catalyst may be used in any amount effective to promote the reaction. The molar ratio of the catalyst to the triazole ring to be formed is preferably 1.0 to 5.0, more preferably 1.05 to 3.0.

The reaction between the iminoether derivative and the hydrazide derivative does not require a catalyst. The target product can be synthesized through heating of the raw materials in a solvent.

The raw materials, solvent, and catalyst used for the reaction may be added in any order. For example, the catalyst or the solvent may be added last. In a preferred process, the nitrile derivative is dispersed or dissolved in the solvent, the catalyst is added to the dispersion or the solution, and the hydrazide derivative is then added to the resultant mixture.

The reaction mixture may be maintained at any temperature effective for the reaction. The temperature is preferably 0 to 150° C., more preferably 20 to 140° C. Water generated during the reaction may be removed during the reaction.

The reaction mixture may be treated by any means. If the catalyst is a base, the reaction mixture is preferably neutralized with an acid. The acid used for neutralization is, for example, hydrochloric acid, sulfuric acid, nitric acid, or acetic acid, and is particularly preferably acetic acid. The acid for neutralization may be used in any amount effective to adjust the pH of the reaction mixture to 4 to 9. The molar ratio of the acid to the base is preferably 0.1 to 3, particularly preferably 0.2 to 1.5.

If the reaction mixture is subjected to extraction with an appropriate organic solvent, the extracted organic phase is preferably washed with water and then concentrated. As used herein, the term "appropriate organic solvent" refers to a water-insoluble solvent, such as ethyl acetate, toluene, dichloromethane, or ether, or a solvent mixture of any of these water-insoluble solvents and tetrahydrofuran or an alcohol solvent. The organic solvent is preferably ethyl acetate.

The compound represented by Formula (1) may be crystallized by any process. In a preferred process, water is added to the neutralized reaction mixture for crystallization, or a solution of the compound represented by Formula (1) in water is neutralized before crystallization.

Exemplary compound 1 can be synthesized through, for example, the following scheme.

(Synthesis of Exemplary Compound 1)

[F90]

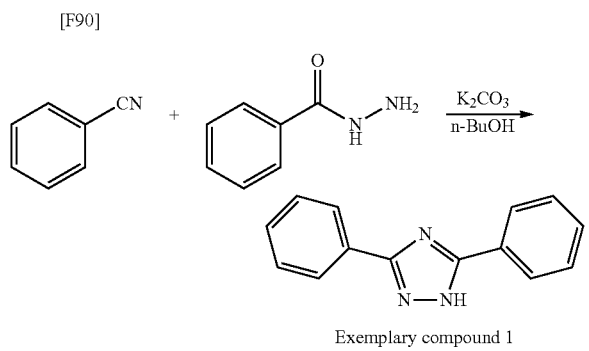

Exemplary compound 1

Benzonitrile (77.3 g, 75.0 mmol), benzoylhydrazine (34.0 g, 25.0 mmol), and potassium carbonate (107.0 g, 77.4 mmol) were added to n-butanol (350 mL), and the mixture was stirred in a nitrogen atmosphere at 120° C. for 24 hours. The reaction mixture was cooled to room temperature, the resultant precipitate was removed through filtration, and the filtrate was concentrated under reduced pressure. 2-Propanol (20 mL) was added to the concentrated product, and the resultant precipitate was recovered through filtration. The precipitate was dissolved in methanol (80 mL), pure water (300 mL) was added to the solution, and acetic acid was added dropwise to the solution, into a pH of 7. The precipitated crystals were collected through filtration and then washed with pure water, followed by blow-drying at 50° C., to produce exemplary compound 1 (38.6 g) at a benzoylhydrazine-based yield of 70%.

$^1$H-NMR spectral data of exemplary compound 1 are as follows:

$^1$H-NMR (400 MHz, solvent: deuterated DMSO, standard: tetramethylsilane) δ (ppm): 7.56-7.48 (6H, m), 7.62-7.61 (4H, m)

(Synthesis of Exemplary Compound 6)

Exemplary compound 6 can be synthesized through the following scheme.

[F91]

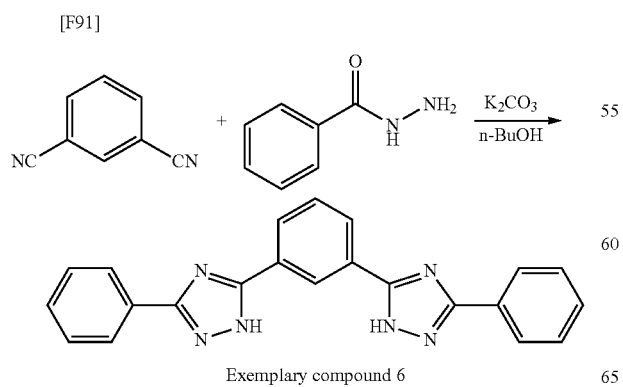

Exemplary compound 6

1,3-Dicyanobenzene (2.5 g, 19.5 mmol), benzoylhydrazine (7.9 g, 58.5 mmol), and potassium carbonate (9.0 g, 68.3 mmol) were added to n-butanol (40 mL), and the mixture was stirred in a nitrogen atmosphere at 120° C. for 24 hours. The reaction mixture was cooled, and pure water (40 mL) was then added to the mixture. The mixture was stirred at room temperature for three hours, and the precipitated solid was filtered out and washed with pure water. Water and ethyl acetate were added to the resultant solid for phase separation, and the organic phase was washed with pure water. The organic phase was dried over magnesium sulfate, and the solvent was removed through evaporation under reduced pressure. The resultant crude crystals were purified by silica gel chromatography (ethyl acetate/heptane), to produce exemplary compound 6 (5.5 g) at a 1,3-dicyanobenzene-based yield of 77%.

$^1$H-NMR spectral data of exemplary compound 6 are as follows:

$^1$H-NMR (400 MHz, solvent: deuterated DMSO, standard: tetramethylsilane) δ (ppm): 8.83 (1H, s), 8.16-8.11 (6H, m), 7.67-7.54 (7H, m)

(Synthesis of Exemplary Compound 176)

Exemplary compound 176 can be synthesized through the following scheme.

[F92]

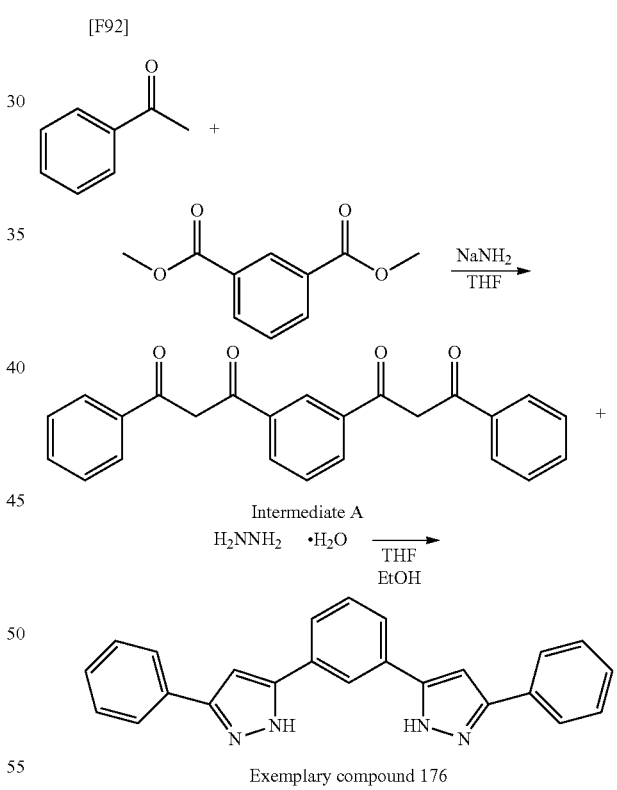

Exemplary compound 176

Acetophenone (80 g, 0.67 mol) and dimethyl isophthalate (52 g, 0.27 mol) were added to dehydrated tetrahydrofuran (520 mL), and sodium amide (52.3 g. 1.34 mol) was added dropwise to the mixture in a nitrogen atmosphere under stirring and cooling with ice water. The resultant mixture was stirred for three hours under cooling with ice water, and then stirred for 12 hours under cooling with water. The reaction mixture was neutralized with concentrated sulfuric acid, and pure water and ethyl acetate were then added to the mixture for phase separation. The organic phase was washed with pure water and dried over magnesium sulfate, and the solvent was removed through evaporation under reduced pressure. The resultant crude crystals were washed by suspending in methanol, to produce intermediate A (55.2 g).

Intermediate A (55 g, 0.15 mol) was added to tetrahydrofuran (300 mL) and ethanol (200 mL), and hydrazine monohydrate (18.6 g, 0.37 mol) was added dropwise to the mixture under stirring at room temperature. After completion of the dropwise addition, the resultant mixture was refluxed under heating for 12 hours. Water and ethyl acetate were added to the reaction mixture for phase separation. The organic phase was washed with pure water and dried over magnesium sulfate, and the solvent was removed through evaporation under reduced pressure. The resultant crude crystals were purified by silica gel chromatography (ethyl acetate/heptane), to produce exemplary compound 176 (27 g).

$^1$H-NMR spectral data of exemplary compound 176 are described below. NMR spectrometry was performed through addition of a few drops of trifluoroacetic acid to a measuring solvent for preventing complication of chemical shifts due to the presence of a tautomer.

$^1$H-NMR (400 MHz, solvent: deuterated DMSO, standard: tetramethylsilane) δ (ppm): 8.34 (1H, s), 7.87-7.81 (6H, m), 7.55-7.51 (1H, m), 7.48-7.44 (4H, m), 7.36-7.33 (2H, m), 7.29 (1H, s)

Other exemplary compounds can be synthesized by a similar process.

<Use of Compound Represented by Formula (1)>

The compound according to the present invention represented by Formula (1) can be incorporated in an appropriate amount into an optical film. The amount of the compound is preferably 1 to 15 mass %, particularly preferably 2 to 10 mass %, relative to the resin (e.g., cellulose ester) forming the optical film. Compounds having a structure represented by Formula (1) may be used alone or in combination. Incorporation of the compound in an amount falling within the aforementioned range can reduce variations in optical values in association with a change in environmental humidity without impairing the mechanical strength of the optical film of the present invention.

The compound represented by Formula (1) may be added in the form of powder to the resin forming the optical film, or may be dissolved in a solvent before being added to the resin.

The present invention provides a universal technique for maintaining stable optical properties of a resin composition during long-term storage or treatment with water. The technique involves application, to a hygroscopic resin, of a plurality of a CH/π interaction sites, which has not yet been used as a means for achieving coexistence of the resin and an additive. The present invention is based on a technical concept quite different from techniques incidentally described in published literature (including patent literature) for using a hygroscopic resin and an aromatic compound in combination. Thus, the present invention, which has been accomplished on the basis of a novel technical concept, should be regarded as an advanced and universal technique which will further develop in the future.

Now will be described the difference between the technical concept of the present invention and that described in published literature (including patent literature) in usage form of a hygroscopic resin and an aromatic compound.

Japanese Unexamined Patent Application Publication No. 2012-215817 (PTL 4) discloses a technique for reducing a humidity-dependent variation in retardation of a cellulose acylate film by incorporation, into the film, of a highly hygroscopic compound exhibiting a difference between moisture contents determined under different conditions of 2% or more in an amorphous state. PTL 4 describes a technical concept on preferential coordination of the highly hygroscopic compound, which has a triazine structure, to water molecules in the cellulose acylate film in a high-humidity environment, and inhibited coordination of water molecules to carbonyl groups of the cellulose acylate, resulting in reduction of a humidity-dependent variation in retardation.

Unfortunately, PTL 4 does not suggest a CH/π interaction, which is a technical concept of the present invention. In addition, the triazine structure, which has an NICS value larger than that of a benzene ring, has low aromaticity and fails to provide a satisfactory CH/π interaction between the triazine structure and the resin. Thus, the technique disclosed in PTL 4 cannot prevent intrusion of water molecules between a hygroscopic resin and an additive, resulting in failure to achieve the advantageous effects of the present invention.

Japanese Unexamined Patent Application Publication No. 2004-243628 (PTL 5) discloses a technique for reducing bleeding-out of a retardation enhancer contained in a cellulose ester. PTL 5 describes a technical concept that bleeding-out of a retardation enhancer is reduced under control of a process of casting a cellulose ester solution containing a triazine compound as the retardation enhancer, and an early stage of a drying process before removal of a film prepared from the cellulose ester solution. PTL 5 also discloses that a triazine compound having a pyrazole structure as a substituent is used in the technique.

Unfortunately, similar to the case of PTL 4, PTL 5 does not suggest a CH/π interaction, which is a technical concept of the present invention. In addition, the triazine structure with a large NICS value has low aromaticity and fails to provide a satisfactory CH/π interaction with the resin. Thus, the technique disclosed in PTL 5 cannot prevent intrusion of water molecules between a hygroscopic resin and an additive, resulting in failure to achieve the advantageous effects of the present invention.

Japanese Unexamined Patent Application Publication No. 2000-111914 (PTL 6) discloses a retardation enhancer for a film of a lower fatty acid ester of cellulose, the retardation enhancer having at least two aromatic rings. PTL 6 describes a technical concept that retardation is increased by a molecular conformation of at least two aromatic rings aligned on the same plane to avoid steric hindrance.

Unfortunately, PTL 6 mentions neither an interaction between the lower fatty acid ester of cellulose and the retardation enhancer, nor a CH/π interaction, which is a technical concept of the present invention. Also, PTL 6 does not state a variation in optical performance of a film of the lower fatty acid ester of cellulose through thermal treatment under humidification. PTL 6 describes a pyrazole compound having a phenyl group on the nitrogen atom at position 1 of the pyrazole ring. In the most stable conformation of this compound, as described below, the benzene ring (b) at position 1 is twisted by about 45° relative to the pyrazole ring (a), and the benzene ring (d) at position 5 is also twisted by about 45° relative to the pyrazole ring (a). Although the rings a and b can form CH/π interaction sites in parallel between the compound and the resin, the rings c and d, which are twisted by about 45° relative to the pyrazole ring, cannot form CH/π interaction sites between the compound and the ring in parallel with the rings a and b. Thus, the technique disclosed in PTL 6 cannot provide a CH/π interaction sufficient for preventing intrusion of water molecules between a hydroscopic resin and an additive; i.e., the technique cannot achieve the advantageous effects of the present invention.

PTL 6 also describes a compound having an aromatic ring of 10-π-electron system, such as benzoxazole or benzotriazole. As described above, the π/π interaction between molecules of such a compound is more dominant than the CH/π interaction between the compound and a resin, resulting in failure to provide a CH/π interaction sufficient for preventing intrusion of water molecules between a hydroscopic resin and an additive.

[F93]

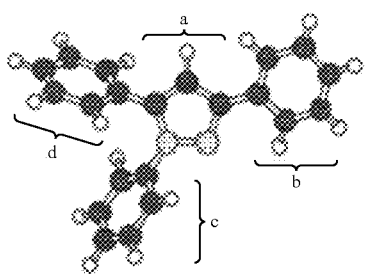

Japanese Unexamined Patent Application Publication No. 2000-275435 (PTL 7) discloses an additive enhancing the wavelength dispersion of retardation of an optically anisotropic film. PTL 7 states that the additive preferably has an absorption peak within a range of 250 nm to 400 nm. PTL 7 also describes a compound having an oxadiazole ring (i.e., an aromatic heterocyclic ring) in Examples.

Japanese Unexamined Patent Application Publication No. 2007-23124 (PTL 8) discloses a technique for reducing the retardation of a film across the thickness of the film while maintaining the in-plane retardation of the film at a specific level. The technique involves use of a composition containing a cellulose compound and a compound having at least two sites at which an aromatic heterocyclic group is bonded to an aromatic hydrocarbon group via a single bond. PTL 8 describes preferred 5-membered or 6-membered aromatic heterocyclic compounds, such as oxadiazole, isoxadiazole, thiadiazole, and isothiadiazole. PTL 8 also describes a compound having two isoxadiazole rings bonded via a phenylene group in Examples.

Unfortunately, PTLs 7 and 8 mention neither an interaction between a resin and an additive, nor a CH/π interaction, which is a technical concept of the present invention. The objects and advantageous effects disclosed in these PTLs are quite different from those of the present invention. Even if the techniques described in these PTLs incidentally involve use of a compound having a plurality of 5-membered aromatic heterocyclic rings or 6-membered aromatic rings, the techniques should be distinguished from the present invention so long as the techniques are not specifically intended to use such a compound for achieving a strong CH/π interaction between a hydroscopic resin and an additive, thereby preventing intrusion of water molecules between the resin and the additive. Despite extensive searches, the present inventors was not able to find disclosure on the technical concept of the present invention in these PTLs. PTLs 7 and 8 describe a compound having an oxadiazole or isoxadiazole ring (i.e., a 5-membered aromatic heterocyclic ring) in Examples. According to the aforementioned literature B, the oxadiazole ring has an NICS value of −10.74 and the isoxadiazole ring has an NICS value of −11.51. These NICS values are more positive than those of the pyrrole ring (−14.86), the imidazole ring (−13.85), and the 1,2,4-triazole ring (−13.66), each of which is a 5-membered aromatic heterocyclic ring containing no oxygen atom. Thus, the techniques disclosed in PTLs 7 and 8 do not utilize a CH/π interaction, and are quite different from the technical concept of the present invention.

As shown in the following reaction schemes, an oxadiazole ring, an isoxadiazole ring, a thiadiazole ring, or an isothiadiazole ring, which has an unstable ring structure, may react with a hydroxy group (—OH) or an amino group (—NH₂) contained in many hygroscopic resins, or may be hydrolyzed with water molecules. The following reactions are described in Chem. Ber., 1892, 25, 1585, J. Org. Chem., 2005, 70, 2322-2324, and Tetrahedron, 2012, 68, 4814-4819.

[F94]

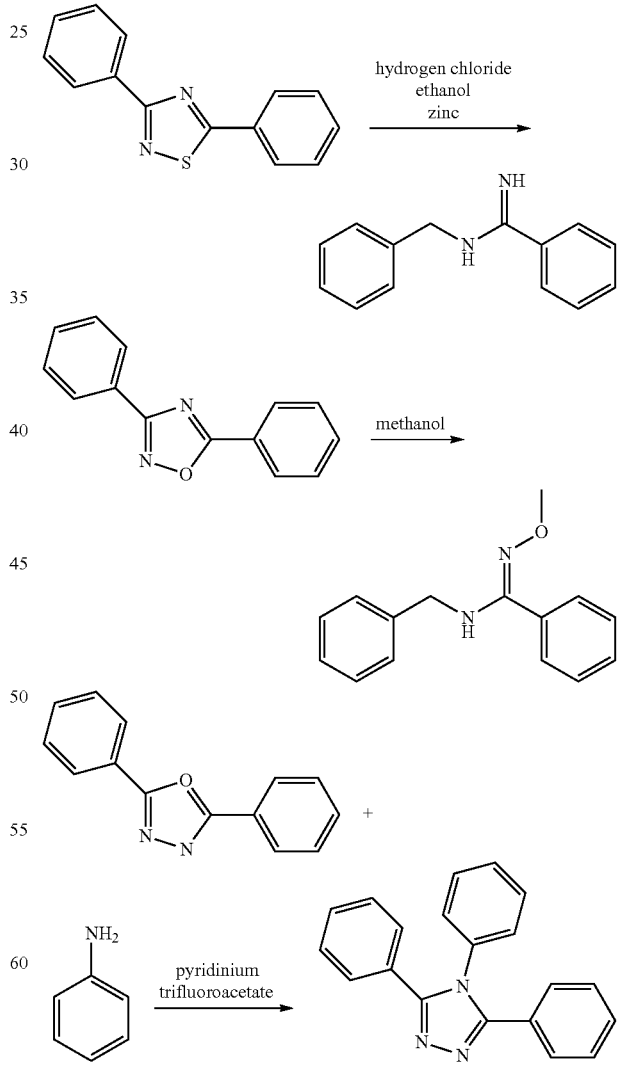

Compounds described in PTLs 7 and 8 have a structure which is likely to cause any reaction or degradation in coexistence with a hygroscopic resin. Thus, these compounds are not suitable for use in optical applications requiring durability, and are less effective for reductions of variations in optical properties, which is an object of the present invention.

<Hygroscopic Resin>

The resin composition of the present invention contains a hygroscopic resin.

The hygroscopic resin may absorb water in association with a change in environmental humidity over time, leading to variations in dimensions and properties, including mechanical properties, such as rigidity and strength, electrical properties, such as resistivity, and optical properties, such as refractive index.

Examples of the hygroscopic resin include acrylic resins (e.g., poly(methyl methacrylate)), polyesters (e.g., poly(ethylene terephthalate)), polyamides (e.g., nylon), polycarbonates, cellophane, cellulose derivatives (e.g., cellulose acetate and ethyl cellulose), poly(vinyl alcohol), poly(vinyl acetate), poly(vinyl formal), poly(vinyl acetal), poly(vinyl formal), polyimides, urea resins, phenolic resins, and melamine resins.

The hygroscopic resin used in the present invention exhibits a water absorption of 0.1% or more. Incorporation of the additive of the present invention into the hygroscopic resin can stabilize optical properties. A significantly high water absorption precludes stable optical properties. Thus, the water absorption is more preferably 0.5 to 10%.

In the present invention, the hygroscopic resin is preferably a cellulose derivative because of its high stabilization effect in optical properties. The hygroscopic resin is particularly preferably a cellulose ester having an acyl group.

As used herein, the term "water absorption" refers to a percent increase in weight of the hygroscopic resin through immersion thereof in water at 23° C. for 24 hours.

In the present invention, the water absorption is specifically determined as described below.

A film prepared from the hygroscopic resin is left in a chamber at 23° C. and 55% RH for four hours or longer, and the weight (W1) of the film is then measured. Subsequently, the film is immersed in distilled water at 23° C. for 24 hours, and the weight (W2) of the film taken out from the water is then measured. The water absorption is determined by the following expression.

Water absorption (%)={(W2−W1)÷W1}×100

The resin composition of the present invention contains the resin and the additive N. The resin may be used as a base material for an optical film or used in an optical lens.

<Optical Film>

Now will be described the optical film of the present invention in detail, as well as the resin contained in the resin composition.

As used herein, the term "optical film" refers to a functional film used in various display devices, such as liquid crystal displays, plasma displays, and organic EL displays. Specific examples of the optical film include protective films for a polarizing plate, retardation films, antireflective films, luminance improving films, hard coat films, antiglare films, antistatic films, and optical compensation films for widening a viewing angle.

The resin contained in the resin composition preferably has a polar group. It is inferred that a strong interaction is established between the polar group of the resin, water, and a 5-membered or 6-membered aromatic hydrocarbon or heterocyclic ring, and the molecular orientation of the resin is maintained even under a change in content of water molecules in the optical film, resulting in a slight or no variation in retardation value.

The polar group may be any organic group polarized by an atom having a high electronegativity, such as oxygen, nitrogen, sulfur, or a halogen. Examples of the resin having a polar group include resins having a hydroxy group, a carbonyl group, a urethane group, an isocyanurate group, a urea group, a carbonate group, an amido group, an ester group, a carboxyl group, an acid anhydride group, an ether group, an epoxy group, an imino group, or an amino group. The resin used in the present invention is preferably a cellulose derivative, such as a cellulose ester resin or a cellulose ether resin.

The cellulose derivative may be used in combination with any of the aforementioned resins. The resin used in combination is preferably a polycarbonate resin, an acrylic resin, or a cyclic olefin resin. If a resin other than the cellulose derivative is used in combination, the amount of the resin is preferably 0 to 50 mass %.

(Cellulose Derivative)

The cellulose derivative is a compound derived from cellulose (i.e., a compound having a cellulose skeleton). Examples of the cellulose derivative include cellulose ethers (e.g., methyl cellulose, ethyl cellulose, hydroxyethyl cellulose, hydroxypropyl cellulose, and cyanoethyl cellulose), cellulose esters (detailed below), cellulose ether esters (e.g., acetyl methyl cellulose, acetyl ethyl cellulose, acetyl hydroxyethyl cellulose, and benzoyl hydroxypropyl cellulose), cellulose carbonates (e.g., cellulose ethylcarbonate), and cellulose carbamates (e.g., cellulose phenylcarbamate). Preferred is a cellulose ester. These cellulose derivatives may be used alone or in combination.

The cellulose ester is a compound prepared through esterification between cellulose and at least one of an aliphatic carboxylic acid having about 2 to 22 carbon atoms and an aromatic carboxylic acid, preferably a compound prepared through esterification between cellulose and a lower fatty acid having six or less carbon atoms.

The acyl group contained in the cellulose ester may be linear or branched, or may form a ring. The acyl group may have a substituent. The acyl group preferably has two to six carbon atoms, more preferably two to four carbon atoms, still more preferably two or three carbon atoms.

Specific examples of the cellulose ester include cellulose acetate, and mixed fatty acid esters of cellulose, such as cellulose acetate propionate, cellulose acetate butyrate, cellulose acetate propionate butyrate, and cellulose acetate phthalate. Preferred are cellulose acetate, cellulose acetate butyrate, and cellulose acetate propionate. The butyryl group contained in the cellulose ester may be linear or branched.

The cellulose ester may have a degree of acylation of about 1.0 to 3.0. The degree of acylation is preferably 2.0 to 2.95 for reducing moisture permeability.

The degree of acylation of the cellulose ester can be determined in accordance with ASTM D817-96.

The cellulose derivative preferably has a number average molecular weight of $6 \times 10^4$ to $3 \times 10^5$, more preferably $7 \times 10^4$ to $2 \times 10^5$, for enhancing the mechanical strength of the resultant film.

The weight average molecular weight (Mw) and the number average molecular weight (Mn) of the cellulose derivative are determined by gel permeation chromatography (GPC). Conditions for measurement are as follows:

Solvent: methylene chloride

Columns: Shodex K806, K805, and K803G (manufactured by Showa Denko K.K., the three columns are connected)

Column temperature: 25° C.
Concentration of sample: 0.1 mass %
Detector: RI Model 504 (manufactured by GL Sciences Inc.)
Pump: L6000 (manufactured by Hitachi, Ltd.)
Flow rate: 1.0 mL/min
Calibration curve: a calibration curve prepared from 13 samples of standard polystyrene STK (manufactured by Tosoh Corporation, Mw: 500 to 1,000,000) is used. The 13 samples are eluted at substantially equal intervals.

The cellulose derivative preferably has a residual sulfuric acid content of 0.1 to 45 mass ppm, more preferably 1 to 30 mass ppm in terms of elemental sulfur. Sulfuric acid would probably remain in the form of salt in the optical film. A residual sulfuric acid content exceeding 45 mass ppm may lead to breakage of the film during thermal stretching or during slitting after thermal stretching. The residual sulfuric acid content can be determined in accordance with ASTM D817-96.

The cellulose derivative preferably has a free acid content of 1 to 500 mass ppm, more preferably 1 to 100 mass ppm, still more preferably 1 to 70 mass ppm. A free acid content falling within the aforementioned range may prevent the film from breaking during thermal stretching or during slitting after thermal stretching. The free acid content can be determined in accordance with ASTM D817-96.

The cellulose derivative may contain a trace amount of a metal component. The trace metal component would probably be derived from water used for synthesis of the cellulose derivative. A minimum possible level of the metal component which may serve as a nucleus of insoluble matter is preferred. In particular, a metal ion, such as iron, calcium, or magnesium ion, may form insoluble matter in the form of salt with a resin decomposed product having an organic acid group. A calcium (Ca) component may form a coordination compound (i.e., complex) with an acid component, such as a carboxylic acid or a sulfonic acid, or with various ligands, to generate a large amount of insoluble scum (insoluble dregs causing turbidity).

Thus, the cellulose derivative preferably has an iron (Fe) content of 1 mass ppm or less. The cellulose derivative preferably has a calcium (Ca) content of 60 mass ppm or less, more preferably 0 to 30 mass ppm. The cellulose derivative preferably has a magnesium (Mg) content of 0 to 70 mass ppm, particularly preferably 0 to 20 mass ppm.

The metal content, such as an iron (Fe), calcium (Ca), or magnesium (Mg) content, can be determined with an inductively coupled plasma-atomic emission spectrometer (ICP-AES) after pretreatment of the absolutely dried cellulose derivative by micro-digest wet decomposition (decomposition with sulfuric acid and nitric acid) and alkali fusion.

The residual alkaline earth metal, residual sulfuric acid, or residual acid content of the synthesized cellulose derivative can be adjusted by thorough washing of the derivative.

The cellulose derivative can be prepared by any process known in the art. Specifically, the cellulose derivative can be synthesized with reference to the method described in Japanese Unexamined Patent Application Publication No. H10-45804. Examples of the cellulose serving as a raw material for the cellulose derivative include, but are not limited to, those derived from cotton linters, wood pulp, and kenaf. Cellulose derivatives prepared from different raw materials may be used in combination.

((Meth)acrylic Resin)

The (meth)acrylic resin used in the present invention may be a homopolymer of a (meth)acrylic acid ester or a copolymer of a (meth)acrylic acid ester and another monomer. (Meth)acrylic resins may be used alone or in combination. The (meth)acrylic acid ester is preferably methyl methacrylate. The copolymer contains a structural unit derived from methyl methacrylate in an amount of preferably 50 mass % or more, more preferably 70 mass % or more.

Examples of the monomer forming the copolymer with methyl methacrylate include alkyl methacrylates containing an alkyl group having 2 to 18 carbon atoms; alkyl acrylates containing an alkyl group having 1 to 18 carbon atoms; alkyl (meth)acrylates having a hydroxy group capable of forming a lactone ring structure described below, and containing an alkyl group having 1 to 18 carbon atoms; α,β-unsaturated acids, such as acrylic acid and methacrylic acid; dicarboxylic acids containing an unsaturated group, such as maleic acid, fumaric acid, and itaconic acid; aromatic vinyl compounds, such as styrene and α-methylstyrene; α,β-unsaturated nitriles, such as acrylonitrile and methacrylonitrile; maleic anhydride; maleimide; N-substituted maleimide; glutaric anhydride; acrylamide derivatives, such as acryloylmorpholine (ACMO); and N-vinylpyrrolidone (VP). These monomers may be used alone or in combination.

Of these, preferred are alkyl acrylates, such as methyl acrylate, ethyl acrylate, n-propyl acrylate, n-butyl acrylate, s-butyl acrylate, and 2-ethylhexyl acrylate, and alkyl (meth)acrylates having a hydroxy group, such as methyl 2-(hydroxymethyl)acrylate and ethyl 2-(hydroxymethyl)acrylate, for enhancing the thermal decomposition resistance and fluidity of the copolymer. Acryloylmorpholine is preferably used for enhancing compatibility of the copolymer with the cellulose ester.

The (meth)acrylic resin preferably has a lactone ring structure for enhancing the heat resistance of the resultant optical film or controlling the photoelastic coefficient of the film. The (meth)acrylic resin preferably has a lactone ring structure represented by Formula (3).

[F95]

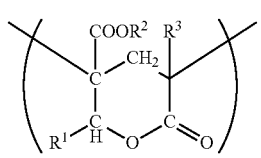

Formula(3)

In Formula (3), $R^1$ to $R^3$ each independently represent a hydrogen atom or an organic residue having 1 to 20 carbon atoms. The organic residue may contain an oxygen atom. Examples of the organic residue include linear or branched alkyl groups, linear or branched alkylene groups, aromatic hydrocarbon groups, —OAc (Ac represents an acetyl group), and —CN.

As described below, the lactone ring structure represented by Formula (3) is derived from an alkyl (meth)acrylate having a hydroxy group.

The (meth)acrylic resin having a lactone ring structure may further have a structural unit derived from an alkyl (meth)acrylate containing an alkyl group having 1 to 18 carbon atoms, and may optionally have a structural unit derived from a monomer having a hydroxy group, an unsaturated carboxylic acid, or a monomer represented by Formula (4).

[F96]

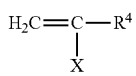

Formula(4)

In Formula (4), $R^4$ represents a hydrogen atom or a methyl group, and X represents a hydrogen atom, an alkyl group having 1 to 20 carbon atoms, an aromatic hydrocarbon group, —OAc (Ac represents an acetyl group), —CN, an acyl group, or —C—OR (R represents a hydrogen atom or an organic residue having 1 to 20 carbon atoms).

The (meth)acrylic resin has a content of lactone ring structure represented by Formula (1) of preferably 5 to 90 mass %, more preferably 10 to 80 mass %, still more preferably 15 to 70 mass %. A lactone ring structure content of 5 mass % or more may lead to formation of a film exhibiting a required retardation and satisfactory heat resistance, solvent resistance, and surface hardness. A lactone ring structure content of 90 mass % or less may cause improvement in moldability, leading to high flexibility of the resultant film.

The (meth)acrylic resin having a lactone ring structure contains structural units derived from alkyl (meth)acrylate in an amount of preferably 10 to 95 mass %, more preferably 20 to 90 mass %, still more preferably 30 to 85 mass %.

The (meth)acrylic resin having a lactone ring structure contains structural units derived from a hydroxy-group-containing monomer, an unsaturated carboxylic acid, or a monomer represented by Formula (2) in an amount of preferably 0 to 30 mass %, more preferably 0 to 20 mass %, still more preferably 0 to 10 mass %.

The (meth)acrylic resin having a lactone ring structure can be produced through a step of preparing a polymer having a hydroxy group and an ester group in the polymer chain by polymerization of a monomer component containing an alkyl (meth)acrylate having a hydroxy group and another alkyl (meth)acrylate, and a step of forming a lactone ring structure in the polymer by thermal treatment of the polymer.

The (meth)acrylic resin has a weight average molecular weight Mw of preferably $8.0 \times 10^4$ to $5.0 \times 10^5$, more preferably $9.0 \times 10^4$ to $4.5 \times 10^5$, still more preferably $1.0 \times 10^5$ to $4.0 \times 10^5$. A weight average molecular weight Mw of $8.0 \times 10^4$ or more may lead to an improvement in strength of the resultant film, whereas a weight average molecular weight Mw of $5.0 \times 10^5$ or less may lead to a reduction in haze of the film.

The weight average molecular weight Mw of the (meth)acrylic resin can be determined by gel permeation chromatography as in the case of the cellulose ester.

The optical film of the present invention may optionally contain any of various additives described below.
(Sugar Ester)

The optical film of the present invention may contain a sugar ester other than the aforementioned cellulose ester for improving the plasticity of the film.

The sugar ester usable in the present invention is a compound having 1 to 12 furanose or pyranose structures, wherein the hydroxy groups of the compound are partially or entirely esterified.

The sugar ester is preferably, for example, a sucrose ester represented by Formula (FA).

[F97]

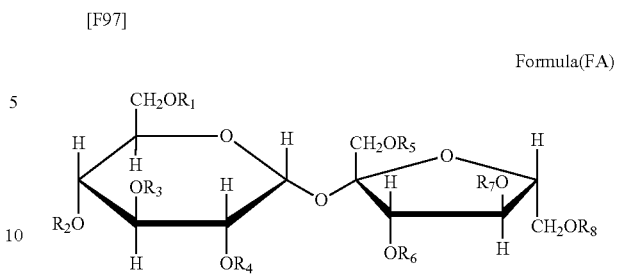

Formula(FA)

In Formula (FA), $R_1$ to $R_8$ each independently represent a hydrogen atom, a substituted or unsubstituted alkylcarbonyl group, or a substituted or unsubstituted arylcarbonyl group. $R_1$ to $R_8$ may be identical to or different from one another.

The substituted or unsubstituted alkylcarbonyl group is preferably a substituted or unsubstituted alkylcarbonyl group having two or more carbon atoms. Examples of the substituted or unsubstituted alkylcarbonyl group include a methylcarbonyl group (acetyl group). Examples of the substituent on the alkyl group include aromatic hydrocarbon groups, such as a phenyl group.

The substituted or unsubstituted arylcarbonyl group is preferably a substituted or unsubstituted arylcarbonyl group having seven or more carbon atoms. Examples of the arylcarbonyl group include a phenylcarbonyl group. Examples of the substituent on the aromatic hydrocarbon group include alkyl groups, such as a methyl group, and alkoxy groups, such as a methoxy group.

The sucrose ester preferably has an average degree of acylation of 3.0 to 7.5. An average degree of acylation falling within this range may lead to satisfactory compatibility of the sucrose ester with the cellulose ester.

Specific examples of the sucrose ester represented by Formula (FA) include exemplary compounds FA-1 to FA-24 described below. The following table shows $R_1$ to $R_8$ in Formula (FA) representing exemplary compounds FA-1 to FA-24 and average degrees of acylation.

| Compound No. | $R_1$~$R_8$ | Average degree of acylation |
|---|---|---|
| [F98] | | |
| FA-1 | 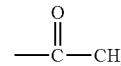 | 3.3 |
| FA-2 |  | 4.2 |
| FA-3 |  | 5.7 |
| FA-4 |  | 6.0 |
| FA-5 |  | 3.5 |
| FA-6 |  | 4.0 |

| Compound No. | $R_1$~$R_8$ | Average degree of acylation |
|---|---|---|
| FA-7 | —C(=O)—C₆H₅ (benzoyl) | 5.5 |
| FA-8 | —C(=O)—C₆H₅ (benzoyl) | 6.0 |
| FA-9 | —C(=O)—C₆H₄—CH₃ (p-toluoyl) | 3.2 |
| FA-10 | —C(=O)—C₆H₄—CH₃ (p-toluoyl) | 4.4 |
| FA-11 | —C(=O)—C₆H₄—CH₃ (p-toluoyl) | 5.5 |
| FA-12 | —C(=O)—C₆H₄—CH₃ (p-toluoyl) | 6.0 |

[F99]

| Compound No. | $R_1$~$R_8$ | Average degree of acylation |
|---|---|---|
| FA-13 | —C(=O)—CH₂—C₆H₅ | 3.0 |
| FA-14 | —C(=O)—CH₂—C₆H₅ | 4.0 |
| FA-15 | —C(=O)—CH₂—C₆H₅ | 5.5 |
| FA-16 | —C(=O)—CH₂—C₆H₅ | 6.0 |
| FA-17 | —C(=O)—C₆H₂(OCH₃)₃ (3,4,5-trimethoxybenzoyl) | 3.1 |
| FA-18 | —C(=O)—C₆H₂(OCH₃)₃ (3,4,5-trimethoxybenzoyl) | 4.7 |
| FA-19 | —C(=O)—C₆H₂(OCH₃)₃ (3,4,5-trimethoxybenzoyl) | 5.3 |
| FA-20 | —C(=O)—C₆H₂(OCH₃)₃ (3,4,5-trimethoxybenzoyl) | 6.0 |

[F100]

| Compound No. | $R_1$~$R_8$ | Average degree of acylation |
|---|---|---|
| FA-21 | —C(=O)—CH(CH₃)—CH₃ (isobutyryl) | 3.5 |
| FA-22 | —C(=O)—CH(CH₃)—CH₃ (isobutyryl) | 4.6 |
| FA-23 | —C(=O)—CH(CH₃)—CH₃ (isobutyryl) | 5.6 |
| FA-24 | —C(=O)—CH(CH₃)—CH₃ (isobutyryl) | 6.0 |

Examples of other sugar esters include compounds described in Japanese Unexamined Patent Application Publication Nos. S62-42996 and H10-237084.

The sugar ester content is preferably 0.5 to 35.0 mass %, more preferably 5.0 to 30.0 mass %, relative to the cellulose ester.

(Plasticizer)

The optical film of the present invention may contain a plasticizer for improving the fluidity of the composition during formation of the film or the flexibility of the film. Examples of the plasticizer include plasticizers of polyesters, polyhydric alcohol esters, polycarboxylic esters (including phthalic esters), glycolates, and other esters (including citric esters, fatty acid esters, phosphate esters, and trimellitic esters). These plasticizers may be used alone or in combination.

The polyester plasticizer is a compound prepared through a reaction between a mono- to tetra-carboxylic acid and a mono- to hexa-hydric alcohol, preferably a compound prepared through a reaction between a dicarboxylic acid and a glycol.

Examples of the dicarboxylic acid include succinic acid, glutaric acid, itaconic acid, adipic acid, phthalic acid, azelaic acid, and sebacic acid. In particular, a compound prepared from a dicarboxylic acid, such as succinic acid, adipic acid, or phthalic acid, enables effective provision of plasticity.

Examples of the glycol include ethylene glycol, propylene glycol, 1,3-butylene glycol, 1,4-butylene glycol, 1,6-hexamethylene glycol, neopentylene glycol, diethylene glycol, triethylene glycol, and dipropylene glycol. Dicarboxylic acids or glycols may be used alone or in combination.

The polyester plasticizer may be in the form of an ester, an oligoester, or a polyester. The polyester plasticizer preferably has a molecular weight of 100 to 10,000. A molecular weight of 600 to 3,000 is more preferred for enhancing a plasticity imparting effect.

The polyester plasticizer has a viscosity depending on its molecular structure or molecular weight. A plasticizer prepared from adipic acid preferably has a viscosity of 200 to 5,000 MPa·s (25° C.) for achieving high compatibility with the cellulose ester and enhancing a plasticity imparting effect. Polyester plasticizers may be used alone or in combination.

The polyhydric alcohol ester plasticizer is an ester compound (alcohol ester) composed of an aliphatic polyhydric alcohol having a valency of 2 or more and a monocarboxylic acid, preferably an aliphatic polyhydric alcohol ester having a valency of 2 to 20. The polyhydric alcohol ester compound preferably has an aromatic ring or a cycloalkyl ring in the molecule.

Examples of the aliphatic polyhydric alcohol include ethylene glycol, propylene glycol, trimethylolpropane, and pentaerythritol.

The monocarboxylic acid may be, for example, an aliphatic monocarboxylic acid, an alicyclic monocarboxylic acid, or an aromatic monocarboxylic acid. Monocarboxylic acids may be used alone or in combination. The OH groups of the aliphatic polyhydric alcohol may be partially or entirely esterified.

The aliphatic monocarboxylic acid is preferably a linear or branched fatty acid having 1 to 32 carbon atoms. The aliphatic monocarboxylic acid more preferably has 1 to 20 carbon atoms, still more preferably 1 to 10 carbon atoms. Examples of the aliphatic monocarboxylic acid include acetic acid, propionic acid, butyric acid, and valeric acid. Acetic acid is preferably used for enhancing compatibility with the cellulose ester.

Examples of the alicyclic monocarboxylic acid include cyclopentanecarboxylic acid, cyclohexanecarboxylic acid, and cyclooctanecarboxylic acid.

Examples of the aromatic monocarboxylic acid include benzoic acid; aromatic monocarboxylic acids prepared through addition of one to three alkyl groups or alkoxy groups (e.g., methoxy group and ethoxy group) to the benzene ring of benzoic acid, such as toluic acid; and aromatic monocarboxylic acids having two or more benzene rings, such as biphenylcarboxylic acid, naphthalenecarboxylic acid, and tetralincarboxylic acid. Preferred is benzoic acid.

The polyhydric alcohol ester plasticizer may have any molecular weight. The molecular weight is preferably 300 to 1,500, more preferably 350 to 750. A larger molecular weight is preferred for reducing volatilization, whereas a smaller molecular weight is preferred for enhancing moisture permeability and achieving high compatibility of the plasticizer with the cellulose ester.

Specific examples of the polyhydric alcohol ester plasticizer include trimethylolpropane triacetate, pentaerythritol tetraacetate, and ester compound (A) represented by Formula (I) described in Japanese Unexamined Patent Application Publication No. 2008-88292.

The polycarboxylic ester plasticizer is an ester compound composed of an alcohol compound and a polycarboxylic acid having a valency of 2 or more, preferably 2 to 20. The polycarboxylic acid is preferably an aliphatic polycarboxylic acid having a valency of 2 to 20, an aromatic polycarboxylic acid having a valency of 3 to 20, or an alicyclic polycarboxylic acid having a valency of 3 to 20.

Examples of the polycarboxylic acid include trivalent or higher-valent aromatic carboxylic acids and derivatives thereof, such as trimellitic acid, trimesic acid, and pyromellitic acid; aliphatic polycarboxylic acids, such as succinic acid, adipic acid, azelaic acid, sebacic acid, oxalic acid, fumaric acid, maleic acid, and tetrahydrophthalic acid; and polyvalent oxycarboxylic acids, such as tartaric acid, tartronic acid, malic acid, and citric acid. Polyvalent oxycarboxylic acids are preferably used, which exhibit reduced volatilization of the plasticizer from the film.

Examples of the alcohol compound include linear or branched saturated aliphatic alcohol compounds, linear or branched unsaturated aliphatic alcohol compounds, alicyclic alcohol compounds, and aromatic alcohol compounds. The saturated aliphatic alcohol compound or the unsaturated aliphatic alcohol compound preferably has 1 to 32 carbon atoms, more preferably 1 to 20 carbon atoms, still more preferably 1 to 10 carbon atoms. Examples of the alicyclic alcohol compound include cyclopentanol and cyclohexanol. Examples of the aromatic alcohol compound include phenol, p-cresol, dimethylphenol, benzyl alcohol, and cinnamyl alcohol. Alcohol compounds may be used alone or in combination.

The polycarboxylic ester plasticizer may have any molecular weight. The molecular weight is preferably 300 to 1,000, more preferably 350 to 750. A larger molecular weight is preferred in view of reduced bleeding-out, whereas a smaller molecular weight is preferred in view of moisture permeability and high compatibility with the cellulose ester.

The polycarboxylic acid ester plasticizer preferably has an acid value of 1 mg KOH/g or less, more preferably 0.2 mg KOH/g or less. The acid value indicates milligrams of potassium hydroxide required for neutralization of the acid (carboxyl groups present in the sample) contained in 1 g of a sample. The acid value is determined in accordance with JIS K0070.

Examples of the polycarboxylic ester plasticizer include ester compounds (B) represented by Formula (II) described in Japanese Unexamined Patent Application Publication No. 2008-88292.

The polycarboxylic ester plasticizer may be a phthalic ester plasticizer. Examples of the phthalic ester plasticizer include diethyl phthalate, dimethoxyethyl phthalate, dimethyl phthalate, dioctyl phthalate, dibutyl phthalate, di-2-ethylhexyl phthalate, dicyclohexyl phthalate, and dicyclohexyl terephthalate.

Examples of the glycolate plasticizer include alkyl phthalyl alkyl glycolates. Examples of the alkyl phthalyl alkyl glycolate include methyl phthalyl methyl glycolate, ethyl phthalyl ethyl glycolate, propyl phthalyl propyl glycolate, butyl phthalyl butyl glycolate, and octyl phthalyl octyl glycolate.

Examples of the ester plasticizer include fatty acid ester plasticizers, citrate ester plasticizers, phosphate ester plasticizers, and trimellitate plasticizers.

Examples of the fatty acid ester plasticizer include butyl oleate, methyl acetyl ricinolate, and dibutyl sebacate. Examples of the citrate ester plasticizer include acetyl trimethyl citrate, acetyl triethyl citrate, and acetyl tributyl citrate. Examples of the phosphate ester plasticizer include triphenyl phosphate, tricresyl phosphate, cresyl diphenyl phosphate, octyl diphenyl phosphate, diphenyl biphenyl phosphate, trioctyl phosphate, and tributyl phosphate. Examples of the trimellitate plasticizer include octyl trimellitate, n-octyl trimellitate, isodecyl trimellitate, and isononyl trimellitate.

The plasticizer content is preferably 0.5 to 30.0 mass % relative to the cellulose ester. A plasticizer content of 30.0 mass % or less leads to reduced bleeding-out in the optical film.

(Ultraviolet Absorber)

The optical film of the present invention may further contain an ultraviolet absorber. The ultraviolet absorber may be, for example, a benzotriazole, 2-hydroxybenzophenone, or phenyl salicylate ultraviolet absorber. Specific examples of the ultraviolet absorber include triazole compounds, such as 2-(5-methyl-2-hydroxyphenyl)benzotriazole, 2-[2-hydroxy-3,5-bis(α,α-dimethylbenzyl)phenyl]-2H-benzotriazole, and 2-(3,5-di-t-butyl-2-hydroxyphenyl)benzotriazole; and benzophenone compounds, such as 2-hydroxy-4-methoxybenzophenone, 2-hydroxy-4-octoxybenzophenone, and 2,2'-dihydroxy-4-methoxybenzophenone.

In particular, an ultraviolet absorber having a molecular weight of 400 or more, which has a high boiling point, is less likely to volatilize or dissipate during high-temperature molding. Thus, addition of a relatively small amount of the ultraviolet absorber can enhance the weatherability of the resultant film.

Examples of the ultraviolet absorber having a molecular weight of 400 or more include benzotriazole compounds, such as 2-[2-hydroxy-3,5-bis(α,α-dimethylbenzyl)phenyl]-2-benzotriazole and 2,2-methylenebis[4-(1,1,3,3-tetrabutyl)-6-(2H-benzotriazol-2-yl)phenol]; hindered amine compounds, such as bis(2,2,6,6-tetramethyl-4-piperidyl) sebacate and bis(1,2,2,6,6-pentamethyl-4-piperidyl) sebacate; and hybrid compounds having both hindered phenol and hindered amine structures in the molecule, such as bis(1,2,2,6,6-pentamethyl-4-piperidyl) 2-(3,5-di-t-butyl-4-hydroxybenzyl)-2-π-butylmalonate and 1-[2-[3-(3,5-di-t-butyl-4-hydroxyphenyl)propionyloxy]ethyl]-4-[3-(3,5-di-t-butyl-4-hydroxyphenyl)propionyloxy]-2,2,6,6-tetramethylpiperidine. Preferred are 2-[2-hydroxy-3,5-bis(α,α-dimethylbenzyl)phenyl]-2-benzotriazole and 2,2-methylenebis[4-(1,1,3,3-tetrabutyl)-6-(2H-benzotriazol-2-yl)phenol]. These ultraviolet absorbers may be used alone or in combination.

(Fine Particles)

The optical film of the present invention may contain fine particles of an inorganic or organic compound.

Examples of the inorganic compound include silicon dioxide, titanium dioxide, aluminum oxide, zirconium oxide, calcium carbonate, calcium carbonate, talc, clay, calcined kaolin, calcined calcium silicate, calcium silicate hydrate, aluminum silicate, magnesium silicate, and calcium phosphate.

Examples of the organic compound include polytetrafluoroethylene, cellulose acetate, polystyrene, poly(methyl methacrylate), poly(propyl methacrylate), poly(methyl acrylate), poly(ethylene carbonate), acrylic-styrene resins, silicone resins, polycarbonate resins, benzoguanamine resins, melamine resins, polyolefin powder, polyester resins, polyamide resins, polyimide resins, pulverized and classified organic polymers (e.g., poly(ethylene fluoride) resins and starches), polymers synthesized by suspension polymerization, and spherical polymers prepared by a spray drying or dispersion process.

Preferred are particles made of silicon-containing compounds (e.g., silicon dioxide), which can maintain the haze of the resultant film at a low level.

Examples of the fine particle of silicon dioxide include Aerosil R972, R972V, R974, R812, 200, 200V, 300, R202, OX50, and TT600 (manufactured by Nippon Aerosil Co., Ltd.).

Particularly preferred are Aerosil 200V and R972V, which can improve the surface smoothness of the optical film while maintaining the haze of the film at a low level.

Examples of the fine particle of zirconium oxide include Aerosil R976 and R811 (manufactured by Nippon Aerosil Co., Ltd.).

Examples of the polymer compound include silicone resins, fluororesins, and (meth)acrylic resins. Preferred are silicone resins, and more preferred are silicone resins having a three-dimensional network structure. Examples of the silicone resins include Tospearl 103, 105, 108, 120, 145, 3120, and 240 (manufactured by Toshiba Silicone).

The fine particles have a mean primary particle size of preferably 5 to 400 nm, more preferably 10 to 300 nm. The fine particles may form secondary agglomerated particles substantially having a particle size of 0.05 to 0.30 Fine particles having a mean particle size of 100 to 400 nm may be present in the form of primary particles without being agglomerated.

The fine particles are preferably incorporated into the optical film such that at least one surface thereof has a dynamic friction coefficient of 0.2 to 1.0.

The content of the fine particle is preferably 0.01 to 1.00 mass %, more preferably 0.05 to 0.50 mass %, relative to the cellulose ester.

(Dispersant)

The optical film of the present invention may further contain a dispersant for improving the dispersion of fine particles. The dispersant is one or more selected from amine dispersants and carboxyl group-containing polymer dispersants.

The amine dispersant is preferably an alkyl amine or an amine salt of a polycarboxylic acid. Specific examples of the amine dispersant include amines prepared from polyester acids, polyether ester acids, fatty acids, fatty acid amides, polycarboxylic acids, alkylene oxides, polyalkylene oxides, polyoxyethylene fatty acid esters, and polyoxyethylene glycerin fatty acid esters. Examples of the amine salt include amidoamine salts, aliphatic amine salts, aromatic amine salts, alkanolamine salts, and polyamine salts.

Specific examples of the amine dispersant include polyoxyethylene fatty acid amides, polyoxyethylene alkylamines, tripropylamine, die thylaminoethylamine, dimethylaminopropylamine, and diethylaminopropylamine. Examples of commercial products include Solsperse series (manufactured by Lubrizol Corporation), Ajisper series (manufactured by Ajinomoto Co., Inc.), BYK series (manufactured by BYK-Chemie), and EFKA series (manufactured by EFKA).

The carboxyl group-containing polymer dispersant is preferably a polycarboxylic acid or a salt thereof; for example, polycarboxylic acid, ammonium polycarboxylate, or sodium polycarboxylate. Specific examples of the carboxyl group-containing polymer dispersant include poly(acrylic acid), poly(ammonium acrylate), poly(sodium acrylate), ammonium acrylate copolymers, poly(maleic acid), poly(ammonium maleate), and poly(sodium maleate).

The amine dispersant or the carboxyl group-containing polymer dispersant may be used in the form of a solution in a solvent or may be used as commercially supplied.

The dispersant content, which may vary depending on the type of the dispersant, is preferably 0.2 mass % or more relative to the fine particles. A dispersant content of 0.2 mass % or more relative to the fine particles leads to sufficiently improved dispersibility of the fine particles.

If the optical film of the present invention further contains a surfactant, the dispersant may be less likely to adsorb on the surfaces of the fine particles than the surfactant, resulting in agglomeration of the fine particles. The dispersant, which is expensive, is preferably incorporated into the film in a minimum possible amount. However, a significantly low dispersant content may lead to insufficient wetting of the fine particles or poor dispersion stability. Thus, if the optical film of the present invention further contains a surfactant, the dispersant content is adjusted to about 0.05 to 10.00 parts by mass relative to 10.00 parts by mass of the fine particles.

(Retardation Controller)

For improvement of the display quality of an image display device (e.g., a liquid crystal display device), the optical film can be provided with optical compensation function by adding a retardation controller to the film, or combining the retardations of a protective film for a polarizing plate and a liquid crystal layer prepared through formation of an orientation film.

Examples of the retardation controller include aromatic compounds having two or more aromatic rings described in European Patent No. 911,656 A2, and rod-like compounds described in Japanese Unexamined Patent Application Publication No. 2006-2025. Two or more aromatic compounds may be used in combination. The aromatic ring of such an aromatic compound is preferably an aromatic hydrocarbon ring and an aromatic heterocyclic ring. The aromatic heterocyclic ring is generally an unsaturated heterocyclic ring. Particularly preferred is a 1,3,5-triazine ring described in Japanese Unexamined Patent Application Publication No, 2006-2026.

The compound represented by Formula (1) also serves as a retardation controller. Thus, the compound represented by Formula (1) exhibits both a retardation controlling effect and an effect of reducing variations in optical values in association with a change in humidity.

The amount of the retardation controller added is preferably 0.5 to 20 mass %, more preferably 1 to 10 mass %, relative to the resin used as a film base material (100 mass %).

(Other Additives)

The optical film of the present invention may further contain an antioxidant, an antistatic, or a flame retardant for preventing thermal decomposition during molding or coloration caused by heat.

The flame retardant may be one or more phosphorus-containing flame retardants selected from red phosphorus, triaryl phosphates, diaryl phosphates, monoaryl phosphates, aryl phosphonate compounds, arylphosphine oxide compounds, condensed aryl phosphates, halogenated alkyl phosphates, halogen-containing condensed phosphate esters, halogen-containing condensed phosphonate esters, and halogen-containing phosphite esters. Specific examples of the phosphorus-containing flame retardant include triphenyl phosphate, 9,10-dihydro-9-oxa-10-phosphaphenanthrene-10-oxide, phenyl phosphonate, tris(β-chloroethyl) phosphate, tris(dichloropropyl) phosphate, and tris(tribromoneopentyl) phosphate.

<Properties of Optical Film>

The optical film of the present invention can be used in image display devices, such as organic EL display devices and liquid crystal display devices. The optical film of the present invention is preferably used in the form of a protective film for a polarizing plate, a retardation film, or an optical compensation film. Preferably, the retardation film or the optical compensation film also serves as the protective film for a polarizing plate.

A λ/4 retardation film has an in-plane retardation value Ro which is about one-quarter of a specific light wavelength (generally within a visible light range). The λ/4 retardation film is preferably formed of a single layer of the optical film of the present invention. The λ/4 retardation film is preferably used in the form of an antireflective film for organic EL display devices.

The optical film of the present invention may have any retardation value. The retardation value can be appropriately adjusted depending on the intended use of the optical film.

If the optical film of the present invention is used as an optical compensation film for a vertically oriented liquid crystal display device, the retardation value of the film preferably satisfies the following conditions 1 and 2 for widening a viewing angle.

Condition 1: an in-plane retardation value Ro (590) of 40 to 100 nm determined by Expression (I) at 23° C., 55% RH, and a light wavelength of 590 nm.

$$Ro=(n_x-n_y)\times d \qquad \text{Expression (I)}$$

Conditions 2: a retardation value Rt (590) across the thickness of the film of 100 to 300 nm determined by Expression (II) at 23° C., 55% RH, and a light wavelength of 590 nm.

$$Rt=\{(n_x+n_y)/2-n_z\}\times d \qquad \text{Expression (II)}$$

wherein $n_x$ is a refractive index in an in-plane slow axis direction of the film; $n_y$ is a refractive index in a direction orthogonal to the in-plane slow axis direction of the film; $n_z$ is a refractive index in a thickness direction of the film; and d is the thickness (nm) of the film.

The retardations can be adjusted to desired values through control of the draw ratio during formation of the film, the amount of a retardation enhancer added, the type of acyl group of the cellulose ester, the degree of acylation, or the thickness of the film.

If the optical film of the present invention is used as a λ/4 retardation film for antireflection in an organic EL display device, in-plane retardation values Ro (450), Ro (550), and Ro (650), which are determined at 23° C. and 55% RH and respectively at light wavelengths of 450 nm, 550 nm, and 650 nm, preferably satisfy Expressions (a1) to (a3).

$$110 \text{ nm} \leq Ro(550) \leq 170 \text{ nm} \qquad (a1)$$

$$0.72 \leq Ro(450)/Ro(550) \leq 0.96 \qquad (a2)$$

$$0.83 \leq Ro(550)/Ro(650) \leq 0.97 \qquad (a3)$$

An optical film having a retardation value Ro (550) satisfying Expression (a1) effectively functions as a λ/4 retardation film. The retardation value more preferably satisfies the expression 120 nm≤Ro (550)≤160 nm, still more preferably the expression 130 nm≤Ro (550)≤150 nm.

An optical film having retardation values Ro (450), Ro (550), and Ro (650) satisfying Expressions (a2) and (a3) exhibits excellent reverse wavelength dispersion and more effectively functions as a λ/4 retardation film. An image display device including the optical film exhibits reduced light leakage in black display. Specifically, satisfaction of Expression (a2) leads to improved blue color reproduction, whereas satisfaction of Expression (a3) leads to improved red color reproduction. The retardation values more preferably satisfy the expression 0.79≤Ro (450)/Ro (550)≤0.89, still more preferably the expression 0.84≤Ro (550)/Ro (650)≤0.93.

The optical film of the present invention preferably has a retardation value Rt (550) across the thickness of the film satisfying the expression 50 nm≤Rt (550)≤250 nm, the retardation value Rt being determined at 23° C., 55% RH, and a light wavelength of 550 nm.

The retardations can be adjusted to desired values through control of the draw ratio during formation of the film, the amount of a retardation enhancer added, the type of acyl group of the cellulose ester, the degree of acylation, or the thickness of the film.

In the optical film of the present invention, a value $N_z$ defined by Expression (a4) preferably satisfies Expression (a5).

$$N_z = Rt(550)/Ro(550) + 0.5 \tag{a4}$$

$$0 \leq N_z \leq 1 \tag{a5}$$

If the value $N_z$ satisfies Expression (a5), the retardation value Rt across the thickness of the film is smaller than the in-plane retardation value Ro. Thus, an image display device including the optical film of the present invention exhibits a small variation in color tone in oblique view.

The angle (orientation angle) between the in-plane slow axis of the optical film and the machine direction of the film is preferably 40 to 50°. If the orientation angle falls within this range, a circularly polarizing plate can be readily produced by a roll-to-roll process involving longitudinal attachment between the optical film withdrawn from a roller and having a slow axis in a direction oblique to the longitudinal direction (machine direction) and a polarizing film withdrawn from another roller and having an absorption axis in a direction parallel to the longitudinal direction (machine direction). This process has productivity advantages because of reduced cutting loss of the films. The orientation angle of the optical film can be determined with an automatic birefringence analyzer (KOBRA-21ADH, manufactured by Oji Scientific Instruments).

The aforementioned Ro and Rt can be determined with an automatic birefringence analyzer, such as AxoScan (manufactured by Axometrics, Inc.) or KOBRA-21ADH (manufactured by Oji Scientific Instruments). A determination process with AxoScan will now be described in detail.

1) The optical film is humidified at 23° C. and 55% RH. The average refractive index of the humidified optical film is measured at a wavelength of 450 nm, 550 nm, 590 nm, or 650 nm with an Abbe refractometer and a spectroscopic light source. The thickness d (nm) of the optical film is measured with a thickness meter.

2) Light having a wavelength of 450 nm, 550 nm, 590 nm, or 650 nm is applied to the humidified optical film in the normal direction of the film, and an in-plane retardation value Ro (450), Ro (550), or Ro(650) is determined with AxoScan at 23° C. and 55% RH.

3) The in-plane slow axis of the optical film is determined with AxoScan. The determined slow axis is regarded as an inclined axis (rotation axis), and light having a wavelength of 450 nm, 550 nm, 590 nm, or 650 nm is applied to the optical film at an incident angle ($\phi$) relative to the normal line of the film, to determine a retardation value R ($\phi$) corresponding to the incident angle. The retardation value R ($\phi$) is determined within an angle $\phi$ range of 0 to 50° (six points for 10°) at 23° C. and 55% RH.

4) The refractive indices $n_x$, $n_y$, and $n_z$ are calculated with AxoScan on the basis of the retardation values Ro (450), Ro (550), Ro (590), and Ro (650) determined in 2), the retardation values R ($\phi$) determined in 3) at 450 nm, 550 nm, 590 nm, and 650 nm, and the average refractive indices and the thickness d determined in 1). The retardation values Rt (450), Rt (550), Rt (590), and Rt (650), which correspond to wavelengths of 450 nm, 550 nm, 590 nm, and 650 nm, respectively, are calculated by Expression (ii).

The optical film preferably has a thickness of 10 to 100 µm in view of reduced thickness of the display device and improved productivity. A thickness of 10 µm or more can maintain the strength or retardation of the film at a certain level or more, whereas a thickness of 100 µm or less leads to a small variation in retardation caused by heat or moisture. The thickness is preferably 20 to 70 µm.

The optical film of the present invention has a variation in thickness (in both thickness and width directions) of preferably 0 to 5 µm, more preferably 0 to 3 µm, still more preferably 0 to 2 µm.

The optical film has a haze (total haze) of preferably less than 1%, more preferably 0.5%, or less, still more preferably 0.2% or less. An optical film having a haze of less than 1% exhibits substantially no reduction in transparency and satisfactory functions.

The haze (total haze) of the optical film can be determined in accordance with JIS K-7136 with a hazemeter NDH-2000 (manufactured by Nippon Denshoku Industries Co., Ltd., light source: halogen bulb (5 V, 9 W), photoreceptor: silicon photo-cell having a relative luminosity filter). The haze can be determined at 23° C. and 55% RH.

The optical film of the present invention preferably has a visible light transmittance of 90% or more, more preferably 93% or more.

The optical film of the present invention has an elongation at break in at least one direction determined in accordance with JIS-K7127-1999 of preferably 10% or more, more preferably 20% or more, still more preferably 30% or more.

<Production of Optical Film>

The optical film of the present invention can be produced by a solution casting process or a melt casting process. The solution casting process is preferred in that it can produce an optical film without defects, such as coloration, intrusion of foreign matter, and die lines. The melt casting process is preferably used for reducing residual solvent in the optical film.

A) Solution Casting Process

The solution casting process for producing the optical film containing a cellulose ester includes A1) a step of preparing a dope by dissolving a cellulose ester and an optional additive in a solvent; A2) a step of casting the dope onto an endless metal support; A3) a step of evaporating the solvent from the cast dope to form a web; A4) a step of removing the web from the metal support; and A5) a step of drying the web and stretching the dried web to produce an optical film.

A1) Dope Preparing Step

A cellulose ester and an optional additive are dissolved in a solvent in a reaction vessel, to prepare a dope.

Any solvent capable of dissolving the cellulose ester and the additive may be used. Examples of the solvent include chlorine-containing organic solvents, such as methylene chloride; and chlorine-free organic solvents, such as methyl acetate, ethyl acetate, amyl acetate, acetone, tetrahydrofuran, 1,3-dioxolane, 1,4-dioxane, cyclohexanone, ethyl formate, 2,2,2-trifluoroethanol, 2,2,3,3-hexafluoro-1-propanol, 1,3-difluoro-2-propanol, 1,1,1,3,3,3-hexafluoro-2-methyl-2-propanol, 1,1,1,3,3,3-hexafluoro-2-propanol, 2,2,3,3,3-pentafluoro-1-propanol, and nitroethane. Preferred are methylene chloride, methyl acetate, ethyl acetate, and acetone.

Preferably, the dope further contains 1 to 40 mass % linear or branched aliphatic alcohol having one to four carbon atoms. A higher alcohol content of the dope leads to gelation of the web, resulting in easy removal of the web from the metal support. Meanwhile, a lower alcohol content of the dope can promote dissolution of cellulose acetate in a chlorine-free organic solvent.

Examples of the linear or branched aliphatic alcohol having one to four carbon atoms include methanol, ethanol, n-propyl alcohol, isopropyl alcohol, n-butyl alcohol, sec-butyl alcohol, and tert-butyl alcohol. Particularly preferred is ethanol, which ensures high stability of the dope, has a relatively low boiling point, and is readily dried.

In particular, the dope preferably contains both methylene chloride and a linear or branched aliphatic alcohol having one to four carbon atoms.

Although a high cellulose ester content of the dope is preferred for reducing drying load, a significantly high cellulose ester content leads to difficulty in filtration. Thus, the cellulose ester content of the dope is preferably 10 to 35 mass %, more preferably 15 to 25 mass %.

The cellulose ester may be dissolved in a solvent under heating and increased pressure. Although a high heating temperature is preferred for enhancing the solubility of the cellulose ester in the solvent, a significantly high heating temperature requires a high pressure, resulting in low productivity. Thus, the heating temperature is preferably 45 to 120° C.

The additive may be added to the dope in a batch manner. Alternatively, the additive may be added in the form of a solution to the dope in an in-line manner. If the additive is fine particle matter, a portion or the entirety of the additive is preferably added in an in-line manner for reducing the load on a filter.

If the additive solution is added in an in-line manner, a small amount of cellulose ester is preferably dissolved in the solution for improving compatibility of the solution with the dope. The thermoplastic resin content of the solution is preferably 1 to 10 parts by mass, more preferably 3 to 5 parts by mass, relative to 100 parts by mass of the solvent.

In-line addition or mixing preferably involves use of an in-line mixer, such as a static mixer (manufactured by Toray Engineering Co., Ltd.) or SWJ (Hi-Mixer, a static in-tube mixer by Toray).

The resultant dope may contain insoluble matter, such as impurities contained in the cellulose ester serving as a raw material. The insoluble matter may form bright spot foreign substances in the resultant film. Thus, the dope is preferably filtered to remove the insoluble matter.

Filtration of the dope is preferably performed such that the number of bright spot foreign substances is reduced to a specific level or less in the resultant film. Specifically, the number of bright spot foreign substances having a size of 0.01 mm or more is 200/cm$^2$ or less, preferably 100/cm$^2$ or less, more preferably 50/cm$^2$ or less, still more preferably 30/cm$^2$ or less, particularly preferably 10/cm$^2$ or less.

The number of bright spot foreign substances having a size of 0.01 mm or less is preferably 200/cm$^2$ or less, more preferably 100/cm$^2$ or less, still more preferably 50/cm$^2$ or less, still more preferably 30/cm$^2$ or less, particularly preferably 10/cm$^2$ or less. Most preferred is no bright spot foreign substance.

The number of bright spot foreign substances in the film is measured as follows:
1) Two polarizing plates are disposed in a cross-Nicol state, and the film is interposed therebetween.
2) While light is applied to one of the polarizing plates, an image is observed on the other polarizing plate. Points at which leakage of light is found are counted as foreign substances.

A2) Casting Step

The dope is supplied through a slit of a pressure die and cast onto an endless metal support.

The metal support used in this step is preferably a stainless steel belt or a cast metal drum having a plated surface. The metal support preferably has a mirror-finished surface.

The casting width may be 1 to 4 m. In the casting step, the surface temperature of the metal support is adjusted to fall within a range from −50° C. to less than the boiling (bubbling) temperature of the solvent. Although a higher temperature is preferred in view of rapid drying of a web, the temperature should be adjusted not to cause bubbling in the web or impaired flatness of the web.

The surface temperature of the metal support is preferably 0 to 100° C., more preferably 5 to 30° C. The metal support may be cooled for gelation of the web, so that the web containing a large amount of residual solvent is removed from the drum.

The temperature of the metal support can be controlled by any technique. For example, hot air or cold air may be blown to the metal support, or the rear surface of the metal support may be brought into contact with hot water. Temperature control with hot water is preferred for effective heat conduction to achieve a predetermined temperature of the metal support within a short time period.

In consideration of a decrease in temperature of the web due to latent heat of vaporization of the solvent, hot air at a temperature higher than the target temperature (e.g., a temperature equal to or higher than the boiling point of the solvent) may be used while preventing bubbling of the solvent. It is particularly preferred that the temperatures of the metal support and drying air be adequately varied between the casting step and the web removing step for achieving effective drying.

A3) Solvent Evaporating Step

The web (dope film formed through casting of the dope onto the metal support) is heated on the metal support, to evaporate the solvent. The web may be dried under the same conditions as described above in A2) casting step.

A4) Removing Step

After evaporation of the solvent, the web is removed from the metal support.

For achievement of high flatness of the resultant film, the residual solvent content of the web removed from the metal support is preferably 10 to 150 mass %, more preferably 20 to 40 mass % or 60 to 130 mass, still more preferably 20 to 30 mass % or 70 to 120 mass %.

The residual solvent content of the web is determined by the following expression.

Residual solvent content (%)={(the mass of the web before thermal treatment−the mass of the web after thermal treatment)/(the mass of the web after thermal treatment)}×100

The thermal treatment for determination of the residual solvent content refers to heating at 115° C. for one hour.

A5) Drying and Stretching Step

The web removed from the metal support is optionally dried and then stretched. The web may be dried while being conveyed with a plurality of vertically disposed rollers. Alternatively, the web may be dried while it is conveyed with its both ends being held with clips.

The web may be dried by any means, such as hot air, infrared rays, heating rollers, and microwaves. Drying with hot air is preferred for convenience.

The dried web is then stretched to produce an optical film having a desired retardation. The retardation of an optical compensation film can be adjusted by controlling the tension applied to the web.

The web is stretched in the transverse direction (TD), the machine direction (MD), or an oblique direction.

If the optical film of the present invention is used as a λ/4 retardation film for antireflection in an organic EL display device, the web is preferably stretched in an oblique direction; specifically, in a direction inclined by 45° relative to the machine direction.

If the web is stretched in the oblique direction, a circularly polarizing plate can be readily produced by a roll-to-roll process involving longitudinal attachment between a polarizing film withdrawn from a roller and having an absorption axis in the longitudinal direction and an optical film withdrawn from another roller and having a slow axis in a direction inclined by 45° relative to the longitudinal direction. This process has an advantage in productivity because of reduced cutting loss of the films.

The web may be monoaxially or biaxially stretched. Biaxial stretching may be performed sequentially or simultaneously.

The draw ratio may vary depending on the thickness of an optical film to be formed or the required retardation of the film. For example, the final draw ratios in the two orthogonal directions are preferably 0.8 to 1.5 in the casting direction and 1.1 to 2.5 in the transverse direction, more preferably 0.8 to 1.0 in the casting direction and 1.2 to 2.0 in the transverse direction. The draw ratio in an oblique direction is preferably 1.1 to 5.0, more preferably 1.2 to 2.5.

The draw ratio is defined by W/W0 in the stretching direction (wherein W represents the length of the film before stretching, and W0 represents the length of the film after stretching). A draw ratio of 1.0 indicates no stretching.

The stretching temperature is preferably 120 to 230° C., more preferably 130 to 220° C., still more preferably a range of higher than 140° C. and 210° C. or lower.

The web can be stretched by any process. For example, the web may be stretched by a roller stretching process involving stretching in the casting direction (machine direction) by a difference in circumferential velocity between a plurality of rollers. Alternatively, the web may be stretched by a tenter stretching process involving stretching in the casting direction by enlarging the distance between clips or pins used for holding of the two edges of the web in the casting direction, stretching in the transverse direction by enlarging the distance between the clips or pins in the transverse direction, or simultaneous stretching in the casting and transverse directions by enlarging the distance between the clips or pins in the casting and transverse directions.

Oblique stretching may be performed with a tenter having means for holding the transverse edges of the web and capable of controlling the holding length (i.e., the distance between an initial holding point and a final holding point) of each edge independently. These stretching processes may be used in combination.

Examples of stretching apparatuses having an oblique stretching mechanism include those described in Example 1 of Japanese Unexamined Patent Application Publication No. 2003-340916, illustrated in FIG. 1 of Japanese Unexamined Patent Application Publication No. 2005-284024, disclosed in Japanese Unexamined Patent Application Publication No. 2007-30466, and used in Example 1 of Japanese Unexamined Patent Application Publication No. 2007-94007.

The residual solvent content of the web at initiation of stretching is preferably 20 mass % or less, more preferably 15 mass % or less.

The stretched film is optionally dried and then wound up. As in the case of the web, the film may be dried while being conveyed with a plurality of vertically disposed rollers (roller system), or the film may be dried while it is conveyed with its both ends being held with clips (tenter system).

B) Melt Casting Process

The melt casting process for producing the optical film of the present invention includes B1) a step of preparing resin pellets (pelletization step); B2) a step of melt-kneading the pellets and extruding the melt-kneaded resin (melting-extrusion step); B3) a step of solidifying the melted resin through cooling to form a web (cooling-solidification step); and B4) a step of stretching the web (stretching step).

B1) Pelletization Step

The resin composition, which contains a thermoplastic resin serving as a main component of the optical film, is preferably kneaded and pelletized in advance by any known process. For example, the resin composition, which contains any of the aforementioned thermoplastic resins and an optical additive (e.g., a plasticizer), is melt-kneaded with an extruder, and the melted resin is extruded into a strand form through a die. The strand melted resin is cooled with water or air, and the cooled resin is cut into pellets.

The raw materials of the pellets are preferably dried before being fed into the extruder for prevention of decomposition.

For mixing of an antioxidant with a thermoplastic resin, these materials may be combined together in the form of solids, the thermoplastic resin may be impregnated with a solution of the antioxidant in a solvent, or the antioxidant may be sprayed onto the thermoplastic resin. A feeder of the extruder or the outlet of a die is preferably surrounded with an atmosphere of dehumidified air or nitrogen gas for preventing degradation of the raw materials of the pellets.

In the extruder, the resin composition is preferably kneaded under a low shearing force or at a low temperature for preventing degradation of the resin (e.g., a decrease in molecular weight, coloration, or gelation). If the resin composition is kneaded with a twin-screw extruder, two screws with deep grooves are preferably rotated in the same direction. For uniform kneading, the two screws are preferably engaged with each other.

Without pelletization of the resin composition containing a thermoplastic resin, the optical film may be produced only from the thermoplastic resin melt-kneaded with the extruder.

B2) Melting-Extrusion Step

The resultant pellets and an optional additive are supplied from a hopper to an extruder. The pellets are preferably supplied under vacuum, under reduced pressure, or in an inert gas atmosphere for preventing oxidative decomposition of the pellets. The pellets (i.e., film material) and the optional additive are melt-kneaded with the extruder.

The melting temperature of the film material in the extruder, which may vary depending on the type of the material, is preferably Tg to (Tg+100)° C., more preferably (Tg+10) to (Tg+90)° C. (wherein Tg represents the glass transition temperature (° C.) of the film material).

If an additive, such as a plasticizer or fine particles, is further added at the middle of the extruder, a mixing device (e.g., a static mixer) may be provided downstream of the extruder for uniform mixing of the additive.

The melted resin discharged from the extruder is optionally filtered with a leaf disk filter. Thereafter, the resultant resin is further agitated with a static mixer and then extruded in a film form through a die.

The extrusion rate is preferably stabilized with a gear pump. The leaf disk filter used for removal of foreign matter is preferably made of sintered stainless steel fiber. This filter is prepared by sintering of entangled and compressed stainless steel fiber filaments. The density or filtration accuracy of the filter can be adjusted under control of the thickness of fiber filaments or the degree of compression.

The melting temperature of the resin at the outlet of the die may be about 200 to 300° C.

B3) Cooling-Solidification Step

The melted resin extruded through the die is nipped between a cooling roller and an elastic touch roller, into a melted film having a specific thickness. The melted resin film is cooled and solidified in a stepwise manner with a plurality of cooling rollers.

The cooling rollers may have a surface temperature equal to or lower than the glass transition temperature Tg (° C.) of the film-form resin. The cooling rollers may have different surface temperatures.

A commercially available elastic touch roller, which may be called a pinching rotator, may be used. The temperature of the film surface in contact with the elastic touch roller may be Tg to (Tg+110)° C.

The solidified film-form resin is removed from the cooling rollers with a removing roller, to produce a web. The tension is preferably controlled during removal of the film-form resin for preventing deformation of the web.

B4) Stretching Step

The resultant web is stretched with a stretching machine, to produce a film. The web is stretched in the transverse direction, the machine direction, or an oblique direction.

If the optical film of the present invention is used as a λ/4 retardation film for antireflection in an organic EL display device, the web is preferably stretched in an oblique direction; specifically, in a direction inclined by 45° relative to the machine direction.

Conditions for stretching the web (e.g., draw ratio and temperature) may be the same as those described above.

<Polarizing Plate>

The optical film of the present invention can be used in the polarizing plate of the present invention or in the liquid crystal display device including the polarizing plate. Preferably, the optical film of the present invention also serves as a protective film for the polarizing plate. This case eliminates the need for another optical film having a retardation function, leading to a reduction in thickness of the liquid crystal display device and simplification of a production process.

The liquid crystal display device of the present invention preferably includes a liquid crystal cell and the polarizing plate of the present invention bonded to each surface of the liquid crystal cell with an adhesive layer.

The polarizing plate of the present invention can be prepared by any typical process. Preferably, a surface of the optical film of the present invention is saponified with an alkali, and the alkali-saponified surface of the optical film is bonded, with an aqueous completely saponified poly(vinyl alcohol) solution, to at least one surface of a polarizer prepared by immersion in an iodine solution and stretching. The other surface of the polarizer may be bonded to another protective film for the polarizing plate. In the liquid crystal display device, the optical film of the present invention is preferably provided on the surface of the polarizer facing the liquid crystal cell. The opposite surface of the polarizer may be provided with a conventional protective film for the polarizing plate.

The conventional protective film is preferably a commercially available cellulose ester film. Examples of the cellulose ester film include Konica Minolta Tac films KC8UX, KC5UX, KC8UCR3, KC8UCR4, KC8UCR5, KC8UY, KC6UY, KC4UY, KC4UE, KC8UE, KC8UY-HA, KC8UX-RHA, KC8UXW-RHA-C, KC8UXW-RHA-NC, and KC4UXW-RHA-NC (manufactured by Konica Minolta Advanced Layers, Inc.).

<Adhesive>

FIG. 1 is a schematic diagram of the configuration of a liquid crystal display device. With reference to FIG. 1, a retardation film 105 is bonded to a polarizer 104 with an active energy ray-curable adhesive layer 103B. The use of an active energy ray-curable adhesive is preferred for effective control of moisture permeability. Examples of the adhesive usable in the present invention include active energy ray-curable adhesives; curable adhesives, such as urethane adhesives, epoxy adhesives, aqueous polymer-isocyanate adhesives, and thermosetting acrylic adhesives; moisture-curable urethane adhesives; anaerobic adhesives, such as polyether-methacrylate, ester-methacrylate, and oxidized polyether-methacrylate adhesives; instant adhesives, such as cyanoacrylate adhesives; and two-component instant adhesives, such as acrylate-peroxide adhesives. The adhesive used may be of a one-component type or a two-component type (i.e., mixing of two components before use). The adhesive may be a solvent adhesive containing an organic solvent medium, an aqueous adhesive in the form of an emulsion, colloid, or aqueous solution containing an aqueous medium, or a non-solvent adhesive. The adhesive content may be appropriately determined depending on the thickness of an adhesive layer to be formed and methods and conditions for application of the adhesive. The adhesive content is generally 0.1 to 50 mass %.

(Active Energy Ray-Curable Adhesive)

The active energy ray-curable adhesive is preferably, for example, an active energy ray-curable adhesive composition disclosed in Japanese Unexamined Patent Application Publication No, 2011-028234. The composition contains (α) a cationically polymerizable compound, (β) a photocationic polymerization initiator, (γ) a photosensitizer exhibiting a maximum absorption of light at 380 nm or more, and (δ) a naphthalene photosensitizing aid. It should be noted that another active energy ray-curable adhesive composition may also be used.

The polarizing plate can be produced by bonding of the optical film of the present invention to one surface of a polarizer with the active energy ray-curable adhesive. If the two surfaces of the retardation film have different adhesive properties, the polarizer is preferably bonded to the surface having higher adhesion.

Now will be described a process for producing the polarizing plate by use of the active energy ray-curable adhesive.

The polarizing plate can be produced by a process including a step of applying the active energy ray-curable adhesive to at least one of a polarizer and a retardation film, to form an adhesive layer; a step of bonding the polarizer and the retardation film via the adhesive layer; and a step of curing the adhesive layer interposed between the polarizer and the retardation film. The process may also include a pretreatment step of treating the surface of the retardation film to be bonded to the polarizer for facilitation of bonding.

(Pretreatment Step)

In this step, the surface of the retardation film to be bonded to the polarizer is subjected to a pretreatment for facilitation of bonding. If the two respective surfaces of the polarizer are bonded to the retardation film and a protective film, the retardation film and the protective film are subjected to the pretreatment. In the subsequent adhesive applying step, the active energy ray-curable adhesive is applied to the pretreated surface (i.e., the surface bonded to the polarizer) of the retardation film. The pretreatment may be corona treatment or plasma treatment.

(Adhesive Applying Step)

In the adhesive applying step, the active energy ray-curable adhesive is applied onto at least one of the polarizer and the retardation film. Any application process can be used for applying the active energy ray-curable adhesive directly onto the surface of the polarizer or the retardation film. Examples of the application process include various wet processes, such as doctor blading, wire bar coating, die coating, comma coating, and gravure coating. The active energy ray-curable adhesive may be applied by casting the adhesive between the polarizer and the retardation film, and applying pressure to the workpiece with rollers to uniformly spread the adhesive.

(Bonding Step)

After application of the active energy ray-curable adhesive, the workpiece is subjected to the bonding step. For example, if the active energy ray-curable adhesive is applied onto the surface of the polarizer in the preceding applying step, the retardation film is disposed thereon. If the active energy ray-curable adhesive is applied onto the surface of the retardation film in the preceding applying step, the polarizer is disposed thereon. If the active energy ray-curable adhesive is cast between the polarizer and the retardation film, the polarizer and the retardation film are disposed each other in this state. If the retardation film and the protective film are bonded to the two respective surfaces of the polarizer with the active energy ray-curable adhesive, these films are disposed on the surfaces of the polarizer via the active energy ray-curable adhesive. In this state, pressure is applied to the workpiece with rollers from both surfaces of the workpiece (e.g., from the polarizer and the retardation film if the retardation film is disposed on one surface of the polarizer, or from the retardation film and the protective film if these films are disposed on both surfaces of the polarizer). Metal or rubber rollers can be used. The rollers disposed on both surfaces of the workpiece may be made of the same material or different materials.

(Curing Step)

In the curing step, the uncured active energy ray-curable adhesive is irradiated with active energy rays, to cure the adhesive, which contains a cationically polymerizable compound (e.g., an epoxy compound or an oxetane compound) or a radically polymerizable compound (e.g., an acrylate compound or an acrylamide compound). Thus, the disposed polarizer and retardation film are bonded together with the active energy ray-curable adhesive. If the retardation film is bonded to one surface of the polarizer, active energy rays may be applied to the polarizer or the retardation film. If the retardation film and the protective film are bonded to both surfaces of the polarizer, preferably, the respective films are disposed on both surfaces of the polarizer via the active energy ray-curable adhesive, and active energy rays are applied to the workpiece to cure the adhesive on both surfaces of the polarizer at the same time.

The active energy rays used for curing may be visible rays, ultraviolet rays, X-rays, or electron beams. In general, electron beams or ultraviolet rays are preferably used in view of easy handling and sufficiently rapid curing.

Electron beam irradiation can be performed under any conditions suitable for curing the adhesive. For example, the accelerating voltage is preferably 5 to 300 kV, more preferably 10 to 250 kV. An accelerating voltage below 5 kV may fail to flight of electron beams to the adhesive, resulting in insufficient curing of the adhesive. Meanwhile, an accelerating voltage exceeding 300 kV may lead to reflection of electron beams caused by strong penetration of the beams through the workpiece, resulting in damage to the retardation film or the polarizer. The irradiation dose is preferably 5 to 100 kGy, more preferably 10 to 75 kGy. An irradiation dose below 5 kGy may lead to insufficient curing of the adhesive, whereas an irradiation dose exceeding 100 kGy may cause damage to the retardation film or the polarizer, leading to impaired mechanical strength or yellowing, resulting in failure to achieve intended optical properties.

Ultraviolet ray irradiation can be performed under any conditions suitable for curing the adhesive. The cumulative irradiation dose of ultraviolet rays is preferably 50 to 1,500 $mJ/cm^2$, more preferably 100 to 500 $mJ/cm^2$.

If the polarizing plate is produced by a continuous line process, the line speed, which may vary depending on the curing time of the adhesive, is preferably 1 to 500 m/min, more preferably 5 to 300 m/min, still more preferably 10 to 100 m/min. A significantly low line speed may cause poor productivity or excessive damage to the retardation film, resulting in failure to produce a polarizing plate capable of passing a durability test. Meanwhile, a significantly high line speed may cause insufficient curing of the adhesive, resulting in failure to achieve intended adhesion.

The adhesive layer of the polarizing plate produced as described above may have any thickness. The thickness is generally 0.01 to 10, preferably 0.5 to 5 µm.

The protective film for the polarizing plate on the front side of the display device is preferably provided with an antiglare layer, a clear hard coat layer, an antireflective layer, an antistatic layer, an antifouling layer, or a back coat layer.

The polarizer, which is a main component of the polarizing plate, can transmit only a light component having a polarization plane in a specific direction. Typically known polarizers include poly(vinyl alcohol) polarizing films. The poly(vinyl alcohol) polarizing films are classified into poly (vinyl alcohol) films dyed with iodine and those dyed with dichroic dyes.

The polarizer is prepared as follows: An aqueous poly (vinyl alcohol) solution is formed into a film, and the film is monoaxially stretched and then dyed, or vice versa. The resultant film is preferably provided with durability by treatment with a boron compound. The polarizer preferably has a thickness of 5 to 30 µm, particularly preferably 10 to 20 µm.

<Liquid Crystal Display Device>

The polarizing plate including the optical film of the present invention can be used in a liquid crystal display device. The image display device of the present invention exhibits excellent visibility.

The optical film and polarizing plate of the present invention can be used in a liquid crystal display device having any driving mode, such as STN, TN, OCE, HAN, VA (MVA or PVA), IPS, or OCB.

The optical film and the polarizing plate are particularly preferably used in a VA (MVA or PVA)-mode liquid crystal display device.

Even if the liquid crystal display device has a 30-inch or larger screen, the display device exhibits reduced light leakage in black display and excellent visibility, such as high front contrast.

<Circularly Polarizing Plate>

The circularly polarizing plate of the present invention includes a polarizer (linearly polarizing film) and the optical film of the present invention disposed on at least one surface of the polarizer. The optical film of the present invention may be bonded directly to the polarizer, or may be bonded to the polarizer via another layer or film.

The polarizer may be a polarizing film dyed with iodine, a polarizing film dyed with a dichroic dye, or a polyene polarizing film. The polarizing film dyed with iodine or dichroic dye may be prepared by monoaxial stretching of a poly(vinyl alcohol) film and subsequent dyeing of the stretched film with iodine or a dichroic dye, or vice versa. The monoaxially stretched film is preferably provided with durability by treatment with a boron compound. The polarizer has a transmission axis parallel to the stretching direction of the film.

The poly(vinyl alcohol) film may be prepared from an aqueous poly(vinyl alcohol) solution. The poly(vinyl alcohol) film is preferably an ethylene-modified poly(vinyl alcohol) film, which exhibits high polarizing performance, high durability, and reduced color unevenness.

Examples of the dichroic dye include azo dyes, stilbene dyes, pyrazolone dyes, triphenylmethane dyes, quinoline dyes, oxazine dyes, thiazine dyes, and anthraquinone dyes.

The polarizer preferably has a thickness of 5 to 30 μm, more preferably 10 to 20 μm.

The angle between the transmission axis of the polarizer and the in-plane slow axis of the optical film of the present invention is 40 to 50°, preferably 45°.

A reflective polarizing plate may be provided between the polarizer and the optical film of the present invention. The reflective polarizing plate transmits linearly polarized light parallel to the transmission axis of the polarizer, and reflects linearly polarized light in a direction different from that of the transmission axis. An organic EL display device including the reflective polarizing plate can more effectively emit light from a light-emitting layer to the outside.

Examples of the reflective polarizing plate include a birefringent polarizer including alternately disposed polymer thin films having different refractive indices in one direction (disclosed in Japanese Translation of PCT International Application Publication No. H08-503312) and a polarization separating film having a cholesteric structure (disclosed in Japanese Unexamined Patent Application Publication No. H11-44816). The polarizer may further have a protective film on a surface thereof.

If one surface of the polarizer is provided with the optical film of the present invention, the other surface of the polarizer may be provided with a transparent protective film other than the optical film. The transparent protective film may be a common cellulose ester film. The cellulose ester film is preferably a commercially available cellulose ester film. Examples of the cellulose ester film include Konica Minolta Tac films KC8UX, KC5UX, KC8UCR3, KC8UCR4, KC8UCR5, KC8UY, KC6UY, KC4UY, KC4UE, KC8UE, KC8UY-HA, KC8UX-RHA, KC8UXW-RHA-C, KC8UXW-RHA-NC, and KC4UXW-RHA-NC (manufactured by Konica Minolta Advanced Layers, Inc.).

The transparent protective film may have any thickness. The thickness is about 10 to 200 μm, preferably 10 to 100 μm, more preferably 10 to 70 μm.

If a transparent protective film or a λ/4 retardation film is provided on the outermost surface of the display, the transparent protective film or the λ/4 retardation film may be provided with, for example, a transparent hard coat layer, an antiglare layer, and/or an antireflective layer.

The circularly polarizing plate can be produced through a step of bonding the polarizer to the optical film of the present invention. The adhesive used for bonding is preferably, for example, an aqueous completely saponified poly(vinyl alcohol) solution.

The circularly polarizing plate is suitable for use in image display devices described below, such as an organic EL display device and a liquid crystal display device.

<Image Display Device>

The image display device of the present invention includes the optical film of the present invention. The image display device of the present invention is, for example, an organic EL display device or a liquid crystal display device.

Figure 2:
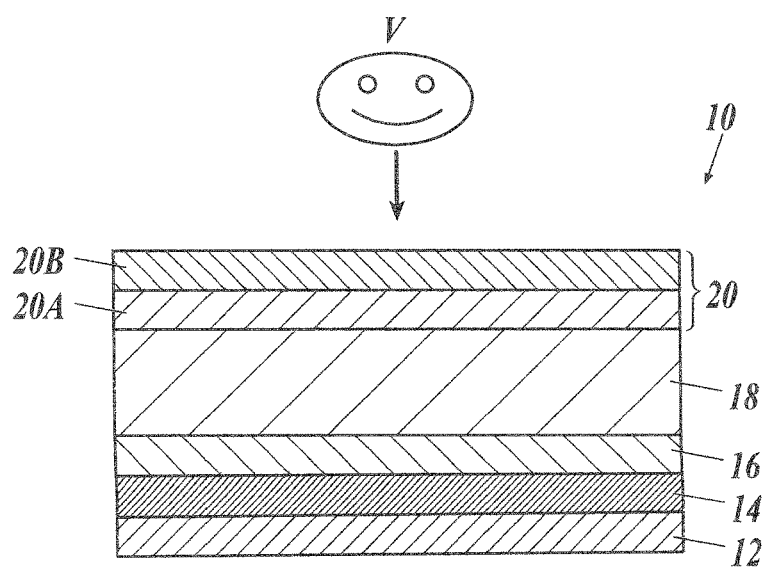
FIG. 2 is a schematic diagram of the configuration of an organic EL display device.

FIG. 2 is a schematic diagram of the configuration of an organic EL display device.

The organic EL display device includes an organic EL element. The organic EL element contains an organic light-emitting material which emits light by current flow between a pair of electrodes. Specifically, the organic EL element emits energy in the form of light generated by recombination of electrons from a cathode and holes from an anode.

With reference to FIG. 2, the organic EL display device 10 includes a light-reflecting electrode 12, a light-emitting layer 14, a transparent electrode layer 16, a transparent substrate 18, and a circularly polarizing plate 20 disposed in sequence. The circularly polarizing plate 20 includes a λ/4 retardation film 20A and a polarizer 20B. The λ/4 retardation film 20A is the optical film of the present invention, and the polarizer 20B is a linearly polarizing film.

The light-reflecting electrode 12 is preferably composed of a metal material having high optical reflectance. Examples of the metal material include Mg, MgAg, MgIn, Al, and LiAl. The light-reflecting electrode 12 preferably has a flat surface for preventing diffuse reflection of light.

The light-reflecting electrode 12 can be formed through sputtering. The light-reflecting electrode 12 may be patterned by etching.

The light-emitting layer 14 includes red (R), green (G), and blue (B) light-emitting sublayers. Each of the light-emitting sublayers contains a light-emitting material. The light-emitting material may be an inorganic or organic compound, and is preferably an organic compound.

Each of the red, green, and blue light-emitting sublayers may also contain a charge transporting material to function as a charge transporting layer. Each light-emitting sublayer may also contain a hole transporting material to function as a hole transporting layer. If each light-emitting sublayer contains neither a charge transporting material nor a hole transporting material, the organic EL display device 10 may further include a charge transporting layer or a hole transporting layer.

The light-emitting layer 14 can be formed through vapor deposition of a light-emitting material. The red, green, and blue light-emitting sublayers are prepared through patterning with, for example, a photomask.

The transparent electrode layer 16 is generally an indium tin oxide (ITO) electrode. The transparent electrode layer 16 can be formed through sputtering. The transparent electrode layer 16 may be patterned by etching.

The transparent substrate 18 is formed of any material which can transmit light, such as a glass substrate or a plastic film.

The circularly polarizing plate 20 is configured such that the λ/4 retardation film 20A is disposed on the transparent substrate 18 and the polarizer 20B is located on the viewing side V.

The organic EL display device 10 can display an image by light emitted from the light-emitting layer 14 through current flow between the light-reflecting electrode 12 and the transparent electrode layer 16. The organic EL display device 10 can display a full-color image because the red, green, and blue light-emitting sublayers enable current to flow therethrough.

The optical film of the present invention or the circularly polarizing plate including the optical film can be applied not only to the aforementioned organic EL display device, but also to organic EL display devices described in International Patent Publication WO1996/34514 and Japanese Unexamined Patent Application Publication Nos. H09-127885 and H11-45058. In such a case, the optical film of the present invention or the circularly polarizing plate is disposed instead of or in addition to antireflective means preliminarily provided in the organic EL display device. The optical film of the present invention or the circularly polarizing plate can also be applied to an inorganic EL display device described in, for example, Toshio Inokuchi, "Electroluminescent Display," Sangyo Tosho Co., 1991.

Figure 3:
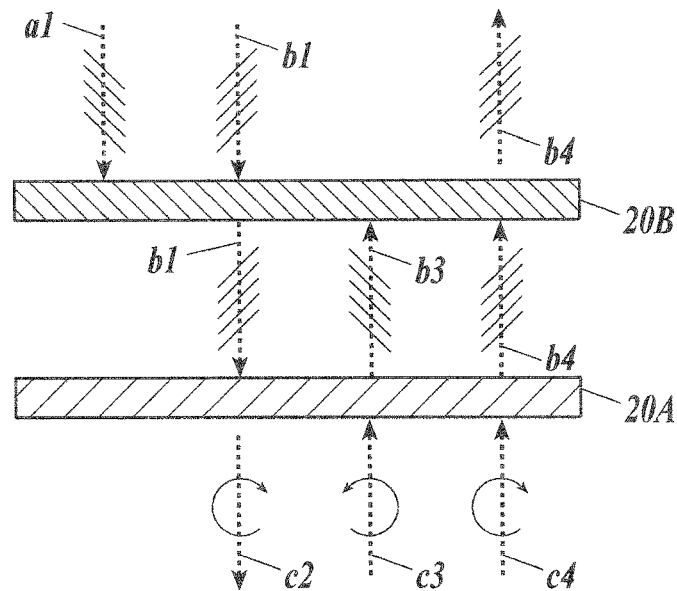
FIG. 3 is a schematic diagram illustrating the antireflective function of a circularly polarizing plate.

FIG. 3 is a schematic diagram illustrating the antireflective function of the circularly polarizing plate 20.

If external light including linearly polarized light components a1 and b1 is applied to the organic EL display device 10 in a direction parallel to the normal line of the display screen of the device 10, only the linearly polarized light component b1, which is parallel to the transmission axis of the polarizer 20B, passes through the polarizer 20B. The linearly polarized light component a1, which is not parallel to the transmission axis of the polarizer 20B, is absorbed by the polarizer 20B. The linearly polarized light component b1 then passes through the λ/4 retardation film 20A and is converted into a circularly polarized light component c2. The circularly polarized light component c2 is reflected by the light-reflecting electrode 12 (see FIG. 2) of the organic EL display device 10 and is converted into an inversely rotating circularly polarized light component c3. The circularly polarized light component c3 then passes through the λ/4 retardation film 20A and is converted into a linearly polarized light component b3 orthogonal to the transmission axis of the polarizer 20B. The linearly polarized light component b3 is absorbed by the polarizer 20B and does not transmit therethrough.

As described above, the external light (including the linearly polarized light components a1 and b1) applied to the organic EL display device 10 is entirely absorbed by the polarizer 20B; i.e., the light reflected by the light-reflecting electrode 12 is not emitted to the outside of the organic EL display device 10. This mechanism can prevent impairment of image display performance, which would be caused by the reflected image from the back face.

Light generated in the organic EL display device 10 (i.e., light emitted from the light-emitting layer 14) includes two circularly polarized light components c3 and c4. As described above, the circularly polarized light component c3 passes through the λ/4 retardation film 20A and is converted into a linearly polarized light component b3. The linearly polarized light component b3 is absorbed by the polarizer 20B and does not transmit therethrough. The circularly polarized light component c4 passes through the λ/4 retardation film 20A and is converted into a linearly polarized light component b4 parallel to the transmission axis of the polarizer 20B. The linearly polarized light component b4 then passes through the polarizer 20B and is recognized as an image.

A reflective polarizing plate (not illustrated) may be disposed between the polarizer 20B and the λ/4 retardation film 20A, so that the linearly polarized light component b3 orthogonal to the transmission axis of the polarizer 20B is reflected by the reflective polarizing plate. Specifically, the linearly polarized light component b3 is reflected by the reflective polarizing plate without being absorbed by the polarizer 20B, and the reflected light component b3 is reflected again by the light-reflecting electrode 12 and converted into a linearly polarized light component b4 parallel to the transmission axis of the polarizer 20B. Thus, disposition of the reflective polarizing plate enables light from the light-emitting layer 14 (including the circularly polarized light components c3 and c4) to entirely emit to the outside of the device.

Figure 4:
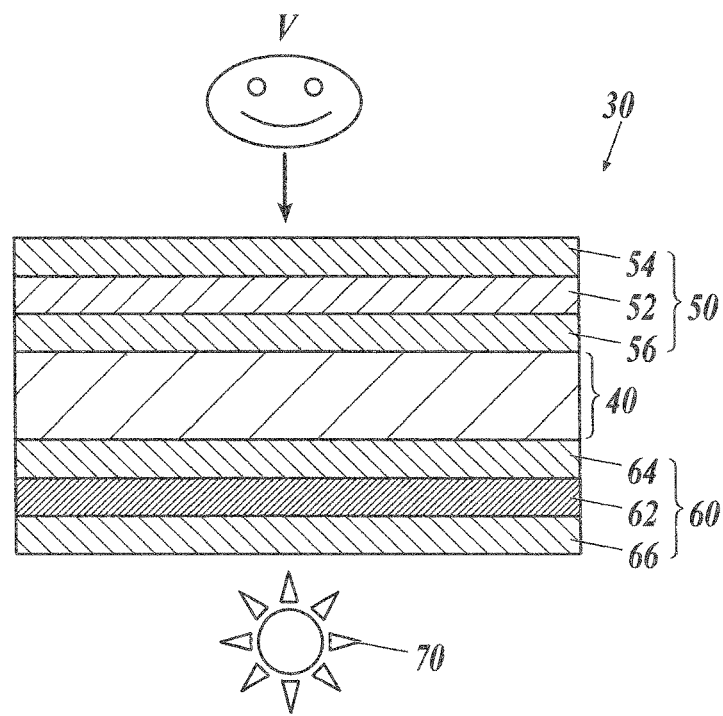
FIG. 4 is a schematic diagram of the configuration of a liquid crystal display device.

FIG. 4 is a schematic diagram of the configuration of a liquid crystal display device.

With reference to FIG. 4, the liquid crystal display device 30 includes a liquid crystal cell 40, two polarizing plates 50 and 60 sandwiching the liquid crystal cell 40, and a backlight unit 70.

The liquid crystal cell 40 may have any driving mode. Examples of the driving mode include twisted nematic (TN), super twisted nematic (STN), in-plane switching (IPS), optically compensated birefringence (OCB), vertical alignment (VA) (including multi-domain vertical alignment (MVA) and patterned vertical alignment (PVA)), and hybrid aligned nematic (HAN) modes. A VA (MVA or PVA) mode is preferred for achieving high contract.

A VA-mode liquid crystal cell includes a pair of transparent substrates and a liquid crystal layer disposed therebetween.

One of the transparent substrates is provided with a pixel electrode for applying voltage to liquid crystal molecules. A counter electrode may be disposed on the transparent substrate having the pixel electrode or on the other transparent substrate.

The liquid crystal layer contains liquid crystal molecules having negative or positive dielectric anisotropy. If no electric field is generated between the pixel electrode and the counter electrode without application of voltage, liquid crystal molecules are oriented such that the major axes thereof are substantially perpendicular to the surface of the transparent substrate by the orientation restricting force of an orientation film provided on the surface of the transparent substrate facing the liquid crystal layer.

In the liquid crystal cell having the aforementioned configuration, an electric field is generated between the pixel electrode and the counter electrode through application, to the pixel electrode, of a voltage corresponding to a pixel signal, whereby liquid crystal molecules oriented perpendicular to the surface of the transparent substrate are oriented such that the major axes thereof are parallel to the surface of the transparent substrate. Thus, an image is displayed by driving the liquid crystal layer to control the transmittance and reflectance of sub-pixels.

The polarizing plate 50, which is disposed on the viewing side V, includes a polarizer 52 and protective films 54 and 56 sandwiching the polarizer 52.

The polarizing plate 60, which is disposed adjacent to the backlight unit 70, includes a polarizer 62 and protective films 64 and 66 sandwiching the polarizer 62. One of the protective films 56 and 64 may optionally be omitted.

Any of the protective films 54, 56, 64, and 66 may be the optical film of the present invention.

<Optical Lens>

The resin composition of the present invention can be used in an optical lens. The optical lens is composed of a hygroscopic resin. Examples of preferred hygroscopic resins include acrylic resins (e.g., poly(methyl methacrylate)), polyesters (e.g., poly(ethylene terephthalate)), polyamides (e.g., nylon), polycarbonates, and cellulose derivatives (e.g., cellulose acetate and ethyl cellulose). Particularly preferred are acrylic resins or cellulose derivatives.

EXAMPLES

The present invention will now be described in more detail by way of Examples, which should not be construed as limiting the invention thereto. Unless otherwise specified, "part(s)" and "%" in Examples denote "part(s) by mass" and "mass %," respectively.

Example 1

Various mixtures were prepared as described below, and the CH/π interaction between an additive N according to the present invention and a hygroscopic resin was examined.

<Preparation of Mixture 1>

Cellulose acetate resin (degree of acetylation: 2.4, number average molecular weight: 200,000) (0.1 g) and tetramethylsilane (3 drops) were completely dissolved in deuterated acetone (1 mL) under stirring at room temperature for 12 hours.

<Preparation of Mixture 2>

Cellulose acetate resin (degree of acetylation: 2.4, number average molecular weight: 200,000) (0.1 g), acetic acid (0.1 g), and tetramethylsilane (3 drops) were completely dissolved in deuterated acetone (1 mL) under stirring at room temperature for 12 hours.

<Preparation of Mixture 3>

Cellulose acetate resin (degree of acetylation: 2.4, number average molecular weight: 200,000) (0.1 g), triethylamine (0.1 g), and tetramethylsilane (3 drops) were completely dissolved in deuterated acetone (1 mL) under stirring at room temperature for 12 hours.

<Preparation of Mixture 4>

Cellulose acetate resin (degree of acetylation: 2.4, number average molecular weight: 200,000) (0.1 g), exemplary compound 6 (0.1 g), and tetramethylsilane (3 drops) were completely dissolved in deuterated acetone (1 mL) under stirring at room temperature for 12 hours.

<$^1$H-NMR Spectrometry>

The results of $^1$H-NMR spectrometry of mixtures 1 to 4 are described below. $^1$H-NMR chemical shifts were determined relative to tetramethylsilane serving as an internal standard (0 ppm).

$^1$H-NMR spectrometry was performed with Lambda 400 (manufactured by JEOL Ltd.) at 400 MHz. The results are shown in FIGS. 5A to 5D. Specifically, FIGS. 5A to 5D are $^1$H-NMR spectra (each illustrating a CH/π bonding) of mixtures 1 to 4, respectively.

Figure 5A:
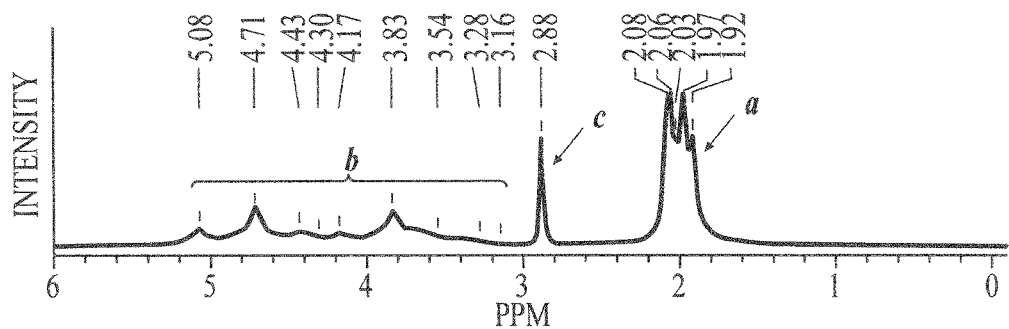
FIG. 5A is a $^1$H-NMR spectrum of comparative mixture 1 showing an example of CH/π bonding.

Referring to FIG. 5A, in the case of comparative mixture 1 containing only the resin, peaks (a) in a range of 1.92 to 2.08 ppm are attributed to the $CH_3$ protons of the acetyl group of cellulose acetate, and peaks b in a range of 3.16 to 5.08 ppm are attributed to the protons on the carbon atoms of a glucose skeleton.

Figure 5B:
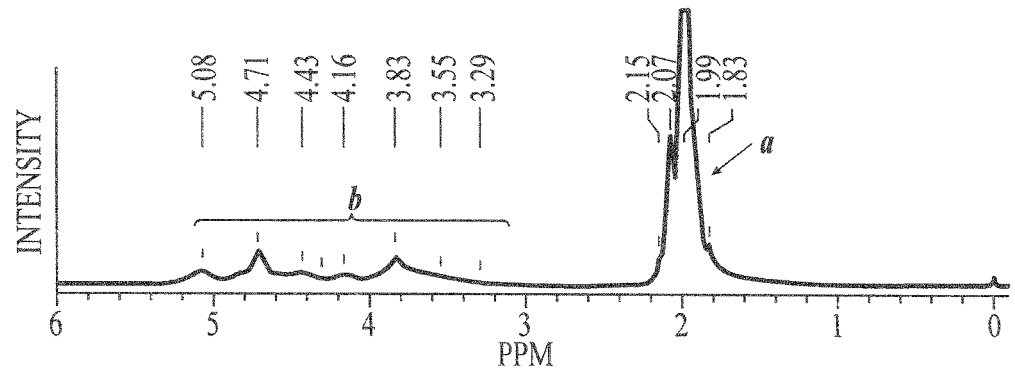
FIG. 5B is a $^1$H-NMR spectrum of comparative mixture 2 showing an example of CH/π bonding.
Figure 5C:
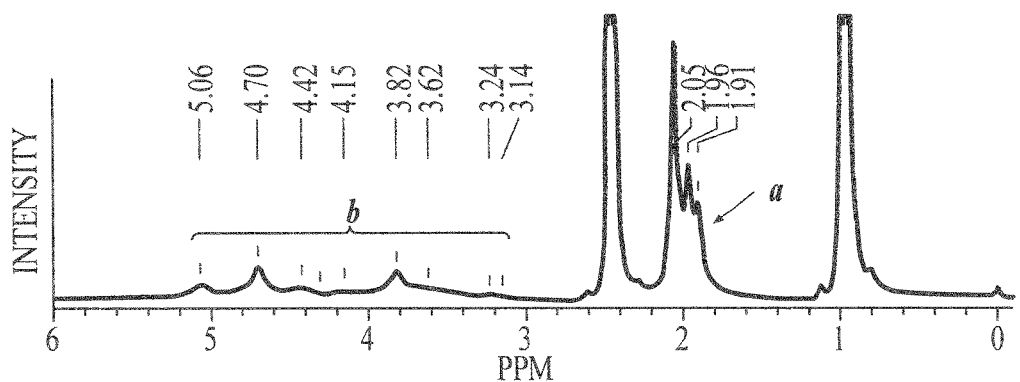
FIG. 5C is a $^1$H-NMR spectrum of comparative mixture 3 showing an example of CH/π bonding.
Figure 5D:
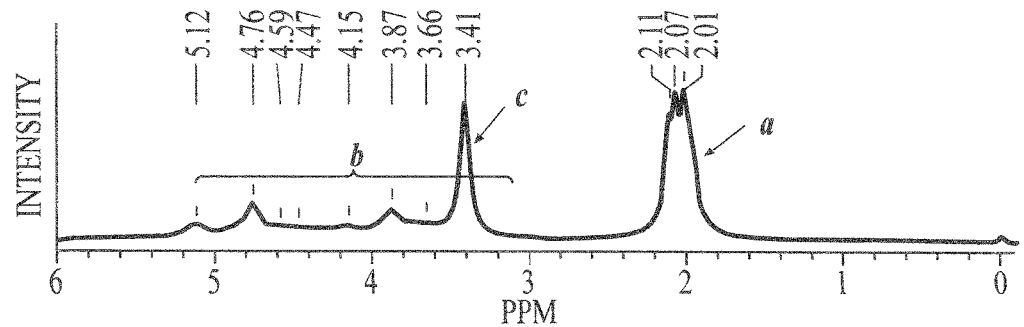
FIG. 5D is a $^1$H-NMR spectrum of mixture 4 showing an example of CH/π bonding.

In the case of comparative mixture 2 containing acetic acid (i.e., a hydrogen donor) or comparative mixture 3 containing triethylamine (i.e., a hydrogen acceptor), the chemical shifts of the protons in the cellulose acetate resin are substantially the same as those observed in comparative mixture 1 (i.e., reference) (see FIGS. 5B and 5C). In contrast, in the case of mixture 4 containing exemplary compound 6 according to the present invention, peaks a and b attributed to the protons in the cellulose acetate resin are chemically shifted to a lower magnetic field as compared with the case of mixture 1 (see FIG. 5D). This indicates that exemplary compound 6 according to the invention is present adjacent to the cellulose acetate resin by the CH/π interaction between the compound and the resin.

Peak c shown in FIGS. 5A to 5D is attributed to the protons of water.

Example 2

[Preparation of Optical Film 101]

The following components were mixed under stirring in a dissolver for 50 minutes, and the mixture was then treated with a Manton-Gaulin homogenizer, to prepare a fine particle dispersion.

| (Fine particle dispersion) | |
|---|---|
| Fine particles (Aerosil R972V, manufactured by Nippon Aerosil Co., Ltd.) | 11 parts by mass |
| Ethanol | 89 parts by mass |

Methylene chloride contained in the fine particle-added mixture shown below was placed into a solution tank, and the above-prepared fine particle dispersion was slowly added thereto in an amount described below under thorough stirring. Subsequently, the mixture was treated with an attritor such that secondary particles had a specific size, followed by filtration with Finemet NF (manufactured by Nippon Seisen Co., Ltd.), to prepare a fine particle-added mixture.

| (Fine particle-added mixture) | |
|---|---|
| Methylene chloride | 99 parts by mass |
| Fine particle dispersion | 5 parts by mass |

Methylene chloride and ethanol contained in the main dope shown below were placed into a pressure solution tank. Subsequently, cellulose derivative C1, sugar ester S, exemplary compound 1, and the above-prepared fine particle-added mixture were added to the tank under stirring, and these components were completely dissolved in the solvent under heating and stirring. The resultant solution was filtered with paper filter No. 244 (manufactured by Azumi Filter Paper Co., Ltd.), to prepare a main dope.

| (Formulation of main dope) | |
|---|---|
| Methylene chloride | 520 parts by mass |
| Ethanol | 45 parts by mass |
| Cellulose derivative C1 | 100 parts by mass |
| Sugar ester S | 5 parts by mass |
| Exemplary compound 1 (compound represented by Formula (1)) | 3 parts by mass |
| Fine particle-added mixture | 1 part by mass |

Now will be described the structure of sugar ester S added as a plasticizer.

[F101]

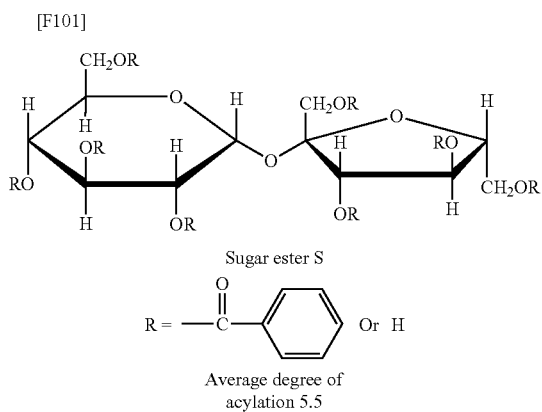

Sugar ester S

Average degree of acylation 5.5

The dope was uniformly cast onto a stainless steel belt support with an endless belt casting apparatus. The solvent contained in the cast dope was evaporated on the stainless steel belt support, into a residual solvent content of 75%. The resultant web was detached from the stainless steel belt support. The web was conveyed while being held with clips of a tenter stretching apparatus. Subsequently, the film was dried while being conveyed with multiple rollers in a drying zone. The transverse edges of the film held with the tenter clips were trimmed by slitting with a laser cutter, and the raw film was then wound on a roller.

The web unwound from the roller was stretched in the transverse direction at a temperature 20° C. higher than the glass transition temperature Tg of the raw film and a draw ratio of 1.35, to prepare optical film 101 having a thickness of 50 μm.

[Preparation of Optical Films 102 to 209]

Optical films 102 to 209 were prepared in the same manner as in optical film 1, except that the type and amount of a cellulose derivative added, the type and amount of another resin added, the type and amount of a plasticizer (e.g., a sugar ester) added, the type of a compound represented by Formula (1) or a comparative compound, the draw ratio of a web, and the thickness of a stretched optical film were modified as shown in Tables 3 to 5. The thickness of each optical film was adjusted by control of the casting rate of the dope.

Optical films 190 to 193 were prepared without stretching.

For preparation of optical films 201 to 207, the raw film was stretched in a direction inclined by 45° relative to the machine direction at a temperature 20° C. higher than the glass transition temperature Tg of the web and a draw ratio of 2.2. Optical film 1 had a thickness of 30 μm. The angle between the in-plane slow axis of each of optical films 201 to 207 and the machine direction was 45°.

Table 2 details cellulose derivatives used.

TABLE 2

| | Cellulose derivative | Number average molecular weight (Mn) |
|---|---|---|
| C 1 | Cellulose acetate (Degree of acetylation: 2.41) | 56000 |
| C 2 | Cellulose acetate propionate (Degree of acetylation: 1.56, Degree of propionylation: 0.9, Total of acylation: 2.46) | 64000 |
| C 3 | Cellulose acetate butyrate (Degree of acetylation: 1.63, Degree of butyrylation: 0.9, Total degree of acylation: 2.53) | 66000 |
| C 4 | Cellulose acetate (Degree of acetylation: 2.87) | 75000 |
| C 5 | Ethyl cellulose (Degree of ethylation: 2.35) | 46000 |
| C 6 | Cellulose acetate propionate (Degree of acetylation: 0.12, Degree of propionylation: 1.53, Total degree of acylation: 1.65) | 55000 |
| C 7 | Cellulose acetate propionate (Degree of acetylation: 1.95, Degree of propionylation: 0.71, Total degree of acylation: 2.66) | 78000 |
| C 8 | Cellulose acetate propionate (Degree of acetylation: 0.19, Degree of propionylation: 2.56, Total degree of acylation: 2.75) | 80000 |

Now will be described the chemical structures of comparative compounds shown in Tables 3 to 7.

[F102]

Polyster compound A1

Comparative compound 1

Aromatic-terminal ester compound P1

Comparative compound 2

Comparative compound 3

Comparative compound 4

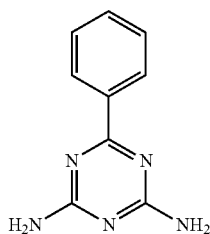

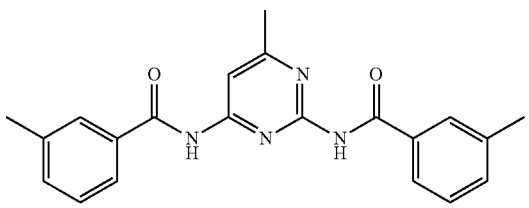

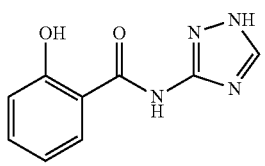

Comparative compound 5

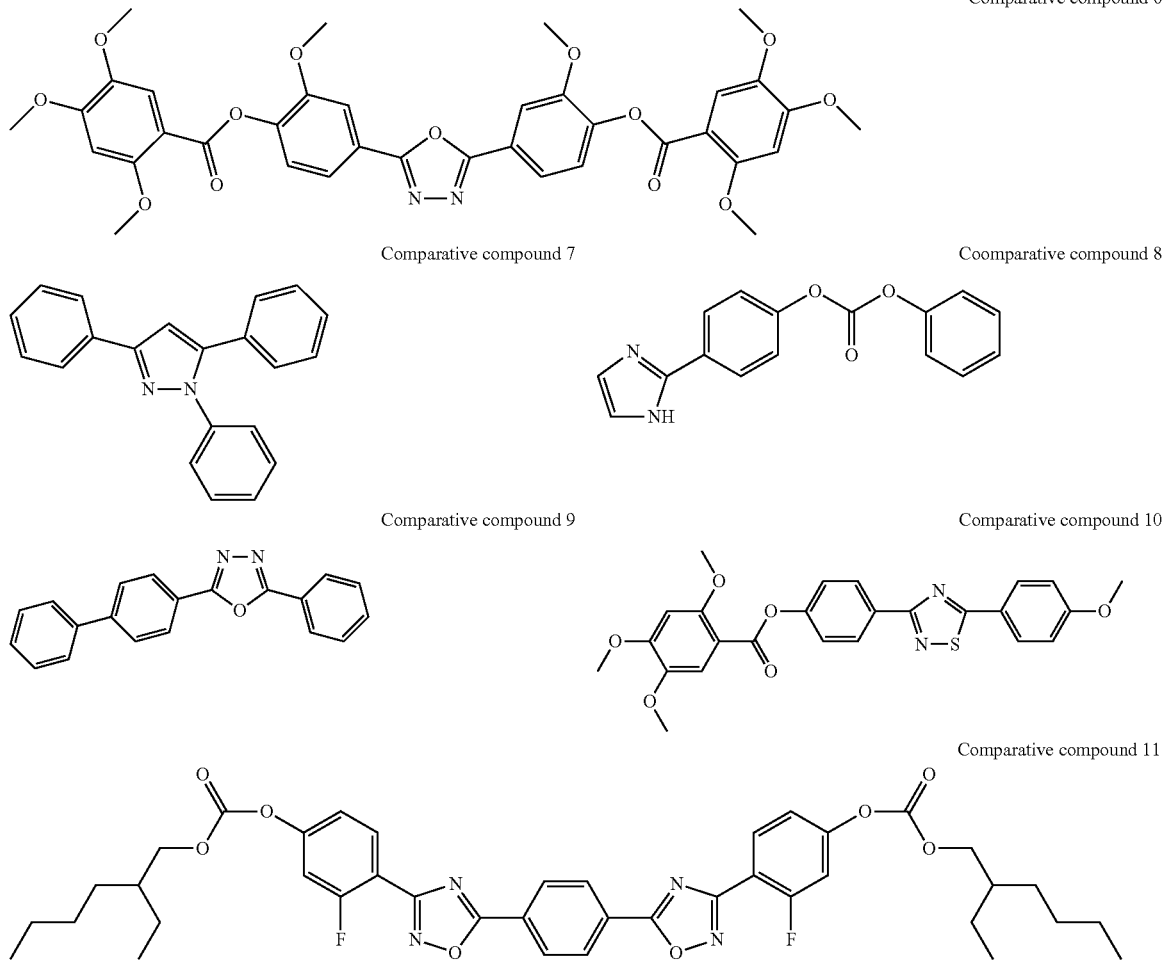

(Synthesis of Polyester Compound A1)

Ethylene glycol (236 parts by mass), 1,4-butylene glycol (683 parts by mass), succinic acid (1,180 parts by mass), and tetrabutyl titanate (0.03 parts by mass) were placed into a reactor equipped with a cooling condenser. The resultant mixture was subjected to dehydration condensation at 140° C. for two hours and at 220° C. for two hours. After removal of the cooling condenser, the mixture was further subjected to dehydration condensation at 220° C. for 20 hours, to yield polyester (A1) having a number average molecular weight of 2,000. The average number of carbon atoms of the glycols was 3.33, and the number of carbon atoms of the dibasic acid was 4.

(Synthesis of Aromatic-Terminal Ester Compound P1)

Phthalic acid (410 parts), benzoic acid (610 parts), dipropylene glycol (737 parts), and tetraisopropyl titanate (0.40 parts) serving as a catalyst were placed into a reactor equipped with a reflux condenser. While excess monohydric alcohol was refluxed with stirring in a stream of nitrogen, the generated water was continuously removed under heating at 130 to 250° C., into an acid value of 2 or less. Subsequently, the distillate was removed at 200 to 230° C. under reduced pressure (100 MPa to 4.00 MPa or less), followed by filtration, to yield an aromatic-terminal polyester having the following properties:

Viscosity (25° C., mPa·s): 43,400
Acid value: 0.2 mg KOH/g (Synthesis of Aromatic-Terminal Ester Compound P2)

1,2-Propylene glycol (251 g), phthalic anhydride (278 g), adipic acid (91 g), benzoic acid (610 g), and tetraisopropyl titanate (0.191 g) serving as an esterification catalyst were placed into a 2-L four-neck flask equipped with a thermometer, an agitator, a slow cooling tube, and a rapid cooling tube. The resultant mixture was gradually heated to 230° C. with stirring in a stream of nitrogen. After dehydration condensation for 15 hours, unreacted 1,2-propylene glycol was distilled off at 200° C. under reduced pressure, to yield aromatic-terminal ester compound P2 having an acid value of 0.10 and a number average molecular weight of 450.

(Synthesis of Aromatic-Terminal Ester Compound P3)

1,2-Propylene glycol (251 g), terephthalic acid (354 g), benzoic acid (610 g), and tetraisopropyl titanate (0.191 g) serving as an esterification catalyst were placed into a 2-L four-neck flask equipped with a thermometer, an agitator, a slow cooling tube, and a rapid cooling tube. The resultant mixture was gradually heated to 230° C. with stirring in a stream of nitrogen. After dehydration condensation for 15 hours, unreacted 1,2-propylene glycol was distilled off at 200° C. under reduced pressure, to yield aromatic-terminal ester compound P3 having an acid value of 0.10 and a number average molecular weight of 400.

<<Evaluation of Optical Film>>

The above-prepared optical films were evaluated for properties described below.

(Determination of Retardation Value)

The retardation values Ro and Rt of each optical film calculated by the following expressions were determined with an automatic birefringence analyzer (KOBRA-21ADH, manufactured by Oji Scientific Instruments) at 23° C., 55% RH, and a light wavelength of 590 nm.

Specifically, three-dimensional refractive indices of the optical film were measured at 10 points at 23° C., 55% RH, and a light wavelength of 590 nm, and the averages of the refractive indices $n_x$, $n_y$, and $n_z$ were determined. Thereafter, the in-plane retardation value Ro and the retardation value Rt across the thickness of the film were calculated by the following expressions:

$$Ro(590)=(n_x-n_y)\times d \quad \text{Expression (I)}$$

$$Rt(590)=\{(n_x+n_y)/2-n_z\}\times d \quad \text{Expression (II)}$$

wherein $n_x$ represents a refractive index in a direction x in which the refractive index is maximum in the in-plane direction of the film; $n_y$ represents a refractive index in a direction y orthogonal to the direction x in the in-plane direction of the film; $n_z$ represents a refractive index in a thickness direction z of the film; and d represents the thickness (nm) of the film.

(Determination of Variation in Retardation Value in Association with Change in Humidity)

(Determination of Variation in Retardation Value Caused by Water Immersion)

A variation in retardation value in association with a change in humidity was determined as described below. The following procedure was performed at 23° C. and 55% RH.

1. An optical film was disposed between two glass slides, and the retardation values Ro1 and Rt1 of the film were determined in this state.

2. The optical film was immersed in pure water for 24 hours, and the humidified optical film was then quickly disposed between two glass slides such that no bubbles entered between each glass slide and the film. The retardation values Ro2 and Rt2 of the film were determined in this state.

3. The variations in retardation value (ΔRo and ΔRt) of the optical film immersed in pure water at 23° C. for 24 hours were calculated from the retardation values Ro1, Rt1, Ro2, and Rt2 determined above in 1 and 2. The variation ΔRo or ΔRt, which is the absolute value of the difference between Ro1 and Ro2 or between Rt1 and Rt2, was calculated by the following expressions:

$$\Delta Ro=|Ro1-Ro2|$$

$$\Delta Rt=|Rt1-Rt2|$$

The effect of the compound of the present invention or a comparative compound in reducing a variation in retardation value was evaluated on the basis of percent reduction of a variation (%) determined by the following expressions:

Percent reduction of a variation in Ro (%)={[(ΔRo of a reference film)−(ΔRo of a sample film)]÷(ΔRo of the reference film)}×100

Percent reduction of a variation in Rt (%)={[(ΔRt of the reference film)−(ΔRt of the sample film)]÷(ΔRt of the reference film)}×100

The effect of the compound according to the present invention or a comparative compound in reducing a variation in retardation value was evaluated on the basis of percent reduction of a variation (%) determined by the aforementioned expressions.

The effect of an additive on a reduced variation in retardation value is evaluated on the basis of percent reduction of a variation in Ro or Rt upon addition of the additive in an amount of 3 parts by mass relative to 100 parts by mass of a resin used as a base material. The percent reduction of a variation in Ro or Rt is preferably 20% or more, more preferably 50% or more. Particularly preferred is that both the percent reduction of a variation in Ro and the percent reduction of a variation in Rt are 70% or more.

Tables 3 to 7 show the results. Abbreviations described in the Tables are as follows:

PMMA1: poly(methyl methacrylate) (weight average molecular weight: 280,000)

PMMA2: poly(methyl methacrylate) (weight average molecular weight: 2,500)

P2: aromatic-terminal ester compound P2

P3: aromatic-terminal ester compound P3

Comparative 1: comparative compound 1 (polyester compound A1)

Comparative 2: comparative compound 2 (aromatic terminal ester compound P1)

Comparative 3: comparative compound 3

Comparative 4: comparative compound 4

Comparative 5: comparative compound 5

Comparative 6: comparative compound 6

Comparative 7: comparative compound 7

Comparative 8: comparative compound 8

Comparative 9: comparative compound 9

Comparative 10: comparative compound 10

Comparative 11: comparative compound 11

In the Tables, numerals shown in the column "compound represented by Formula (1)" correspond to reference numerals of exemplary compounds 1 to 695 described in [F15] to [F89].

The water absorptions of hygroscopic resins used in Examples are described below. The water absorption of each hygroscopic resin was determined by the aforementioned method on the basis of the mass after immersion of the resin in distilled water at 23° C. for 24 hours.

C1: 5.5%, C2: 5.0%, C3: 4.5%, C4: 3.5%, C5: 2.5%, C6: 6.3%, C7: 4.5%, C8: 4.0%, PMMA1: 0.8%

TABLE 3

| | Cellulose derivative | | Another resin | | Plasticizer | | Compound represented by Formula (1) or comparative compound | | Production process | |
|---|---|---|---|---|---|---|---|---|---|---|
| Optical film No. | Type | Amount (parts by mass) | Type | Amount (parts by mass) | Type | Amount (parts by mass) | Type | Amount (parts by mass) | Draw ratio | Thickness (μm) |
| 101 | C 1 | 100 | None | — | Sugar ester S | 5 | 1 | 3 | 1.35 | 50 |
| 102 | C 1 | 100 | None | — | Sugar ester S | 5 | 1 | 6 | 1.35 | 50 |

TABLE 3-continued

| | | | | | | | | | | |
|---|---|---|---|---|---|---|---|---|---|---|
| 103 | C 1 | 100 | None | — | Sugar ester S | 5 | 2 | 3 | 1.35 | 50 |
| 104 | C 1 | 100 | None | — | Sugar ester S | 5 | 3 | 3 | 1.35 | 50 |
| 105 | C 1 | 100 | None | — | Sugar ester S | 5 | 4 | 3 | 1.35 | 50 |
| 106 | C 1 | 100 | None | — | Sugar ester S | 5 | 5 | 3 | 1.35 | 50 |
| 107 | C 1 | 100 | None | — | Sugar ester S | 5 | 6 | 3 | 1.35 | 50 |
| 108 | C 1 | 100 | None | — | Sugar ester S | 5 | 6 | 1 | 1.35 | 50 |
| 109 | C 1 | 100 | None | — | Sugar ester S | 5 | 7 | 3 | 1.35 | 50 |
| 110 | C 1 | 100 | None | — | Sugar ester S | 5 | 8 | 3 | 1.35 | 50 |
| 111 | C 1 | 100 | None | — | Sugar ester S | 5 | 9 | 3 | 1.35 | 50 |
| 112 | C 1 | 100 | None | — | Sugar ester S | 5 | 10 | 1 | 1.35 | 50 |
| 113 | C 1 | 100 | None | — | Sugar ester S | 5 | 11 | 3 | 1.35 | 50 |
| 114 | C 1 | 100 | None | — | Sugar ester S | 5 | 12 | 3 | 1.35 | 50 |
| 115 | C 1 | 100 | None | — | Sugar ester S | 5 | 200 | 3 | 1.35 | 50 |
| 116 | C 1 | 100 | None | — | Sugar ester S | 5 | 172 | 3 | 1.35 | 50 |
| 117 | C 1 | 100 | None | — | Sugar ester S | 5 | 176 | 1 | 1.35 | 50 |
| 118 | C 1 | 100 | None | — | Sugar ester S | 5 | 176 | 3 | 1.35 | 50 |
| 119 | C 1 | 100 | None | — | Sugar ester S | 5 | 223 | 3 | 1.35 | 50 |
| 120 | C 1 | 100 | None | — | Sugar ester S | 5 | 204 | 3 | 1.35 | 50 |
| 121 | C 1 | 100 | None | — | Sugar ester S | 5 | 233 | 3 | 1.35 | 50 |
| 122 | C 1 | 100 | None | — | Sugar ester S | 5 | 236 | 3 | 1.35 | 50 |
| 123 | C 1 | 100 | None | — | Sugar ester S | 5 | 250 | 3 | 1.35 | 50 |
| 124 | C 1 | 100 | None | — | Sugar ester S | 5 | 254 | 3 | 1.35 | 50 |
| 125 | C 1 | 100 | None | — | Sugar ester S | 5 | 547 | 3 | 1.35 | 50 |

| | Optical properties of film | | | | | | |
|---|---|---|---|---|---|---|---|
| Optical film No. | Ro (nm) | Rt (nm) | ΔRo (nm) | ΔRt (nm) | Percent reduction of variation Ro(%) | Rt(%) | Note |
| 101 | 66 | 155 | 4 | 10 | 69 | 71 | Inventive sample |
| 102 | 76 | 170 | 2 | 3 | 85 | 91 | Inventive sample |
| 103 | 64 | 154 | 9 | 20 | 31 | 43 | Inventive sample |
| 104 | 59 | 147 | 10 | 24 | 23 | 31 | Inventive sample |
| 105 | 62 | 157 | 4 | 11 | 69 | 69 | Inventive sample |
| 106 | 61 | 150 | 10 | 22 | 23 | 37 | Inventive sample |
| 107 | 80 | 179 | 0 | 1 | 100 | 97 | Inventive sample |
| 108 | 69 | 158 | 4 | 12 | 69 | 66 | Inventive sample |
| 109 | 79 | 188 | 0 | 1 | 100 | 97 | Inventive sample |
| 110 | 66 | 168 | 3 | 5 | 77 | 86 | Inventive sample |
| 111 | 63 | 164 | 2 | 3 | 85 | 91 | Inventive sample |
| 112 | 68 | 160 | 4 | 10 | 69 | 71 | Inventive sample |
| 113 | 73 | 169 | 3 | 6 | 77 | 83 | Inventive sample |
| 114 | 76 | 175 | 3 | 6 | 77 | 83 | Inventive sample |
| 115 | 67 | 158 | 3 | 9 | 77 | 74 | Inventive sample |
| 116 | 69 | 158 | 3 | 9 | 77 | 74 | Inventive sample |
| 117 | 67 | 156 | 3 | 10 | 77 | 71 | Inventive sample |
| 118 | 81 | 182 | 0 | 0 | 100 | 100 | Inventive sample |
| 119 | 70 | 165 | 7 | 14 | 46 | 60 | Inventive sample |
| 120 | 63 | 152 | 4 | 10 | 69 | 71 | Inventive sample |
| 121 | 62 | 145 | 8 | 18 | 38 | 49 | Inventive sample |
| 122 | 70 | 165 | 3 | 5 | 77 | 86 | Inventive sample |
| 123 | 71 | 168 | 3 | 5 | 77 | 86 | Inventive sample |
| 124 | 66 | 165 | 3 | 6 | 77 | 83 | Inventive sample |
| 125 | 68 | 160 | 4 | 7 | 69 | 80 | Inventive sample |

TABLE 4

| | Cellulose derivative | | Another resin | | Plasticizer | | Compound represented by Formula (1) or comparative compound | | Production process | |
|---|---|---|---|---|---|---|---|---|---|---|
| Optical film No. | Type | Amount (parts by mass) | Type | Amount (parts by mass) | Type | Amount (parts by mass) | Type | Amount (parts by mass) | Draw ratio | Thickness (μm) |
| 126 | C 1 | 100 | None | — | Sugar ester S | 5 | 546 | 3 | 1.35 | 50 |
| 127 | C 1 | 100 | None | — | Sugar ester S | 5 | 265 | 3 | 1.35 | 50 |
| 128 | C 1 | 100 | None | — | Sugar ester S | 5 | 416 | 3 | 1.35 | 50 |
| 129 | C 1 | 100 | None | — | Sugar ester S | 5 | 270 | 3 | 1.35 | 50 |
| 130 | C 1 | 100 | None | — | Sugar ester S | 5 | 566 | 3 | 1.35 | 50 |
| 131 | C 1 | 100 | None | — | Sugar ester S | 5 | 421 | 3 | 1.35 | 50 |
| 132 | C 1 | 100 | None | — | Sugar ester S | 5 | 557 | 3 | 1.35 | 50 |
| 133 | C 1 | 100 | None | — | Sugar ester S | 5 | 277 | 3 | 1.35 | 50 |
| 134 | C 1 | 100 | None | — | Sugar ester S | 5 | 279 | 3 | 1.35 | 50 |

TABLE 4-continued

| | | | | | | | | | | |
|---|---|---|---|---|---|---|---|---|---|---|
| 135 | C 1 | 100 | None | — | Sugar ester S | 5 | 430 | 3 | 1.35 | 50 |
| 136 | C 1 | 100 | None | — | Sugar ester S | 5 | 575 | 3 | 1.35 | 50 |
| 137 | C 1 | 100 | None | — | Sugar ester S | 5 | 579 | 3 | 1.35 | 50 |
| 138 | C 1 | 100 | None | — | Sugar ester S | 5 | 284 | 3 | 1.35 | 50 |
| 139 | C 1 | 100 | None | — | Sugar ester S | 5 | 584 | 3 | 1.35 | 50 |
| 140 | C 1 | 100 | None | — | Sugar ester S | 5 | 307 | 3 | 1.35 | 50 |
| 141 | C 1 | 100 | None | — | Sugar ester S | 5 | 328 | 3 | 1.35 | 50 |
| 142 | C 1 | 100 | None | — | Sugar ester S | 5 | 330 | 3 | 1.35 | 50 |
| 143 | C 1 | 100 | None | — | Sugar ester S | 5 | 624 | 3 | 1.35 | 50 |
| 144 | C 1 | 100 | None | — | Sugar ester S | 5 | 479 | 3 | 1.35 | 50 |
| 145 | C 1 | 100 | None | — | Sugar ester S | 5 | 490 | 3 | 1.35 | 50 |
| 146 | C 1 | 100 | None | — | Sugar ester S | 5 | 363 | 3 | 1.35 | 50 |
| 147 | C 1 | 100 | None | — | Sugar ester S | 5 | 378 | 3 | 1.35 | 50 |
| 148 | C 1 | 100 | None | — | Sugar ester S | 5 | 519 | 3 | 1.35 | 50 |
| 149 | C 1 | 100 | None | — | Sugar ester S | 5 | 447 | 3 | 1.35 | 50 |
| 150 | C 1 | 100 | None | — | Sugar ester S | 5 | 465 | 3 | 1.35 | 50 |

| | Optical properties of film | | | | | | |
|---|---|---|---|---|---|---|---|
| Optical film No. | Ro (nm) | Rt (nm) | ΔRo (nm) | ΔRt (nm) | Percent reduction of variation Ro(%) | Rt(%) | Note |
| 126 | 64 | 168 | 4 | 8 | 69 | 77 | Inventive sample |
| 127 | 72 | 170 | 3 | 5 | 77 | 86 | Inventive sample |
| 128 | 67 | 167 | 4 | 6 | 69 | 83 | Inventive sample |
| 129 | 68 | 170 | 3 | 5 | 77 | 86 | Inventive sample |
| 130 | 59 | 164 | 5 | 8 | 62 | 77 | Inventive sample |
| 131 | 66 | 166 | 4 | 6 | 69 | 83 | Inventive sample |
| 132 | 68 | 168 | 4 | 6 | 69 | 83 | Inventive sample |
| 133 | 69 | 170 | 2 | 4 | 85 | 89 | Inventive sample |
| 134 | 76 | 178 | 1 | 1 | 92 | 97 | Inventive sample |
| 135 | 64 | 164 | 4 | 5 | 69 | 86 | Inventive sample |
| 136 | 74 | 175 | 4 | 5 | 69 | 86 | Inventive sample |
| 137 | 80 | 180 | 3 | 5 | 77 | 86 | Inventive sample |
| 138 | 76 | 176 | 3 | 4 | 77 | 89 | Inventive sample |
| 139 | 73 | 173 | 4 | 6 | 69 | 83 | Inventive sample |
| 140 | 77 | 176 | 2 | 2 | 85 | 94 | Inventive sample |
| 141 | 80 | 180 | 1 | 1 | 92 | 97 | Inventive sample |
| 142 | 78 | 179 | 1 | 1 | 92 | 97 | Inventive sample |
| 143 | 74 | 174 | 3 | 4 | 77 | 89 | Inventive sample |
| 144 | 73 | 172 | 3 | 5 | 77 | 86 | Inventive sample |
| 145 | 80 | 179 | 1 | 1 | 92 | 97 | Inventive sample |
| 146 | 76 | 175 | 1 | 1 | 92 | 97 | Inventive sample |
| 147 | 80 | 179 | 0 | 1 | 100 | 97 | Inventive sample |
| 148 | 73 | 170 | 3 | 5 | 77 | 86 | Inventive sample |
| 149 | 77 | 177 | 1 | 1 | 92 | 97 | Inventive sample |
| 150 | 73 | 176 | 0 | 2 | 100 | 94 | Inventive sample |

TABLE 5

| Optical film No. | Cellulose derivative | | Another resin | | Another resin | | Compound represented by Formula (1) or comparative compound | | Production process | | Optical properties of film | | | | Percent reduction of variation | | Note |
|---|---|---|---|---|---|---|---|---|---|---|---|---|---|---|---|---|---|
| | Type | Amount (parts by mass) | Type | Amount (parts by mass) | Type | Amount (parts by mass) | Type | Amount (parts by mass) | Draw ratio | Thickness (μm) | Ro (nm) | Rt (nm) | ΔRo (nm) | ΔRt (nm) | Ro (%) | Rt (%) | |
| 151 | C 1 | 100 | None | — | | | Sugar ester S | 5 | 481 | 3 | 1.35 | 50 | 70 | 170 | 3 | 4 | 77 | 89 | *1 |
| 152 | C 1 | 100 | None | — | | | Sugar ester S | 5 | 507 | 3 | 1.35 | 50 | 77 | 175 | 0 | 1 | 100 | 97 | *1 |
| 153 | C 1 | 100 | None | — | | | Sugar ester S | 5 | 617 | 3 | 1.35 | 50 | 75 | 175 | 3 | 5 | 77 | 86 | *1 |
| 154 | C 1 | 100 | None | — | | | Sugar ester S | 5 | 627 | 3 | 1.35 | 50 | 68 | 169 | 4 | 7 | 69 | 80 | *1 |
| 155 | C 1 | 100 | None | — | | | Sugar ester S | 5 | 509 | 3 | 1.35 | 50 | 73 | 175 | 1 | 1 | 92 | 97 | *1 |

TABLE 5-continued

| Optical film No. | Cellulose derivative Type | Amount (parts by mass) | Another resin Type | Amount (parts by mass) | Another resin Type | Amount (parts by mass) | Compound represented by Formula (1) or comparative compound Type | Amount (parts by mass) | Production process Draw ratio | Thickness (μm) | Ro (nm) | Rt (nm) | ΔRo (nm) | ΔRt (nm) | Percent reduction of variation Ro (%) | Rt (%) | Note |
|---|---|---|---|---|---|---|---|---|---|---|---|---|---|---|---|---|---|
| 156 | C 1 | 100 | None | — | Sugar ester S | 5 | 387 | 3 | 1.35 | 50 | 77 | 178 | 6 | 8 | 54 | 77 | *1 |
| 157 | C 1 | 100 | None | — | Sugar ester S | 5 | 530 | 3 | 1.35 | 50 | 77 | 177 | 7 | 9 | 46 | 74 | *1 |
| 158 | C 1 | 100 | None | — | Sugar ester S | 5 | 667 | 3 | 1.35 | 50 | 75 | 175 | 7 | 10 | 46 | 71 | *1 |
| 159 | C 1 | 100 | None | — | Sugar ester S | 5 | 402 | 3 | 1.35 | 50 | 73 | 169 | 3 | 5 | 77 | 86 | *1 |
| 160 | C 1 | 100 | None | — | Sugar ester S | 5 | 535 | 3 | 1.35 | 50 | 70 | 170 | 3 | 5 | 77 | 86 | *1 |
| 161 | C 1 | 100 | None | — | Sugar ester S | 5 | 407 | 3 | 1.35 | 50 | 74 | 172 | 2 | 4 | 85 | 89 | *1 |
| 162 | C 1 | 100 | None | — | Sugar ester S | 5 | 397 | 3 | 1.35 | 50 | 78 | 180 | 9 | 20 | 31 | 43 | *1 |
| 163 | C 1 | 100 | None | — | Sugar ester S | 5 | 678 | 3 | 1.35 | 50 | 76 | 176 | 9 | 22 | 31 | 37 | *1 |
| 164 | C 1 | 100 | None | — | Sugar ester S | 5 | 183 | 1 | 1.35 | 50 | 68 | 160 | 4 | 9 | 69 | 74 | *1 |
| 165 | C 1 | 100 | None | — | Sugar ester S | 5 | 693 | 1 | 1.35 | 50 | 67 | 161 | 4 | 9 | 69 | 74 | *1 |
| 166 | C 1 | 100 | None | — | Sugar ester S | 5 | Comparative 1 | 10 | 1.35 | 50 | 64 | 149 | 12 | 32 | 8 | 9 | *2 |
|  |  |  |  |  | Sugar ester S | 5 | Comparative 2 | 5 |  |  |  |  |  |  |  |  |  |
| 167 | C 1 | 100 | None | — | Sugar ester S | 5 | Comparative 3 | 3 | 1.35 | 50 | 65 | 152 | 11 | 30 | 15 | 14 | *2 |
| 168 | C 1 | 100 | None | — | Sugar ester S | 5 | Comparative 4 | 3 | 1.35 | 50 | 71 | 166 | 11 | 30 | 15 | 14 | *2 |
| 169 | C 1 | 100 | None | — | Sugar ester S | 5 | Comparative 5 | 3 | 1.35 | 50 | 58 | 139 | 12 | 34 | 8 | 3 | *2 |
| 170 | C 1 | 100 | None | — | Sugar ester S | 5 | Comparative 6 | 3 | 1.35 | 50 | 74 | 173 | 12 | 33 | 8 | 6 | *2 |
| 171 | C 1 | 100 | None | — | Sugar ester S | 5 | Comparative 7 | 3 | 1.35 | 50 | 62 | 150 | 11 | 30 | 15 | 14 | *2 |
| 172 | C 1 | 100 | None | — | Sugar ester S | 5 | Comparative 8 | 3 | 1.35 | 50 | 62 | 147 | 12 | 33 | 8 | 6 | *2 |
| 173 | C 1 | 100 | None | — | Sugar ester S | 5 | None | — | 1.35 | 50 | 59 | 145 | 13 | 35 | *3 | *3 | *2 |
| 174 | C 1 | 100 | None | — | Sugar ester S | 10 | 1 | 4 | 1.35 | 50 | 50 | 130 | 3 | 7 | 67 | 72 | *1 |

*1: Inventive sample
*2: Comparative sample
*3: Reference

TABLE 6

| Optical film No. | Cellulose derivative Type | Cellulose derivative Amount (parts by mass) | Another resin Type | Another resin Amount (parts by mass) | Plasticizer Type | Plasticizer Amount (parts by mass) | Compound represented by Formula (1) or comparative compound Type | Compound represented by Formula (1) or comparative compound Amount (parts by mass) | Production process Draw ratio | Thickness (μm) |
|---|---|---|---|---|---|---|---|---|---|---|
| 175 | C 1 | 100 | None | — | Sugar ester S | 10 | 6 | 4 | 1.35 | 35 |
| 176 | C 1 | 100 | None | — | Sugar ester S | 10 | None | — | 1.35 | 35 |
| 177 | C 1 | 100 | None | — | Sugar ester S | 8 | 1 | 4 | 1.35 | 35 |
|     |     |     |      |   | P 2 | 2 |   |   |      |    |
| 178 | C 1 | 100 | None | — | Sugar ester S | 8 | None | 0 | 1.35 | 35 |
|     |     |     |      |   | P 2 | 2 |   |   |      |    |
| 179 | C 1 | 100 | None | — | Sugar ester S | 8 | 1 | 4 | 1.35 | 35 |
|     |     |     |      |   | P 3 | 2 |   |   |      |    |
| 180 | C 1 | 100 | None | — | Sugar ester S | 8 | None | 0 | 1.35 | 35 |
|     |     |     |      |   | P 3 | 2 |   |   |      |    |
| 181 | C 1 | 100 | None | — | Sugar ester S | 6 | 1 | 4 | 1.35 | 35 |
|     |     |     |      |   | P 2 | 4 |   |   |      |    |
| 182 | C 1 | 100 | None | — | Sugar ester S | 6 | None | 0 | 1.35 | 35 |
|     |     |     |      |   | P 2 | 4 |   |   |      |    |
| 183 | C 1 | 100 | None | — | Sugar ester S | 6 | 1 | 4 | 1.35 | 35 |
|     |     |     |      |   | P 3 | 4 |   |   |      |    |
| 184 | C 1 | 100 | None | — | Sugar ester S | 6 | None | 0 | 1.35 | 35 |
|     |     |     |      |   | P 3 | 4 |   |   |      |    |
| 185 | C 2 | 100 | None | — | Sugar ester S | 5 | 6 | 3 | 1.35 | 50 |
| 186 | C 2 | 100 | None | — | Sugar ester S | 5 | Comparative 4 | 3 | 1.35 | 50 |
| 187 | C 2 | 100 | None | — | Sugar ester S | 5 | None | — | 1.35 | 50 |
| 188 | C 3 | 100 | None | — | Sugar ester S | 5 | 6 | 3 | 1.35 | 50 |
| 189 | C 3 | 100 | None | — | Sugar ester S | 5 | None | — | 1.35 | 50 |
| 190 | C 4 | 100 | None | — | Sugar ester S | 5 | 1 | 3 | 1.00 | 60 |
| 191 | C 4 | 100 | None | — | Sugar ester S | 5 | None | — | 1.00 | 60 |

| Optical film No. | Ro (nm) | Rt (nm) | ΔRo (nm) | ΔRt (nm) | Percent reduction of variation Ro(%) | Percent reduction of variation Rt(%) | Note |
|---|---|---|---|---|---|---|---|
| 175 | 56 | 139 | 0 | 1 | 100 | 96 | *1 |
| 176 | 44 | 115 | 9 | 25 | *3 | *3 | *2 |
| 177 | 52 | 130 | 4 | 8 | 60 | 68 | *1 |
| 178 | 44 | 115 | 10 | 25 | *3 | *3 | *2 |
| 179 | 54 | 125 | 3 | 7 | 67 | 72 | *1 |
| 180 | 44 | 115 | 9 | 25 | *3 | *3 | *2 |
| 181 | 51 | 127 | 3 | 8 | 67 | 67 | *1 |
| 182 | 44 | 115 | 9 | 24 | *3 | *3 | *2 |
| 183 | 54 | 125 | 3 | 6 | 67 | 75 | *1 |
| 184 | 44 | 115 | 9 | 24 | *3 | *3 | *2 |
| 185 | 65 | 168 | 1 | 2 | 91 | 94 | *1 |
| 186 | 63 | 161 | 10 | 29 | 9 | 12 | *2 |
| 187 | 54 | 138 | 11 | 33 | *3 | *3 | *2 |
| 188 | 50 | 145 | 0 | 1 | 100 | 97 | *1 |
| 189 | 40 | 104 | 9 | 31 | *3 | *3 | *2 |
| 190 | 0 | 60 | 1 | 8 | 67 | 62 | *1 |
| 191 | 0 | 30 | 3 | 21 | *3 | *3 | *2 |

*1: Inventive sample
*2: Comparative sample
*3: Reference

TABLE 7

| Optical film No. | Cellulose derivative Type | Amount (parts by mass) | Another resin Type | Amount (parts by mass) | Plasticizer Type | Amount (parts by mass) | Compound represented by Formula (1) or comparative compound Type | Amount (parts by mass) | Production process Draw ratio | Thickness (μm) |
|---|---|---|---|---|---|---|---|---|---|---|
| 192 | C 5 | 100 | None | — | Sugar ester S | 5 | 6 | 3 | 1.00 | 40 |
| 193 | C 5 | 100 | None | — | Sugar ester S | 5 | None | — | 1.00 | 40 |
| 194 | C 1 | 90 | C5 | 10 | Sugar ester S | 5 | 6 | 3 | 1.30 | 40 |
| 195 | C 1 | 90 | C5 | 10 | Sugar ester S | 5 | None | — | 1.30 | 40 |
| 196 | C 8 | 35 | PMMA1 | 65 | Sugar ester S | 5 | 6 | 3 | 1.30 | 40 |
| 197 | C 8 | 35 | PMMA1 | 65 | Sugar ester S | 5 | None | — | 1.30 | 40 |
| 198 | C 6 | 65 | PMMA2 | 35 | Sugar ester S | 5 | 6 | 3 | 1.30 | 40 |
| 199 | C 6 | 65 | PMMA2 | 35 | Sugar ester S | 5 | Comparative 4 | 3 | 1.30 | 40 |
| 200 | C 6 | 65 | PMMA2 | 35 | Sugar ester S | 5 | None | — | 1.30 | 40 |
| 201 | C 1 | 100 | None | — | Sugar ester S | 5 | 1 | 3 | 2.20 | 30 |
| 202 | C 1 | 100 | None | — | Sugar ester S | 5 | 6 | 3 | 2.20 | 30 |
| 203 | C 1 | 100 | None | — | Sugar ester S | 5 | Comparative 4 | 3 | 2.20 | 30 |
| 204 | C 1 | 100 | None | — | Sugar ester S | 5 | None | — | 2.20 | 30 |
| 205 | C 7 | 100 | None | — | Sugar ester S | 5 | 8 | 3 | 2.20 | 30 |
| 206 | C 7 | 100 | None | — | Sugar ester S | 5 | Comparative 4 | 3 | 2.20 | 30 |
| 207 | C 7 | 100 | None | — | Sugar ester S | 5 | None | — | 2.20 | 30 |
| 208 | — | — | PMMA1 | 100 | Sugar ester S | 5 | 6 | 3 | 1.30 | 40 |
| 209 | — | — | PMMA1 | 100 | Sugar ester S | 5 | None | — | 1.30 | 40 |

| Optical film No. | Optical properties of film | | | | | | |
|---|---|---|---|---|---|---|---|
| | Ro (nm) | Rt (nm) | ΔRo (nm) | ΔRt (nm) | Percent reduction of variation Ro(%) | Rt(%) | Note |
| 192 | 16 | 348 | 1 | 4 | 50 | 87 | *1 |
| 193 | 14 | 327 | 2 | 30 | Reference | Reference | *2 |
| 194 | 77 | 179 | 1 | 1 | 91 | 97 | *1 |
| 195 | 49 | 166 | 11 | 38 | Reference | Reference | *2 |
| 196 | 4 | 5 | 1 | 1 | 50 | 67 | *1 |
| 197 | 2 | 3 | 2 | 3 | Reference | Reference | *2 |
| 198 | 60 | 157 | 2 | 3 | 67 | 83 | *1 |
| 199 | 56 | 151 | 5 | 16 | 17 | 11 | *2 |
| 200 | 52 | 145 | 6 | 18 | Reference | Reference | *2 |
| 201 | 105 | 96 | 9 | 8 | 61 | 67 | *1 |
| 202 | 142 | 130 | −1 | 0 | 104 | 100 | *1 |
| 203 | 99 | 93 | 19 | 21 | 17 | 13 | *2 |
| 204 | 70 | 72 | 23 | 24 | Reference | Reference | *2 |
| 205 | 104 | 95 | 0 | 1 | 100 | 95 | *1 |
| 206 | 65 | 66 | 17 | 19 | 15 | 10 | *2 |
| 207 | 42 | 45 | 20 | 21 | Reference | Reference | *2 |
| 208 | 6 | 4 | 1 | 2 | 50 | 33 | *1 |
| 209 | 4 | −4 | 2 | 3 | Reference | Reference | *2 |

* PMMA1: Poly(methyl methacrylate) (Weight average molecular: 280000)
* PMMA2: Poly(methyl methacrylate) (Weight average molecular: 2500)
*1: Inventive sample
*2: Comparative sample The results indicate that an optical film prepared from the resin composition of the present invention exhibits excellent moisture resistance.

Example 3

<<Preparation of Resin Composition>>
[Preparation of Resin Composition 201]

Methylene chloride and ethanol contained in the main dope shown below were placed into a pressure solution tank. Subsequently, cellulose derivative C1 and exemplary compound 1 were added to the tank under stirring, and these components were completely dissolved in the solvent under heating and stirring. The resultant solution was filtered with paper filter No. 244 (manufactured by Azumi Filter Paper Co., Ltd.), to prepare a main dope.

| (Formulation of main dope) | |
|---|---|
| Methylene chloride | 520 parts by mass |
| Ethanol | 45 parts by mass |
| Cellulose derivative C1 | 100 parts by mass |
| Exemplary compound 1 | 5 parts by mass |

The dope was uniformly cast onto a stainless steel belt support with an endless belt casting apparatus. The solvent contained in the cast dope was evaporated on the stainless steel belt support, into a residual solvent content of 75%. The resultant web was detached from the stainless steel belt support. The web was conveyed while being held with clips of a tenter stretching apparatus. Subsequently, the film was dried while being conveyed with multiple rollers in a drying zone. The transverse edges of the web held with the tenter clips were trimmed by slitting with a laser cutter, and the raw film was then wound on a roller.

Thus, resin composition 201 having a thickness of 60 μm was prepared.

[Preparation of Resin Compositions 202 to 223]

Resin compositions 202 to 223 each having a thickness of 60 μm were prepared in the same manner as in resin composition 201, except that the types of a resin and an exemplary compound were modified as shown in Table 8.

(Determination of Variation in Refractive Index)

Each of the above-prepared samples was left at 23° C. and 20% RH for 24 hours for controlling humidity, and the average refractive index n1 of the sample was then measured in the same environment with an Abbe refractometer 4T (manufactured by Atago Co., Ltd.) using a light source of 590 nm.

Subsequently, the sample was humidified at 23° C. and 80% RH for 24 hours, and the average refractive index n2 of the sample was then measured in the same environment with an Abbe refractometer 4T using a light source of 590 nm.

A variation in refractive index Δn (n2−n1) was determined. A sample having a smaller Δn value exhibits more excellent moisture resistance, and is more suitable for use in an optical lens. Table 8 shows data on variation in refractive index.

TABLE 8

| Resin composition No. | Type of resin | Compound represented by Formula (1) or comparative compound | Variation in refractive index (Δn) | Note |
| --- | --- | --- | --- | --- |
| 201 | C 1 | 1 | −0.0032 | Inventive sample |
| 202 | C 1 | 6 | −0.0020 | Inventive sample |
| 203 | C 1 | 12 | −0.0027 | Inventive sample |
| 204 | C 1 | 200 | −0.0030 | Inventive sample |
| 205 | C 1 | 172 | −0.0030 | Inventive sample |
| 206 | C 1 | 176 | −0.0015 | Inventive sample |
| 207 | C 1 | 223 | −0.0040 | Inventive sample |
| 208 | C 1 | 4 | −0.0053 | Comparative sample |
| 209 | C 1 | 5 | −0.0054 | Comparative sample |
| 210 | C 1 | 6 | −0.0055 | Comparative sample |
| 211 | C 1 | Comparative 7 | −0.0057 | Comparative sample |
| 212 | C 1 | Comparative 8 | −0.0054 | Comparative sample |
| 213 | C 1 | None | −0.0055 | Comparative sample |
| 214 | PMMA1 | 1 | 0.0007 | Inventive sample |
| 215 | PMMA1 | 6 | 0.0004 | Inventive sample |
| 216 | PMMA1 | 172 | 0.0006 | Inventive sample |
| 217 | PMMA1 | 176 | 0.0003 | Inventive sample |
| 218 | PMMA1 | 4 | 0.0013 | Comparative sample |
| 219 | PMMA1 | 5 | 0.0011 | Comparative sample |
| 220 | PMMA1 | 6 | 0.0012 | Comparative sample |
| 221 | PMMA1 | Comparative 7 | 0.0012 | Comparative sample |
| 222 | PMMA1 | Comparative 8 | 0.0013 | Comparative sample |
| 223 | PMMA1 | None | 0.0012 | Comparative sample |

※ PMMA1: Poly(methyl methacrylate) (Weight average molecular: 280000)

The results shown in Table 8 indicate that the resin composition of the present invention exhibits a substantially constant refractive index independent of environmental humidity. Thus, the resin composition is suitable for use in optical lenses, such as imaging lenses, pickup lenses, and lenses for eyeglasses, and optical fibers.

Example 4

[Preparation of Optical Film 301]

Methylene chloride and ethanol contained in the main dope shown below were placed into a pressure solution tank. Subsequently, cellulose derivative C1 and exemplary compound 1 were added to the tank under stirring, and these components were completely dissolved in the solvent under heating and stirring. The resultant solution was filtered with paper filter No. 244 (manufactured by Azumi Filter Paper Co., Ltd.), to prepare a main dope.

| (Formulation of main dope) | |
| --- | --- |
| Methylene chloride | 520 parts by mass |
| Ethanol | 45 parts by mass |
| Cellulose derivative C1 | 100 parts by mass |
| Exemplary compound 1 | 5 parts by mass |

The dope was uniformly cast onto a stainless steel belt support with an endless belt casting apparatus. The solvent contained in the cast dope was evaporated on the stainless steel belt support, into a residual solvent content of 75%. The resultant web was detached from the stainless steel belt support. The web was conveyed while being held with clips of a tenter stretching apparatus. Subsequently, the film was dried while being conveyed with multiple rollers in a drying zone. The transverse edges of the film held with the tenter clips were trimmed by slitting with a laser cutter. The resultant optical film was wound on a roller.

A sample film having a thickness of 60 μm was thereby prepared.

[Preparation of Optical Films 302 to 309]

Optical films 302 to 309 each having a thickness of 60 μm were prepared in the same manner as in optical film 301, except that the type of an exemplary compound was modified as shown in Table 9.

(Variation in Optical Value, During Moisture and Heat Resistance Test)

The retardation value Rt1 of each optical film across the thickness thereof was determined at 23° C. and 55% RH. Subsequently, the film was subjected to a moisture and heat resistance test at 80° C. and 90% RH for 1,000 hours. Thereafter, the retardation value Rt2 of the film across the thickness thereof was determined at 23° C. and 55% RH.

The percent variation in optical value (%) during the moisture and heat resistance test was determined by the following expression: {(Rt1−Rt2)÷Rt1}×100.

Table 9 shows the results.

TABLE 9

| Optical film No. | Compound represented by Formula (1) or comparative compound | Percent variation in optical value during resistance test (%) | Note |
| --- | --- | --- | --- |
| 301 | 1 | 4 | Inventive sample |
| 302 | 6 | 3 | Inventive sample |
| 303 | 172 | 4 | Inventive sample |
| 304 | 176 | 2 | Inventive sample |
| 305 | 135 | 6 | Inventive sample |
| 306 | 155 | 8 | Inventive sample |
| 307 | Comparative 9 | 40 | Comparative sample |
| 308 | Comparative 10 | 50 | Comparative sample |
| 309 | Comparative 11 | 40 | Comparative sample |

Although inventive optical films exhibited no change in appearance during the moisture and heat resistance test, comparative films were yellowed during the test.

The results shown in Table 9 indicate that the optical film of the present invention exhibits a small variation in retardation value during the moisture and heat resistance test; i.e., the optical film has excellent moisture and heat resistance.

Example 5

<<Preparation of Polarizing Plate>>
[Preparation of Polarizing Plate 101]
(Preparation of Polarizer)

A poly(vinyl alcohol) film having a thickness of 30 μm was swollen in water at 35° C. The resultant film was immersed in an aqueous solution containing iodine (0.075 g), potassium iodide (5 g), and water (100 g) for 60 seconds, and then immersed in an aqueous solution containing potassium iodide (3 g), boric acid (7.5 g), and water (100 g) at 45° C. The resultant film was monoaxially stretched at 55° C. and a draw ratio of 5. The monoaxially stretched film was washed with water and then dried, to prepare a polarizer having a thickness of 10 μm.
(Preparation of Active Energy Ray-Curable Adhesive: Cationic Polymerization)

The following components were mixed, followed by defoaming, to prepare an active energy ray-curable adhesive. Triarylsulfonium hexafluorophosphate was incorporated in the form of 50% solution in propylene carbonate. In the following formulation, the amount of triarylsulfonium hexafluorophosphate corresponds to the solid content of the solution.

| | |
|---|---|
| 3,4-Epoxycyclohexylmethyl-3,4-epoxycyclohexane carboxylate | 45 parts by mass |
| Epoleed GT-301 (alicyclic epoxy resin, manufactured by Daicel Corporation) | 40 parts by mass |
| 1,4-Butanediol diglycidyl ether | 15 parts by mass |
| Triarylsulfonium hexafluorophosphate | 2.3 parts by mass |
| 9,10-Dibutoxyanthracene | 0.1 parts by mass |
| 1,4-Diethoxynaphthalene | 2.0 parts by mass |

(Preparation of Polarizing Plate 101)

Polarizing plate 101 having the configuration of the polarizing plate 101A illustrated in FIG. 1 was prepared by a process described below. In the following description, reference numerals in parentheses correspond to those of the components illustrated in FIG. 1.

KC6UA film (manufactured by Konica Minolta Advanced Layers, Inc.) was provided as a protective film (102). The above-prepared active energy ray-curable adhesive was applied onto the protective film (102) with a micro gravure coater (gravure roller: #300, rotation speed: 140%/line speed), to form an active energy ray-curable adhesive layer (103A) having a thickness of 5 μm.

Subsequently, the active energy ray-curable adhesive was applied onto the above-prepared optical film 101 (105) in the same manner as described above, to form an active energy ray-curable adhesive layer (103B) having a thickness of 5 μm.

The above-prepared poly(vinyl alcohol)-iodine polarizer (104) was disposed between the active energy ray-curable adhesive layers (103A) and (103B), and these layers were bonded together through rollers such that the slow axis of the optical film (105) was orthogonal to the absorption axis of the polarizer (104), to prepare a laminate of the protective film 1 (102), the active energy ray-curable adhesive layer (103A), the polarizer (104), the active energy ray-curable adhesive layer (1033), and the optical film 101 (105).

Both surfaces of the laminate were irradiated with electron beams, to prepare polarizing plate 101 (101A).

Preparation of polarizing plate 101 (101A) was performed under the following conditions: line speed: 20 m/min, accelerating voltage: 250 kV, and irradiation dose: 20 kGy.
[Preparation of Polarizing Plates 102 to 140]

Polarizing plates 102 to 140 were prepared in the same manner as in polarizing plate 101, except that optical film 101 was replaced with optical films 102 to 121 and 166 to 184.
<<Preparation of Liquid Crystal Display Device>>

A commercially available VA-mode liquid crystal display device (40-inch display KLV-40J3000, manufactured by Sony Corporation) was provided, and the polarizing plates of the display device were detached from both surfaces of the liquid crystal cell. Each of the above-prepared polarizing plates 101 to 140 was bonded to each surface of the liquid crystal cell as illustrated in FIG. 1, to prepare liquid crystal display devices 101 to 140. For preparation of each liquid crystal display device, the absorption axis of the polarizing plate was oriented in the same direction as that of the originally bonded polarizing plate.
<<Evaluation of Liquid Crystal Display Device>>

Each of the above-prepared liquid crystal display devices was evaluated as described below.
(Evaluation of Moisture Resistance Based on Color Unevenness in Humidified Environment)

The liquid crystal display device was covered with water-impregnated Bemcot (manufactured by Asahi Kasei Fibers Corporation) for 30 hours while avoiding evaporation of moisture. Subsequently, the liquid crystal display device was turned on and visually inspected for color uniformity in the display screen. The liquid crystal display device was evaluated for moisture resistance based on the following criteria.

A: No color unevenness
B: Substantially no color unevenness
C: Slight color unevenness but practically acceptable
D: Noticeable color unevenness
E: Quite noticeable color unevenness and unacceptable moisture resistance

TABLE 10

| Liquid crystal display device No. | Optical film No. | Color unevenness | Note |
|---|---|---|---|
| 101 | 101 | B | Inventive sample |
| 102 | 102 | A | Inventive sample |
| 103 | 103 | C | Inventive sample |
| 104 | 104 | C | Inventive sample |
| 105 | 105 | B | Inventive sample |
| 106 | 106 | C | Inventive sample |
| 107 | 107 | A | Inventive sample |
| 108 | 108 | B | Inventive sample |
| 109 | 109 | A | Inventive sample |
| 110 | 110 | A | Inventive sample |
| 111 | 111 | A | Inventive sample |
| 112 | 112 | B | Inventive sample |
| 113 | 113 | A | Inventive sample |
| 114 | 114 | A | Inventive sample |
| 115 | 115 | B | Inventive sample |
| 116 | 116 | B | Inventive sample |
| 117 | 117 | B | Inventive sample |
| 118 | 118 | A | Inventive sample |
| 119 | 119 | C | Inventive sample |
| 120 | 120 | B | Inventive sample |
| 121 | 121 | C | Inventive sample |
| 122 | 166 | E | Comparative sample |
| 123 | 167 | D | Comparative sample |
| 124 | 168 | D | Comparative sample |
| 125 | 169 | E | Comparative sample |
| 126 | 170 | E | Comparative sample |
| 127 | 171 | D | Comparative sample |
| 128 | 172 | E | Comparative sample |

TABLE 10-continued

| Liquid crystal display device No. | Optical film No. | Color unevenness | Note |
|---|---|---|---|
| 129 | 173 | E | Comparative sample |
| 130 | 174 | B | Inventive sample |
| 131 | 175 | A | Inventive sample |
| 132 | 176 | E | Comparative sample |
| 133 | 177 | B | Inventive sample |
| 134 | 178 | E | Comparative sample |
| 135 | 179 | B | Inventive sample |
| 136 | 180 | E | Comparative sample |
| 137 | 181 | B | Inventive sample |
| 138 | 182 | E | Comparative sample |
| 139 | 183 | B | Inventive sample |
| 140 | 184 | E | Comparative sample |

The results shown in Table 10 indicate that the image display device (liquid crystal display device) of the present invention exhibits excellent moisture resistance.

Example 6

[Preparation of Circularly Polarizing Plate 201]
(Preparation of Polarizer)

A poly(vinyl alcohol) film having a thickness of 120 μm was monoaxially stretched at 110° C. and a draw ratio of 5. The stretched film was immersed in an aqueous solution containing iodine (0.075 g), potassium iodide (5 g), and water (100 g) for 60 seconds, and then immersed in an aqueous solution containing potassium iodide (6 g), boric acid (7.5 g), and water (100 g) at 68° C. The resultant film was washed with water and dried, to prepare a polarizer having a thickness of 20 μm.

A surface of optical film 201 prepared in Example 1 was saponified with an alkali. A surface of a Konica Minolta Tac film KC6UA (manufactured by Konica Minolta Advanced Layers, Inc.) was also saponified with an alkali. The saponified surfaces are to be bonded to a polarizer. One surface of the polarizer was bonded to the saponified surface of optical film 201 with 5% aqueous poly(vinyl alcohol) solution serving as an adhesive. The other surface of the polarizer was boned to the saponified surface of Konica Minolta Tac film KC6UA with 5% aqueous poly(vinyl alcohol) solution, to prepare circularly polarizing plate 201. Optical film 201 and the polarizer were bonded such that the angle between the transmission axis of the polarizer and the slow axis of optical film 201 was 45°.

[Preparation of Circularly Polarizing Plates 201 to 204]

Circularly polarizing plates 202 to 204 were prepared in the same manner as in circularly polarizing plate 201, except that optical film 201 was replaced with optical films 202 to 204.

[Preparation of Organic EL Display Device 201]

A chromium light-reflecting electrode having a thickness of 80 nm was formed on a glass substrate by sputtering. An ITO thin film having a thickness of 40 nm, serving as an anode, was formed on the light-reflecting electrode. Subsequently, a hole transporting layer having a thickness of 80 nm was formed on the anode using poly(3,4-ethylenedioxythiophene)-poly(styrene sulfonate) (PEDOT:PSS) by sputtering. Red (R), green (G), and blue (B) light-emitting layers each having a thickness of 100 nm were then formed on the hole transporting layer by patterning through a shadow mask. The red light-emitting layer was formed by codeposition of tris(8-hydroxyquinolinato)aluminum ($Alq_3$) as a host and [4-(dicyanomethylene)-2-methyl-6(p-dimethylaminostyryl)-4H-pyran] (DCM) as a luminescent compound (mass ratio=99:1). The green light-emitting layer was formed by codeposition of $Alq_3$ as a host and coumarin 6 as a luminescent compound (mass ratio=99:1). The blue light-emitting layer was formed by codeposition of the following compound BAlq as a host and perylene as a luminescent compound (mass ratio=90:10).

[F103]

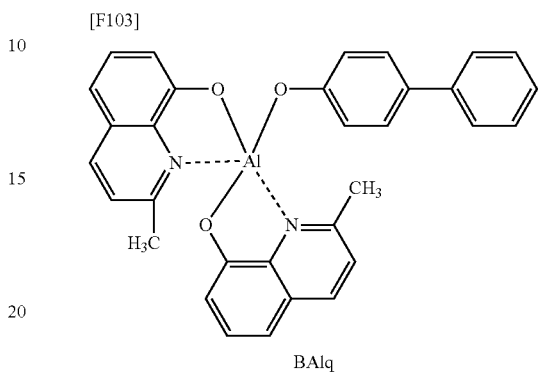

BAlq

On the red (R), green (G), and blue (B) light-emitting layers was formed a thin film having a thickness of 4 nm from calcium (i.e., a metal having a low work function) by vacuum deposition, the thin film serving as a first cathode capable of effective electron injection. On the first cathode was formed an aluminum thin film having a thickness of 2 nm serving as a second cathode, to prepare an organic light-emitting layer. Aluminum used in the second cathode plays a role in preventing the chemical alteration of calcium in the first cathode during formation of a transparent electrode on the second cathode by sputtering.

Subsequently, an ITO transparent conductive film having a thickness of 80 nm was formed on the second cathode by sputtering (the first and second cathodes and the transparent conductive film will be collectively referred to as "transparent electrode layer"). A silicon nitride thin film having a thickness of 200 nm serving as an insulating film (transparent substrate) was formed on the transparent conductive film by CVD.

Circularly polarizing plate 201 was bonded to the insulating film (transparent substrate) with an adhesive such that optical film 201 was located adjacent to the insulating film, to prepare organic EL display device 157.

[Preparation of Organic EL Display Devices 202 to 204]

Organic EL display devices 202 to 204 were prepared in the same manner as in organic EL display device 201, except that circularly polarizing plate 201 was replaced with circularly polarizing plates 202 to 204.

<<Evaluation of Organic EL Display Device>>

Each of the above-prepared organic EL display devices was evaluated as described below.

(Evaluation of Moisture Resistance Based on Color Unevenness in Humidified Environment)

The organic EL display device was covered with water-impregnated Bemcot (manufactured by Asahi Kasei Fibers Corporation) for 30 hours while avoiding evaporation of moisture. Subsequently, the organic EL display device was turned on and visually inspected for color uniformity in the display screen. The organic EL display device was evaluated for moisture resistance based on the following criteria.

A: No color unevenness
B: Substantially no color unevenness
C: Slight color unevenness but practically acceptable
D: Noticeable color unevenness
E: Quite noticeable color unevenness and unacceptable moisture resistance

TABLE 11

| Organic EL display device No. | Optical film No. | Color unevenness | Note |
|---|---|---|---|
| 201 | 201 | B | Inventive sample |
| 202 | 202 | A | Inventive sample |
| 203 | 203 | E | Comparative sample |
| 204 | 204 | E | Comparative sample |

The results shown in Table 11 indicate that the organic EL display device of the present invention exhibits excellent properties from a viewpoint of color unevenness.

Example 7

Optical films 401 to 405 were prepared in the same manner as in optical film 1 of Example 2, except that the type and amount of a cellulose derivative added, the type of a plasticizer, a compound represented by Formula (1), or a comparative compound, the draw ratio of a web, and the thickness of a stretched optical film were modified as shown in Table 12. The thickness of each optical film was adjusted by control of the casting rate of the dope. For preparation of optical films 401 to 405, the film was stretched in a direction inclined by 45° relative to the machine direction at a temperature 20° C. higher than the glass transition temperature Tg of the raw film and a draw ratio of 2.2. The angle between the in-plane slow axis of each of optical films 401 to 405 and the machine direction was 45°.

<<Evaluation of Optical Film>>

The above-prepared optical films were evaluated in the same manner as in Example 2. Specifically, a variation in retardation value Ro caused by water immersion was determined, and a percent reduction of a variation in Ro (%) was also determined.

In addition, three-dimensional refractive indices of each optical film were measured at 10 points at 23° C., 55% RH, and a wavelength of 450 nm, 550 nm, or 650 nm, and the averages of the refractive indices $n_x$, $n_y$, and $n_z$ were determined. Thereafter, the in-plane retardation values Ro (450), Ro (550), and Ro (650), corresponding to wavelengths of 450 nm, 550 nm, or 650 nm, respectively, of the film were determined in the same manner as in Example 2, Table 12 shows the results.

TABLE 12

| | Cellulose derivative | | | Compound represented by Formula (1) or comparative compound | | Production process | |
|---|---|---|---|---|---|---|---|
| Optical film No. | Type | Amount (parts by mass) | Plasticizer Type | Type | Amount (parts by mass) | Draw ratio | Thickness (μm) |
| 401 | C 1 | 100 | None | 1 | 3 | 2.20 | 110 |
| 402 | C 1 | 100 | None | 6 | 3 | 2.20 | 110 |
| 403 | C 1 | 100 | None | 176 | 3 | 2.20 | 110 |
| 404 | C 1 | 100 | None | Comparative 6 | 3 | 2.20 | 110 |
| 405 | C 1 | 100 | None | None | — | 2.20 | 110 |

| | Optical properties of film | | | | | | |
|---|---|---|---|---|---|---|---|
| Optical film No. | Ro(590) (nm) | ΔRo(590) (nm) | Percent reduction of variation Ro (%) | Ro(550) (nm) | Ro(450)/ Ro(550) | Ro(550)/ Ro(650) | Note |
| 401 | 120 | 20 | 75 | 115 | 0.82 | 0.91 | Inventive sample |
| 402 | 145 | 7 | 91 | 140 | 0.84 | 0.93 | Inventive sample |
| 403 | 149 | 5 | 94 | 144 | 0.85 | 0.93 | Inventive sample |
| 404 | 150 | 68 | 15 | 150 | 1.00 | 1.01 | Comparative sample |
| 405 | 90 | 80 | Reference | 100 | 1.40 | 1.26 | Comparative sample |

The results shown in Table 12 indicate that an optical film prepared from the resin of the present invention exhibits high moisture resistance, excellent optical properties, and excellent reverse wavelength dispersion.

Example 8

[Preparation of Circularly Polarizing Plates 401 to 405]

Circularly polarizing plates 401 to 405 were prepared in the same manner as in circularly polarizing plate 201 of Example 6, except that optical film 201 was replaced with optical films 401 to 405.

[Preparation of Organic EL Display Devices 401 to 405]

Organic EL display devices 401 to 405 were prepared in the same manner as in organic EL display device 157 of Example 6, except that circularly polarizing plate 201 in organic EL display device 201 was replaced with circularly polarizing plates 401 to 405.

<<Evaluation of Organic EL Display Device>>

The above-prepared organic EL display devices were evaluated from the viewpoint of color unevenness.

Table 13 shows the results.

TABLE 13

| Organic EL display device No. | Optical film No. | Color unevenness | Note |
|---|---|---|---|
| 401 | 401 | B | Inventive sample |
| 402 | 402 | A | Inventive sample |
| 403 | 403 | A | Inventive sample |
| 404 | 404 | E | Comparative sample |
| 405 | 405 | E | Comparative sample |

The results shown in Table 13 indicate that the organic EL display device of the present invention exhibits excellent properties in a viewpoint of color unevenness.

INDUSTRIAL APPLICABILITY

The present invention can provide a resin composition exhibiting a small humidity-dependent variation in optical values. The present invention can also provide an optical film and an optical lens, each of which is prepared from the resin composition and exhibits a small humidity-dependent variation in optical values. The present invention can also provide a polarizing plate, a circularly polarizing plate, and an image display device, each of which includes the optical film and exhibits excellent moisture resistance.

REFERENCE SIGNS LIST

101A: polarizing plate
102: protective film
103A, 103B: active energy ray-curable adhesive layer
104: polarizer
105: retardation film
106: protective film
107: liquid crystal cell
108: liquid crystal display device
BL: backlight
10: organic EL display device
12: light-reflecting electrode
14: light-emitting layer
16: transparent electrode layer
18: transparent substrate
20: circularly polarizing plate
20A: λ/4 retardation film
20B: polarizer (linearly polarizing film)
a1, b1, b3, b4: linearly polarized light component
c1, c2, c3, c4: circularly polarized light component
30: liquid crystal display device
40: liquid crystal cell
50, 60: polarizing plate
52, 62: polarizer
54, 56, 64, 66: protective film
70: backlight unit
V: viewing side

The invention claimed is:

1. A resin composition comprising:
a resin and
a compound which has a structure represented by the following formula:

[F2]

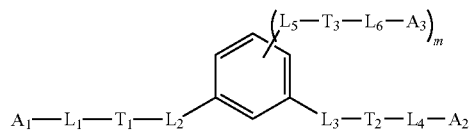

Formula(2)

wherein $A_1$, $A_2$ and $A_3$ each independently represent an alkyl group, a cycloalkyl group, an aromatic hydrocarbon ring, or an aromatic heterocyclic ring; $T_1$, $T_2$ and $T_3$ each independently represent a pyrrole ring, a pyrazole ring, an imidazole ring, a 1,2,3-triazole ring, or a 1,2,4-triazole ring; $L_1$, $L_2$, $L_3$, $L_4$, $L_5$ and $L_6$ each independently represent a single bond or a divalent linking group; and m represents an integer of 0 to 4.

2. The resin composition according to claim 1, wherein the resin is a hygroscopic resin.

3. The resin composition according to claim 2, wherein the hygroscopic resin exhibits a water absorption of 0.5 to 10 mass % at 23° C.

4. The resin composition according to claim 2, wherein the hygroscopic resin is a cellulose compound.

5. The resin composition according to claim 2, wherein the hygroscopic resin is a cellulose ester.

6. The resin composition according to claim 1, wherein the compound has a pyrrole ring, a pyrazole ring, an imidazole ring, a 1,2,3-triazole ring, or a 1,2,4-triazole ring having a nucleus-independent chemical shift value smaller than that of a benzene ring.

7. A resin composition comprising a resin and a compound having a formula selected from the group consisting of

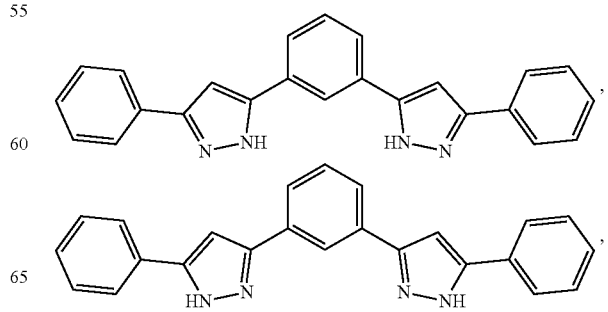

-continued
and
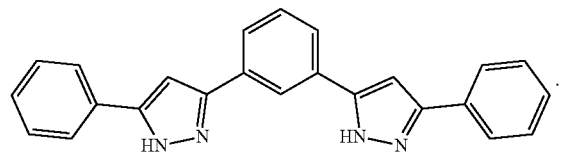
* * * * *